(12) United States Patent
Ahmed et al.

(10) Patent No.: US 11,844,634 B2
(45) Date of Patent: *Dec. 19, 2023

(54) MOBILE PATIENT ALARM DISPLAY

(71) Applicant: MASIMO CORPORATION, Irvine, CA (US)

(72) Inventors: Omar Ahmed, Lake Forest, CA (US); Bilal Muhsin, San Clemente, CA (US); Massi Joe E. Kiani, Irvine, CA (US); Keith Ward Indorf, Riverside, CA (US); Sebastian T. Frey, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 17/372,328

(22) Filed: Jul. 9, 2021

(65) Prior Publication Data

US 2021/0330270 A1 Oct. 28, 2021

Related U.S. Application Data

(63) Continuation of application No. 16/889,263, filed on Jun. 1, 2020, now Pat. No. 11,109,818, which is a (Continued)

(51) Int. Cl.
*G08B 21/02* (2006.01)
*A61B 5/00* (2006.01)

(52) U.S. Cl.
CPC ............ *A61B 5/746* (2013.01); *A61B 5/002* (2013.01); *A61B 5/742* (2013.01); *A61B 2562/08* (2013.01)

(58) Field of Classification Search
USPC ............ 340/573.1, 572.1–572.9, 573.3, 683, 340/825.29, 825.36, 7.6, 539.12
See application file for complete search history.

(56) References Cited

U.S. PATENT DOCUMENTS

| | | |
|---|---|---|
| 3,646,606 A | 2/1972 | Buxton et al. |
| 3,690,313 A | 9/1972 | Weppner et al. |
| (Continued) | | |

FOREIGN PATENT DOCUMENTS

| | | |
|---|---|---|
| CN | 202889636 | 4/2013 |
| EP | 0 735 499 | 10/1996 |
| (Continued) | | |

OTHER PUBLICATIONS

US 8,845,543 B2, 09/2014, Diab et al. (withdrawn)
(Continued)

*Primary Examiner* — Daniel Previl
(74) *Attorney, Agent, or Firm* — Knobbe, Martens, Olson & Bear, LLP

(57) ABSTRACT

This disclosure describes example alarm notification systems that can enable a clinician to respond to an alarm notification received via a computing device, which may have more advanced functionality than a pager. The clinician device may be a mobile device, such as a cellphone or smartphone, tablet, laptop, personal digital assistant (PDA), or the like. The clinician device may communicate with a remote server to obtain patient data generated by a patient device at the point-of-care (such as a bedside device or patient-worn monitor). This patient data may be continuous monitoring data for one or more patients. A mobile application (optionally a browser application) on the clinician device can enable the clinician to view continuous monitoring data for multiple patients, as well as view and respond to alarms and alerts, all from the clinician device, regardless of location.

15 Claims, 108 Drawing Sheets

Related U.S. Application Data continuation of application No. 16/388,637, filed on Apr. 18, 2019, now Pat. No. 10,667,764.

(60) Provisional application No. 62/712,154, filed on Jul. 30, 2018, provisional application No. 62/678,848, filed on May 31, 2018, provisional application No. 62/659,961, filed on Apr. 19, 2018.

(56) References Cited

U.S. PATENT DOCUMENTS

| | | |
|---|---|---|
| 3,810,102 A | 5/1974 | Parks, III et al. |
| 3,815,583 A | 6/1974 | Scheidt |
| 3,972,320 A | 8/1976 | Kalman |
| 3,978,849 A | 9/1976 | Geneen |
| 4,108,166 A | 8/1978 | Schmid |
| 4,231,354 A | 11/1980 | Kurtz et al. |
| 4,589,415 A | 5/1986 | Haaga |
| 4,662,378 A | 5/1987 | Thomis |
| 4,827,943 A | 5/1989 | Bornn et al. |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,318,037 A | 6/1994 | Evans et al. |
| 5,319,355 A | 6/1994 | Russek |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Shimizu |
| 5,375,604 A | 12/1994 | Kelly et al. |
| 5,377,676 A | 1/1995 | Vari et al. |
| 5,400,794 A | 3/1995 | Gorman |
| D357,982 S | 5/1995 | Dahl et al. |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,462,051 A | 10/1995 | Oka et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,537,289 A | 7/1996 | Dahl |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,671,914 A | 9/1997 | Kalkhoran et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang et al. |
| 5,724,580 A | 3/1998 | Levin et al. |
| 5,724,983 A | 3/1998 | Selker et al. |
| 5,725,308 A | 3/1998 | Smith et al. |
| 5,726,440 A | 3/1998 | Kalkhoran et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,754,111 A | 5/1998 | Garcia |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,813,403 A | 9/1998 | Soller et al. |
| 5,822,544 A | 10/1998 | Chaco et al. |
| 5,822,546 A | 10/1998 | George |
| 5,823,950 A | 10/1998 | Diab et al. |
| 5,829,723 A | 11/1998 | Brunner |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |
| 5,876,351 A | 3/1999 | Rohde |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,931,791 A | 8/1999 | Saltzstein et al. |
| 5,934,925 A | 8/1999 | Tobler et al. |
| 5,940,182 A | 8/1999 | Lepper, Jr. et al. |
| 5,942,986 A | 8/1999 | Shabot et al. |
| 5,951,469 A | 9/1999 | Yamaura |
| 5,987,343 A | 11/1999 | Kinast |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,006,119 A | 12/1999 | Soller et al. |
| 6,010,937 A | 1/2000 | Karam et al. |
| 6,011,986 A | 1/2000 | Diab et al. |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang et al. |
| 6,036,642 A | 3/2000 | Diab et al. |
| 6,036,718 A | 3/2000 | Ledford et al. |
| 6,040,578 A | 3/2000 | Malin et al. |

(56) References Cited

U.S. PATENT DOCUMENTS

| | | | |
|---|---|---|---|
| 6,045,509 A | 4/2000 | Caro et al. |
| 6,045,527 A | 4/2000 | Appelbaum et al. |
| 6,057,758 A | 5/2000 | Dempsey et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,175,752 B1 | 1/2001 | Say et al. |
| 6,183,417 B1 | 2/2001 | Gehab et al. |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,241,684 B1 | 6/2001 | Amano et al. |
| 6,251,113 B1 | 6/2001 | Appelbaum |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,304,767 B1 | 10/2001 | Soller et al. |
| 6,308,089 B1 | 10/2001 | von der Ruhr et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,325,761 B1 | 12/2001 | Jay |
| 6,329,139 B1 | 12/2001 | Nova et al. |
| 6,332,100 B1 | 12/2001 | Sahai et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,352,504 B1 | 3/2002 | Ise |
| 6,354,235 B1 | 3/2002 | Davies |
| 6,360,114 B1 | 3/2002 | Diab et al. |
| 6,364,834 B1 | 4/2002 | Reuss et al. |
| 6,364,839 B1 | 4/2002 | Little et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,406,426 B1 | 6/2002 | Reuss et al. |
| 6,407,335 B1 | 6/2002 | Franklin-Lees |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,470,893 B1 | 10/2002 | Boesen |
| 6,480,505 B1 | 11/2002 | Johansson et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,516,289 B2 | 2/2003 | David et al. |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,570,592 B1 | 5/2003 | Sajdak et al. |
| 6,578,428 B1 | 6/2003 | Dromms et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,641,533 B2 | 11/2003 | Causey et al. |
| 6,643,530 B2 | 11/2003 | Diab et al. |
| 6,646,556 B1 | 11/2003 | Smith et al. |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| 6,658,276 B2 | 12/2003 | Kianl et al. |
| 6,661,161 B1 | 12/2003 | Lanzo et al. |
| 6,663,570 B2 | 12/2003 | Mott et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,725,086 B2 | 4/2004 | Marinello |
| 6,728,560 B2 | 4/2004 | Kollias et al. |
| 6,730,026 B2 | 5/2004 | Christ et al. |
| 6,735,459 B2 | 5/2004 | Parker |
| 6,738,652 B2 | 5/2004 | Mattu et al. |
| 6,745,060 B2 | 6/2004 | Diab et al. |
| 6,746,406 B2 | 6/2004 | Lia et al. |
| 6,750,463 B1 | 6/2004 | Riley |
| 6,751,492 B2 | 6/2004 | Ben-haim |
| 6,760,607 B2 | 7/2004 | Al-Ali |

(56) References Cited

U.S. PATENT DOCUMENTS

| | | |
|---|---|---|
| 6,766,188 B2 | 7/2004 | Soller |
| 6,770,028 B1 | 8/2004 | Ali et al. |
| 6,771,994 B2 | 8/2004 | Kiani et al. |
| 6,783,492 B2 | 8/2004 | Dominguez |
| 6,788,965 B2 | 9/2004 | Ruchti et al. |
| 6,790,178 B1 | 9/2004 | Mault et al. |
| 6,792,300 B1 | 9/2004 | Diab et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,241 B2 | 11/2004 | Grubisic |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,876,931 B2 | 4/2005 | Lorenz et al. |
| 6,893,396 B2 | 5/2005 | Schulze et al. |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,952,340 B2 | 10/2005 | Son et al. |
| 6,956,649 B2 | 10/2005 | Acosta et al. |
| 6,957,107 B2 | 10/2005 | Rogers et al. |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,988,989 B2 | 1/2006 | Weiner et al. |
| 6,990,087 B2 | 1/2006 | Rao et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,042,338 B1 | 5/2006 | Weber |
| 7,044,918 B2 | 5/2006 | Diab |
| 7,044,930 B2 | 5/2006 | Stromberg |
| 7,048,687 B1 | 5/2006 | Reuss et al. |
| 7,063,666 B2 | 6/2006 | Weng et al. |
| 7,067,893 B2 | 6/2006 | Mills et al. |
| 7,079,035 B2 | 7/2006 | Bock et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,256,708 B2 | 8/2007 | Rosenfeld |
| 7,261,691 B1 | 8/2007 | Asomani |
| 7,261,697 B2 | 8/2007 | Berstein |
| 7,264,616 B2 | 9/2007 | Shehada et al. |
| 7,267,671 B2 | 9/2007 | Shehada et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,285,090 B2 | 10/2007 | Stivoric et al. |
| 7,289,835 B2 | 10/2007 | Mansfield et al. |
| 7,292,141 B2 | 11/2007 | Staats et al. |
| 7,292,883 B2 | 11/2007 | De Felice et al. |
| 7,295,866 B2 | 11/2007 | Al-Ali |
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,327,219 B2 | 2/2008 | Lederer |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,378,975 B1 | 5/2008 | Smith et al. |
| 7,382,247 B2 | 6/2008 | Welch et al. |
| 7,383,070 B2 | 6/2008 | Diab et al. |
| 7,390,299 B2 | 6/2008 | Weiner et al. |
| 7,395,158 B2 | 7/2008 | Monfre et al. |
| 7,395,216 B2 | 7/2008 | Rosenfeld |
| 7,402,338 B2 | 7/2008 | Weintritt et al. |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,787 B2 | 10/2008 | Diab |

(56) References Cited

U.S. PATENT DOCUMENTS

| | | |
|---|---|---|
| 7,454,240 B2 | 11/2008 | Diab et al. |
| 7,454,359 B2 | 11/2008 | Rosenfeld |
| 7,454,360 B2 | 11/2008 | Rosenfeld |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,043 B2 | 4/2009 | Welch et al. |
| 7,515,044 B2 | 4/2009 | Welch et al. |
| 7,519,406 B2 | 4/2009 | Blank et al. |
| 7,523,044 B2 | 4/2009 | Rosenblood |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,551,717 B2 | 6/2009 | Tome et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,590,950 B2 | 9/2009 | Collins et al. |
| 7,593,230 B2 | 9/2009 | Abul-Haj et al. |
| 7,596,398 B2 | 9/2009 | Al-Ali et al. |
| 7,597,665 B2 | 10/2009 | Wilk et al. |
| 7,606,608 B2 | 10/2009 | Blank et al. |
| 7,612,999 B2 | 11/2009 | Clark et al. |
| 7,616,303 B2 | 11/2009 | Yang et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,639,145 B2 | 12/2009 | Lawson et al. |
| 7,640,140 B2 | 12/2009 | Ruchti et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,671,733 B2 | 3/2010 | McNeal et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,740,590 B2 | 6/2010 | Bernstein |
| 7,749,164 B2 | 7/2010 | Davis |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,806,830 B2 | 10/2010 | Bernstein |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,884,314 B2 | 2/2011 | Hamada |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,942,844 B2 | 5/2011 | Moberg et al. |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,978,062 B2 | 7/2011 | LaLonde et al. |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Ali et al. |
| 7,991,463 B2 | 8/2011 | Kelleher et al. |
| 7,991,625 B2 | 8/2011 | Rosenfeld |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| 8,094,013 B1 | 1/2012 | Lee et al. |
| RE43,169 E | 2/2012 | Parker |
| 8,118,620 B2 | 2/2012 | Al-Ali et al. |

(56) References Cited

U.S. PATENT DOCUMENTS

| | | |
|---|---|---|
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,180,650 B2 | 5/2012 | Graves et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,200,308 B2 | 6/2012 | Zhang et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,224,667 B1 | 7/2012 | Miller et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,294,588 B2 | 10/2012 | Fisher et al. |
| 8,294,716 B2 | 10/2012 | Lord et al. |
| 8,298,153 B2 | 10/2012 | Boute et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| RE43,860 E | 12/2012 | Parker |
| 8,326,649 B2 | 12/2012 | Rosenfeld |
| 8,327,002 B1 | 12/2012 | Van Dussen et al. |
| 8,328,793 B2 | 12/2012 | Birkenbach et al. |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| D679,018 S | 3/2013 | Fullerton et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,423,378 B1 | 4/2013 | Golderg |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,167 B2 | 7/2013 | Buxton et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,565,847 B2 | 10/2013 | Buxton et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,578,082 B2 | 11/2013 | Medina et al. |
| 8,579,813 B2 | 11/2013 | Causey, III et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,588,924 B2 | 11/2013 | Dion |
| 8,597,287 B2 | 12/2013 | Benamou et al. |
| 8,600,467 B2 | 12/2013 | Al-Ali et al. |
| 8,600,777 B2 | 12/2013 | Schoenberg |
| 8,606,342 B2 | 12/2013 | Diab |
| 8,612,260 B2 | 12/2013 | Hasan et al. |
| 8,620,678 B2 | 12/2013 | Gotlib |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,655,680 B2 | 2/2014 | Bechtel et al. |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,771 B2 | 4/2014 | Wekell et al. |
| 8,690,799 B2 | 4/2014 | Telfort et al. |
| 8,694,331 B2 | 4/2014 | DeBelser et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,717,909 B1 | 5/2014 | Shekhar et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |

(56) References Cited

U.S. PATENT DOCUMENTS

| | | |
|---|---|---|
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,758,020 B2 | 6/2014 | Burdea et al. |
| 8,761,850 B2 | 6/2014 | Lamego |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,950 B2 | 7/2014 | Larsen et al. |
| 8,801,613 B2 | 8/2014 | Al-Ali et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,054 B2 | 9/2014 | Weiss |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,873,035 B2 | 10/2014 | Yang et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,907,287 B2 | 12/2014 | Vanderpohl |
| 8,909,310 B2 | 12/2014 | Lamego et al. |
| 8,909,330 B2 | 12/2014 | McCombie et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,951,248 B2 | 2/2015 | Messerly et al. |
| 8,956,292 B2 | 2/2015 | Wekell et al. |
| 8,956,294 B2 | 2/2015 | McCombie et al. |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 8,998,830 B2 | 4/2015 | Halperin et al. |
| 9,028,429 B2 | 5/2015 | Telfort et al. |
| 9,037,207 B2 | 5/2015 | Al-Ali et al. |
| 9,041,530 B2 | 5/2015 | Sprigg et al. |
| 9,057,689 B2 | 6/2015 | Soller |
| 9,058,635 B1 | 6/2015 | Rybkin |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,291 B2 | 8/2015 | Soller |
| 9,095,316 B2 | 8/2015 | Welch et al. |
| 9,104,789 B2 | 8/2015 | Gross et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,125,578 B2 | 9/2015 | Grunwald |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,262,586 B2 | 2/2016 | Steiger et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,384,652 B2 | 7/2016 | Gilham et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,529,762 B2 | 12/2016 | Gisler et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |

(56) References Cited

U.S. PATENT DOCUMENTS

| | | |
|---|---|---|
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Al-Ali et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |

(56) References Cited

U.S. PATENT DOCUMENTS

| | | |
|---|---|---|
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Sherim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,109,818 B2 | 9/2021 | Ahmed et al. |
| 11,114,188 B2 | 9/2021 | Poeze et al. |
| D933,232 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| 2001/0011355 A1 | 8/2001 | Kawai |
| 2001/0031922 A1 | 10/2001 | Weng et al. |
| 2001/0034477 A1 | 10/2001 | Mansfield et al. |
| 2001/0039483 A1 | 11/2001 | Brand et al. |
| 2001/0046366 A1 | 11/2001 | Susskind |
| 2001/0051765 A1 | 12/2001 | Walker et al. |
| 2002/0010401 A1 | 1/2002 | Bushmakin et al. |
| 2002/0038392 A1 | 3/2002 | De La Huerga |
| 2002/0045836 A1 | 4/2002 | Alkawwas |
| 2002/0052311 A1 | 5/2002 | Solomon et al. |
| 2002/0058864 A1 | 5/2002 | Mansfield et al. |
| 2002/0062230 A1 | 5/2002 | Morag et al. |
| 2002/0063690 A1 | 5/2002 | Chung et al. |
| 2002/0099275 A1 | 7/2002 | Schmidt et al. |
| 2002/0133080 A1 | 9/2002 | Apruzzese et al. |
| 2002/0177758 A1 | 11/2002 | Schoenberg |
| 2002/0198445 A1 | 12/2002 | Dominguez et al. |
| 2003/0013975 A1 | 1/2003 | Kiani |
| 2003/0018243 A1 | 1/2003 | Gerhardt et al. |
| 2003/0027326 A1 | 2/2003 | Ulmsten et al. |
| 2003/0036683 A1 | 2/2003 | Kehr et al. |
| 2003/0052787 A1 | 3/2003 | Zerhusen et al. |
| 2003/0058838 A1 | 3/2003 | Wengrovitz |
| 2003/0144582 A1 | 7/2003 | Cohen et al. |
| 2003/0149598 A1 | 8/2003 | Santoso et al. |
| 2003/0156288 A1 | 8/2003 | Barnum et al. |
| 2003/0158466 A1 | 8/2003 | Lynn et al. |
| 2003/0172940 A1 | 9/2003 | Rogers et al. |
| 2003/0212312 A1 | 11/2003 | Coffin, IV et al. |
| 2003/0216670 A1 | 11/2003 | Beggs |
| 2004/0013647 A1 | 1/2004 | Solomon et al. |
| 2004/0059599 A1 | 3/2004 | McIvor |
| 2004/0106163 A1 | 6/2004 | Workman, Jr. et al. |
| 2004/0122787 A1 | 6/2004 | Avinash et al. |
| 2004/0126007 A1 | 7/2004 | Ziel et al. |
| 2004/0139571 A1 | 7/2004 | Chang et al. |
| 2004/0147818 A1 | 7/2004 | Levy et al. |
| 2004/0172222 A1 | 9/2004 | Simpson et al. |
| 2004/0172302 A1 | 9/2004 | Martucci et al. |
| 2004/0186357 A1 | 9/2004 | Soderberg et al. |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0249670 A1 | 12/2004 | Noguchi et al. |
| 2004/0254431 A1 | 12/2004 | Shehada et al. |
| 2004/0254432 A1 | 12/2004 | Shehada et al. |
| 2004/0267103 A1 | 12/2004 | Li et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0055276 A1 | 3/2005 | Kiani et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1 | 6/2005 | Mack et al. |
| 2005/0125256 A1 | 6/2005 | Schoenberg |
| 2005/0143671 A1 | 6/2005 | Hastings et al. |
| 2005/0146431 A1 | 7/2005 | Hastings et al. |
| 2005/0148890 A1 | 7/2005 | Hastings |
| 2005/0164933 A1 | 7/2005 | Tymianski et al. |
| 2005/0190747 A1 | 9/2005 | Sindhwani et al. |

(56) References Cited

U.S. PATENT DOCUMENTS

| | | |
|---|---|---|
| 2005/0191294 A1 | 9/2005 | Arap et al. |
| 2005/0203775 A1 | 9/2005 | Achan |
| 2005/0234317 A1 | 10/2005 | Kiani |
| 2005/0268401 A1 | 12/2005 | Dixon et al. |
| 2005/0277872 A1 | 12/2005 | Colby, Jr. et al. |
| 2006/0049936 A1 | 3/2006 | Collins, Jr. et al. |
| 2006/0058647 A1 | 3/2006 | Strommer et al. |
| 2006/0073719 A1 | 4/2006 | Kiani |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0161054 A1 | 7/2006 | Reuss et al. |
| 2006/0169773 A1 | 8/2006 | Lyons et al. |
| 2006/0189871 A1 | 8/2006 | Al-Ali et al. |
| 2006/0190833 A1 | 8/2006 | SanGiovanni et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0002533 A1 | 1/2007 | Kogan et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0073116 A1 | 3/2007 | Kiani et al. |
| 2007/0073555 A1 | 3/2007 | Buist |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0156033 A1 | 7/2007 | Causey et al. |
| 2007/0157285 A1 | 7/2007 | Frank et al. |
| 2007/0159332 A1 | 7/2007 | Koblasz |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0185739 A1 | 8/2007 | Ober et al. |
| 2007/0192140 A1 | 8/2007 | Gropper |
| 2007/0213600 A1 | 9/2007 | John et al. |
| 2007/0232941 A1 | 10/2007 | Rabinovich |
| 2007/0244377 A1 | 10/2007 | Cozad et al. |
| 2007/0244724 A1 | 10/2007 | Pendergast et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg et al. |
| 2008/0000479 A1 | 1/2008 | Elaz et al. |
| 2008/0001735 A1 | 1/2008 | Tran |
| 2008/0003200 A1 | 1/2008 | Arap et al. |
| 2008/0015903 A1* | 1/2008 | Rodgers ............... G06Q 30/02 705/3 |
| 2008/0021854 A1 | 1/2008 | Jung et al. |
| 2008/0033661 A1 | 2/2008 | Syroid et al. |
| 2008/0053438 A1 | 3/2008 | DeVries et al. |
| 2008/0058657 A1 | 3/2008 | Schwartz et al. |
| 2008/0064965 A1 | 3/2008 | Jay et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0094228 A1 | 4/2008 | Welch et al. |
| 2008/0097167 A1 | 4/2008 | Yudkovitch et al. |
| 2008/0099366 A1 | 5/2008 | Niemiec et al. |
| 2008/0119412 A1 | 5/2008 | Tymianski et al. |
| 2008/0138278 A1 | 6/2008 | Scherz et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0201174 A1 | 8/2008 | Ramasubramanian et al. |
| 2008/0208912 A1 | 8/2008 | Garibaldi |
| 2008/0221396 A1 | 9/2008 | Garces et al. |
| 2008/0221418 A1 | 9/2008 | Al-Ali et al. |
| 2008/0228077 A1 | 9/2008 | Wilk et al. |
| 2008/0249804 A1 | 10/2008 | Kim |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0319275 A1 | 12/2008 | Chiu et al. |
| 2008/0319354 A1 | 12/2008 | Bell et al. |
| 2009/0005651 A1 | 1/2009 | Ward et al. |
| 2009/0018808 A1 | 1/2009 | Bronstein et al. |
| 2009/0024008 A1 | 1/2009 | Brunner et al. |
| 2009/0036759 A1 | 2/2009 | Ault et al. |
| 2009/0043172 A1 | 2/2009 | Zagorchev et al. |
| 2009/0046837 A1 | 2/2009 | Thiel |
| 2009/0052623 A1 | 2/2009 | Tome et al. |
| 2009/0054735 A1 | 2/2009 | Higgins et al. |
| 2009/0054743 A1 | 2/2009 | Wekell et al. |
| 2009/0062682 A1 | 3/2009 | Bland et al. |
| 2009/0069642 A1 | 3/2009 | Gao et al. |
| 2009/0093687 A1 | 4/2009 | Telfort et al. |
| 2009/0095926 A1 | 4/2009 | MacNeish, III |
| 2009/0099480 A1 | 4/2009 | Salgo et al. |
| 2009/0119843 A1 | 5/2009 | Rodgers et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0146822 A1 | 6/2009 | Soliman |
| 2009/0157058 A1 | 6/2009 | Ferren et al. |
| 2009/0164236 A1 | 6/2009 | Gounares et al. |
| 2009/0171170 A1 | 7/2009 | Li et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0204977 A1 | 8/2009 | Tavares et al. |
| 2009/0221880 A1 | 9/2009 | Soderberg et al. |
| 2009/0226372 A1 | 9/2009 | Ruoslahti et al. |
| 2009/0247984 A1 | 10/2009 | Lamego et al. |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0309755 A1 | 12/2009 | Williamson |
| 2009/0322540 A1 | 12/2009 | Richardson et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0088121 A1 | 4/2010 | Shih et al. |
| 2010/0099964 A1 | 4/2010 | O'Reilly et al. |
| 2010/0125217 A1 | 5/2010 | Kuo et al. |
| 2010/0144627 A1 | 6/2010 | Vitek et al. |
| 2010/0185101 A1 | 7/2010 | Sakai et al. |
| 2010/0188230 A1 | 7/2010 | Lindsay |
| 2010/0198622 A1 | 8/2010 | Gajic et al. |
| 2010/0210958 A1 | 8/2010 | Manwaring et al. |
| 2010/0234718 A1 | 9/2010 | Sampath et al. |
| 2010/0270257 A1 | 10/2010 | Wachman et al. |
| 2010/0298650 A1 | 11/2010 | Moon et al. |
| 2010/0298659 A1 | 11/2010 | McCombie et al. |
| 2010/0298661 A1 | 11/2010 | McCombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317951 A1 | 12/2010 | Rutkowski et al. |
| 2011/0001605 A1 | 1/2011 | Kiani et al. |
| 2011/0021930 A1 | 1/2011 | Mazzeo et al. |
| 2011/0023130 A1 | 1/2011 | Gudgel et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0046495 A1 | 2/2011 | Osypka |

(56) References Cited

U.S. PATENT DOCUMENTS

| | | |
|---|---|---|
| 2011/0066051 A1 | 3/2011 | Moon et al. |
| 2011/0077473 A1 | 3/2011 | Lisogurski |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087081 A1 | 4/2011 | Kiani et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105854 A1 | 5/2011 | Kiani et al. |
| 2011/0105956 A1 | 5/2011 | Hirth |
| 2011/0106561 A1 | 5/2011 | Eaton, Jr. et al. |
| 2011/0106565 A1 | 5/2011 | Compton et al. |
| 2011/0117878 A1 | 5/2011 | Barash et al. |
| 2011/0118561 A1 | 5/2011 | Tari et al. |
| 2011/0118573 A1 | 5/2011 | Mckenna |
| 2011/0125060 A1 | 5/2011 | Telfort et al. |
| 2011/0130636 A1 | 6/2011 | Daniel et al. |
| 2011/0137297 A1 | 6/2011 | Kiani et al. |
| 2011/0152629 A1 | 6/2011 | Eaton et al. |
| 2011/0166465 A1 | 7/2011 | Clements et al. |
| 2011/0167133 A1 | 7/2011 | Jain |
| 2011/0172498 A1 | 7/2011 | Olsen et al. |
| 2011/0172967 A1 | 7/2011 | Al-Ali et al. |
| 2011/0178373 A1 | 7/2011 | Pacey et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208073 A1 | 8/2011 | Matsukawa et al. |
| 2011/0212090 A1 | 9/2011 | Pedersen et al. |
| 2011/0213210 A1 | 9/2011 | Temby et al. |
| 2011/0227739 A1 | 9/2011 | Gilham et al. |
| 2011/0230733 A1 | 9/2011 | Al-Ali |
| 2011/0257544 A1 | 10/2011 | Kaasinen et al. |
| 2011/0263950 A1 | 10/2011 | Larson et al. |
| 2011/0295094 A1 | 12/2011 | Doyle et al. |
| 2012/0002791 A1 | 1/2012 | Kraus et al. |
| 2012/0004579 A1 | 1/2012 | Luo et al. |
| 2012/0025992 A1 | 2/2012 | Tallent et al. |
| 2012/0029300 A1 | 2/2012 | Paquet |
| 2012/0029304 A1 | 2/2012 | Medina et al. |
| 2012/0029879 A1 | 2/2012 | Sing et al. |
| 2012/0041783 A1 | 2/2012 | McKee et al. |
| 2012/0059230 A1 | 3/2012 | Teller et al. |
| 2012/0071771 A1 | 3/2012 | Behar |
| 2012/0075464 A1 | 3/2012 | Derenne et al. |
| 2012/0095778 A1 | 4/2012 | Gross et al. |
| 2012/0101353 A1 | 4/2012 | Reggiardo et al. |
| 2012/0112903 A1 | 5/2012 | Kaib et al. |
| 2012/0123231 A1 | 5/2012 | O'Reilly |
| 2012/0123799 A1 | 5/2012 | Nolen et al. |
| 2012/0134257 A1 | 5/2012 | Knox |
| 2012/0136221 A1 | 5/2012 | Killen et al. |
| 2012/0165629 A1 | 6/2012 | Merritt et al. |
| 2012/0184120 A1 | 7/2012 | Basta et al. |
| 2012/0197619 A1 | 8/2012 | Namer Yelin et al. |
| 2012/0203078 A1 | 8/2012 | Sze et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0226160 A1 | 9/2012 | Kudoh |
| 2012/0239434 A1 | 9/2012 | Breslow et al. |
| 2012/0242501 A1 | 9/2012 | Tran et al. |
| 2012/0259233 A1 | 10/2012 | Chan et al. |
| 2012/0265039 A1* | 10/2012 | Kiani ............... A61B 5/412 600/323 |
| 2012/0278104 A1 | 11/2012 | Traughber et al. |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0293323 A1 | 11/2012 | Kaib et al. |
| 2012/0294801 A1 | 11/2012 | Scherz et al. |
| 2012/0303476 A1 | 11/2012 | Krzyzanowski et al. |
| 2012/0306881 A1 | 12/2012 | Nemoto |
| 2013/0006131 A1 | 1/2013 | Narayan et al. |
| 2013/0006151 A1 | 1/2013 | Main et al. |
| 2013/0012830 A1 | 1/2013 | Leininger |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0045685 A1 | 2/2013 | Kiani |
| 2013/0046197 A1 | 2/2013 | Dlugos, Jr. et al. |
| 2013/0060147 A1 | 3/2013 | Welch et al. |
| 2013/0069802 A1 | 3/2013 | Foghel et al. |
| 2013/0092805 A1 | 4/2013 | Funk et al. |
| 2013/0096405 A1 | 4/2013 | Garfio |
| 2013/0096936 A1 | 4/2013 | Sampath et al. |
| 2013/0109929 A1 | 5/2013 | Menzel |
| 2013/0123616 A1 | 5/2013 | Merritt et al. |
| 2013/0197364 A1 | 8/2013 | Han |
| 2013/0243021 A1 | 9/2013 | Siskavich |
| 2013/0261494 A1 | 10/2013 | Bloom et al. |
| 2013/0279109 A1 | 10/2013 | Lindblad et al. |
| 2013/0296672 A1 | 11/2013 | O'Neil et al. |
| 2013/0304559 A1 | 11/2013 | Stone et al. |
| 2013/0317393 A1 | 11/2013 | Weiss et al. |
| 2013/0324804 A1 | 12/2013 | McKeown et al. |
| 2013/0324808 A1 | 12/2013 | Al-Ali et al. |
| 2013/0331660 A1 | 12/2013 | Al-Ali et al. |
| 2013/0340176 A1 | 12/2013 | Stevens et al. |
| 2013/0345921 A1 | 12/2013 | Al-Ali et al. |
| 2014/0012100 A1 | 1/2014 | Al-Ali et al. |
| 2014/0022081 A1 | 1/2014 | Ribble et al. |
| 2014/0046674 A1 | 2/2014 | Rosenfeld |
| 2014/0051953 A1 | 2/2014 | Lamego et al. |
| 2014/0081090 A1 | 3/2014 | Picard et al. |
| 2014/0097961 A1 | 4/2014 | Vaglio et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0152673 A1 | 6/2014 | Lynn et al. |
| 2014/0162598 A1* | 6/2014 | Villa-Real ............... H04M 1/66 455/411 |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0188516 A1 | 7/2014 | Kamen |
| 2014/0194711 A1* | 7/2014 | Al-Ali ............... A61B 5/14551 600/323 |
| 2014/0213864 A1 | 7/2014 | Abdul-Hafiz et al. |
| 2014/0257057 A1 | 9/2014 | Reis Cunha et al. |
| 2014/0266787 A1 | 9/2014 | Tran |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330098 A1 | 11/2014 | Merritt et al. |
| 2014/0343889 A1 | 11/2014 | Ben Shalom et al. |
| 2014/0357966 A1 | 12/2014 | Al-Ali et al. |
| 2014/0358574 A1 | 12/2014 | Tara et al. |
| 2015/0001302 A1 | 1/2015 | Gelay et al. |
| 2015/0005600 A1 | 1/2015 | Blank et al. |
| 2015/0011907 A1 | 1/2015 | Purdon et al. |
| 2015/0019231 A1 | 1/2015 | Sadler et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0094618 A1 | 4/2015 | Russell et al. |
| 2015/0099950 A1 | 4/2015 | Al-Ali et al. |

(56) References Cited

U.S. PATENT DOCUMENTS

| | | |
|---|---|---|
| 2015/0101844 A1 | 4/2015 | Al-Ali et al. |
| 2015/0106121 A1 | 4/2015 | Muhsin et al. |
| 2015/0196249 A1 | 7/2015 | Brown et al. |
| 2015/0213217 A1 | 7/2015 | Amarasingham et al. |
| 2015/0216459 A1 | 8/2015 | Al-Ali et al. |
| 2015/0220696 A1 | 8/2015 | Lekutai et al. |
| 2015/0223705 A1 | 8/2015 | Sadhu |
| 2015/0238722 A1 | 8/2015 | Al-Ali |
| 2015/0257689 A1 | 9/2015 | Al-Ali et al. |
| 2015/0351697 A1 | 12/2015 | Weber et al. |
| 2015/0366507 A1 | 12/2015 | Blank et al. |
| 2016/0029932 A1 | 2/2016 | Al-Ali |
| 2016/0066824 A1 | 3/2016 | Al-Ali et al. |
| 2016/0078747 A1* | 3/2016 | King ................. G16Z 99/00 340/539.12 |
| 2016/0081552 A1 | 3/2016 | Wojtczuk et al. |
| 2016/0095543 A1 | 4/2016 | Telfort et al. |
| 2016/0103598 A1 | 4/2016 | Al-Ali et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0270735 A1 | 9/2016 | Diab et al. |
| 2016/0283665 A1 | 9/2016 | Sampath et al. |
| 2016/0285717 A1 | 9/2016 | Kim et al. |
| 2016/0287786 A1 | 10/2016 | Kiani |
| 2016/0314260 A1 | 10/2016 | Kiani |
| 2016/0321904 A1 | 11/2016 | Johnson et al. |
| 2016/0324488 A1 | 11/2016 | Olsen |
| 2016/0327984 A1 | 11/2016 | Al-Ali et al. |
| 2016/0367173 A1 | 12/2016 | Dalvi et al. |
| 2017/0000394 A1 | 1/2017 | Al-Ali et al. |
| 2017/0014083 A1 | 1/2017 | Diab et al. |
| 2017/0024748 A1 | 1/2017 | Haider |
| 2017/0042488 A1 | 2/2017 | Muhsin |
| 2017/0055882 A1 | 3/2017 | Al-Ali et al. |
| 2017/0102901 A1 | 4/2017 | Burke |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0196464 A1 | 7/2017 | Jansen et al. |
| 2017/0196470 A1 | 7/2017 | Lamego et al. |
| 2017/0228516 A1 | 8/2017 | Sampath et al. |
| 2017/0235910 A1 | 8/2017 | Cantillon et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0311891 A1 | 11/2017 | Kiani et al. |
| 2017/0340293 A1 | 11/2017 | Al-Ali et al. |
| 2017/0360310 A1 | 12/2017 | Kiani et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0168491 A1 | 6/2018 | Al-Ali et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0285094 A1 | 10/2018 | Housel et al. |
| 2018/0289325 A1 | 10/2018 | Poeze et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0130730 A1* | 5/2019 | Boyer ................. G16Z 99/00 |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |

(56) References Cited

U.S. PATENT DOCUMENTS

| | | |
|---|---|---|
| 2019/0307377 A1 | 10/2019 | Perea et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0219335 A1 | 7/2020 | Gintz et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |

FOREIGN PATENT DOCUMENTS

| | | |
|---|---|---|
| EP | 1 075 831 | 2/2001 |
| EP | 1 226 783 | 7/2002 |
| JP | 10-336064 | 12/1998 |
| JP | 2002-513602 | 5/2002 |
| JP | 2002-165764 | 6/2002 |
| JP | 2002-172096 | 6/2002 |
| JP | 2002-542493 | 12/2002 |
| JP | 2005-218036 | 8/2005 |
| JP | 2005-295375 | 10/2005 |
| JP | 2007-021213 | 2/2007 |
| JP | 2007-095365 | 4/2007 |
| JP | 2007-174051 | 7/2007 |
| JP | 2008-519635 | 6/2008 |
| JP | 2008-541045 | 11/2008 |
| JP | 2009-017959 | 1/2009 |
| JP | 2009-207836 | 9/2009 |
| JP | 2010-503134 | 1/2010 |
| JP | 2010-524510 | 7/2010 |
| JP | 2011-519607 | 7/2011 |
| JP | 2011-519684 | 7/2011 |
| JP | 2011-152261 | 8/2011 |
| WO | WO 98/029790 | 7/1998 |
| WO | WO 99/013766 | 3/1999 |
| WO | WO 99/056613 | 11/1999 |
| WO | WO 00/063713 | 10/2000 |
| WO | WO 2004/056266 | 7/2004 |
| WO | WO 2004/059551 | 7/2004 |
| WO | WO 2006/051461 | 5/2006 |
| WO | WO 2011/001302 | 1/2011 |
| WO | WO 2011/002904 | 1/2011 |
| WO | WO 2011/025549 | 3/2011 |
| WO | WO 2013/056160 | 4/2013 |
| WO | WO 2013/119982 | 8/2013 |
| WO | WO 2015/054665 | 4/2015 |
| WO | WO 2019/204368 | 10/2019 |

OTHER PUBLICATIONS

Babich, Nick, "Designing a User-Friendly Homepage Carousel", <https://uxplanet.org/designing-a-user-friendly-homepage-carousel-f664c9f2b50e>, Aug. 13, 2016, pp. 11.

Cahalin et al., "The Six-Minute Walk Test Predicts Peak Oxygen Uptake and Survival in Patients with Advanced Heart Failure", Chest, 110(2):325-332, (Aug. 1996), Downloaded from http://journal.publications.chestnet.org/ on Oct. 16, 2013.

Capuano et al., "Remote Telemetry—New Twists for Old Technology", Nursing Management, Jul. 1995, vol. 26, No. 7, pp. 26-32.

Dilger, Daniel, "First look at Apple's new multiuser FaceTime 5.0 for macOS Mojave", Jun. 27, 2018, <https://appleinsider.com/articles/18/06/27/first-look-at-apples-new-multiuser-facetime-50-for-macos-mojave>, pp. 5.

Daäger, "Advanced Anesthesia Solutions", Dräger Apollo® Anesthesia Workstation, Drägerwerk AG & Co. KG aA, 2017, pp. 8.

Elmer-Dewitt, Philip, "Apple's iWatch: The killer apps may be in hospitals, not health clubs", Fortune.com, Feb. 3, 2014, http://fortune.com/2014/02/03/apples-iwatch-the-killer-apps-may-be-in-hospitals-not-health-clubs/, 4 pages.

Grundy et al., "Telemedicine in Critical Care: An Experiment in Health Care Delivery", JACEP, Oct. 1977, vol. 6, No. 10, pp. 439-444.

Grundy et al., "Telemedicine in Critical Care: Problems in Design, Implementation and Assessment", Jul. 1982, vol. 10, No. 7, pp. 471-475.

Arab Health, "Masimo—Arab Health TV 2018," available at https://www.youtube.com/watch?v=1vpg414Ezrg, as published Feb. 2, 2018, pp. 32. [Including transcpript and selected relevant images].

Masimo, "Kite—Apps on Google Play", May 22, 2018, https://play.google/com/store/apps/details?id=com.masimo.kite, pp. 2.

Masimo, "Kite™ Expanded Visibility of Patient Data", 2017, pp. 2.

Masimo, "Kite Supplemental Display", Operator's Manual, 2017, pp. 30.

Masimo, "Rad-97™ Pulse CO-Oximeter®", 2017, pp. 2.

"Multihoming"—Wikipedia, the free encyclopedia, Retrieved from http://en.wikipedia.org/w/index.php?title=Multihoming&oldid=511630157 on Sep. 25, 2012.

Pahl, Lisa, MSN, RN, "Alarm Management with Philips Monitoring Solutions", Philips, Jan. 25, 2016, pp. 22.

Philips, "A Comprehensive View . . . and Smartphone Alerts", Koninklijke Philips N.V., 2015, pp. 4.

Philips, "IntelliVue: MP5 Patient Monitor", Koninklijke Philips N.V., Jun. 2015, pp. 6.

Ruppen et al., "A Wot Approach to eHealth: Case Study of a Hospital Laboratory Alert Escalation System", Proceedings of the Third International Workshop on the Web of Things; 2012, vol. 1. No. 6, pp. 6.

Rysavy, Peter, "Making the Call with Two-Way Paging", Network Computing, Published Jan. 15, 1997, www.rysavy.com/Articles/twoway.htm, pp. 5.

Wachter et al., "The Employment of an Iterative Design Process to Develop a Pulmonary Graphical Display", Journal of the American Medical Informatics Association, vol. 10, No. 4, Jul./Aug. 2003, pp. 363-372.

(56) References Cited

OTHER PUBLICATIONS

Zebra et al., "The TC25 Rugged Smartphone", including Spec Sheet, Feb. 2, 2018, pp. 4.
International Search Report & Written Opinion in PCT Application No. PCT/US2019/027772, dated Aug. 29, 2019.

\* cited by examiner

ALARM LIMITS

SpO2
upper --
lower 88

SpHb
upper 17
lower 7

SpCO
upper 10
lower --

Cancel  Submit

FIG. 19A

MOBILE PATIENT ALARM DISPLAY

RELATED APPLICATIONS

The present application is a continuation of U.S. patent application Ser. No. 16/889,263, filed Jun. 1, 2020, titled Mobile Patient Alarm Display, which is a continuation of U.S. patent application Ser. No. 16/388,637, filed Apr. 18, 2019, titled Mobile Patient Alarm Display, now U.S. Pat. No. 10,667,764, which claims priority to U.S. Provisional Patent Application Ser. No. 62/659,961, filed Apr. 19, 2018, titled Mobile Patient Alarm Display, U.S. Provisional Patent Application Ser. No. 62/678,848, filed May 31, 2018, titled Mobile Patient Alarm Display, and U.S. Provisional Patent Application Ser. No. 62/712,154, filed Jul. 30, 2018, titled Mobile Patient Alarm Display. All of the foregoing applications are hereby incorporated by reference in their entirety.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, SpO2 level, pulse, and blood pressure, among others. Clinicians, including doctors, nurses, physician's assistants, and other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

Patient monitors capable of measuring pulse oximetry parameters, such as SpO2 and pulse rate in addition to advanced parameters, such as HbCO, HbMet and total hemoglobin (Hbt, THb, or SpHb) and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Masimo Laboratories, Irvine, CA (Masimo Labs) and both incorporated by reference herein. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index, signal quality, HbCO, and HbMet among other parameters are also available from Masimo Corporation, Irvine, CA (Masimo).

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt or SpHb), as a few examples. Advanced physiological monitors and corresponding multiple wavelength optical sensors capable of measuring parameters in addition to SpO2, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366, 208, filed Mar. 1, 2006, titled Noninvasive Multi-Parameter Patient Monitor, which are each hereby incorporated by reference herein in their entirety. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index (PI), signal quality (SiQ), pulse variability index (PVI), HbCO and HbMet among other parameters are also available from Masimo.

SUMMARY

This disclosure describes example alarm notification systems that can enable a clinician to respond to an alarm notification received via a computing device, which may have more advanced functionality than a pager. The clinician device may be a mobile device, such as a cellphone or smartphone, tablet, laptop, personal digital assistant (PDA), or the like. The clinician device may communicate with a remote server to obtain patient data generated by a patient device at the point-of-care (such as a bedside device or patient-worn monitor). This patient data may be continuous monitoring data for one or more patients. A mobile application (optionally a browser application) on the clinician device can enable the clinician to view continuous monitoring data for multiple patients, as well as view and respond to alarms and alerts, all from the clinician device, regardless of location. Many additional example features of the alarm notification systems are described in greater detail below.

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers are re-used to indicate correspondence between referenced elements. The drawings are provided to illustrate embodiments of the inventions described herein and not to limit the scope thereof.

FIGS. 19A and 19B depict example alarm limit settings user interfaces.

DETAILED DESCRIPTION

I. Introduction

Figure 1:
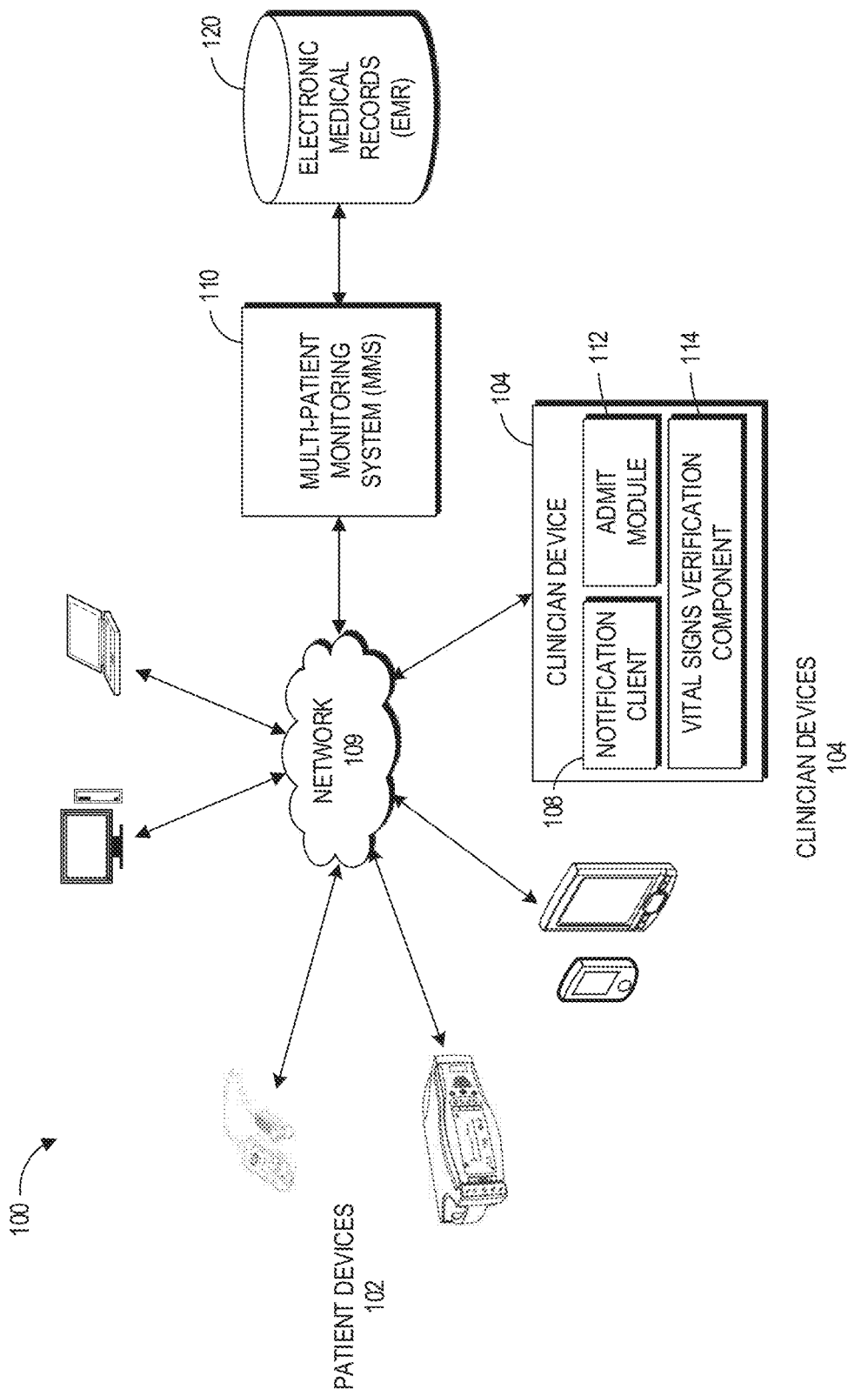
FIG. 1 depicts an example clinical computing environment that includes a multi-patient monitoring system.

Patient monitors typically monitor patients' physiological parameters to determine whether the parameters are within safe limits. If a physiological parameter exceeds a safety limit or threshold, or is otherwise trending toward a dangerous condition, a patient monitor can generate an alarm. The alarm may have audible and/or visual characteristics. Typically, the patient monitor sounds an alarm to attract the attention of nearby clinicians to alert the clinicians that the patient may need medical attention. In addition, some patient monitors send alarms over a network to a computer system at a nurse's station or over a network to a paging system, which pages clinicians. A typical pager system forwards a simple alarm message to one or more clinicians' pagers. The alarm message may include information about the patient's name or room number and possibly limited information about the alarm itself (such as "low SpO2").

This disclosure describes embodiments of alarm notification systems that can enable a clinician to respond to an alarm notification received via a computing device, which may have more advanced functionality than a pager. The clinician device may be a mobile device, such as a cellphone or smartphone, tablet, laptop, personal digital assistant (PDA), or the like. As such, the clinician device can include one or more hardware processors, memory, and a display (which may be a touchscreen). Because the clinician device may have more capability than a pager, the clinician device can confirm receipt of messages and permit clinicians to accept or forward alarms. As a result, escalation can occur more rapidly and response times can decrease, improving patient safety and care.

The clinician device may communicate with a remote server to obtain patient data generated by a patient device at the point-of-care (such as a bedside device or patient-worn monitor). This patient data may be continuous monitoring data for one or more patients. A mobile application (optionally a browser application) on the clinician device can enable the clinician to view continuous monitoring data for multiple patients, as well as view and respond to alarms and alerts, all from the clinician device, regardless of location.

The mobile application can also display data relayed by the remote server from connected bedside devices, such as patient monitors, ventilators, infusion pumps, patient beds, and vital signs monitors. The mobile application can also display high fidelity data, such as waveforms and trend data, in real time. The mobile application can also access and display historical data (such as up to 96 hours or more), aiding assessment of potential deterioration over time. The collation of data from multiple disparate sources in a single location can provide clinicians with a more complete picture of patient status at a glance.

The mobile application can feature intelligent two-way alarm and alert notification technology that can offer significant advantages over systems which send out rudimentary, one-way notifications. The remote server can route and escalate detailed, color-coded alarm and alert notifications to active clinician devices, reaching on-duty and available clinicians. Clinicians can respond to notifications from the mobile application—choosing to accept or forward—and optionally see if other clinicians have already responded. By combining detailed monitoring data with intelligent notification, the mobile application can help to improve clinical collaboration, promoting informed, timely response and effective clinical coordination.

Given the high patient-to-clinician ratios common in many areas, such as the medical-surgical floor, there is an increasing need for continuous remote visibility into patient status. The mobile application can intelligently and reliably deliver valuable patient data and notifications to clinicians wherever they may be, thus helping them to respond and intervene as effectively and efficiently as possible.

II. Example Clinical Computing Environment

Turning to FIG. 1, an example of a clinical computing environment 100 is shown. The clinical computing environment 100 may be implemented in one or more hospitals or other clinical facilities. Further, the clinical computing environment 100 can facilitate monitoring patients within their homes if such patients are using network-enabled monitoring equipment. Additional details of the example environment 100 are described in U.S. Pub. No. 2015/0106121, titled "Alarm Notification System," filed Oct. 10, 2014 ("the '121 publication"), the disclosure of which is hereby incorporated by reference in its entirety. Any of the features described in the '121 publication can be implemented together with any of the features described herein.

In the clinical computing environment 100, various patient devices 102, clinician devices 104, and nurse's station systems or kiosks 106 communicate over a network 109 with a multi-patient monitoring system (MMS) 110. The MMS 110 is an example of a remote server that can communicate with patient devices and clinician devices. The network 109 may include a local area network (LAN), a wide area network (WAN), a public network (such as the Internet), a private network, or any combination of the same. For instance, the network 109 can include a wireless and/or wired hospital network or a network that connects multiple clinical facilities. As another example, a patient device 102 can connect with the MMS 110 from a patient's home, over the network 109. In that situation, the network 109 may be a hospital network that exposes a virtual public network (VPN) connection to the patient devices 102. Further, the MMS 110 may be implemented in a cloud infrastructure that permits remote connection from patient devices 102 at home or in any other location. In some embodiments, applications running on connected devices utilize an encryption layer to provide additional security. For example, communications between the connected devices may encrypted by the sending device and decrypted by the receiving device. Using encryption at the application layer allows devices on different networks and using different network protocols to communicate securely.

The patient devices 102 may be any of the patient monitors or monitoring devices described herein and may include bedside monitors, ambulatory or mobile monitors, in-home monitors, and the like. The patient devices 102 can be point-of-care devices, such as bedside devices or patient-worn devices. The patient devices 102 can receive input from physiological sensors coupled with a patient and may measure parameters such as oxygen saturation or SpO2, respiratory rate, blood pressure, heart rate or pulse rate perfusion, other blood gas parameters, brain activity, brain oxygen saturation, any of the other parameters described herein, and the like. The patient devices 102 can provide information about a patient's status, including current values of physiological parameters, waveforms, trend values, and historical values of physiological parameters over the network 109 to the MMS 110. The MMS 110 can in turn store this data in an electronic medical records (EMR) system 120.

In addition, the MMS 110 can provide this data to the nurse's station systems 106. The nurse's station systems 106 can include any type of computing device including, but not limited to, a desktop, laptop, tablet, phone or the like. The nurse's station systems 106 may also include clinical facility kiosks such as computers on wheels (COWs) (which may use laptop or tablet computers), which may be dispersed throughout a clinical facility. The nurse's station systems 106 can communicate with a plurality of patient devices 102 to receive information of a plurality of patients so that the nurse's station systems 106 can provide clinicians with the ability to monitor physiological parameter data for a plurality of patients.

The clinician devices 104 can include any mobile device, such as a laptop, tablet, cell phone, smartphone, personal digital assistant (PDA), or any other device. In some cases, the clinician devices can include desktop systems. In the depicted example, the clinician devices 104 include a notification client 108 that can receive alarm notifications from the patient devices 102 through the MMS 110. In an example, when a patient device 102 detects that a parameter of a patient has exceeded a threshold set in the patient device 102 (or otherwise triggered an alarm condition), the patient device 102 can send an alarm over the network 109 to the MMS 110. In turn, the MMS 110 can send the alarm or a message representing the alarm to the nurse's station systems 106 and/or the clinician devices 104.

The patient devices 102 may have network capability that enables the patient devices 102 to send the alarm notifications directly over the network 109 to the nurse's station systems 106 and/or to the clinician devices 104. Further, the patient devices 102 may also send alarms to the MMS 110, the nurse's station systems 106, and/or the clinician devices 104. Some alarms can include nonclinical alarms that may not represent that a physiological parameter has exceeded a threshold but instead may include information about a sensor that has been disconnected or otherwise has fallen off (often referred to as a probe-off condition). Likewise, a brief power outage or surge can cause the patient device 102 to reset and send a nonclinical alarm to the other devices shown. Such nonclinical alarms are sometimes referred to herein as alerts to distinguish from alarms that may be clinically actionable.

The notification client 108 can enable two-way communication with the patient devices 102 and the MMS 110 (and/or the nurse's station systems 106) in the event of an alarm. For instance, an alarm sent from a patient device 102 through the network 109 to the MMS 110 could be routed to the clinician device 104. The notification client 108 can receive this alarm and respond back to the MMS 110 or any other component of the computing environment 100, replying that the message was received. This provision of a reply to the alarm made by the notification client 108 can enable the MMS 110 to determine whether to escalate the alarm or not. Since the MMS 110 has received the indication that the notification client 108 received the message, the MMS 110 may determine to wait a period of time before escalating the alarm to an escalated condition (which will be described in greater detail below).

If the notification client 108 does not respond indicating that the client device 104 has received the alarm message, the MMS 110 may determine that some error (whether of the network 109, the clinician device 104 or otherwise) has caused the clinician device 104 to not receive the message. As a result, the MMS 110 can immediately or otherwise rapidly escalate the alarm to one or more other clinicians without having to wait a set period of time. Thus, the two-way communication ability of the clinician device 104 can facilitate this rapid escalation because the MMS 110 can assume that if a response is not provided by the notification client 108, that the clinician device 104 likely did not receive the alarm.

For convenience, this specification primarily describes alarms as being routed through the MMS 110 to the notification client 108 and corresponding response messages being sent from the notification client 108 to the MMS 110 and optionally on to the patient devices 102. However, in other examples the notification client 108 can communicate directly with the patient devices 102 or nurse's station systems 106.

In the depicted example, the clinician device 104 also includes an optional admit module 112 and an optional vital signs verification component 114. These modules are described in detail in the '121 publication, incorporated by reference above.

Reliability of a hospital network may be key to enabling communications of patient data and alarms with clinician devices. Without reliability, an alarm may go unheeded, which could negatively affect patient outcomes. Although many aspects of network reliability may be out of the control of even the most careful medical device manufacturer or network provider, in a clinical network (such as in a hospital or doctor's office), it may be preferable to use the most reliable routers for wireless communication from the point-of-care devices to the MMS 110. Currently, routers or access points using the IEEE 802.11a WiFi standard tend to be more reliable and more secure (for example, due to encryption) than other 802.11x devices. Thus, 802.11a (or 802.11ac) routers or access points can advantageously be used in a clinical network to facilitate reliable delivery of the alarm notifications and escalations described herein. However, a cellular network can also be used, alone or together with a WiFi or other network, for any of the networking functionality described herein.

However, it may be counterintuitive to use 802.11a routers because other standards are more popular and because 802.11a devices tend to have a shorter range (about 25-75 feet unobstructed) than other 802.11x devices (about 150 feet or more unobstructed). Thus, if 802.11a routers are used, more routers are likely needed to be installed in a clinical network than other longer range 802.11x routers to adjust for the reduced range versus other 802.11x routers. The 802.11a routers may be more reliable when installed closer to the point-of-care devices. For example, more 802.11a routers can be installed closer together and/or closer to the point-of-care devices than other 802.11x routers. However, 802.11x routers other than 802.11a routers can be used in other implementations. Further, reliability of wireless routers can advantageously be tested to confirm reliability.

III. Example Multi-Patient Monitoring System Features

Figure 2:
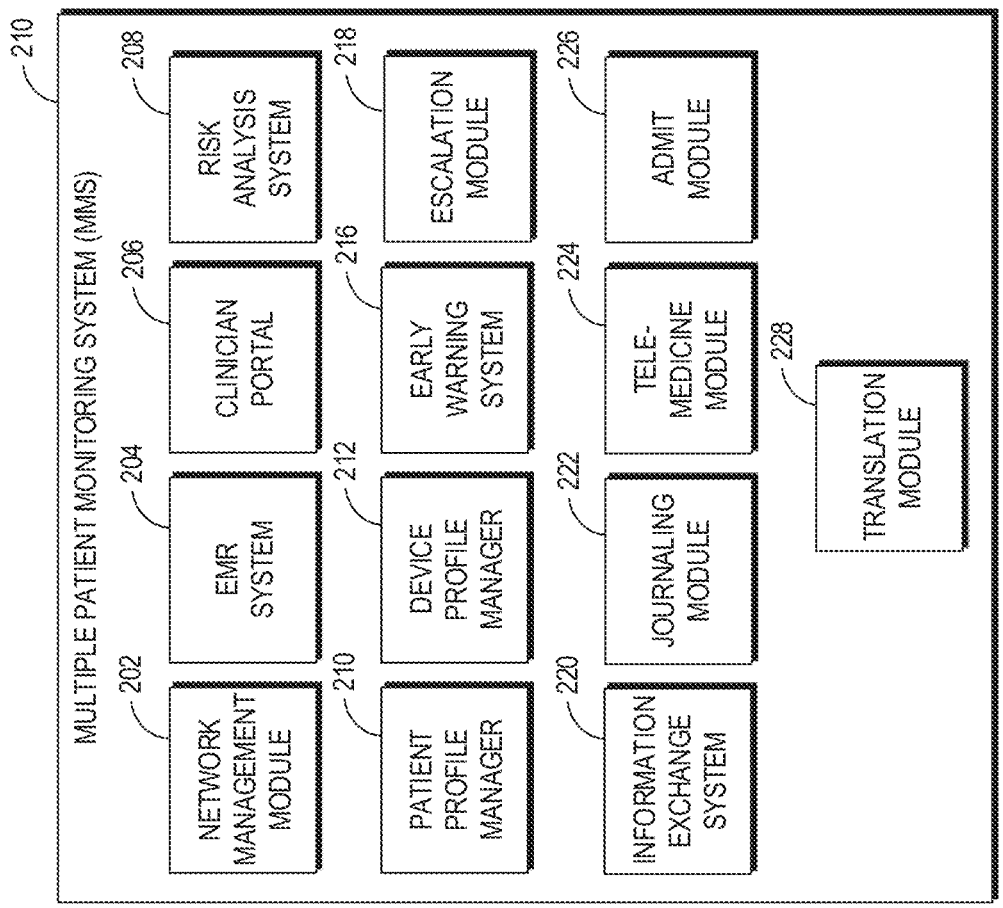
FIG. 2 depicts a more detailed example of the multi-patient monitoring system of FIG. 1.

Turning to FIG. 2, a more detailed example of a multi-patient monitoring system (MMS) 110 is shown, namely, an MMS 210. The MMS 210 can have all of the features of the MMS 110 described above. In the depicted example, the MMS has several subsystems or modules that can be implemented in hardware and/or software. The example modules or components shown group functionality of examples of the MMS 210 together under logical descriptions. It should be understood, however, that the various modules and systems shown in the MMS 210 or portions thereof could be implemented together in a single system. In addition, not all of the systems or modules shown need be implemented on the same computing device but could instead be implemented in separate computing devices. Further, some of the modules shown may be omitted in various examples. These modules are also described in greater detail in the '121 publication, incorporated by reference above.

Certain aspects of the MMS 210 are described as being implemented across multiple clinical facilities. However, the MMS 210 may be implemented in a single clinical facility in other examples, and thus, some of the features described herein may be less applicable or not applicable at all to a single-facility installation of the MMS 210. More detailed example features of the MMS 210, any of which may be combined with the features described herein, are disclosed in U.S. application Ser. No. 14/030,360, filed Sep. 18, 2013, titled "Intelligent Medical Network Edge Router" ("the '360 application"), the disclosure of which is hereby incorporated by reference in its entirety.

The MMS 210 includes, for example, a network management module 202. The network management module 202 can manage network communications with other networks, including networks in hospitals and other facilities as well as communications with mobile patient devices and clinician devices. The MMS 210 also includes an EMR system 204 that can generally store patient data from any facility, including data collected from patient monitoring devices in patients' homes or while patients are mobile outside of their homes or out of facilities.

A clinician portal 206 of the MMS 210 can provide a user interface or user interfaces that can be accessed by clinicians via their clinician devices to monitor the health status of their patients for whom they are responsible. The clinician portal 206 may, for example, be implemented in one or more web pages, mobile applications, or other network applications and may provide information about the wellness or relative wellness of each patient. In one example, a wellness score or index is computed for some or all patients by a risk analysis system 208 of the MMS 210, and the clinician portal 206 can depict these wellness indices among other parameter data, trend data and alarms for each patient.

The MMS 210 also includes a patient profile manager 211. The patient profile manager 211 can manage patient profiles, which can include information about patient demographics, patient alarm settings, including alarm settings from previous visits to potentially multiple different facilities, patient conditions and so forth, and example features of which are described in greater detail below with respect to FIG. 3. The MMS 210 further includes a device profile manager 212 that can manage and store device profiles for medical devices that interact with the MMS 210 as well as optionally other computing devices. The profiles may have information about rules that can be used to track the usage of these devices as well as a variety of other features.

The MMS 210 also includes an early warning system 216. The early warning system 216 can issue early warning alarms based on parameter measurements, indices such as the wellness index or other indices. The early warning system 216 can look for patterns in patients to facilitate detecting never events, including events that should occur never or rarely, like a patient dying in bed without any intervention, particularly when a patient is home and would not ordinarily be under the care of a hospital or have access to a system like the risk analysis system 208 or the early warning system 216.

An information exchange system 220 of the MMS 210 can facilitate communicating information about patients to government or research institutions 118. One scenario where patient information may be submitted (anonymously) to government or research institutions is where a disease outbreak has occurred.

A journaling module 222 of the MMS 210 can capture clinician interactions with medical devices that are in the institutions and/or that are in patients' homes or that are body worn in mobile situations. A telemedicine module 224 of the MMS 210 can facilitate telecommunications between clinicians and patients, including telepresence communications where clinicians can diagnosis, treat, or otherwise attend to the needs of patients remotely using audio visual systems or the like. In some examples, the telemedicine module 224 can also be used in conjunction with features of the escalation module 218. The escalation module 218 can provide functionality for escalating alarms from a first or primary care provider to a second or subsequent care provider in case the primary care provider is unavailable.

The MMS 210 also includes an admit module 226. The admit module 226 may communicate with the admit module 112 optionally installed in the clinician device(s) 104. As described above, the admit module 112 in the clinician device(s) 104 may include a scanner application or the like that can scan a patient tag and a device or location tag, obtain identifiers from each tag, and couple the tags in physical computer storage (such as in an electronic medical records system). This coupling can include sending a message from the admit module 112 to the admit module 226. The admit module 226 can receive the patient identifier and device or location identifier(s) from the admit module 112 and associate the identifiers in physical computer storage, such as in the EMR system or another database.

The MMS 210 also includes a translation module 228 that can receive serial data from third party devices (see FIGS. 6 and 7), translate the serial data into a format recognizable by the patient device 102, and provide the serial data to the patient device 102 (among possibly other devices).

IV. Example Alarm Notification Processes

Figure 3:
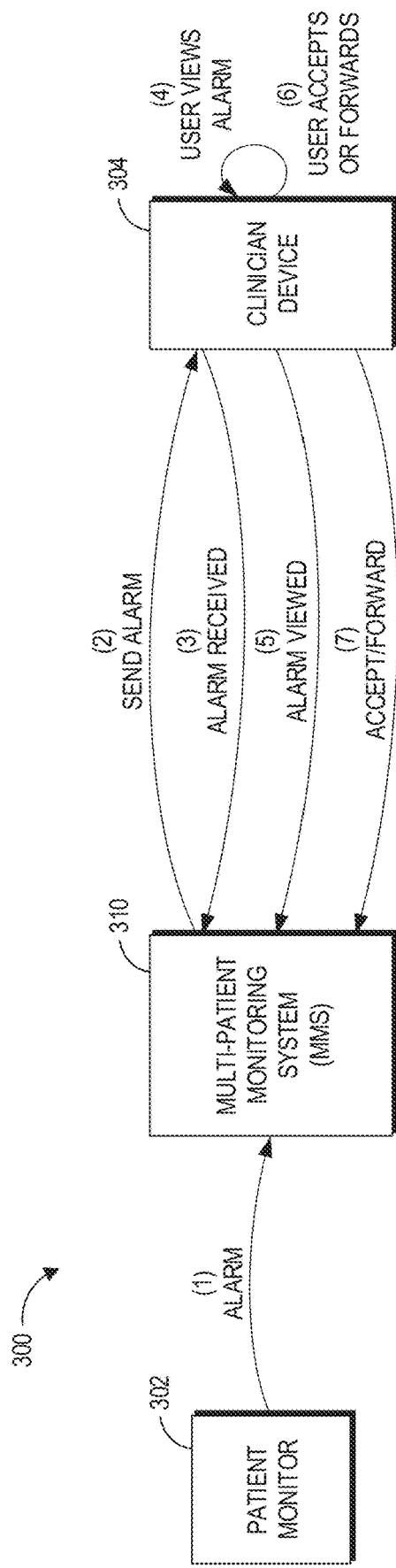
FIG. 3 depicts an example alarm lifecycle flow diagram.

Turning to FIG. 3, an example alarm lifecycle flow 300 is shown. The flow 300 depicts an example state flow of an alarm notification message from a patient monitor 302 to receipt by a clinician device 304. In an example, the lifecycle flow 300 depicts examples of how the clinician device 304 can respond to the alarm so as to improve patient outcomes. The patient monitor 302 is an example of the patient monitor 102. Likewise, the clinician device 304 is an example of the clinician device 104. Also shown is a multi-patient monitoring system (MMS) 310, which may have some or all the functionality of any of the example MMSs disclosed herein, including the MMS 110 or 210.

In the depicted example, the patient monitor 302 at state 1 issues an alarm to the MMS 310. The alarm may be a clinical alarm or a nonclinical alarm as described above. At state 2, the MMS 310 sends an alarm notification message to the clinician device 304. A notification client (not shown; see FIG. 1) in the clinician device 304 can indicate that the alarm was received at state 3 by providing a return message to the MMS 310. As a result, the MMS 310 can know that the alarm was received by the clinician device 304 and therefore justifiably wait a period of time to escalate. In contrast, if the alarm had not been indicated as being received by the clinician device 304 to the MMS 310, the MMS 310 may rapidly escalate (see, e.g., FIG. 4).

At state 4, a user of the clinician device 304 may view the alarm using, for example, the notification client 108. The user may view the alarm in a variety of ways. Generally speaking, the notification client 108 can depict a user interface that shows some aspect of the alarm on a lock screen of the notification client 108, on an active alerts screen, or on an application screen of the notification client 108. The notification client 108 may consider the alarm as being viewed if the clinician device 304 changes state from locked to unlocked (for example, via button press by the clinician) and if the lock screen depicts the alarm (see, for example, FIG. 5 below). In another example, the notification client 108 considers the alarm as being viewed if the clinician unlocks the lock screen and views a list of alarms including this particular alarm (see, for example, FIG. 6). In another example, the notification client 108 considers the alarm as being viewed if the clinician unlocks the lock screen, views a list of alarms including this particular alarm, and then selects this particular alarm (see, for example, FIG. 7).

At state 5, the clinician device 304 reports to the MMS 310 that the alarm has been viewed. This state may also be implemented by the notification client 108 by reporting that the alarm has been viewed. The notification client 108 of the clinician device 304 can enable the MMS 310 to know that the clinician is now aware of the alarm and not just that the clinician's device 304 has received the alarm. Knowing (or, equivalently, receiving or storing an indication in the MMS 310) that the clinician has viewed the alarm can further increase confidence that the clinician may respond to the alarm. Conversely, if the alarm had been received by the clinician device 304 but had not been indicated as being viewed by the clinician, the MMS 310 might hasten escalation to another clinician or set of clinicians (see, e.g., FIG. 4).

At state 6, the user can accept the alarm or forward the alarm, for example, by inputting an indication of acceptance or forwarding to the clinician device 304. The clinician device 304 can, for instance, output a user interface that includes elements or options for accepting an alarm or forwarding the alarm to one or more other clinician(s) (see, for example, FIGS. 10-12, discussed below). By forwarding the alarm to another clinician, the clinician can decline the alarm. Upon selection of the forward option, as discussed below, the clinician device can report this selection to the MMS 310, which can automatically select one or more clinicians to receive an escalated alarm. The user interface at the clinician device 304 may also give the clinician the ability to specify which clinician to forward the alarm to (for example, by providing a drop-down list of available clinicians or by providing a text box that allows a clinician's name to be typed in).

The notification client 108 may, in some examples, infer the clinician's decision to accept handling or decline handling the alarm based on the user's input. For instance, if the clinician marks an alarm notification message as "unread" (e.g., similar to marking an email as unread) or otherwise selects an option to decline the alarm, then the notification device client 108 may infer that the clinician has decided not to handle the alarm. At state 7, the clinician device 304 reports to the MMS 310 whether the clinician has decided to accept or forward the alarm. If the clinician has forwarded the alarm, the MMS 310 can rapidly or immediately escalate the alarm to another clinician or set of clinicians (either chosen by the MMS 310 or optionally selected by the clinician as described above). If the clinician accepts the alarm but does not enter the patient's room and silence the alarm at the bedside device within a period of time, the alarm can be escalated (or re-escalated).

In one example, acceptance is not provided as an option in the notification client 108 because a clinician may directly respond to the alarm without indicating his acceptance of the alarm. Likewise, many other aspects described herein are optional and may be omitted or added thereto.

Figure 4:
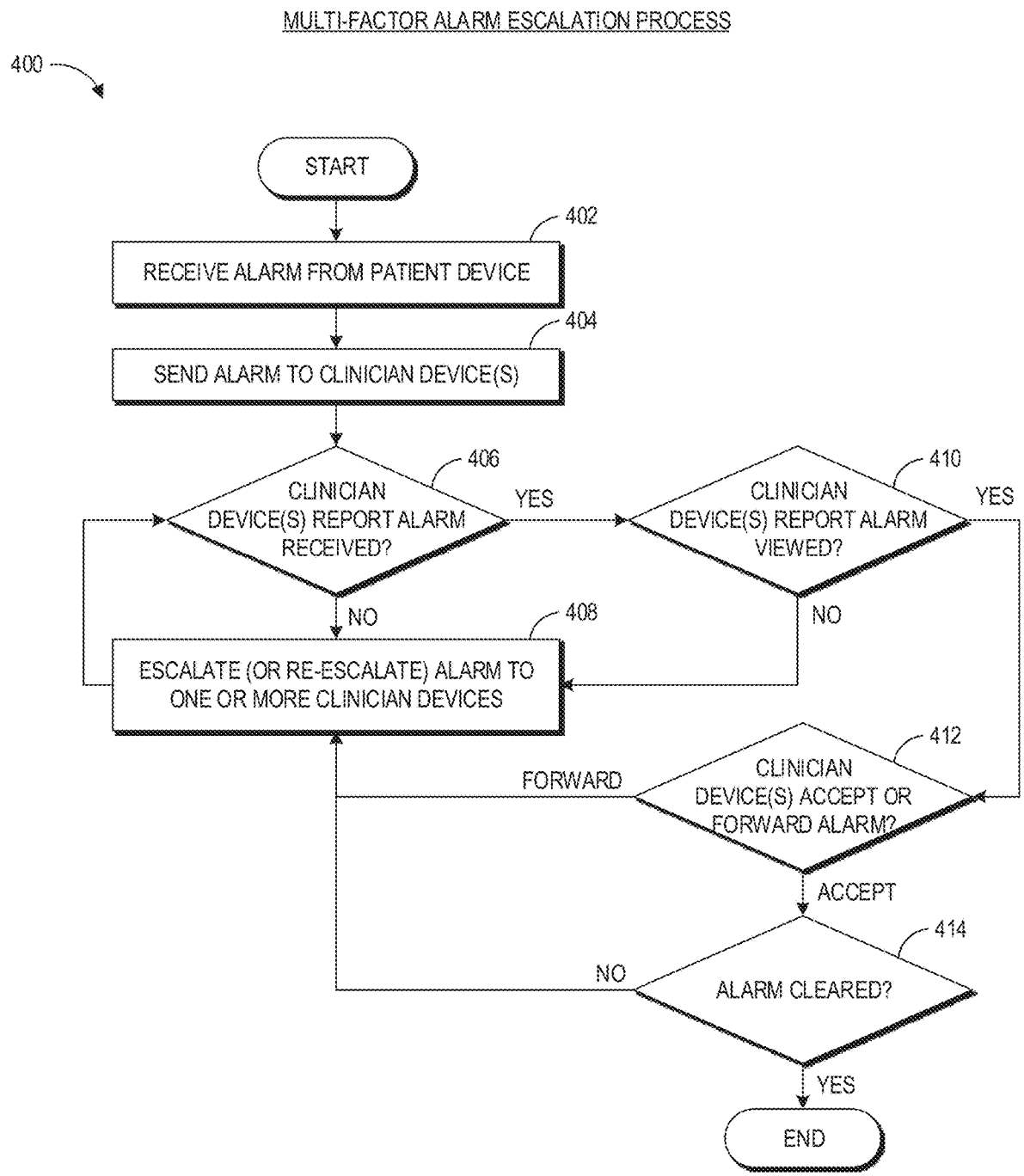
FIG. 4 depicts an example multi-factor alarm escalation process.

Turning to FIG. 4, an example of a multi-factor or two-way alarm escalation process 400 is shown. The alarm escalation process 400 may be implemented by any of the MMSs described herein including the MMS 110, MMS 210, or MMS 310. For convenience, the alarm escalation process 400 will be described in the context of the escalation module 218 of the MMS 210, although other computing systems not described herein may implement the alarm escalation process 400. In certain examples, the alarm escalation process 400 can advantageously provide improved patient outcomes by more rapidly escalating alarms due to the two-way nature of the alarm message lifecycle described herein.

At block 402, the escalation module 218 receives an alarm from a patient device and sends the alarm to a clinician device or devices at block 404. At decision block 406, it is determined by the escalation module 218 whether the clinician device or devices report the alarm having been received. If not, at block 408, the escalation module 218 escalates the alarm to one or more other clinician devices, which may but need not include the initial clinician device or devices to which the initial message was sent.

In some embodiments, the escalation module 218 can dynamically determine which clinicians to notify of an alarm. The escalation module 218 can determine which clinicians to transmit an alarm based on respective clinician devices that are available on the network or that a particular clinician has logged into the clinician device. Thus, the escalation module 218 can omit transmitting alarms to recipients that appear to be unavailable.

In an example, if the initial message was sent to a single clinician device and at block 406, it is determined that the clinician device did not report receiving the message, escalation happens automatically at block 408. In another example, when the initial message is sent to a plurality of clinician devices, block 406 does not trigger escalation at block 408 until it is determined that none of the clinician devices reported receiving the alarm. Alternatively, the escalation module 218 can implement a hybrid approach where if any of a plurality of client devices have not responded as receiving the message, the escalation module 218 can escalate at block 408. In another example, the escalation module 218 escalates if a majority of the client devices did not receive the alarm or indicate having received the alarm message. Other implementations are possible.

If, at decision block 406, the clinician device or devices reported receiving the alarm, then it is further determined by the escalation module 218 at block 410 whether the clinician device or devices reported the alarm being viewed by a user. If not, then the escalation module 218 can escalate or re-escalate the alarm at block 408 to one or more clinician devices. As used herein, in addition to having its ordinary meaning, the term "re-escalate" can refer to escalating a second time or any successive time after a previous escalation has occurred.

As with the decision block 406, the decision block 410 can select a different output depending on the number of clinician devices to which the alarm was sent. If a plurality of clinician devices received the alarm, then the escalation module 218 may proceed to block 408 and escalate if just one of them did not indicate that the user viewed the message. In another example, escalation occurs at block 408 if a majority did not view the message, or if all did not view the message, or the like.

If the clinician device or devices reported the alarm being viewed at block 410, the process 400 proceeds to block 412. At block 412, the escalation module determines whether the clinician device or devices accepted or forwarded the alarm. If the clinician device or devices forwarded (and thus declined) the alarm, then the escalation module 218 proceeds to escalate or re-escalate at block 408. As with the previous decision block 406 and 410, the escalation may occur at block 408 via block 412 if a single device declined the alarm or if a majority or all of the devices forwarded the alarm, depending on the implementation. If one or more devices instead accepted the alarm at block 412, then the escalation module 218 can suspend or silence the alarm at the patient device. Suspending an alarm can include temporarily disabling an audible alarm, for example, for 60 seconds or some other time. Silencing an alarm can include permanently disabling an audible alarm. Even after silencing an alarm, an audible alarm can be triggered again later by the patient data exceeding safe limits. Further, at block 414, the escalation module 218 can await to determine whether the alarm has been cleared. If the alarm has been cleared at the point-of-care device (for example, in person, by a clinician who accepted the alarm or by anyone else), the process 400 ends. Otherwise, the escalation module 218 escalates or re-escalates at block 408.

If multiple parameters are alarming at the same time or together (e.g., one after another and the first has not yet been cleared by clinician or on its own), the process 400 may be modified. For instance, any step in the process may be truncated in time, for example, by shortening wait times, to escalate faster at any point in the process 400. The amount of delay can be configurable, for instance, according to hospital policies. For example, delays between sending an alarm to a clinician device and determining whether to escalate, between clinicians reporting alarms viewed and determining whether to escalate, between accepting an alarm and clearing an alarm or escalating, can all be determined and saved in the MMS.

In another example implementation, block 410 is omitted, and the "yes" path from block 406 proceeds directly to block 412. In yet another example implementation, blocks 406 and 410 are omitted, and escalation is determined solely based on the conditions set forth in blocks 412 and 414.

An advantage of the multi-factor escalation process 400 is that data from the process 400 can be used for reporting purposes. A report can be generated that indicates statistics regarding clinicians' responses, such as the response times of clinicians or who is responding to notifications. For example, a report can indicate if a particular clinician declines many or all of his or her notifications. As another example, a report can be generated that shows the number of alarms in particular geographic areas, such as a wing, domain, or area of a hospital, such that more clinicians can be allocated to those areas. Thus, reviewers of such reports can identify and potentially resolve bottlenecks or inefficiencies in the patient alarm process.

V. Example Point-of-Care Devices

Figure 5:
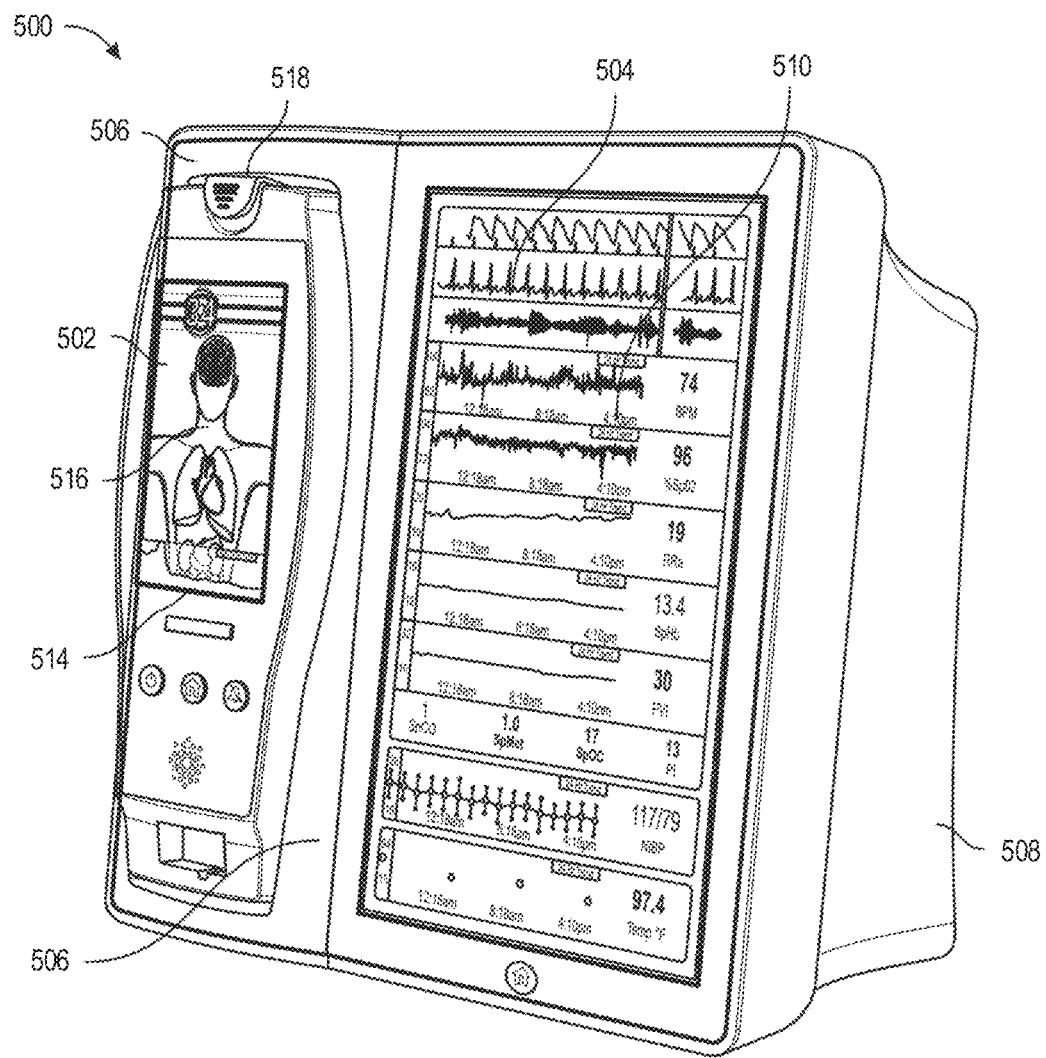
FIG. 5 depicts an example patient monitor or monitoring hub.

FIG. 5 illustrates an example point-of-care device, a bedside device that can function as a patient monitor and a monitoring hub. For convenience, the device shown is referred to herein as a monitoring hub 500 or simply hub 500. The hub 500 includes an example docked portable patient monitor 502. The hub 500 includes a display 504, and a docking station 506, which in an example is configured to mechanically and electrically mate with the portable patient monitor 502, each housed in a movable, mountable and portable housing 508. The housing 508 includes a generally upright inclined shape configured to rest on a horizontal flat surface, although the housing 508 can be affixed in a wide variety of positions and mountings and comprise a wide variety of shapes and sizes. The hub 500 is described in greater detail in U.S. Pat. No. 9,943,269, titled "System for Displaying Medical Monitoring Data," issued Apr. 17, 2018 ("the '269 patent"), the disclosure of which is hereby incorporated by reference in its entirety.

Figure 6:
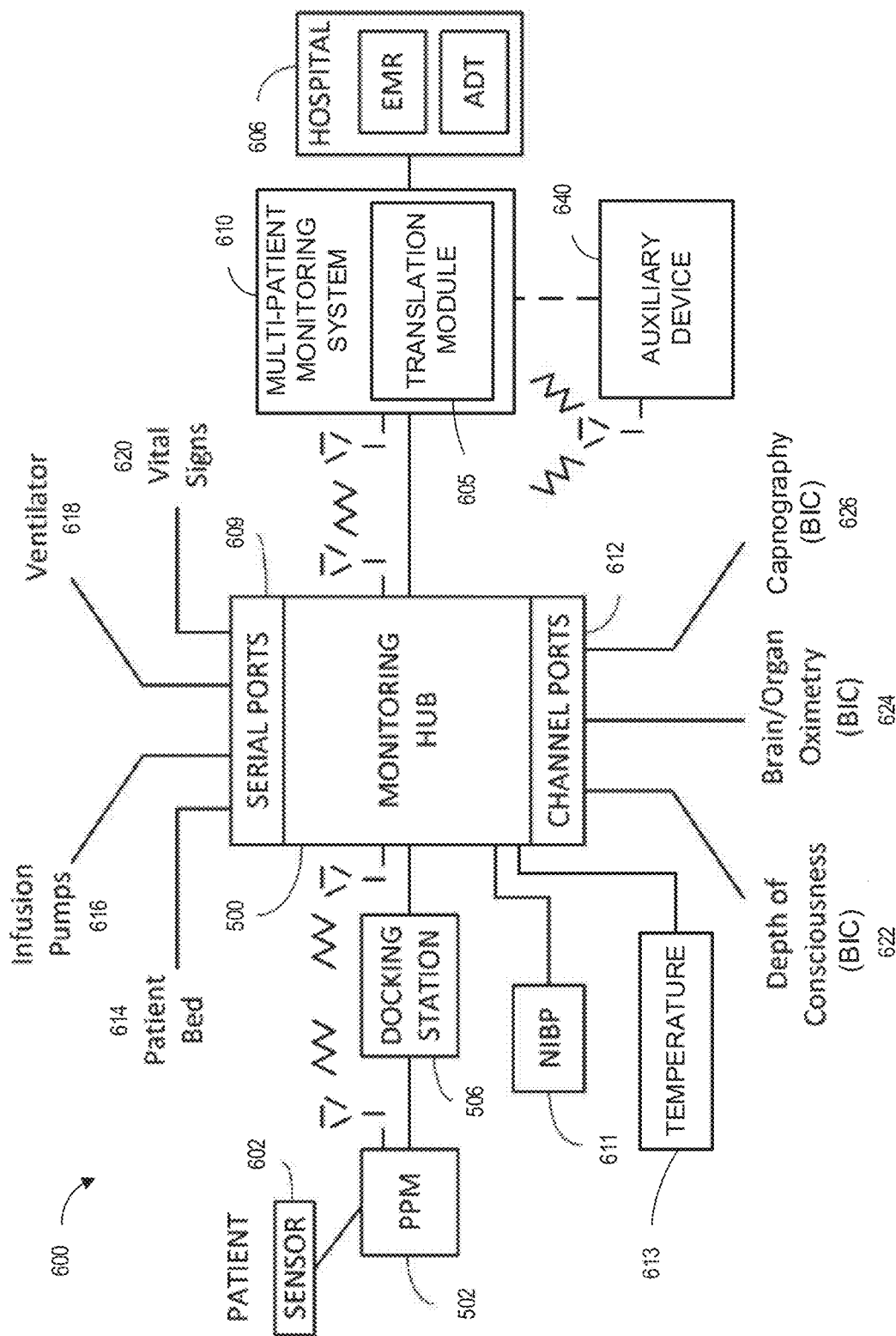
FIG. 6 depicts an example clinical computing environment that includes the patient monitor or monitoring hub of FIG. 5.

FIG. 6 illustrates a block diagram of an exemplary monitoring environment 600 including the hub 500 of FIG. 5. As shown in FIG. 6, the environment may include the portable patient monitor 502 communicating with one or more patient sensors 602, such as, for example, oximetry optical sensors, acoustic sensors, blood pressure sensors, respiration sensors or the like. In an example, additional sensors, such as, for example, a NIBP sensor or system 611 and a temperature sensor or sensor system 613 may communicate directly with the hub 500. The sensors 602, 611 and 613 when in use are typically in proximity to the patient being monitored if not actually attached to the patient at a measurement site. The monitoring environment 600 is also described in greater detail in the '269 patent.

The portable patient monitor 502 can communicate with the hub 500, for example, through the docking station 506 when docked and, for example, wirelessly when undocked; however, such undocked communication is not required. The hub 500 can communicate with one or more multi-patient monitoring systems 610 or server systems, such as, for example, those disclosed with in U.S. Pat. Pub. Nos. 2011/0105854, 2011/0169644, and 2007/0180140. The system 610 is an example of the system 110. The system 610 can communicate with caregiver backend systems 606 such as EMR and/or ADT systems.

FIG. 6 also shows the hub 500 communicating through serial data ports 609 and channel data ports 612. The serial data ports 609 may provide data from a wide variety of patient medical devices, including electronic patient bed systems 614, infusion pump systems 616 including closed loop control systems, ventilator systems 618, blood pressure or other vital sign measurement systems 620, or the like (see also FIG. 7). Similarly, the channel data ports 612 may provide data from a wide variety of patient medical devices, including any of the foregoing, and other medical devices. For example, the channel data ports 612 may receive data from depth of consciousness monitors 622, such as those commercially available from SedLine™, brain or other organ oximeter devices 624, noninvasive blood pressure or acoustic devices 626, or the like. In an example, a channel device may include board-in-cable ("BIC") solutions where the processing algorithms and the signal processing devices that accomplish those algorithms are mounted to a board housed in a cable or cable connector, which in some examples has no additional display technologies. The BIC solution can output its measured parameter data to the channel port 612 to be displayed on the display 504 of hub 500. In an example, the hub 500 may advantageously be entirely or partially formed as a BIC solution that communicates with other systems, such as, for example, tablets, smartphones, or other computing systems.

The auxiliary device 640 shown can be a computing device having physical computer hardware, a display, and the like. For example, the auxiliary device 640 may be a handheld computing device used by a clinician, such as a tablet, laptop, cellphone or smartphone, personal digital assistant (PDA), a wearable computer (such as a smart watch or glasses), or the like. The auxiliary device 640 may also be simply a display device, such as a computer monitor or digital television. In an example, the auxiliary device 640 provides second screen functionality for the hub 500, PPM 502, or MMS 610. As such, the auxiliary device 640 can communicate wirelessly or through a wired connection with the hub 500, MMS 610, or PPM 502.

As a second screen device, the auxiliary device 640 can depict a copy of at least a portion of the display of the hub 500 (or the PPM 502) or a different version of the hub 500 (or the PPM 502) display. For instance, the auxiliary device 640 can receive physiological parameter data, trend data, or waveforms from the hub 500, PPM 502, or MMS 640 and display the parameter data, trend data, or waveforms. The auxiliary device 640 can output any information available to the hub 500, PPM 502, or MMS 610. One use of the auxiliary device 640 is as a clinician device usable by a clinician to view data from the hub 500, PPM 502, or MMS 610 while away from a patient's room (or even while in a patient's room). A clinician can use the auxiliary device 640 to view more detailed information about physiological parameters than is displayed on the hub 500 or PPM 502. For instance, the auxiliary device 640 may include zoom functionality or the like that enables a clinician to zoom into trends or waveforms to more closely inspect parameter activity. In some cases, the auxiliary device 640 can perform at least some processing of physiological parameters, including any of the functionality of the monitoring hub 500. For instance, the auxiliary device 640 may include a translation module 605 (which can have the same or similar functionality as the translation module 228). Additional example features of the translation module 605 are described in greater detail in U.S. Pat. No. 9,943,269, titled "System for Displaying Medical Monitoring Data," filed Oct. 10, 2014 ("the '269 patent"), the disclosure of which is hereby incorporated by reference in its entirety.

VI. Example Alarm Notification User Interfaces

FIGS. 8 through 19 depict example clinician device user interfaces. These user interfaces can be output by the clinician devices 104 described above using, for example, patient data received from the MMS 110-610. The MMS 110-610 can obtain the patient data from a point-of-care device, such as any of the point-of-care devices described above with respect to FIGS. 1, 5, and 6. The user interfaces shown may be output by the notification client 108 of FIG. 1, which may be a mobile application or web application (accessed, for example, via browser). Thus, each of the user interfaces shown may be output for presentation by electronic hardware as graphical user interfaces.

Each of the user interfaces shown includes one or more user interface elements or controls that can be selected by a user. The user interface elements shown are merely illustrative examples and can be varied in other embodiments. For instance, any of the user interface elements shown may be substituted with other types of user interface elements. Some examples of user interface elements that may be used include buttons, dropdown boxes, select boxes, text boxes or text fields, checkboxes, radio buttons, toggles, breadcrumbs (e.g., identifying a page or interface that is displayed), sliders, search fields, pagination elements, tags, icons, tooltips, progress bars, notifications, message boxes, image carousels, modal windows (such as pop-ups), date and/or time pickers, accordions (e.g., a vertically stacked list with show/hide functionality), and the like. Additional user interface elements not listed here may be used.

Further, the user interfaces shown may be combined or divided into other user interfaces such that similar functionality or the same functionality may be provided fewer or more screens. Moreover, each of the user interface elements may be selected by a user using one or more input options, such as a mouse, touch screen input (e.g., finger or pen), or keyboard input, among other user interface input options.

Although each of these user interfaces are shown implemented in a mobile device, the user interfaces or similar user interfaces can be output by any computing device, examples of which are described above.

Figure 8:
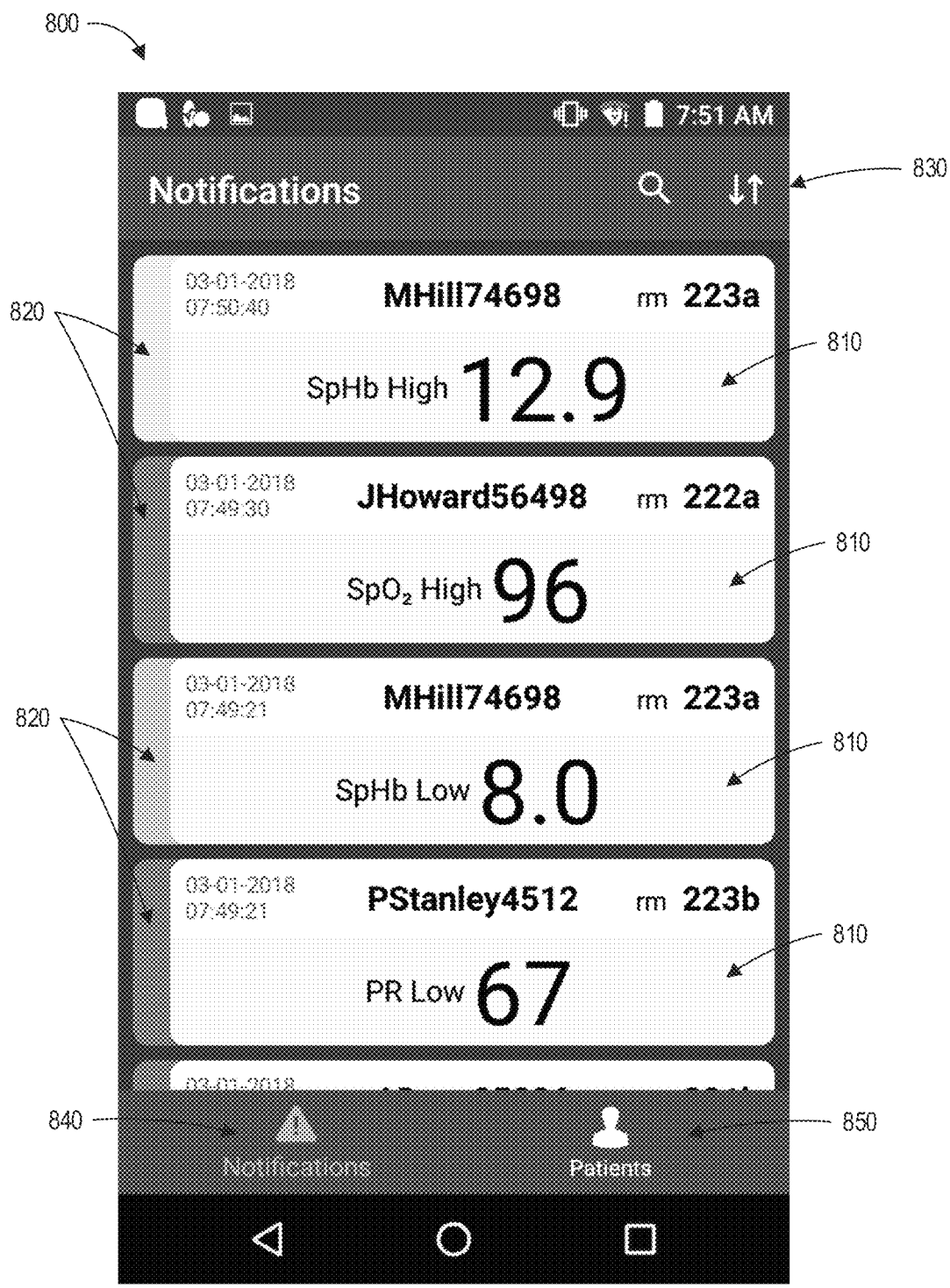
FIG. 8 depicts an example notifications user interface for a clinician device.

FIG. 8 depicts an example notifications screen 800 that may be accessed by the clinician devices described above. The notifications screen 800 is shown as a mobile device user interface, such as a smart phone screen (although for ease of illustration, the smart phone itself is not shown). Although the user interface 800 and subsequent user interfaces are shown shaped as smart phone screens, each of these user interfaces can be adjusted in size and/or shape to fit other types of mobile devices as discussed above.

The notifications screen 800 is an example default view for the mobile application described above, such as the notification client 108. The notifications screen 800 can provide notifications of alarms for a plurality of patients to a clinician. These notifications may be obtained or sent from a remote server, such as the MMS 110-610.

The notifications screen 800 includes a plurality of alarm notifications 810. Each alarm notification 810 is shown as a rectangular box with rounded corners. More generally, each alarm notification 810 may include a region, area, or portion of the display that may, but need not, be box-shaped. Each alarm notification 810 can display information about a patient, such as a label or identifier that may have been assigned to the patient at time of admission (for example MHill74698 and JHoward56498) as well as optionally the room number, the time and date of the notification, and an indication of what the alarm is about. For example, the first alarm notification 810 shown at the top of the notifications screen 800 indicates that the alarm relates to SpHb, which is high and has a value of 12.9 (g/dL). Admission of a patient to a device is described in greater detail in the '121 publication, incorporated by reference above.

To the left of each alarm notification 810 is a notification state indicator 820. Each notification state indicator 820 is a small, nearly rectangular-shaped vertical box to the left of each alarm notification, which forms a part of the alarm notification 810 box. The notification state indicator 820 can have a certain color or other characteristic that provides information about the alarm notification to which it is appended. For example, the notification state indicator 820 can have one of a plurality of colors such as the following: yellow, which can indicate that an alarm notification 810 is an initial notification; orange, which can indicate that an alarm notification 810 is a second or escalated alarm notification 810; red, which can indicate that an alarm notification 810 is a third notification or reescalation; or grey, which can indicate that the alarm notification 810 has been completed or otherwise cleared.

At the bottom of the notifications screen 800 are two user interface elements 840 and 850. The element 840 is a notifications screen element. This element 840 is shown as a different color than the element 850 (such as blue) in this particular screen 800, which can signify that this element 840 is in the selected state. Selecting the element 840 from a different screen, for instance, can result in the notifications screen 800 being displayed. The other element 850 is a patients screen element 850. Selecting the patients screen element 850 can provide a view of a plurality of patients that are assigned to the clinician who is using the clinician device. Example patients screens are shown and described below with respect to FIGS. 14 and 15.

The alarm notifications 810 can be user selectable in any of a variety of ways. For instance, an alarm notification 810 may be selected by pressing, long-pressing, or 3-D pressing the alarm notification or by swiping the alarm notification to left and/or right. Swiping the alarm notification may provide different options, which are discussed below with respect to FIGS. 9, 10, and 11, and pressing, long-pressing, or 3-D pressing an alarm notification 810 can output a user interface as described below with respect to FIG. 12.

Figure 9:
FIGS. 9 and 10 depict example detailed options from the user interface of FIG. 8.

Turning now to FIG. 9, a close-up view of the alarm notification 810 is shown with the alarm notification swiped to the right (as indicated by an arrow 902) to review a detail option 910. The detail option 910 can be selected by a user, for example by pressing it, to view a patient data screen. The patient data screen can provide a view of patient data that is similar to or the same as a view shown on the point-of-care device. For example, the patient data screen may (but need not) be a mirror image of the view on the patient device. Example patient data screens are described below with respect to FIGS. 16 and 17.

Figure 10:
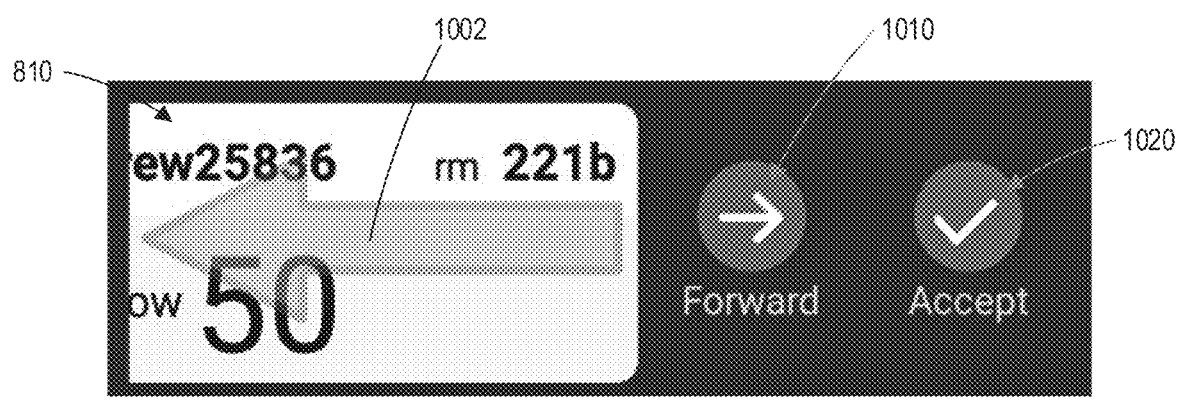

Turning to FIG. 10, a close-up view of the alarm notification 810 is shown being swiped to the left (as indicated by an arrow 1002). Swiping the alarm notification 810 to the left can reveal two options: a forward option 1010, and an accept option 1020. The forward option 1010 can allow the clinician to decline the alarm so that the alarm will be forwarded or escalated to the next available clinician. The clinician who the alarm is forwarded to or set of clinicians may be determined by hospital policy, which may be stored in the MMS 110-610. Alternatively, the user may specify a clinician to forward the alarm to when selecting the forward option 1010. The selection of the forward option 1010 can enable escalation to happen more quickly than with one way notification or pager systems because unlike the one way notification or pager system that would wait a predetermined time before escalating the system can immediately escalate once the forward option 1010 is selected. The forward option is an example of the "forward alarm" option discussed above with respect to FIG. 4 (block 412).

Upon selection of the accept option 1020, the mobile device can send an indication to the MMS 110-610 that the clinician has accepted the alarm and therefore escalation may not occur at this time. Selection of the accept option 1020 may but need not cause the audible alarm that may be occurring at the point-of-care device to suspend or silence. Further options for suspending or silencing an audible alarm are discussed below. The accept option is an example of the "accept" option discussed above with respect to FIG. 4 (block 412). However as described above with respect to FIG. 4, even if the clinician selects the accept option, if the clinician does not actually clear the alarm at the point-of-care device (for example by pressing a button to stop the alarm on the point-of-care device), then the MMS 110-610 may escalate the alarm. Further, by pressing the "accept" option, the alarm can be automatically silenced at the point of care.

Figure 11:
FIG. 11 depicts another example notifications user interface for a clinician device, which incorporates the features of FIG. 10 into the user interface of FIG. 8.

Turning to FIG. 11 another example notification screen 1100 is shown which is similar to the notifications screen 800 except that one of the alarm notifications 810 is shown being swiped to the left as in FIG. 10 to reveal the options 1010 and 1020. Although not shown, it should be understood that the close-up view of the alarm notification 810 in FIG. 9 could likewise be shown in the context of a full notification screen.

Figure 12:
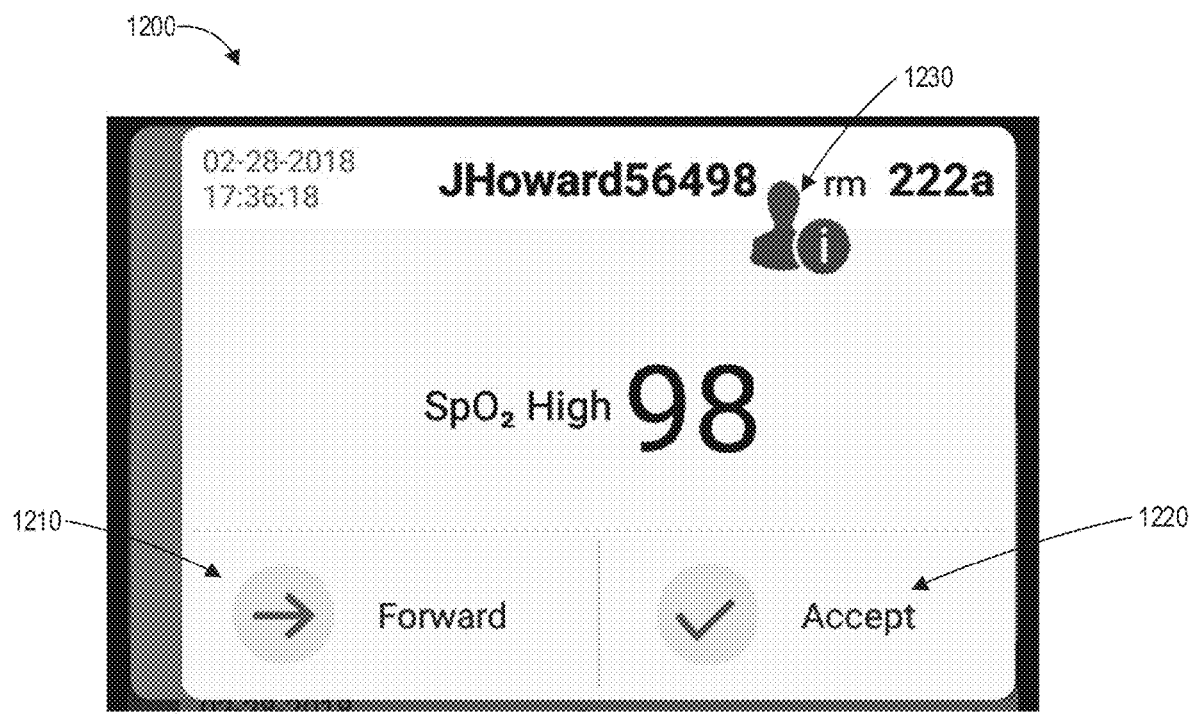
FIG. 12 depicts example detailed options from the user interface of FIG. 8.

Turning to FIG. 12, another example user interface 1200 is shown that may be reached by a user at the notifications screen 800 pressing or long-pressing one of the alarm notifications 810. By doing so, options 1210, 1220 and 1230 may be shown. The option 1210 can have the same functionality as the forward option 1010 of FIG. 10, and the option 1220 can have the same functionality as the accept option 1020 of FIG. 10. The option 1230 can have the same functionality as the option 910 of FIG. 9. Selecting any of these options may have the same functionality of their corresponding options described above.

Figure 13:
FIG. 13 depicts an example popup or lock screen notification.
Figure 16:
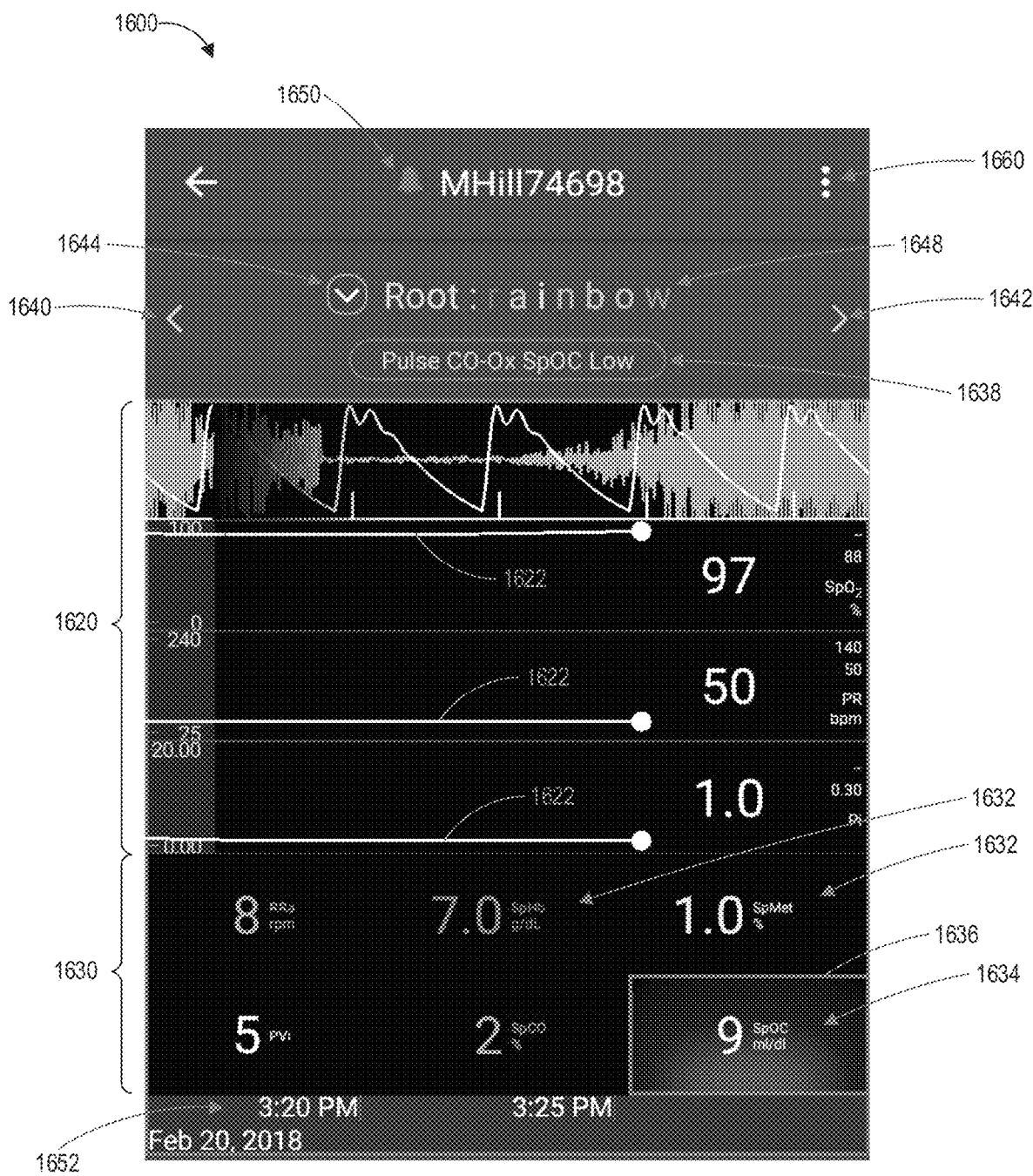
FIGS. 16 and 17 depict example patient monitor view user interfaces.
Figure 17:
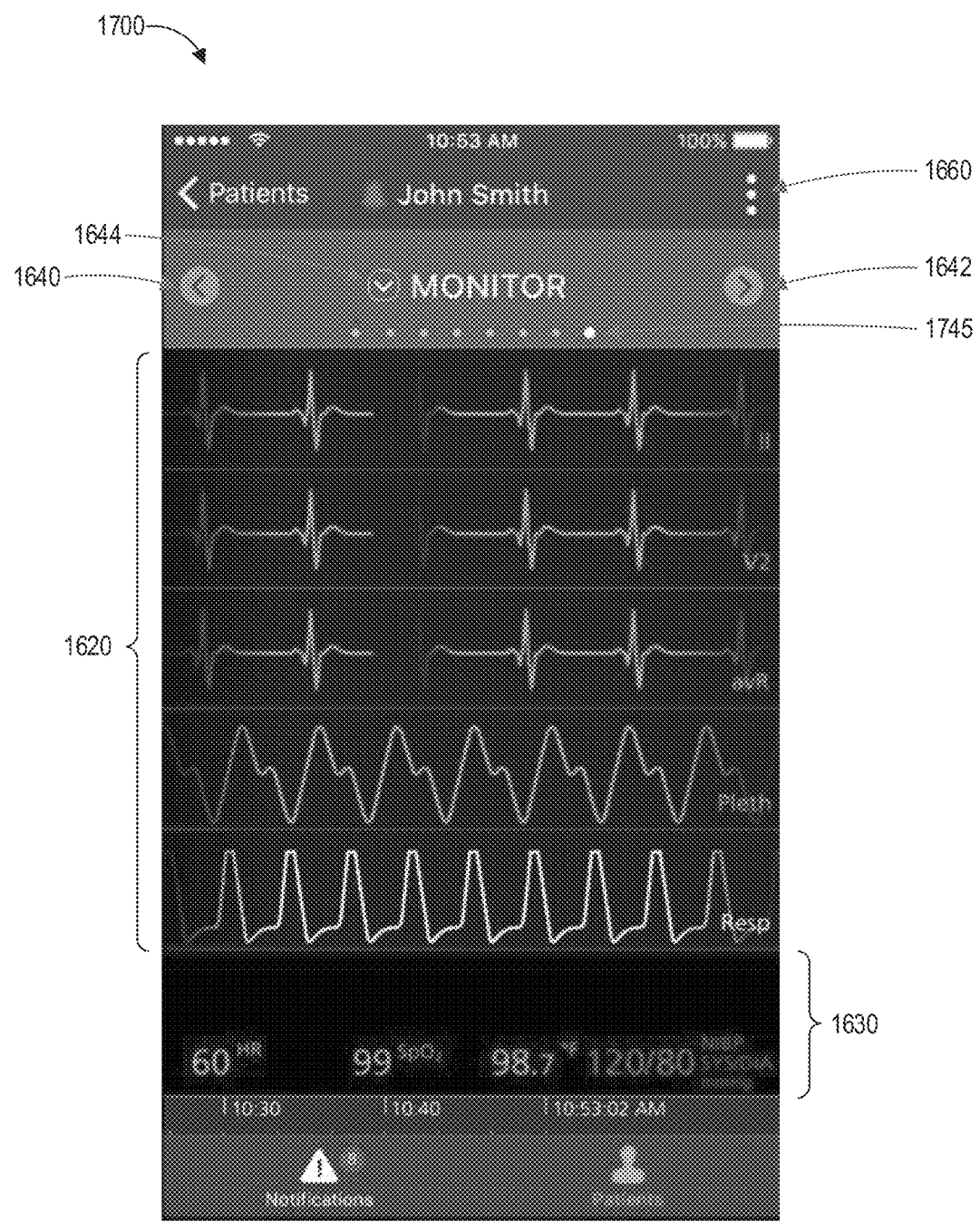

Turning to FIG. 13, an example notification popup 1300 is shown. The example notification popup may appear on a lock screen of the mobile device or may pop up over any other application (including the mobile application itself) if an alarm occurs. The notification popup 1300 lists the patient identifier as well as information about the alarm (in this case, SpHb High 14.0) as well as the time and optionally date of the alarm. Other configurations of the notification popup 1300 are possible. Selection of the notification popup 1300 can result in the mobile device outputting a patient data screen, such as is shown in FIG. 16 or 17, or another screen shown herein.

Figure 14:
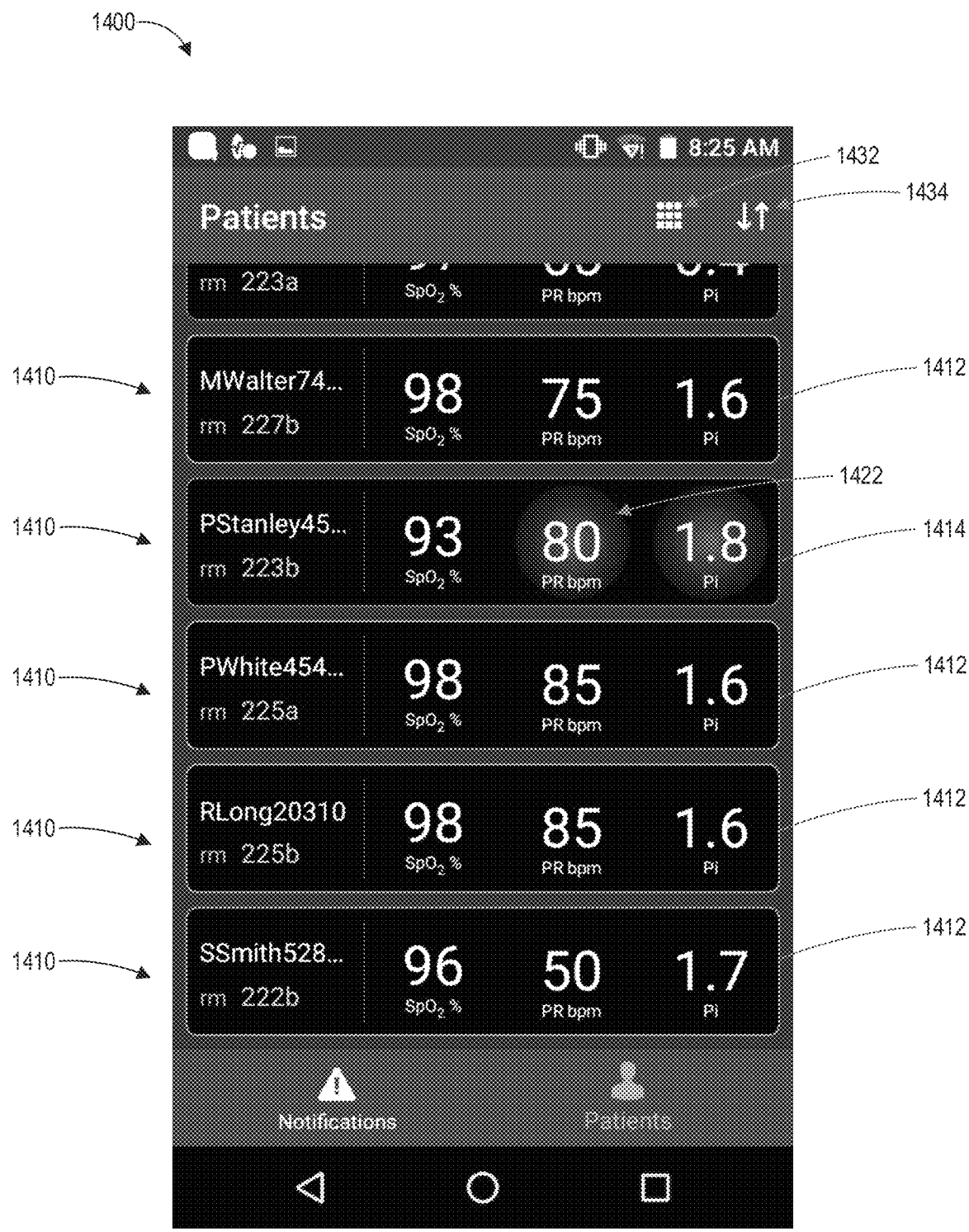
FIG. 14 depicts an example patient list view user interface.

Turning to FIG. 14, an example patients screen 1400 is shown (list view). The patients screen 1400 may be reached by selecting the patients screen element 850 from the notifications screen 800. The patients screen 1400 includes a plurality of tiles 1410 of patient data, arranged in rows. Each tile 1410 can be approximately oblong or rectangular, optionally with rounded corners or other graphical features, and can list the patient identifier, room number, and three physiological parameters. In this example, the physiological parameters shown include SpO$_2$, pulse rate, and perfusion index (Pi). Other parameters, including more or fewer parameters, may be displayed on the tiles 1410 in other implementations.

Each of the tiles 1410 of patient data is surrounded by a border 1412 or 1414 to form a box or rectangle (for example, with rounded corners). The border 1412 or 1414 may be color-coded to indicate a status of the patient. For instance, the border 1412 can be a green border, which can indicate that no alarm is currently taking place, whereas the border 1414 can be a red border, which can indicate that an alarm is taking place. A green border can further indicate successful admission and connection with a point-of-care device. A yellow border can indicate successful connection to a point-of-care device without actual admission to that device. For example, a patient may be connected to a device via sensors but may not yet be admitted to the device using the techniques of the '121 publication described above. A yellow border can also indicate a potential probe-off condition, where the sensor may have fallen off the patient, may be improperly placed on the patient, or where a cable has become disconnected from either the sensor or the monitor. A red border 1414 can indicate that a device is alarming, and a grey border can indicate that a device is disconnected from the patient or from the network. Other highlighting techniques can also be used. For example, the various patient boxes can include shading in different colors as an alternative or in addition to changing the color of the borders.

A glow graphic 1422 behind the alarming parameter(s) can further indicate that an alarm is taking place. The glow graphic 1422 in this example depicts a diffuse circular colored area, which can serve to further draw a clinician's attention to the alarm. The color of the glow graphic 1422 may be red or yellow for alarms, or some other color (for example, according to any of the color schemes described herein). The glow graphic 1422 could also be overlaid in front of the parameter value but be partially transparent to permit viewing of both the glow graphic 1422 and the parameter value. The glow graphic 1422 can flash or blink (optionally pulsing, or fading in and out) to further indicate the presence of the alarm.

Figure 15:
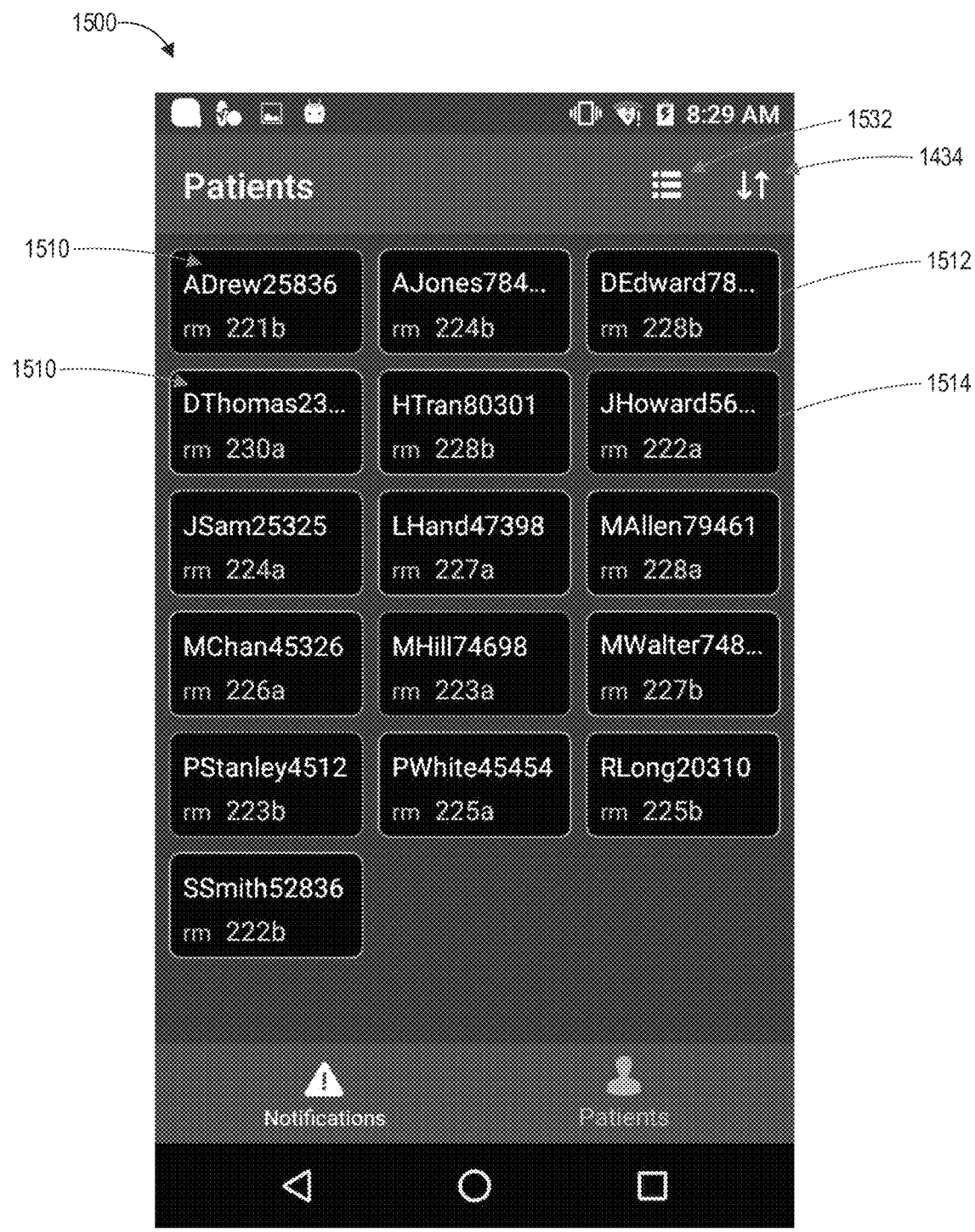
FIG. 15 depicts an example patient grid view user interface.

FIG. 15 depicts another example patients screen 1500. The patients screen 1500 is similar to the patients screen 1400 except that the patients screen 1500 is a grid view of patients, whereas the patients screen 1400 is a list view of patients. The patients screen 1500 may be accessed, for example, by selecting a grid view element 1432 in FIG. 14. In the patients screen 1500, a plurality of patients are shown represented by patient boxes 1510. Each patient box 1510 includes a patient identifier and a room number. For illustrative purposes, the example patient boxes 1510 are shown with rounded corners, but the corners need not be rounded in other implementations. More generally, the patient boxes 1510 can be oblong, rectangular, or square, or have some other similar shape.

Unlike the patients screen 1400, where the tiles 1410 of patient data include physiological parameter values, no physiological parameter values are shown in the patient boxes 1510. One benefit of not showing these values can be that more patients can be shown in one screen. This can be a benefit because mobile devices may have small screens and may present a fuller view of the clinician's assigned patients. In addition, by omitting the physiological parameter values from the screen 1500, the screen 1500 may present a view without frequently changing numbers and can therefore be less visually distracting.

Yet each of the patient boxes 1510 can provide a quick, at-a-glance view of patient status. The status of the patients can be represented by status borders 1512 and 1514 surrounding the boxes 1510. The status borders 1512, 1514 can have different colors, such as any of the colors described above with respect to FIG. 14. For instance, the status borders 1512 can be green, representing a patient that is not in an alarm condition, whereas the status border 1514 can be red or yellow, indicating that an alarm has occurred (with the red and yellow colors optionally having meanings described above). A gray border may indicate that a device is not connected to a patient. Other colors and conditions may also be used.

Also shown is a list view element 1532, which can enable a user to access the list view of the patients screen 1400 (see FIG. 14). Also shown is a sort element 1434 (see also FIG. 8, element 830), which can enable a user to sort the patients either by alarm severity, alarm recency, patient identifier, or room number, among possibly other options. Alarm severity can be determined based on escalation level. For example, an alarm that has been re-escalated may be more severe than an alarm that has been escalated once, which may be more severe than an alarm that has not been escalated. Alarm severity can also be determined based on a degree to which a patient's physiological parameter or wellness index has deviated from a threshold, baseline, minimum, or maximum value. For example, an alarm with a lower SpO2 value than another patient may be considered more severe.

Patients or alarm notifications can be automatically sorted by a clinician's most recent sort option. If alarm severity were the most recent option, for instance, any new incoming alarm notification (or patient in the list) may cause a reordering of existing alarm notifications (or patients) based on severity. However, one downside of automatically reordering patients or notifications by severity may be that the display may perform the reordering just as a user is about to select one of the notifications or patients, causing a missed selection. Missed selections due to automatic re-ordering could be frustrating for users. Thus, sorting based on alarm severity may be disabled or omitted from the application.

In either the patients screen 1400 or 1500, the swipe functionality of the notifications screen 800 may be used.

For instance, any row 1410 of FIG. 14 may be swiped left or right just like an alarm notification, as described above with respect to FIGS. 8-12. If an alarm is present, the row 1410 may be swiped in one direction to access accept or forward options, as discussed above. Indeed, when a row 1410 contains an alarm, the row 1410 may be considered to be an alarm notification. Whether an alarm is present or not, any row 1410 can be swiped in the other direction to access further details about the patient (such as are shown in the patient data screen of FIG. 16). Short or long pressing the row 1410 can also access more details about the patient (see FIG. 16). Similarly, any of the boxes 1510 in the grid of FIG. 15 may be swiped or long-pressed to view similar options as described above with respect to FIGS. 8-12. Boxes 1510 that indicate alarms can also be considered to be alarm notifications.

Turning to FIG. 16, an example patient data screen 1600 is shown. The patient data screen 1600 depicts a more detailed view of a patient's physiological parameters, including physiological parameter values, trend lines, and waveforms. The patient data screen 1600 can be accessed from any of the previous screens, as described above. The patient data screen 1600 can provide a similar view as the display on the point-of-care device used by the patient.

In general, a patient data screen can have an identical or similar display to a point-of-care device that sends data through the MMS to the mobile device. Accordingly, a clinician can view whatever he or she could view at the patient's side remotely. Mimicking or replicating the point-of-care display (or a similar version thereof, such as more than half of the point-of-care display) on a mobile clinician device can enable clinicians to make more informed remote decisions about patients than could be done in the past with pagers or even simple mobile device applications. With such a patient data screen, a clinician can formulate an action plan for treating a patient while on the way to clearing an alarm, rather than after the clinician reaches the patient's side and sees the full data for the first time. This ability to plan ahead, provided by the patient data screen's robust data display, can save valuable time that can translate into saved lives and improved patient outcomes.

Because some mobile devices may be more constrained in screen real estate than some point-of-care devices, the patient data screen may display less information or a condensed view of the point-of-care device screen. Still other point-of-care devices, such as some patient-worn devices, have smaller displays than many mobile devices. For these point-of-care devices, the patient data screen can be identical or include even more information than is shown on the point-of-care devices (such as by adding waveforms if waveforms do not natively fit on the point-of-care devices).

Other configurations are also possible. For instance, a patient data screen corresponding to the same point-of-care device can be formatted differently for a laptop or tablet display, which may have a larger screen area than a smartphone display. The laptop or tablet patient data screen may have an identical or nearly identical display as the point-of-care device, while the smartphone display may have a condensed view such as the screen 1600 discussed below.

Referring specifically to FIG. 16, the patient data screen 1600 displays patient data 1620 and 1630. This patient data is organized in rows 1620 and a grid 1630 of boxes 1632. The rows 1620 include a first row that depicts waveforms and other rows that depict trend lines 1622 and parameter values (here, $SpO_2$, PR, and Pi). More or fewer rows of trend and parameter data or wave form data may be shown in different implementations (see, for example, FIG. 17).

The rows 1620 can be panned or zoomed, for example, using finger gestures like taps, finger drags, and pinch zooms. Accordingly, a clinician can view more data than is displayed on one current screen. The rows of data 1620 show relatively flat trend lines 1622 because the time scale 1652 at the bottom of this example screen 1600 is about 10 minutes, but panning or zooming may show more detail in the trend lines 1622.

The grid 1630 of patient data includes two rows and three columns of parameter value boxes 1632. Each parameter value box 1632 includes a physiological parameter value (such as 8) and a label (such as RRa, rpm—respiratory rate (acoustic), respirations (or breaths) per minute). The parameter value boxes 1632 are borderless in the depicted example except for one box 1634, which has a red border 1636 and a glow graphic behind the parameter value that indicates that this particular parameter is alarming. The indicator 1638 can provide a notification descriptor, such as "Pulse CO-Ox SpOC Low." The color of the border 1636 and the glow graphic may be the same or similar to the color schemes provided above or a different type of color scheme. Further, the parameter value—the actual number—that is the subject of the alarm may also have a color that indicates an alarm place of or in addition to the glow graphic behind the parameter and/or the border 1636. The box 1634 can also blink in a red, yellow, or some other color to draw attention to the alarm. Near the top of the display, below a current instrument name 1648 (discussed below), is an indication of the alarm, replicating the alarm indication in the box 1634. The grid 1630 can also be scrollable if enough parameters are included in the grid 1630. For instance, if enough parameters are included in the grid to exceed two rows worth of boxes, the grid 1630 may become scrollable. Additional examples of scrollable grids and example criteria for making a grid scrollable are described in detail below.

The boxes 1632 in the grid 1630 can be user selectable to switch boxes 1632 in the grid 1630 with rows 1620. A user can select and drag and drop one of the boxes 1632 to the area of the screen that depicts the rows 1620. Once this has occurred, the parameter represented in the dragged and dropped box 1632 can be expanded to have its own row 1620, which may take the place of or may be in addition to one of the existing rows 1620. When placed as a row, the parameter that is in the box 1632 may have the characteristics of either the row 1620 (for example, depicting a wave form, trend, and/or a parameter value).

Thus, if a user wants to see more detailed parameter information about one of the parameters in the grid 1630, the user can move that parameter from the grid 1630 to the rows 1620 area of the display to see a trend, wave form, and/or parameter value together. When the user does so, one of the existing rows 1620 may then be collapsed into one of the boxes 1632 in the grid 1630. For example, if the SpHb parameter value box 1632 were dragged to the rows 1620 section of the display, then one of the rows 1620 (such as the last one for Pi) may disappear and the parameter value for that row may show up in the grid 1630 in place of the SpHb box.

In other example implementations, dragging a box 1632 to the rows 1620 may add a new row without causing an existing row to disappear. The rows 1620 may become scrollable, for instance, so that not all of the rows 1620 may be displayed at once but rather can be scrolled through (for example, up and down). In another example, adding another row by dragging a box to the rows 1620 area can cause the existing rows 1620 to shrink in the vertical dimension to accommodate the new row. Likewise the grid 1630 could shrink to accommodate the new row, or both the grid and the existing rows 1620 may shrink. Further, the rows 1620 may be split into two horizontal columns of rows so that more rows may be displayed (with or without a grid 1630). If multiple boxes 1632 are dragged to the rows 1620, then the grid 1630 may ultimately be reduced to a single row of boxes 1632 instead of two rows. In that case, more rows of detailed data may be shown above the grid 1630. In yet another example, the grid 1630 is omitted and all parameters are shown in rows, which may be scrollable if not enough screen real estate exists to depict all the rows at once.

Further, the placement of the grid 1630 with respect to the rows 1620 may not be fixed and may instead be moved above the rows or below the rows, between rows, or to the left or the right of the rows. The screen 1600 may be rotated to automatically cause the grid 1630 to dock to the left or right of the screen 1600, giving more screen real estate in the vertical axis for showing more rows 1620. The grid 1630 or the rows 1620 may be minimized to provide more screen real estate for one or the other. Many other configurations are also possible.

Toward the top of the screen 1600 are instrument selectors 1640 and 1642. The instrument selectors 1640 and 1642 are user interface elements, arrows in this example, which can enable a user to select a different instrument view. The example instrument selected for viewing in the patient data screen 1600 is indicated as the current instrument 1648, labeled "Root: rainbow." Another instrument selector 1644 is next to the current instrument 1648 and is in the form of an arrow pointing downward. A user can select the instrument selector 1644 to obtain a drop-down box that can allow a quick selection of an instrument from a list. In contrast, the instrument selectors 1640 and 1642 can operate in a carousel fashion, where selection of either selector 1640, 1642 causes the next instrument in the list to automatically be displayed. Another example instrument display is discussed below with respect to FIG. 17.

Selecting any of the instrument selectors 1640 through 1642 can cause the mobile application to obtain patient data from the server (for example, the MMS 110-610) corresponding to a different point-of-care instrument. Multiple point-of-care instruments may be connected to a patient. There may be, for example, (referring to FIG. 7) a monitoring hub 500, an infusion pump 616, a ventilator 618, and a vital signs monitor 620, among other options. Therefore, selecting the instrument selector 1640 through 1644 can enable the clinician to view a different instrument view (such as any of the instruments in FIG. 7 or others), which may be the same or similar to the actual view on the point-of-care device itself, as discussed above with respect to FIG. 16.

It is possible for the point-of-care device to send a preformatted image of the display on the point-of-care device to the server MMS 110-610, which can in turn provide the preformatted display to the clinician device. However, it may be more practical in some implementations for the MMS 110-610 to obtain the patient data from the point-of-care device and forward this information on to the clinician device or mobile device. The clinician device can include one or more graphics libraries and/or stored images corresponding to the point-of-care devices. Using currently-available or custom graphics library commands and/or stored images, the mobile application at the clinician device can construct a patient data screen to display a view the same as or similar to the point-of-care device display.

Turning to FIG. 17, another example patient data screen 1700 is shown. The patient data screen 1700 is similar in many respects to the patient data screen 1600. Both of these screens 1600, 1700 can be output by the mobile application on the clinician device. The screen 1700 may be accessed from any of the instrument selectors 1640-1644. Those instrument selectors 1640-1644 are also shown here in the patient data screen 1700 (so that the screen 1600 or another screen may also be accessed).

In addition, an instrument selector indicator 1745 is shown to indicate which of how many screens is being depicted. The instrument indicator 1745 is essentially a carousel indicator that shows a larger dot next to smaller dots. The larger dot represents the screen in the carousel of screens that is selected. Selecting the instrument selector 1640 can cause the next dot to the left of the largest dot to become the largest dot and to indicate that it is showing that selected monitor with the right instrument selector 1642 having the opposite functionality. Selecting the instrument selector 1642 can cause the carousel to loop to the first screen, represented by the leftmost dot (which would then become the largest dot), and so on.

The patient data screen 1700 corresponds to a different monitor than the one used to derive the patient data screen 1600. The monitor that has data displayed measures ECG parameters as well as a plethysmograph and respiration. This data is represented in rows 1620 of patient data (as in FIG. 16), which in this example are ECG wave forms with corresponding labels such as II, V2, avR, as well as Pleth and Resp waveforms, but not including physiological parameter values. A grid 1630 of other patient data is also shown (similar to FIG. 16). The grid 1630 has a single row with four columns representing four boxes of data. This display 1700 can correspond to a vital signs monitor such as the vital signs monitor 620 of FIG. 7.

Another example display that could be shown on the clinician device, selected by an instrument selector, is a display of the auxiliary device 640, which may be a television, tablet or the like in the hospital room. The auxiliary device 640 and its associated displays are described in greater detail in the '269 patent, incorporated above, as well as in U.S. Provisional Application No. 62/574,726, filed Oct. 19, 2017, titled "Medical Monitoring Hub," the disclosure of which is hereby incorporated by reference in its entirety. Since the auxiliary device 640 may be a television or otherwise have a larger display than the clinician device, the display from the auxiliary device 640 shown on the clinician device may be appropriately condensed.

Figure 18:
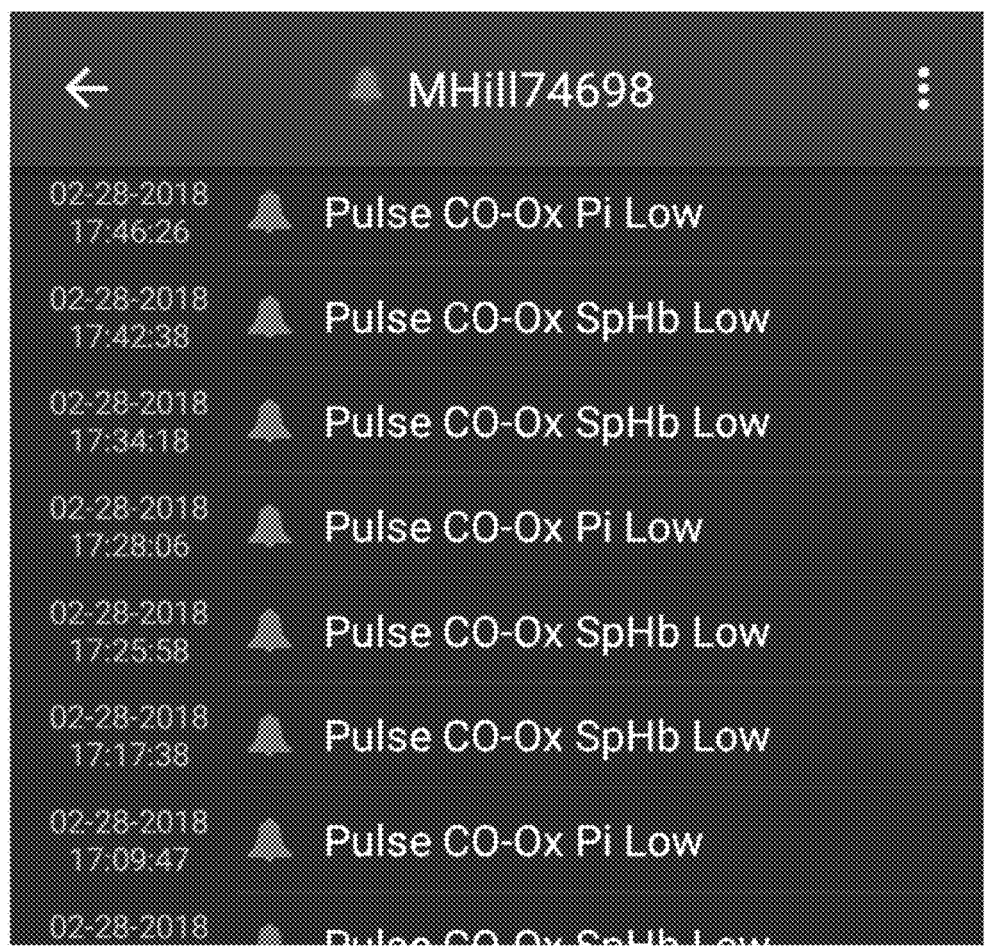
FIG. 18 depicts an example alarm list user interface.

Both FIG. 16 and FIG. 17 (as well as other figures) depict a patient info selector 1660 in the upper right-hand corner of the display. The patient information selector 1660 can be selected to view a patient information screen, which can permit performing changes to alarm settings or viewing a timeline of patient data. For example, FIG. 18 depicts an example timeline view screen 1800 that can be reached from a patient information screen. The timeline view screen 1800 includes a timeline 1810 of patient alarm events.

FIG. 19A depicts an example alarm settings screen 1900 that can be reached from a patient information screen, alarm settings screen (discussed below), or the like. The alarm settings screen 1900 can enable a user to change alarm settings at the point-of-care device remotely. By accessing the alarm settings screen 1900, the clinician can remotely adjust alarm limits. Example user interface elements 1910 and 1920 and 1930 are provided for adjusting alarm limits as shown. These elements includes sliders 1910 for upper and lower alarm limits as well as boxes 1920 that show the upper and lower alarm limits. Finally, cancel and submit boxes 1930 can allow the alarm limit changes to be submitted or cancelled.

VII. Additional Examples

Figure 19B:
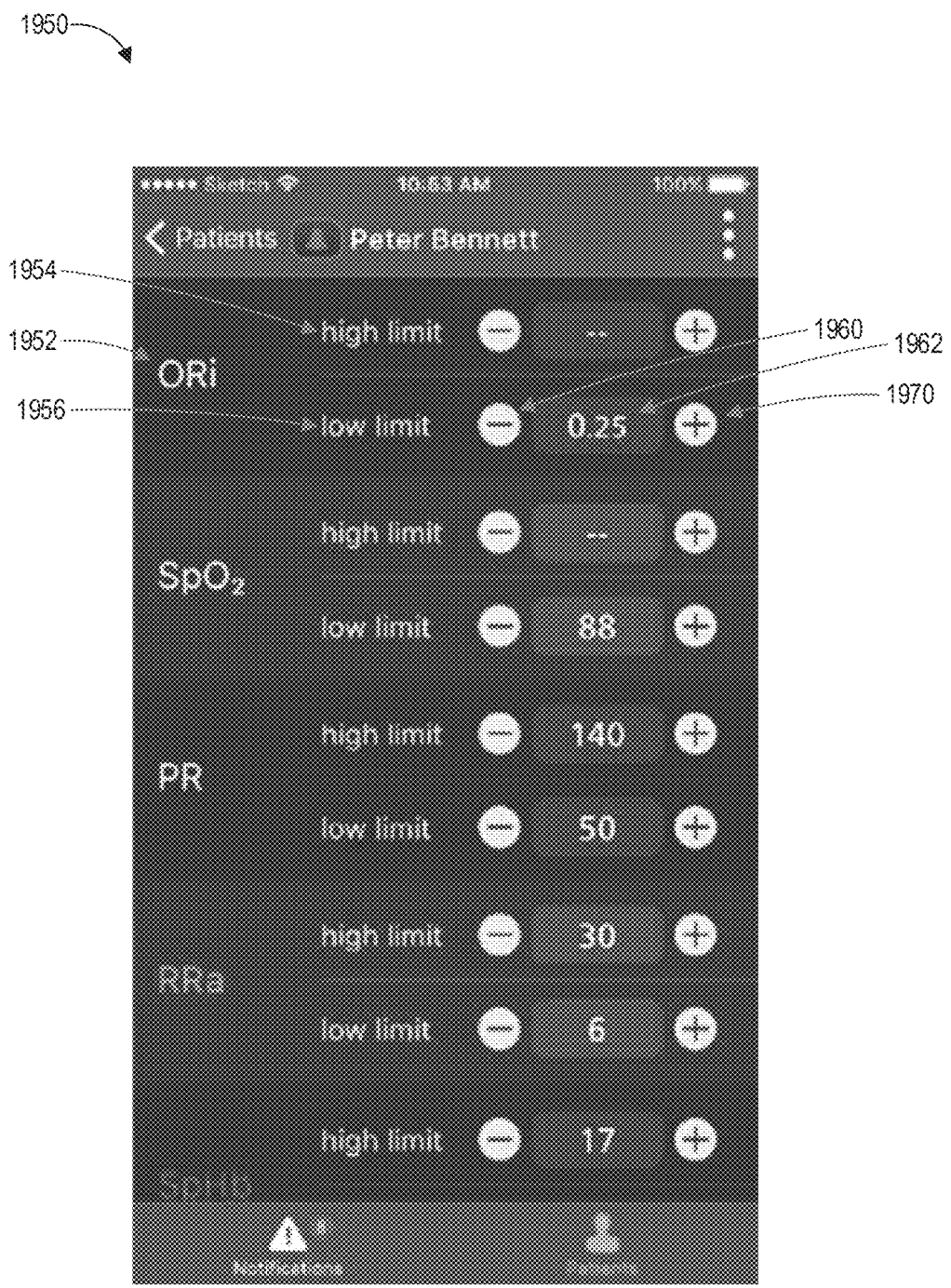

Turning to FIG. 19B, another example alarm setting screen 1950 is shown. The alarm setting screen 1950 can be accessed from a settings menu. For example, a settings menu option 2001 shown in FIG. 20 (discussed below) and in subsequent figures can provide access to the alarm setting screen 1950 (or 1900). A user can also left swipe or right swipe on the user interface 1950 (or any other of the user interfaces described herein) to reach the alarm setting screen 1950.

In the example alarm setting screen 1950, several different example physiological parameters 1952 are shown including ORi (oxygen reserve index), $SpO_2$, PR (pulse rate), and RRa, as well as SpHb. Alarm settings 1954, 1956 are shown for each parameter 1952, including a high limit 1954 and a low limit 1956. Both limits may not be applicable to all parameters. For example, some parameters (such as $SpO_2$) may have a low limit 1956 but not a high limit 1954. User interface elements 1960 and 1970 in the form of minus and plus signs are provided to be user selectable so as to adjust each of the alarm limits 1954, 1956. A value 1962 is shown displayed between the UI elements 1960 and 1970, which can be the value of the alarm limit being adjusted by the UI elements 1960, 1970.

Figure 20:
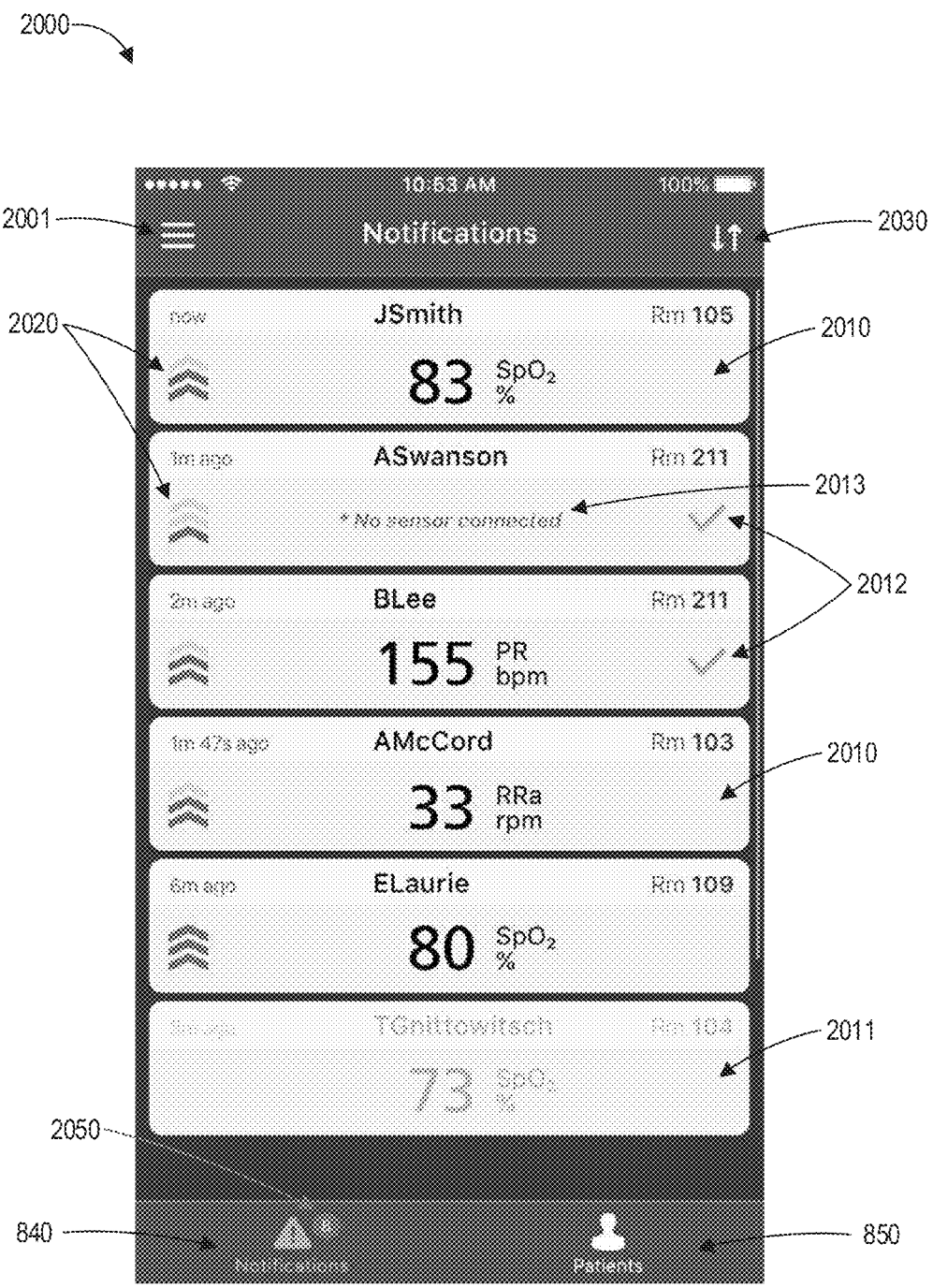
FIGS. 20 through 48 depict additional example user interfaces for a clinician device.

Turning to FIG. 20, another example notifications screen 2000 is shown. The notifications screen 2000 is similar in many respects to the notifications screen 800 of FIG. 8. For example, the notifications screen 2000 includes several alarm notification tiles 2010. Each alarm notification tile 2010 can represent a different alarm notification provided to the clinician's device from the bedside monitor (which may be routed through a remote server such as the MMS 110). Each of the alarm notification tiles 2010 can be oblong or rectangular or otherwise elongated with rounded edges. Variations in appearance to the alarm tiles are possible, such as by sharpening the corners or by providing square tiles. Fewer (or no) alarm notification tiles 2010 may be shown when fewer (or no) alarms for a clinician's patients have occurred.

Each of the alarm notification tiles 2010 can include a patient label (such as J. Smith—which can be a shortened version of the patient's name, full name, or some other identifier), a room number, and one or more parameter values that gave rise to the alarm (such as 83% $SpO_2$) or an error message 2013 such as "No sensor connected." Notification state indicators 2020 are also provided on the left side of each alarm notification tile 2010. The notification state indicators 2020 can be similar to the notification state indicators 820 in function. Instead of being colored rectangular bars, however, the notification state indicators 2020 are represented as inverted arrows or chevrons on the left side of the alarm notification tiles 2010. Of course, the location of the notification state indicators 2020 may be varied.

In the depicted example, each notification state indicator 2020 includes three inverted arrows or chevrons, some of which are shown in color and others of which are greyed out. One colored arrow in the notification state indicators 2020 can indicate that the alarm is an initial alarm. Two colored arrows can indicate that the alarm has been escalated, and three colored arrows can indicate that the alarm has been re-escalated. While three inverted arrows are shown, in other implementations fewer or more arrows (or other symbols) may be used to represent alarms, escalations, and re-escalations.

When an alarm notification is first received at the clinician device, if the device is currently locked, an alarm notification tile 2010 can be displayed on the lock screen of the device (not shown). The alarm notification tile 2010 can include any of the features described herein, including the notification state indicators 2020. A clinician can interact directly with the alarm notification tile 2010 from the lock screen in a similar manner as if the alarm notification tile 2010 were depicted on the user interface 2000.

Many different options can be used for determining when to escalate and re-escalate alarms, including any of the options described above. Hospital policy, for example, may specify when an alarm may be escalated or re-escalated. For instance, one hospital policy can be to escalate alarms after a minute has passed without any action being taken at the bedside monitor to disable the alarm. Another hospital policy can be to re-escalate an alarm if five minutes have passed after initial escalation without any interaction at the bedside monitor. These time periods may vary in different implementations.

Another difference from the alarm notification screen 2000 and the notification screen 800 is that some of the alarm notification tiles 2010 can include clinician response indicators 2012. In this example, the clinician response indicators 2012 are depicted as checkmarks. The checkmark clinician response indicator 2012 can indicate that a clinician has accepted the alarm, whereas an X indicator (not shown) or an arrow indicator (see FIG. 27) can indicate that the clinician has declined or forwarded the alarm.

For alarm notification tiles 2010 that do not have a clinician response indicator 2012, the lack of indicator may mean that no clinician has yet responded or that the clinician using the user interface 2000 has not responded. Having an empty clinician response indicator 2012 can also indicate that another clinician has responded. Optionally, a different indicator may be provided to show that another clinician has responded. The clinician response indicators 2012 can be output based on the forward and accept options described above and which are further described in greater detail below. The clinician response indicators 2012 may also be used in conjunction with the notification screen 800. More generally, any of the features of the notification screen 2000 can be combined with the notification screen 800 and vice versa.

One tile 2011 looks like the other alarm notification tiles 2010 except that it is greyed out. This tile 2011 is greyed out because the tile 2011 used to represent an alarm notification but now indicates that an alarm has been addressed. However, greying out previous alarm notification tiles 2010 is one of multiple possible options for dealing with completed alarms. Another option is to cause such tiles to disappear from view automatically. Alternatively a greyed-out tile 2011 can disappear from view at some later time.

As in FIG. 8, in FIG. 20 there are notifications and patient user interface elements 840 and 850. The notifications user interface element 840 can be shown (as here) with a color such as blue to indicate that the notification screen 2000 is currently selected. The patients user interface element 850 is shown in a different color such as white to indicate that it is selectable to go to a patients screen. Examples of patients screens are described above as well as below. If another screen were currently displayed, the notifications user interface element 840 may be selectable to cause the user interface 2000 (or one like it) to be displayed. Also shown on the notifications user interface element 840 is an indicator 2050 that indicates the number of alarm notifications that may currently be actionable (not all of which are shown as tiles 2010; however, scrolling down can expose the additional tiles 2010).

Figure 21:
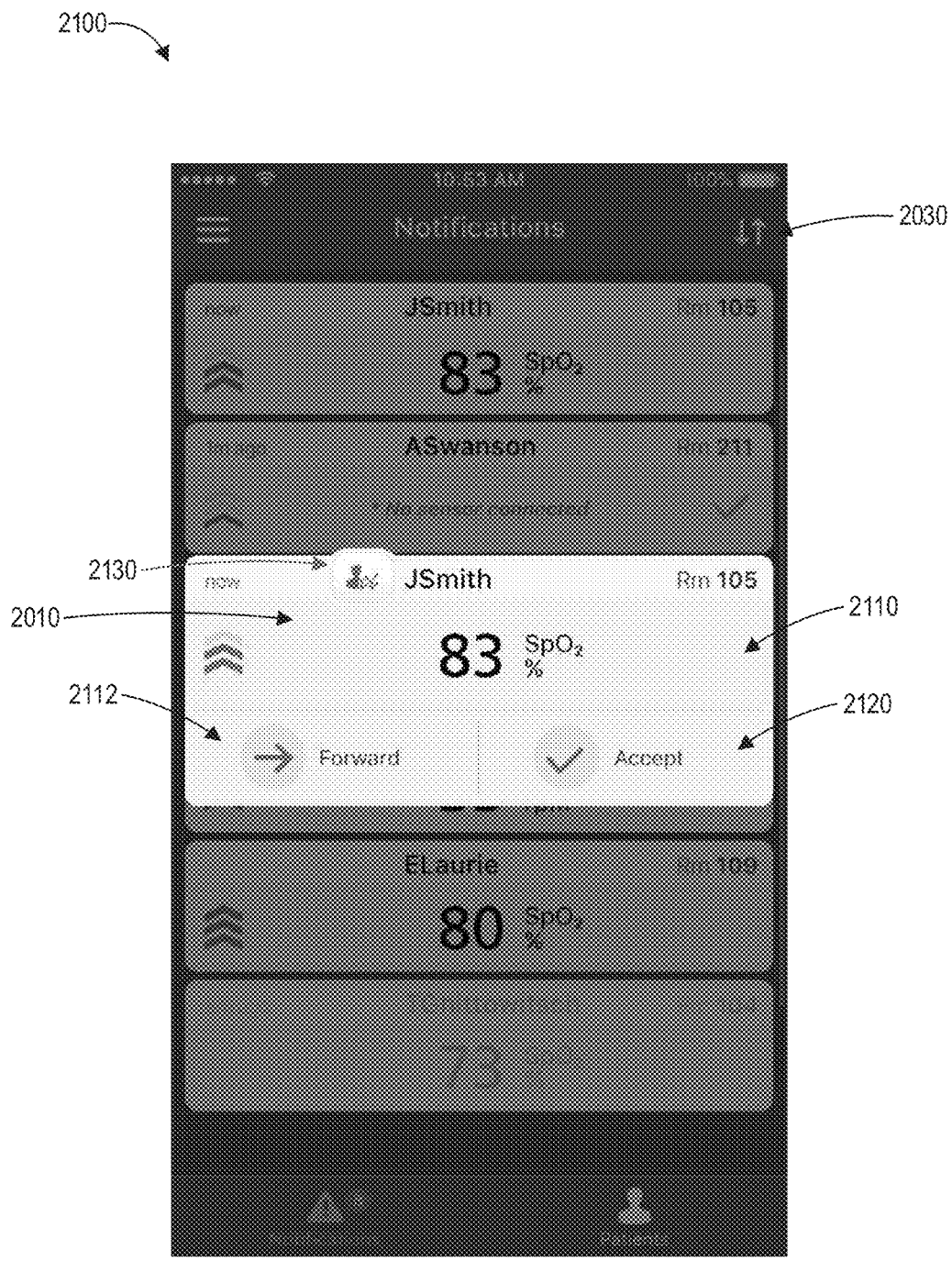

Turning to FIG. 21, another example notification screen 2100 is shown. The notification screen 2100 is very similar to the notification screen 2000, except that as in FIG. 12, one of the alarm notification tiles (2110) has been long-pressed. As a result, options 2112, 2120 and 2130 are displayed, and the remainder of the display is grayed out. These options 2112, 2120 and 2130 include the forward option 2112, the accept option 2120, and the detail option 2130 discussed above. The detail option 2130, for instance, can be selected to view the patient detail display as described above with respect to FIGS. 16 and 17 or any of the patient data screens described below with respect to FIGS. 33 through 44.

Figure 22:
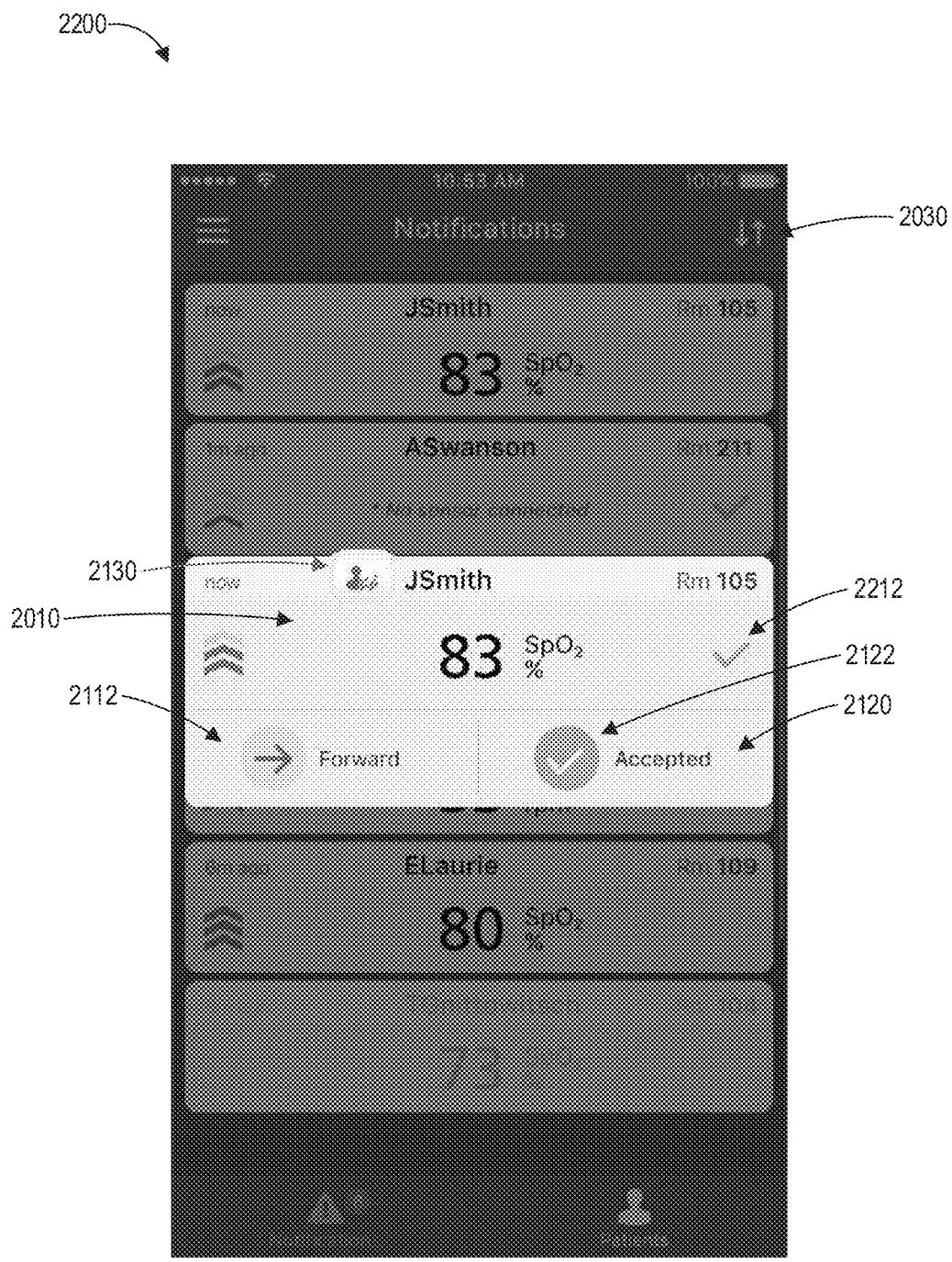

Turning to FIG. 22, another example notification screen 2200 is shown, which is similar to the notification screen 2100 except that the accept option 2120 has been selected. A shaded checkmark icon 2122 indicates that the accept option 2120 has been selected. In addition, in view of the accept option 2120 being selected a clinician response indicator 2212 is shown in the form of a checkmark on the alarm notification tile 2010. The clinician response indicator 2212 is another example of the clinician response indicator 2012 described above with respect to FIG. 20.

Figure 23:
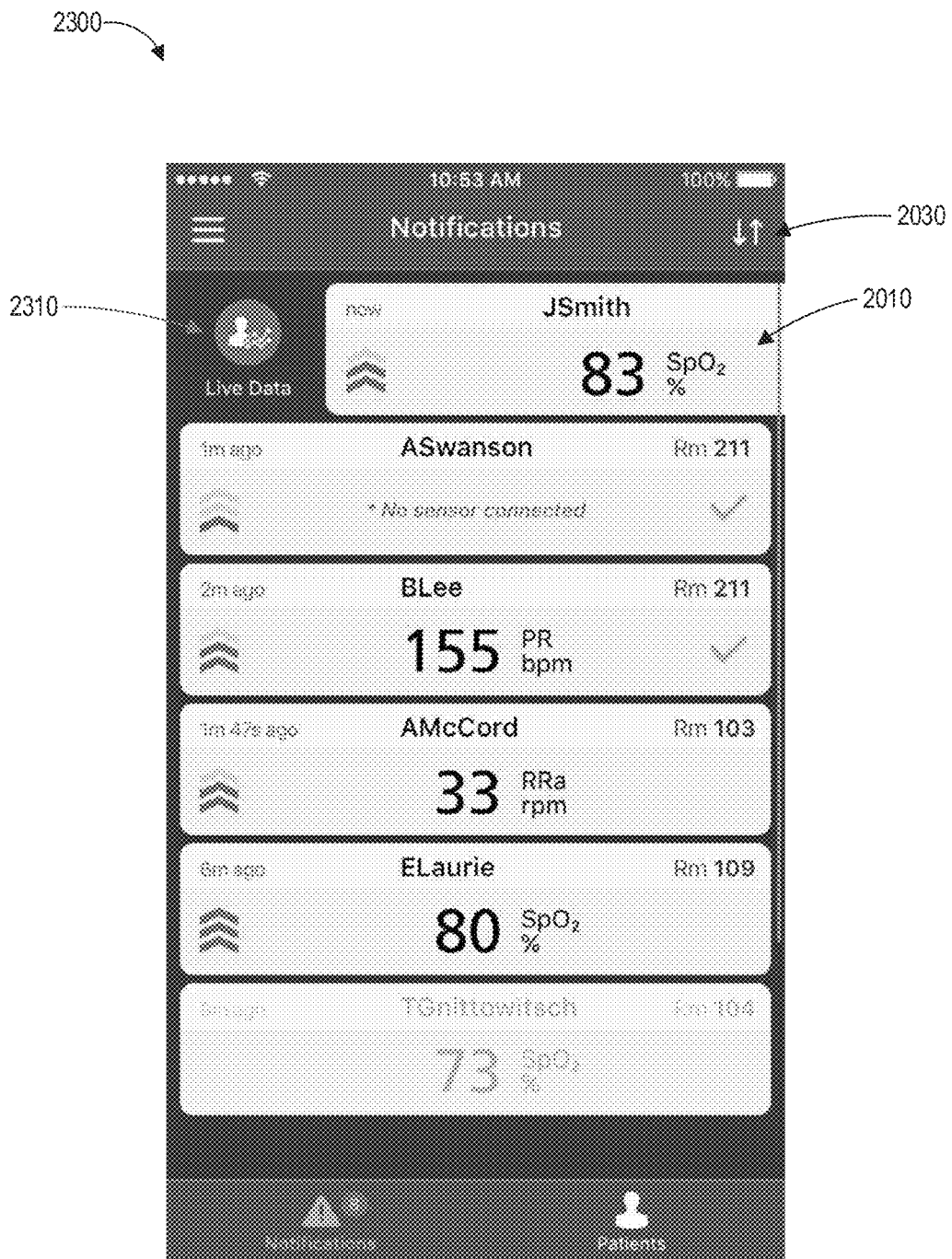

Turning to FIG. 23, another example notification screen 2300 is provided. The notification screen 2300 is similar to the notification screen 2000 except that one of the alarm notification tiles 2010 has been swiped to the right to expose a detail option 2310, which can have similar functionality as the detail option 910 described above with respect to FIG. 9.

Figure 24:
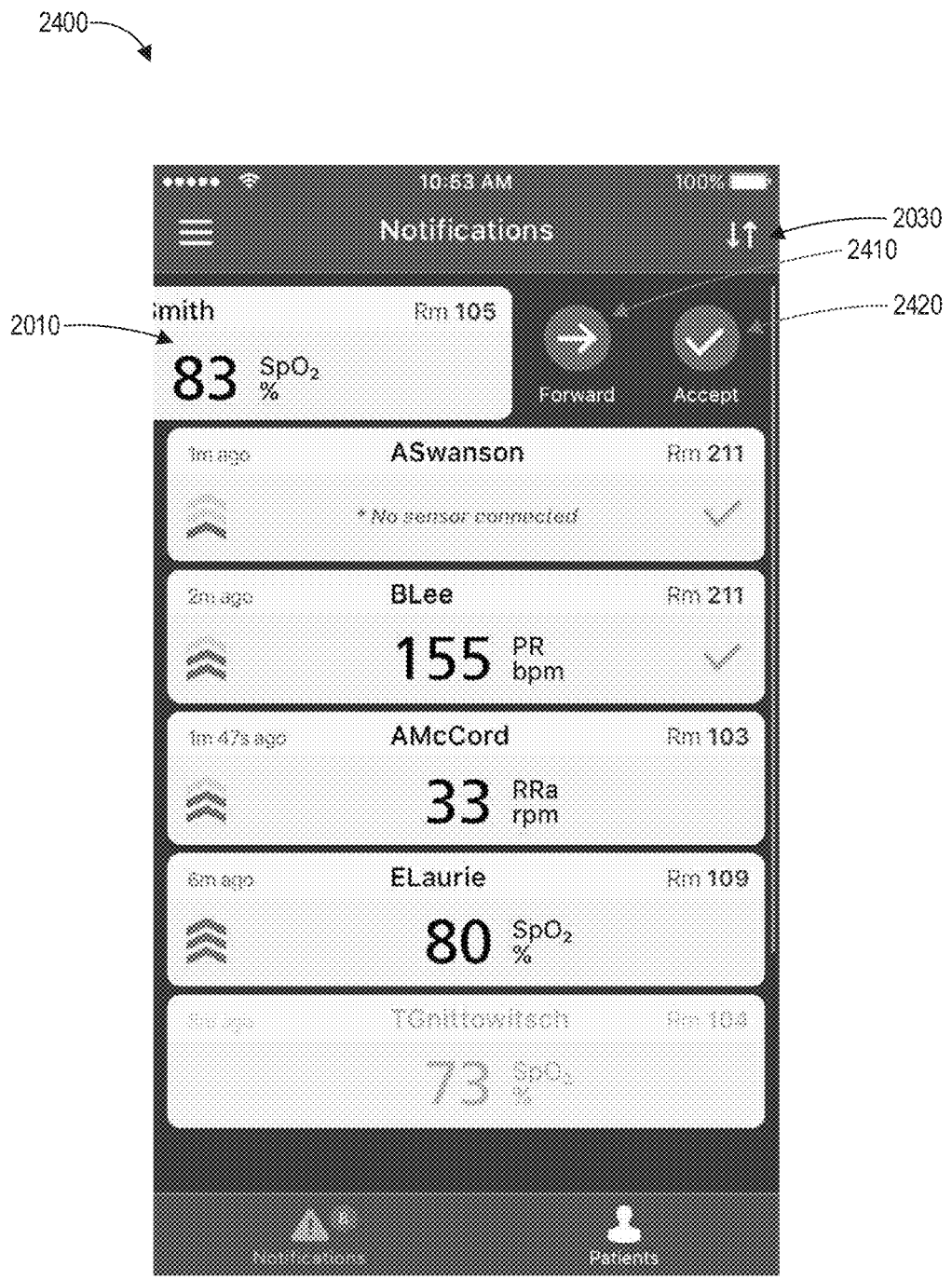

Likewise, turning to FIG. 24, another example notification screen 2400 is shown where one of the alarm notification tiles 2010 has been swiped to the left, exposing forward and accept options 2410, 2420, which can have similar functionality as described above with respect to FIGS. 10 and 22.

Figure 25:

In FIG. 25, similar to FIG. 24, another example notification screen 2500 shows a shaded accept option 2510 with a shaded checkmark to indicate that it has been selected. Also, a clinician response indicator 2012 is shown on the alarm notification tile 2010 to indicate that the alarm has been accepted.

Figure 26:

Turning to FIG. 26, another notification screen 2600 is shown similar to the notification screen 2500, except that instead of the accept option 2420 being shaded, the forward option 2610 is shaded. This shading can indicate that the alarm has been forwarded. Likewise, the alarm notification tile 2010 includes a clinician response indicator 2614 arrow that is similar to the shaded forwarded option arrow, indicating that the alarm has been forwarded.

Figure 27:
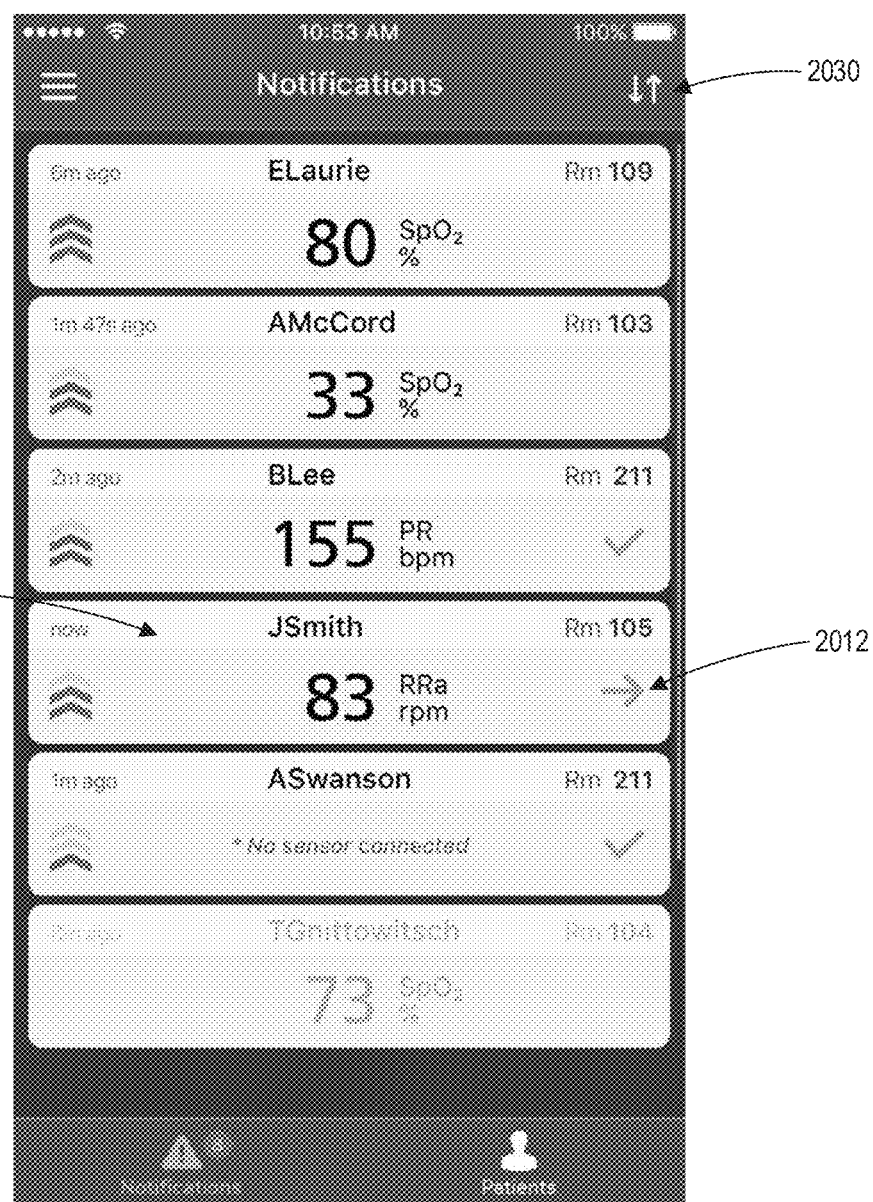
Figure 28:
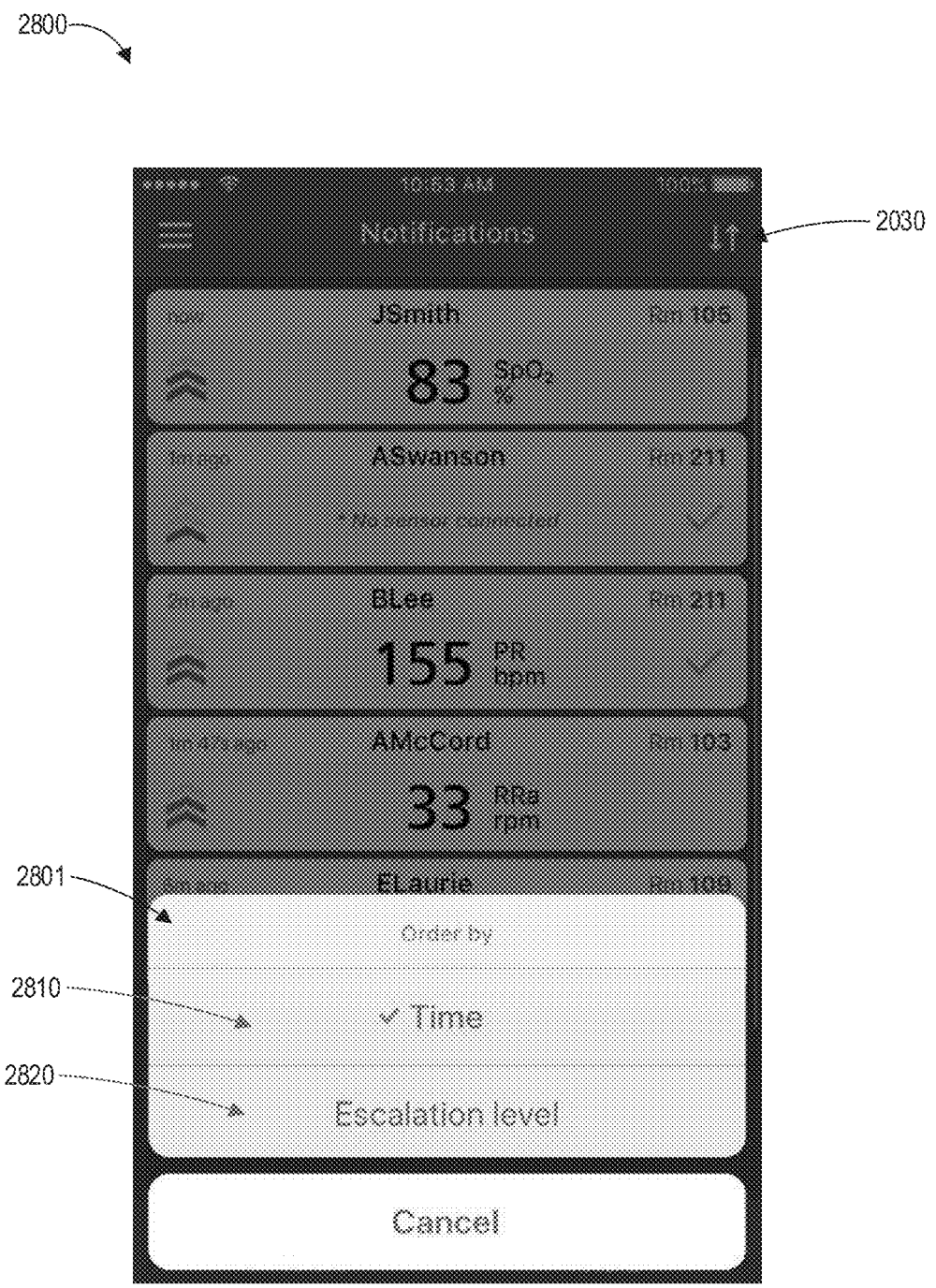

Turning to FIG. 27, another example notification screen 2700 is shown, which includes an alarm tile 2010 with a clinician response indicator 2012 of an arrow from the previous notification screen 2600. In this screen and in other notification screens described herein, an option 2030 is provided that can be selected to sort the alarm notification tiles shown. Sorting behavior can be the same or similar as discussed above. For example, selection of this option 2030 can cause a display such as the user interface 2800 of FIG. 28 to be displayed. In this display, an overlay 2801 is provided. The overlay 2801 includes sorting options 2810 and 2820 to sort the alarm notifications by time or escalation level. The current display or user interface 2800 can sort the alarm notifications by time. Selecting the escalation level option 2820 can result in the sorting shown in the notification screen 2700 of FIG. 27.

Figure 29:
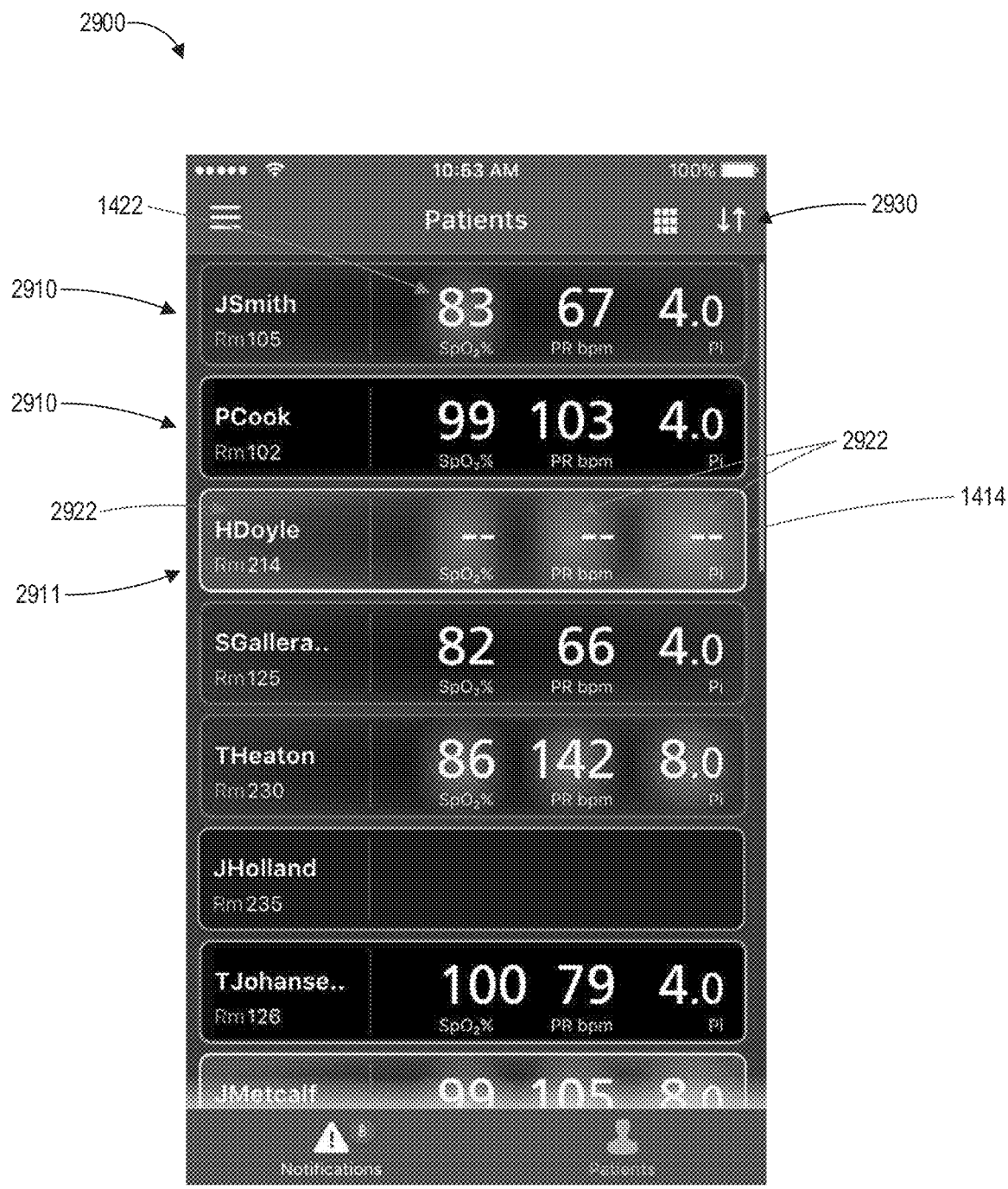

Turning to FIG. 29, an example patients screen 2900 is shown. The patients screen 2900 is similar to the patients screen of FIG. 14 and presents a list view of patients. The patients screen 2900 organizes patients according to tiles 2910. These tiles 2910 are formed in rows and include boxes or oblong or rectangular shapes bounded by a border 1414. Each of the tiles 2910 can include information about a patient, including the patient label, room number, and at least a subset of available parameter data. In this example, the tiles 2910 include three physiological parameter values: SpO2 percentage, pulse rate, and PI (perfusion index). However, in other implementations, the tiles 2910 may depict more, fewer, or other parameters.

As described above with respect to FIG. 14, in FIG. 29, various characteristics of the tiles 2910 can change to indicate that an alarm is occurring. For instance, as described above the color of the border 1414 of a given tile may change to red or yellow to indicate (for example) that there is an alarm as described above. Further, a glow graphic 1422 may appear behind a parameter for which there is no alarm as described above. The glow graphic can pulse, flash, blink, or fade in and out. In addition, there may be a gradient through some or all of the tile 2910 to indicate the alarm. An example gradient 2922 is shown in some of the tiles 2910. This gradient is shown as various glowing areas, which may have the same color corresponding to the alarm border 1414 such as red or yellow. The gradient may also pulse, flash, blink, fade in and out or the like to draw a clinician's attention. Further, the gradient 2922 may be shown even when a parameter other than the parameters shown is responsible for the alarm. Further, as another example, in the tile 2911, blank spots are shown instead of parameter values, due to a probe-off alarm (indicated by yellow border 1414 and yellow gradient 2922), meaning that parameter values cannot be calculated because the probe is disconnected.

Figure 30:
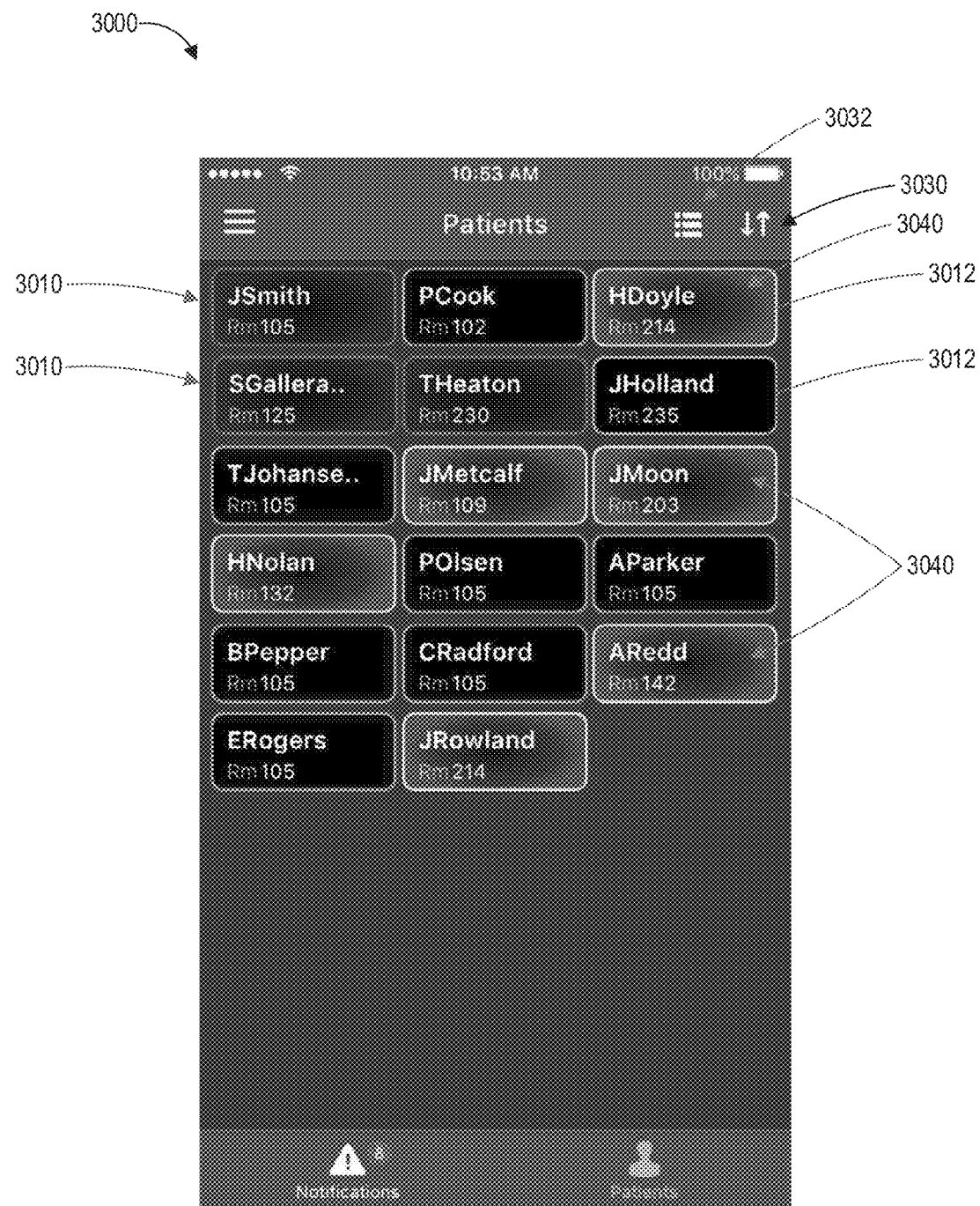

A grid view element 2934 can also be selected to cause a patients screen 3000 or the like to be displayed as shown in FIG. 30. The patients screen 3000 is similar to the patients screen 1500 of FIG. 15. In the patients screen 3000, a grid of patient boxes 3010 are displayed. Each of the patient boxes 3010 can be oblong, rectangular, square or some other similar shape and can include a patient label and room number. However, like the patient boxes described above with respect to FIG. 15, the patient boxes 3010 in this example do not include any physiological parameter data. The boxes 3010 can, like the tiles 2910, have a different color and/or a pulse based on whether an alarm has occurred. For instance, a border 3012 can be provided that changes color, and a gradient 3040 may be provided that indicates that an alarm has occurred. The gradient may pulse, blink, flash, fade in and out, or the like.

Figure 31:
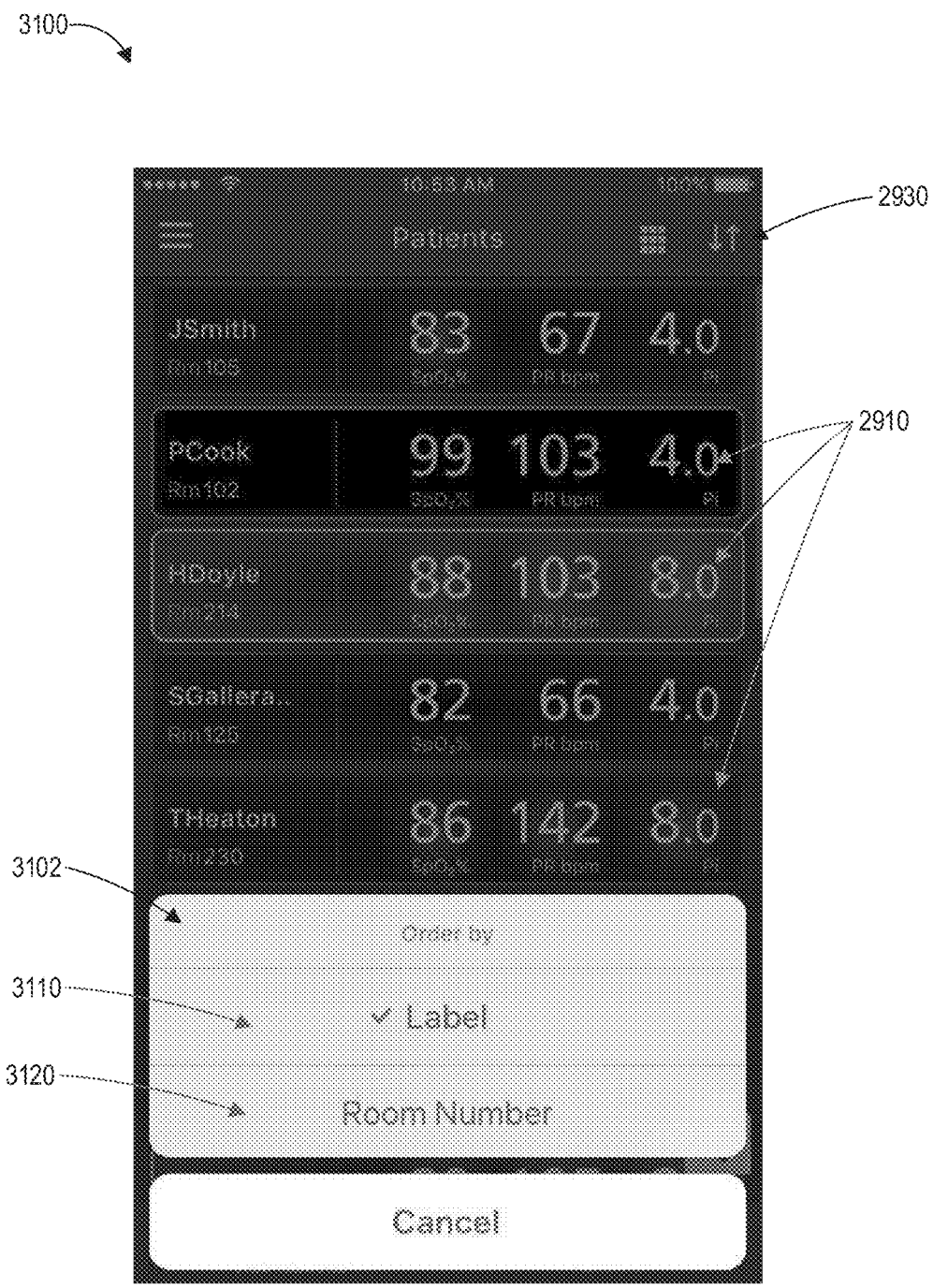
Figure 32:
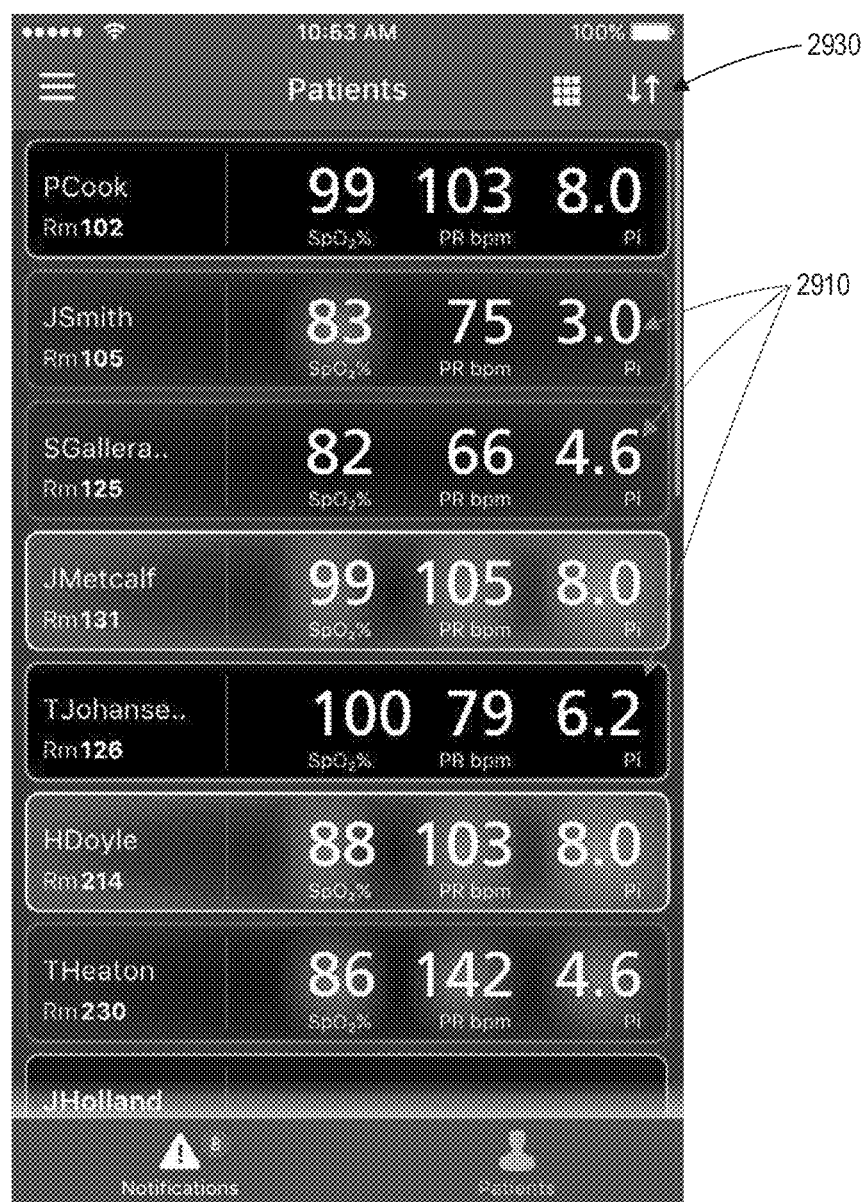

Referring again to FIG. 29, an example sort element 2930 is provided. Selection of the sort element can cause a patients screen 3100 to be displayed like the one shown in FIG. 31. The patients screen 3100 includes the patient tiles 2910 of the patients screen 2900 but also includes an overlay 3102 (with the rest of the display grayed out). The overlay 3102 includes options 3110, 3120 for sorting the tiles 2910, for example, by label (3110) or room number (3120). Other options may be provided, such as sorting by severity of alarms or any other sorting options discussed above. For example, turning to FIG. 32, a user interface 3200 is shown that orders the tiles 2910 by room number (upon selection of the option 3120).

FIGS. 33 through 44 depict additional example patient data screens. These patient data screens are similar in many ways to the patient data screens shown in FIGS. 16 and 17. The screens in FIGS. 33 through 44 may have similar or the same functionality as the patient data screens of FIGS. 16 and 17.

Figure 33:
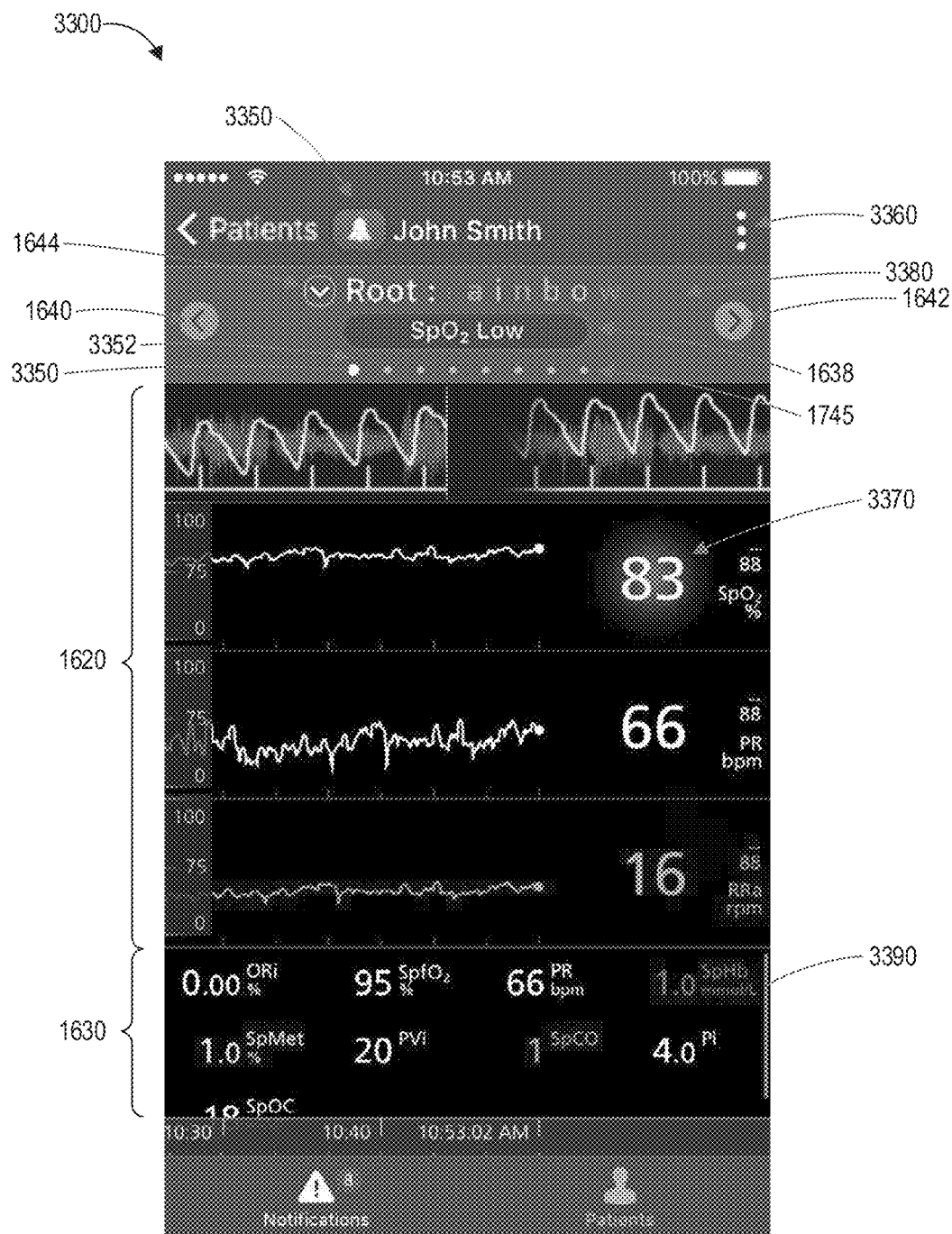

Referring specifically to FIG. 33, a patient data screen 3300 is shown. The patient data screen 3300 is similar in many respects to the patient data screen 1600 of FIG. 16. For example, rows 1620 of data and a grid 1630 of patient data are provided. In one of the rows 1620, an alarm glow graphic 3370 is supplied behind a physiological parameter value to indicate that this parameter is alarming. The alarm glow graphic 3370 may have the functionality of any of the glow graphics described above.

In the grid 1630, a scroll bar 3390 is provided to indicate that the grid 1630 may be scrolled to view additional parameters. The scroll bar 3390 can indicate the relative position of the grid. The scrollbar 3390 itself may be selectable to scroll the grid up and down. When the grid 1630 has three or more rows of data, the grid may be scrollable. Alternatively, when the grid 1630 occupies a relatively smaller area of the screen than the rows, the grid may be scrollable with fewer than three rows. The grid 1630 may also scroll from side to side instead of vertically. The grid 1630 can also scroll like a ticker automatically, from one side to the other.

Toward the top of the patient data screen 3300, an instrument selector region 3380 is provided that includes several different elements. The instrument selector region 3380 depicts a name of the patient device and/or channel of that device that corresponds to the patient data being displayed. In this example, the patient device name is "Root," which is an example patient device available from Masimo Corporation of Irvine, California Next to the device name is a channel name, called "rainbow." This channel is also available from Masimo and corresponds to optically-derived parameters such as SpO2, pulse rate, and respiratory rate, as well as other parameters. In general, a channel can correspond to a subset of the functionality of an instrument. A channel may also correspond to add-on functionality through another sensor or board-in-cable (BIC) connected to the instrument. Example BICs that can be used with any of the functionality herein are described in the '269 patent, incorporated by reference above.

Also shown in the instrument selector region 3380 is an instrument selector 1644 (see also FIG. 16). As a patient may be connected to multiple instruments and channels, the instrument selector 1644 is shown as a drop-down arrow that can be selected to choose from different instruments or channels connected to the patient. Example output that may be displayed upon selection of the instrument selector 1644 is described below with respect to FIGS. 45 and 46.

The arrows 1640 and 1642 from FIG. 16 are also shown to enable selection of a different instrument or channel. In addition, the entire instrument selector region 3380 may be user selectable to be swiped from left to right or right to left to select a different instrument or channel. An instrument carousel 1745 can provide an indication of which instrument or channel has been selected. A selected instrument indicator 3350 on the instrument carousel 1745 indicates where in the carousel of possible instrument displays that the current display is located. In the depicted example, the selected instrument indicator 3350 is at a left-most point in the carousel 1745, such that swiping to the right can result in viewing another instrument display. Optionally swiping to the left can wrap around to the right-most indicator of the carousel 1745 to show a corresponding instrument display.

Another alarm indicator 3352, shown as a red dot above the carousel 1745, indicates that an alarm is occurring on the instrument or channel corresponding to the portion of the carousel 1745 which the red dot is above. There may be multiple alarm indicators 3352 shown if multiple instruments or channels are alarming. Moreover, an alarm control button 3350 can allow a user to suspend or silence an alarm at the point of care, as described above.

Figure 34:
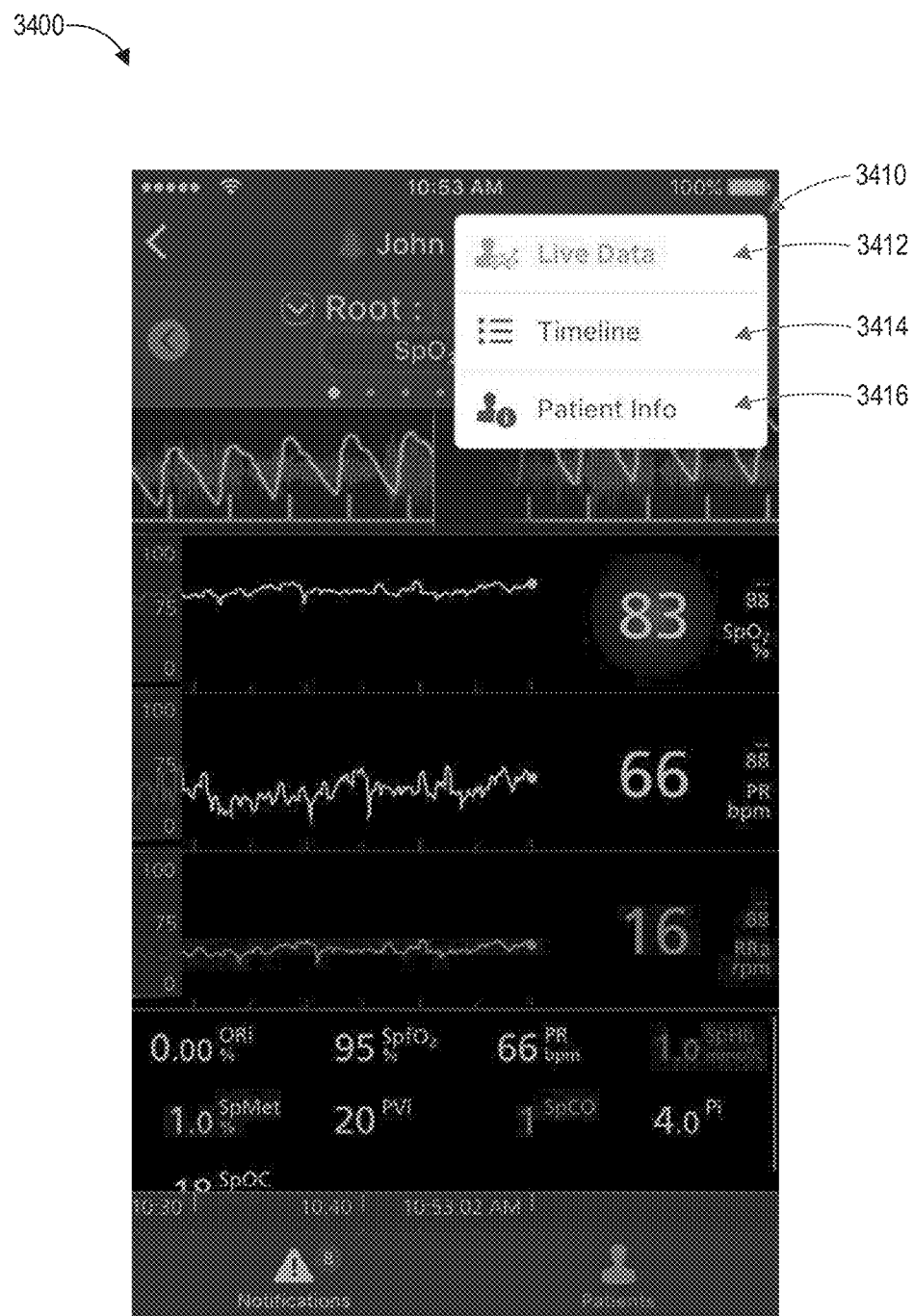
Figure 47:
Figure 48:
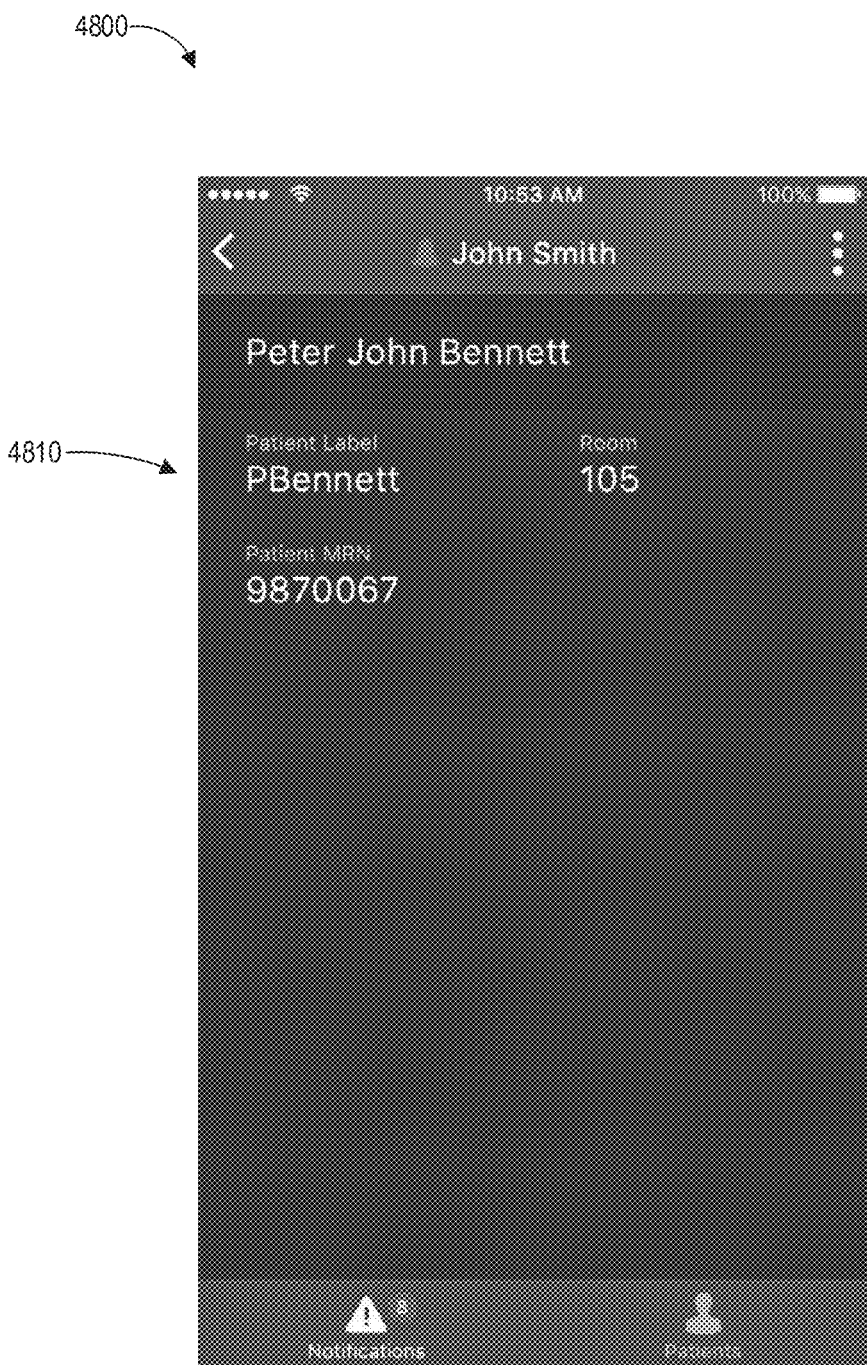

Turning to FIG. 34, another example patient data screen is shown. The patient data screen 3400 of FIG. 4 can output an option menu 3410 as an overlay to the patient data screen 3300 and may be selected by selecting an option selector 3360 in FIG. 33. The option menu 3410 includes three example options, a live data option 3412, a timeline option 3414, and a patient information option 3416. The live data option 3412 can be colored, for example in blue, to indicate that it is the currently-selected option. The timeline option 3414 can be selected to view a timeline view such as shown in FIGS. 18 and 47. The patient information option 3416 can be selected to see a view such as shown in FIG. 48.

Figure 35:
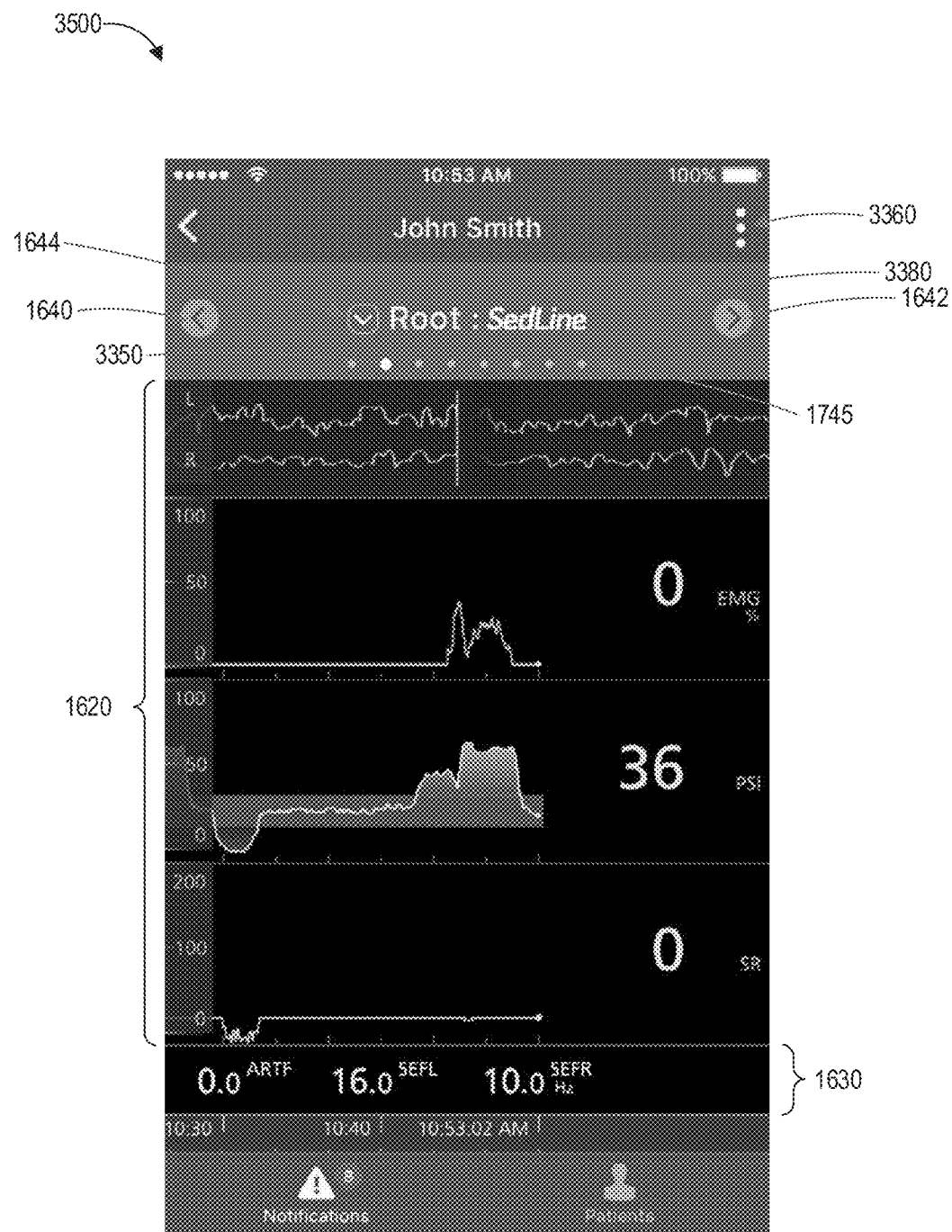

Turning to FIG. 35, another example patient data screen 3500 is shown. The patient data screen 3500 depicts patient data corresponding to the Root device (described above) and a SedLine™ channel of that device. The SedLine™ channel can correspond to brain function monitoring using an add-on EEG board-in-cable connected to the Masimo Root device. The instrument carousel 1745 and the selected instrument indicator 3350 indicate that the display from FIG. 33 has been swiped or moved to the right to output the display shown. For example, the selected instrument indicator 3250 is now one circle to the right in the carousel 1745 compared with the position the selected instrument indicator was in FIG. 33. As before, row data 1620 and grid data 1630 are provided in this example.

Figure 36:
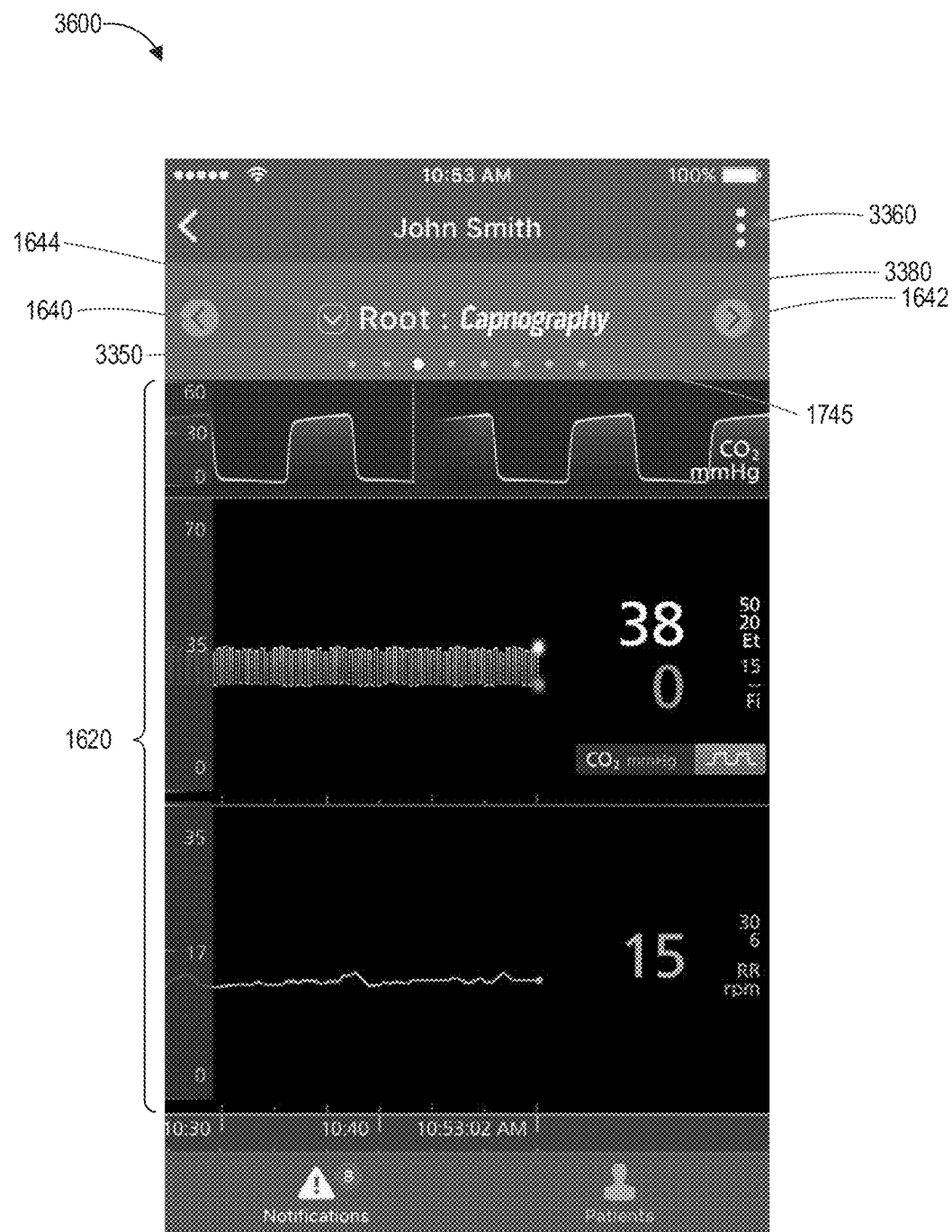

Turning to FIG. 36, another example patient data screen 3600 is shown. The patient data screen 3600 is depicted for the Root device with a capnography channel as indicated in the instrument selector region 3380. The carousel 1745 shows that the selected instrument indicator 3350 has moved one over to the right from FIG. 35, such that (for example) swiping to the right in FIG. 35 can cause the display of the FIG. 36 to be shown. In this particular example, patient rows 1620 are shown but no grid, as there are not enough parameters in this example to also warrant a grid.

Figure 37:
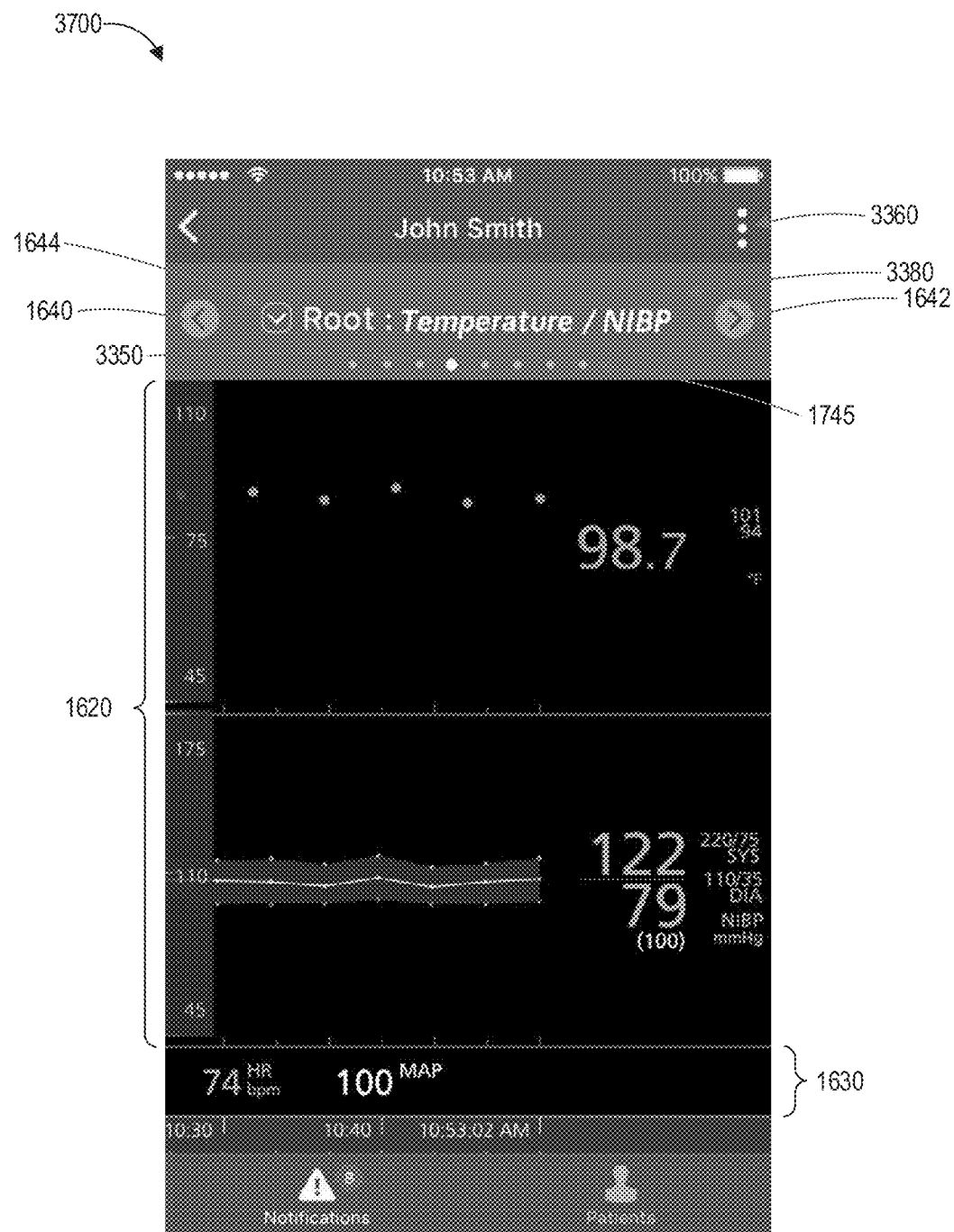

Turning to FIG. 37, an example patient data screen 3700 is shown. The patient data screen 3700 indicates in the instrument selector region 3380 that the Root instrument is selected and a Temperature/NIBP (non-invasive blood pressure) channel is selected. Rows 1620 and a grid 1630 of data are provided. The carousel 1745 and the selected instrument indicator 3350 indicate that swiping right from FIG. 36 has resulted in the display shown in FIG. 37.

Figure 38:
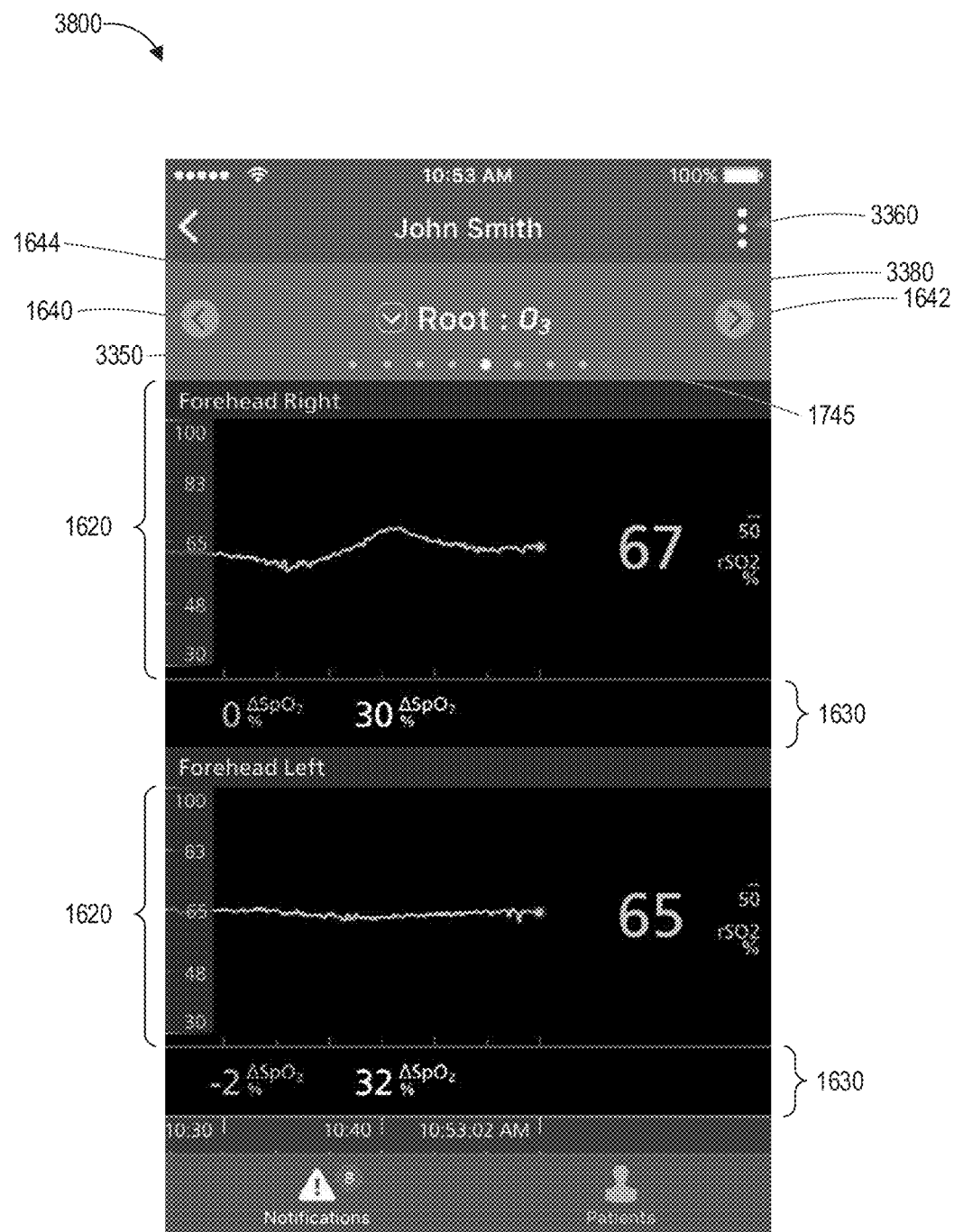

Turning to FIG. 38, another example patient data screen 3800 is shown. The instrument selector region 3380 indicates that the Root device is selected and an O3 channel is also selected. O3 can refer to regional oximetry, which can be used to measure cerebral blood oxygen saturation. The rows 1620 and the grid 1630 are also shown. In fact, two grids 1630 are shown. One aspect that differentiates this patient data screen 3800 from previous screens is that there are two separate grids 1630 separated by rows 1620. Each grid 1630 can correspond to the data in the row 1620 above it. Thus, the placement of the grid may be below or above one or more rows. The grid may also be placed to the left or to the right of a row or set of rows.

Figure 39:
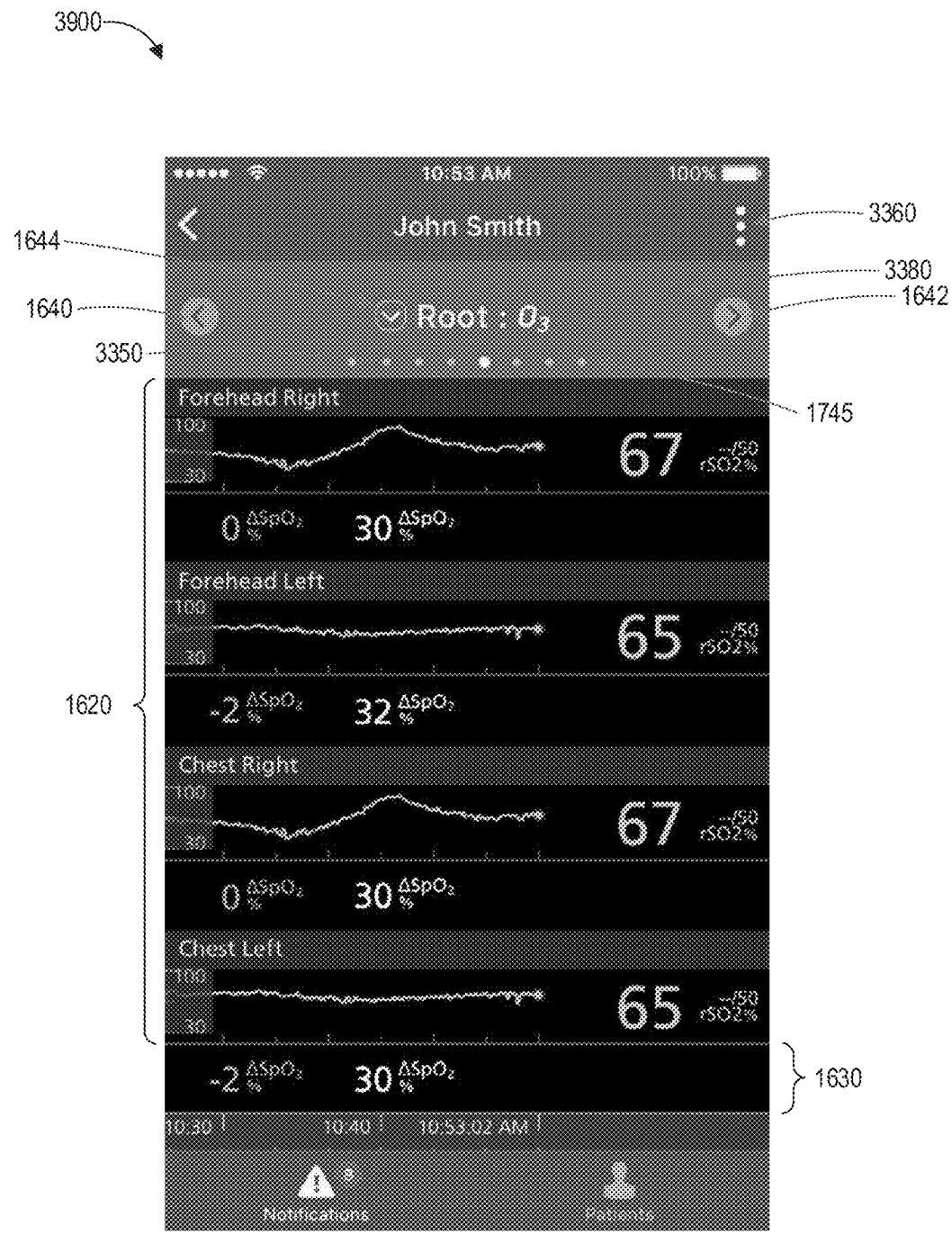

Turning to FIG. 39, an example patient data screen 3900 is shown that is similar in many respects to the patient data screen 3800. This patient data screen 3900 is again for the Root device, O3 channel, but is also used for chest pulse oximetry. The patient data screen 3900 includes four rows 1620 interspersed with four grids 1630. Thus, any suitable number of rows and grids may be provided in various displays.

Figure 40:
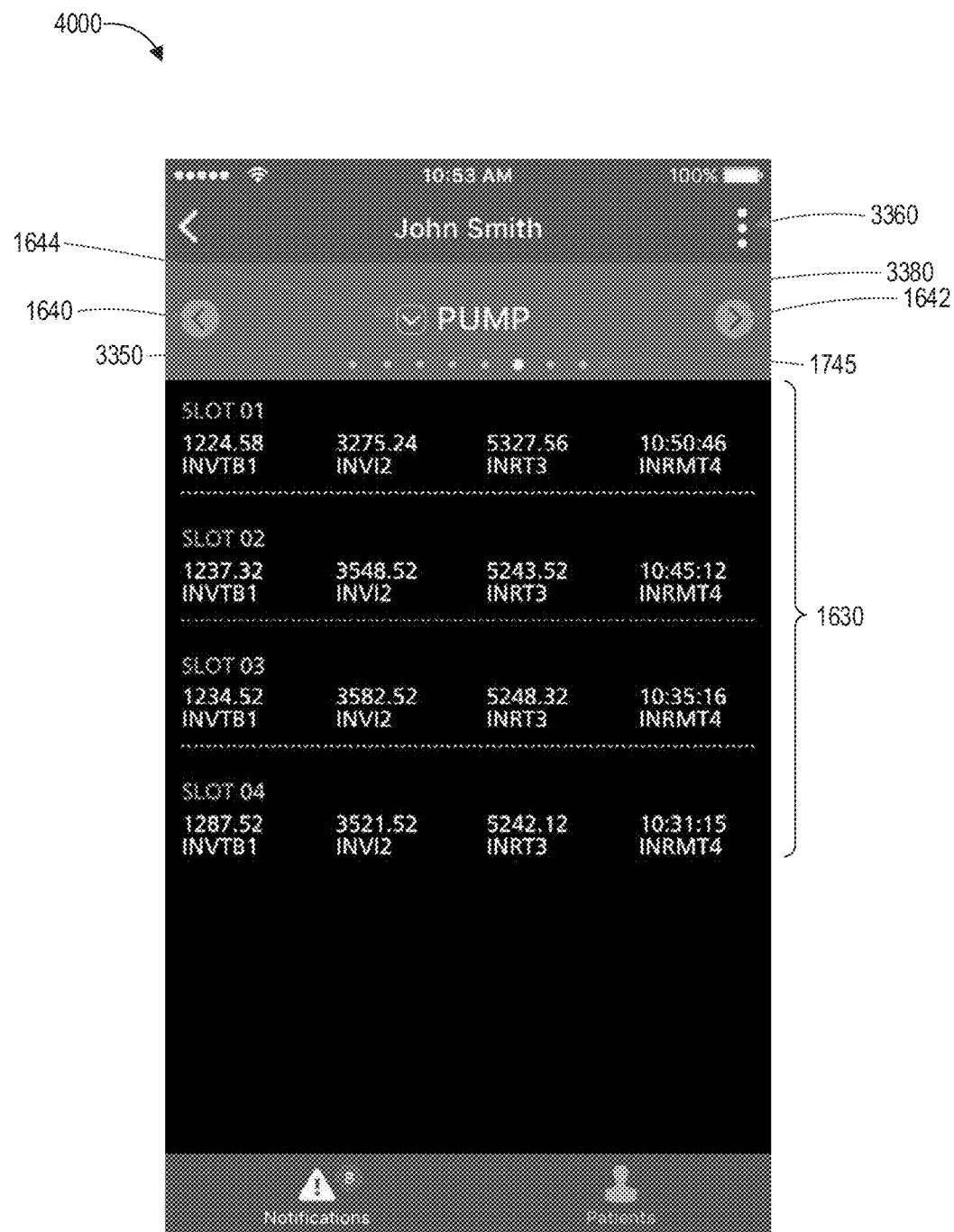

Turning to FIG. 40, an example patient data screen 4000 is shown for an intravenous (IV) pump as indicated in the instrument selector region 3380. Also shown is a grid 1630 of data. Rows of data are not provided in this example. This screen 4000 can be selected by the instrument selector 1644 or by swiping on the instrument selector region 3380 or by selecting either of the arrows 1640 or 1642, as in previous screens.

Figure 41:
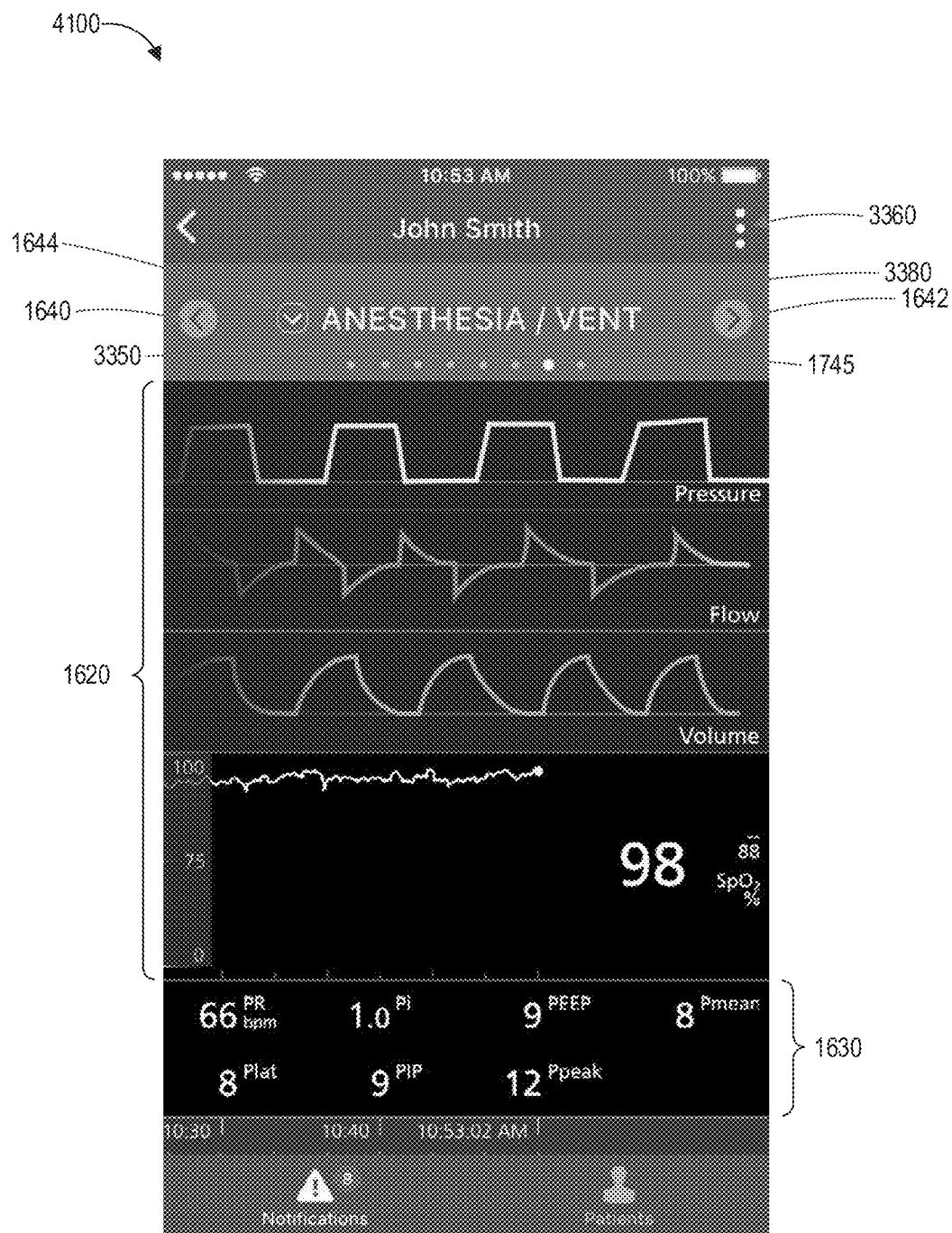
Figure 42:
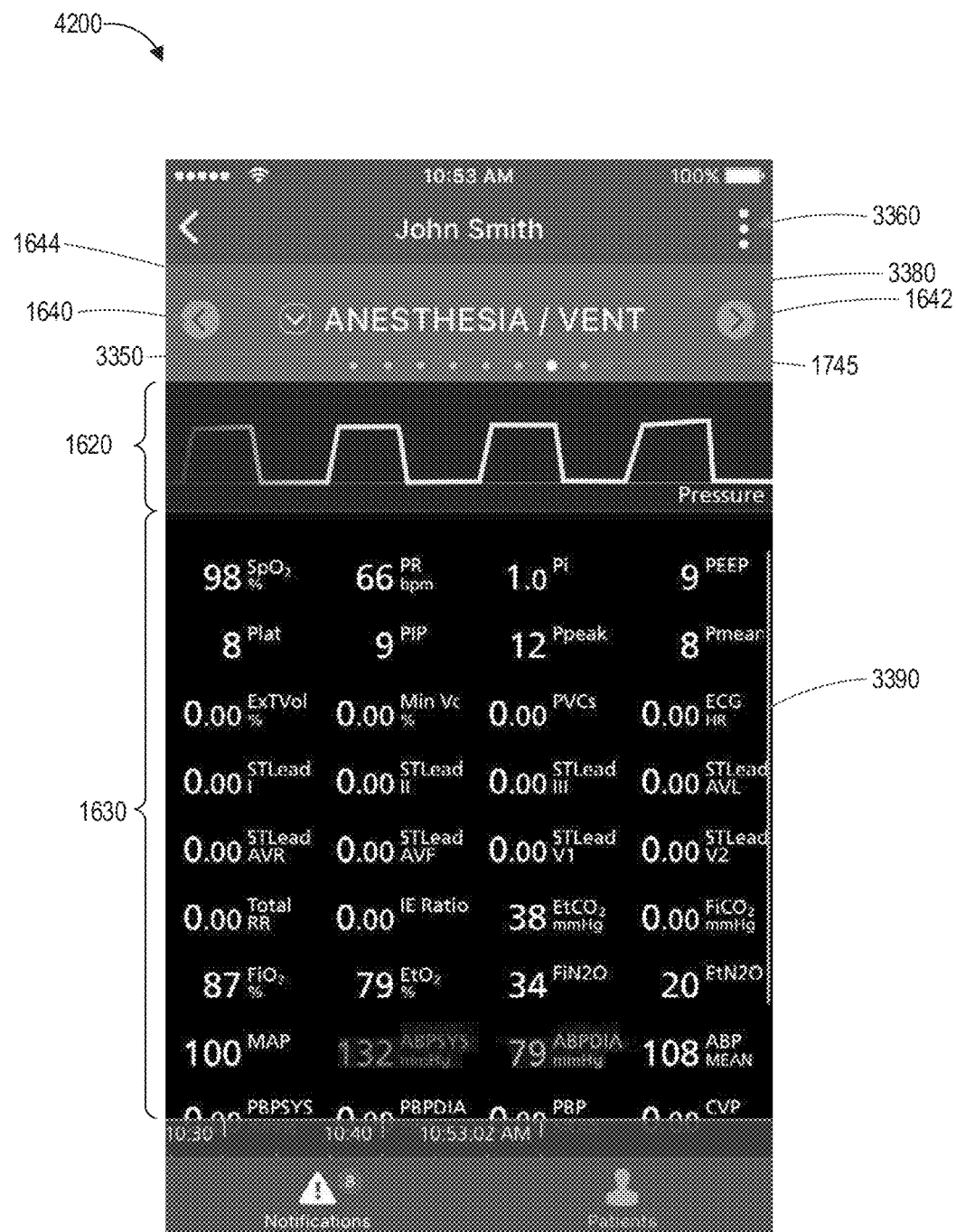

FIGS. 41 and 42 depict different example patient data screens 4100 and 4200 for an anesthesia device/ventilator or vent. Each screen 4100, 4200 depicts rows 1620 and a grid 1630, although the grid 1630 takes up most of the display in FIG. 42 whereas the rows 1620 in FIG. 41 take up most of the display. As indicated in this carousel 1745, either of these screens can be reached by swiping from a previous display.

Figure 7:
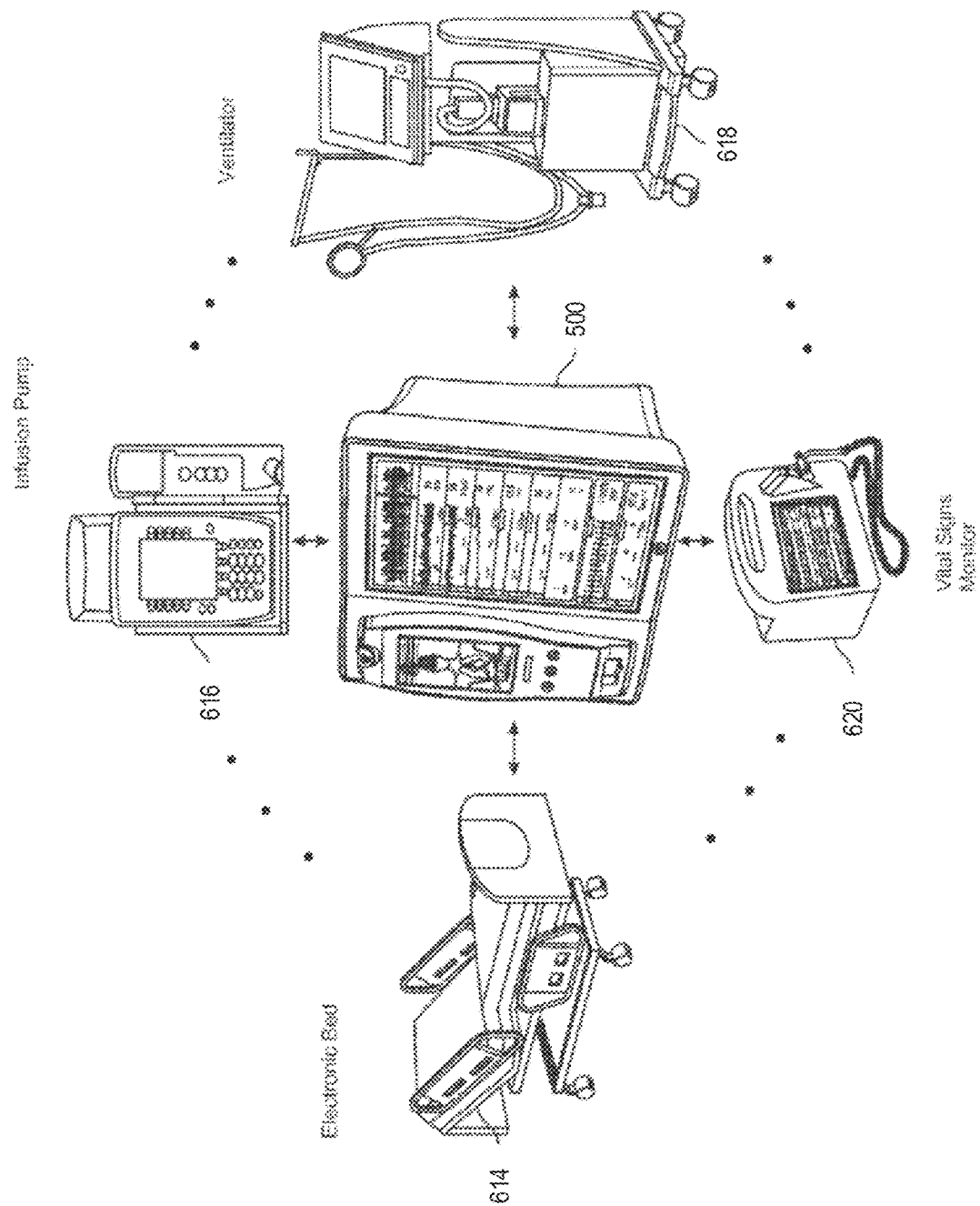
FIG. 7 depicts another example clinical computing environment that includes the patient monitor or monitoring hub of FIG. 5.
Figure 43:
Figure 44:
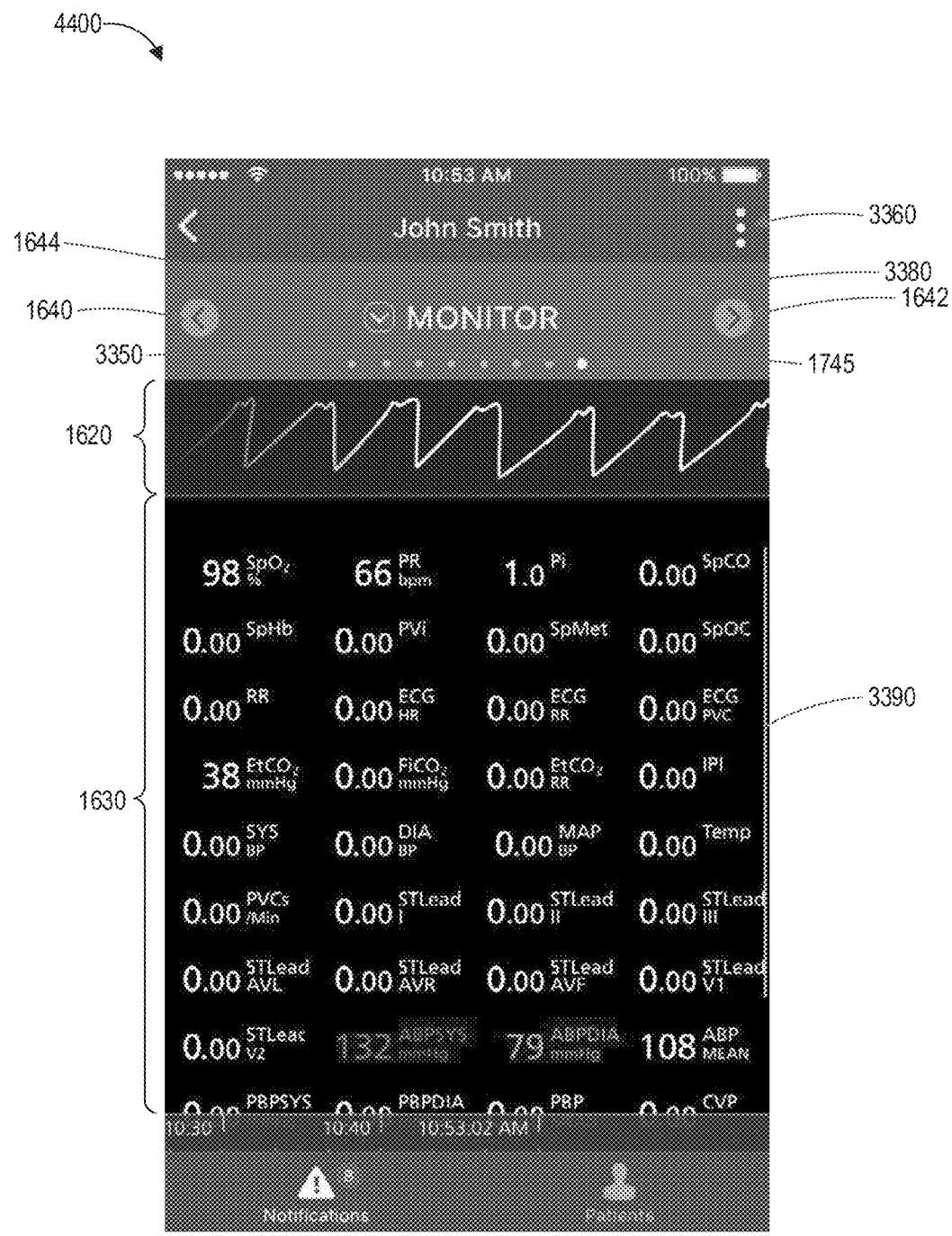

FIGS. 43 and 44 depict example patient data screens 4300, 4400 for a vital signs monitor (for example the monitor 620 of FIG. 7). Each display depicts rows 1620 and the grid 1630 of data, except that only a single row 1620 and a much larger grid 1630 are shown in FIG. 44 as compared with FIG. 43. The carousel 1745 and indicator 3350 indicate that the display of FIG. 43 and FIG. 44 can be reached by swiping from another screen.

Figure 45:
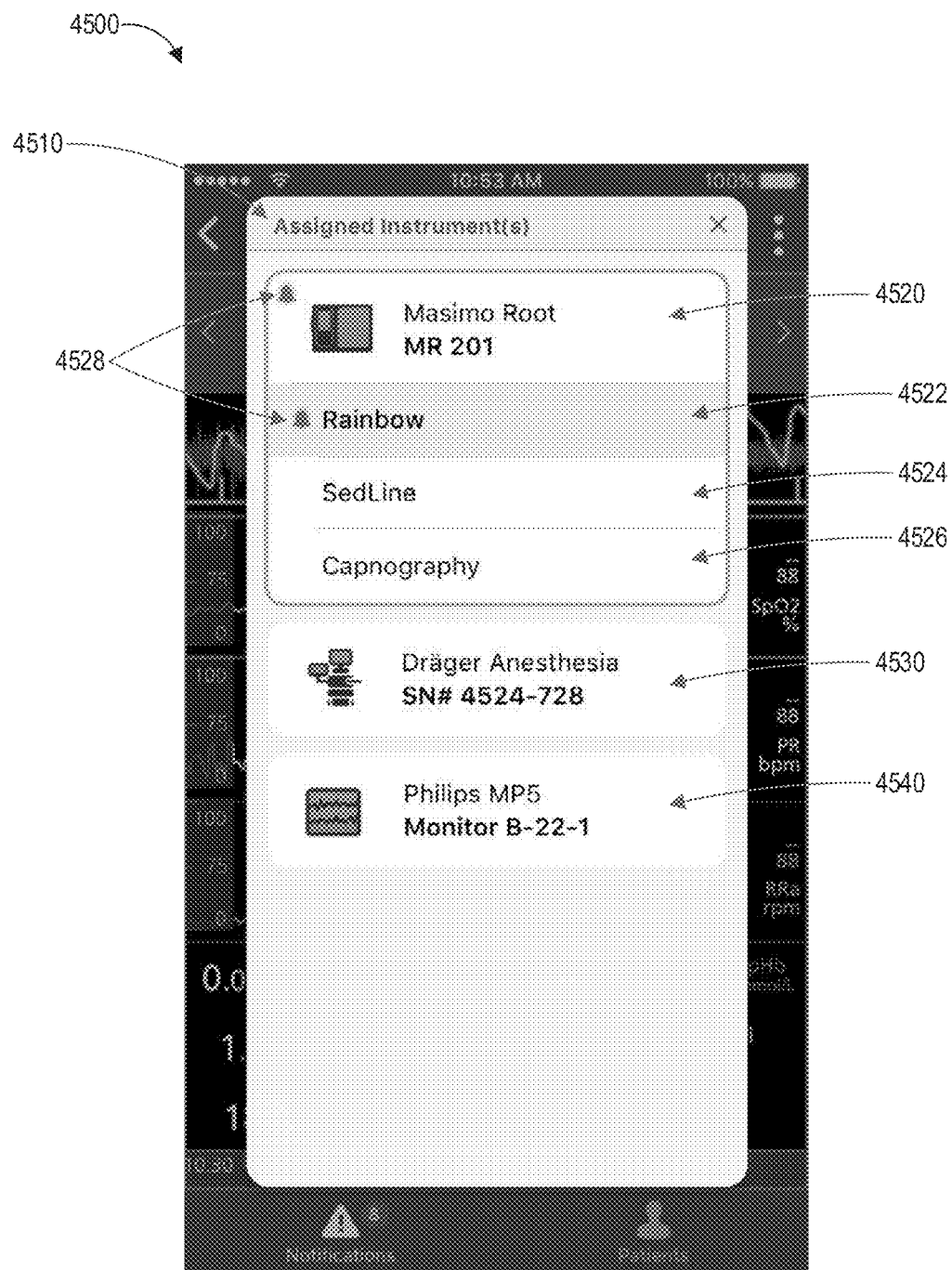

Turning to FIG. 45, an example user interface 4500 is shown that is an example of one of the patient data screens above overlaid with an assigned instruments overlay 4510. The overlay 4510 can be output by selecting the instrument selector 1644 in any of the previous patient data screens described herein. The overlay 4510 can depict a selected instrument 4520 as well as other available instruments 4530 and 4540. The selected instrument 4520 is the Root instrument in this example, and the other non-selected instruments for the current display are a Draeger anesthesia device and a Philips MPS vital signs monitor. Within the selected Root instrument, a rainbow channel 4522 is selected. Either of the instruments 4530 or 4540 or other channels 4524, 4526 may be selected (for example, by finger press) to show a patient data screen corresponding to that instrument. For example, the anesthesia screens shown in FIGS. 41 and 42 may be viewed by selecting the Draeger anesthesia instrument 4530, whereas the vital signs screen shown in FIGS. 43 and 44 may be selected by selecting the Philips MPS instrument 4540. Thus, the overlay 4510 provides yet another way to view the output of different instruments and channels.

Additional instruments may be connected to the hub (see FIGS. 6 and 7), of which the Masimo Root is an example. Thus, when additional instruments are connected to the hub, they may become available for selection in the overlay 4510 and with the other selection options described above (such as swiping, arrows, and drop-down boxes). When other instruments 5430 or 5440 are not connected to the hub, for example, as shown in FIG. 46, they may be greyed out (see 4530 in FIG. 46).

Figure 46:
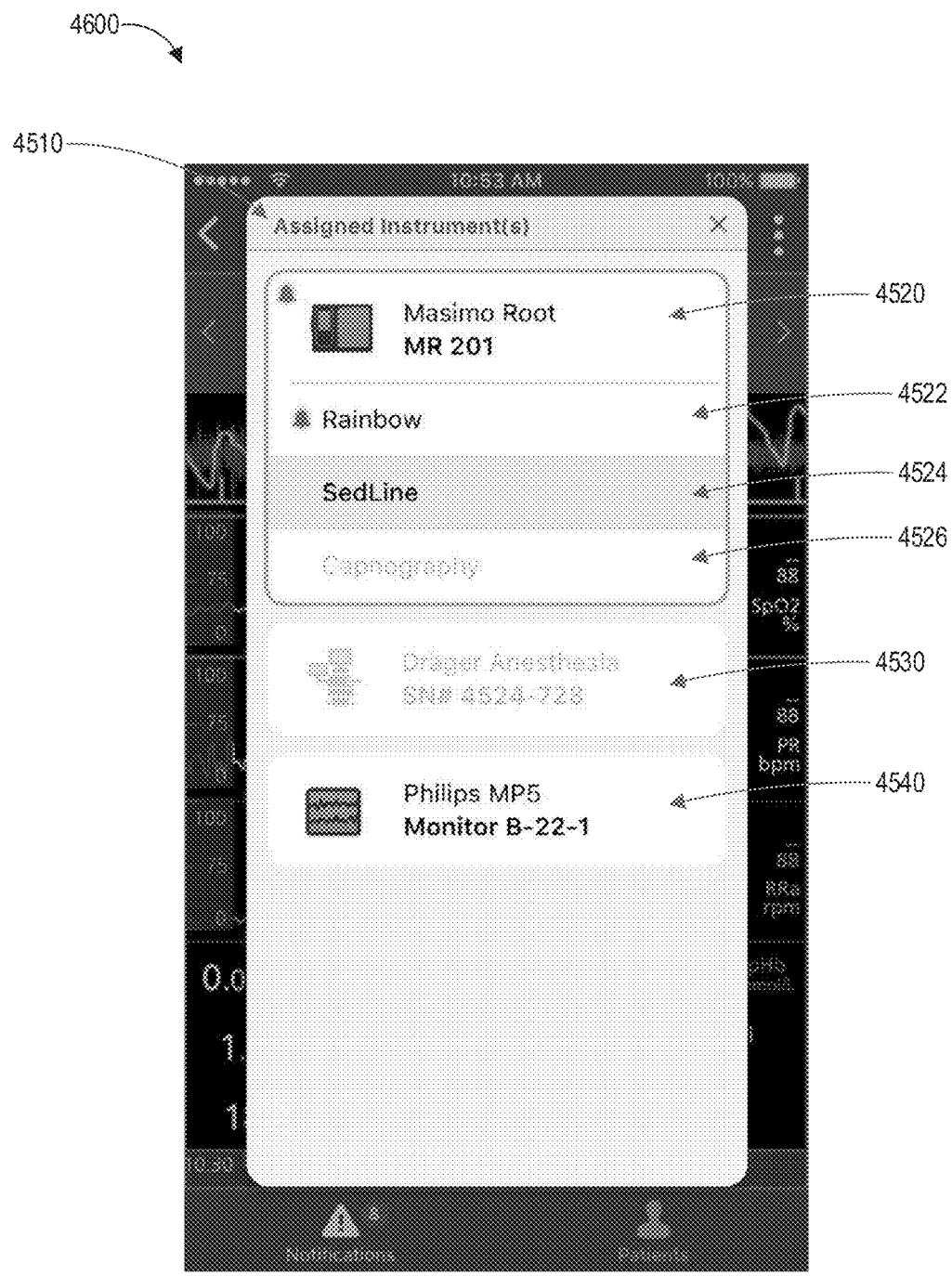

With continued reference to FIG. 46, within the instrument 4520 there are three available channels in this example: the rainbow channel 4522, a SedLine™ channel 4524, and a capnography channel 4526. The rainbow channel 4522 is shaded, indicating that it is currently selected so that exiting out of the overlay 4510 will depict the patient data screen corresponding to the rainbow parameters. The other channels 4524, 4526 may be selected to view their respective displays, except that the capnography channel 4526 is grayed out because it is currently unavailable (for example, a capnography BIC may not be connected to the instrument 4520). For instance, selecting the SedLine™ channel 4524 can cause a user interface such as is shown in FIG. 35 to be displayed, whereas selecting the capnography channel 4526 can cause a user interface such as is shown in FIG. 36 to be displayed. Thus, channels of patient data or instruments may be selected for display from the assigned instruments overlay 4510 or by moving serially from screen to screen as described above. Moreover, alarm icons 4528 indicate the device and/or channel that may be alarming.

Turning to FIG. 47, an example user interface 4700 is shown that depicts a timeline 4710 of patient events. The user interface 4700 can be similar to the timeline 1810 of FIG. 18. The user interface 4700 may be accessed from the timeline option 3414 of FIG. 34, for example.

Turning to FIG. 48, an example user interface is shown that depicts patient information 4810, including patient's full name, label, room and patient medical record number (MRN). The user interface 4800 may be accessed from the patient information option 3416 of FIG. 34, for example.

Figure 107:
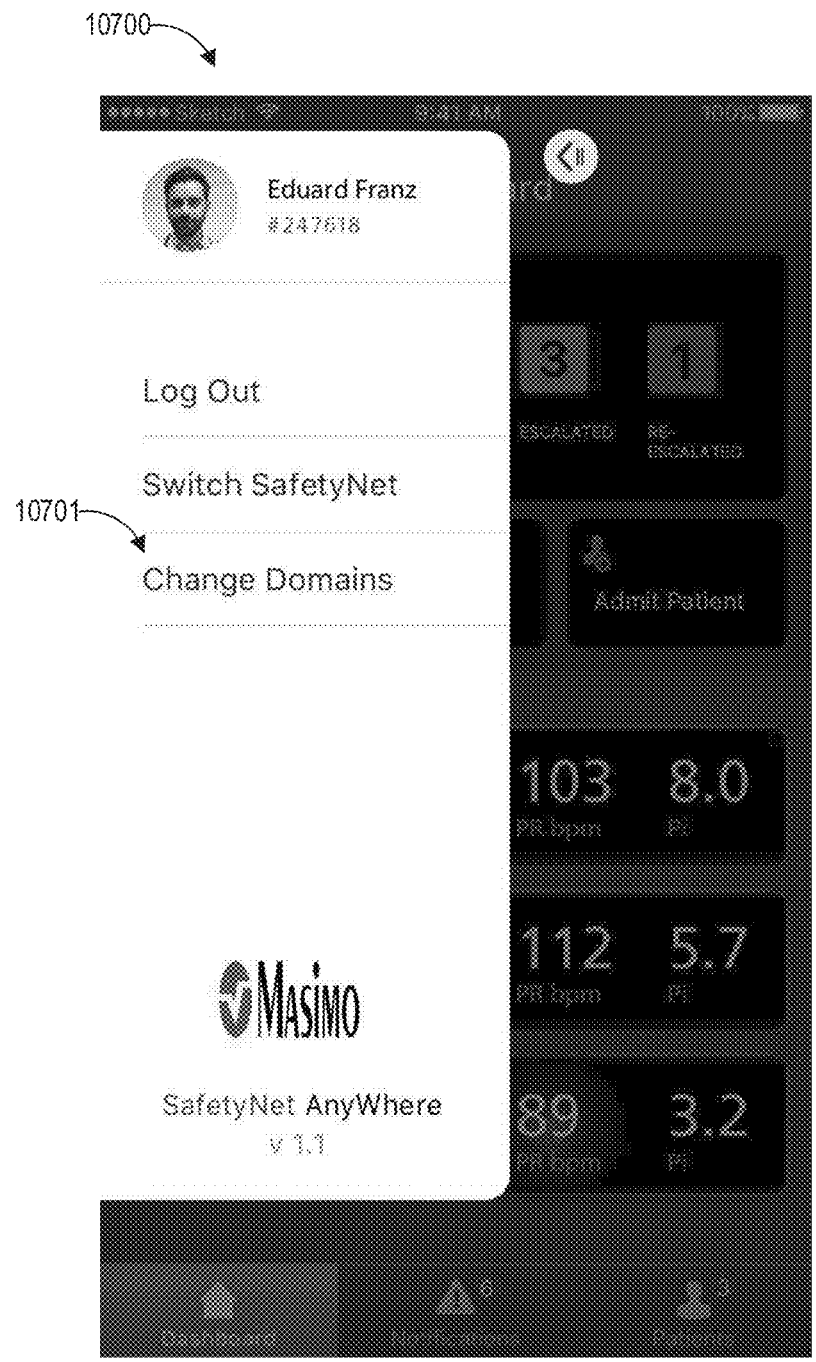
FIG. 107 depicts an example menu user interface.
Figure 108:
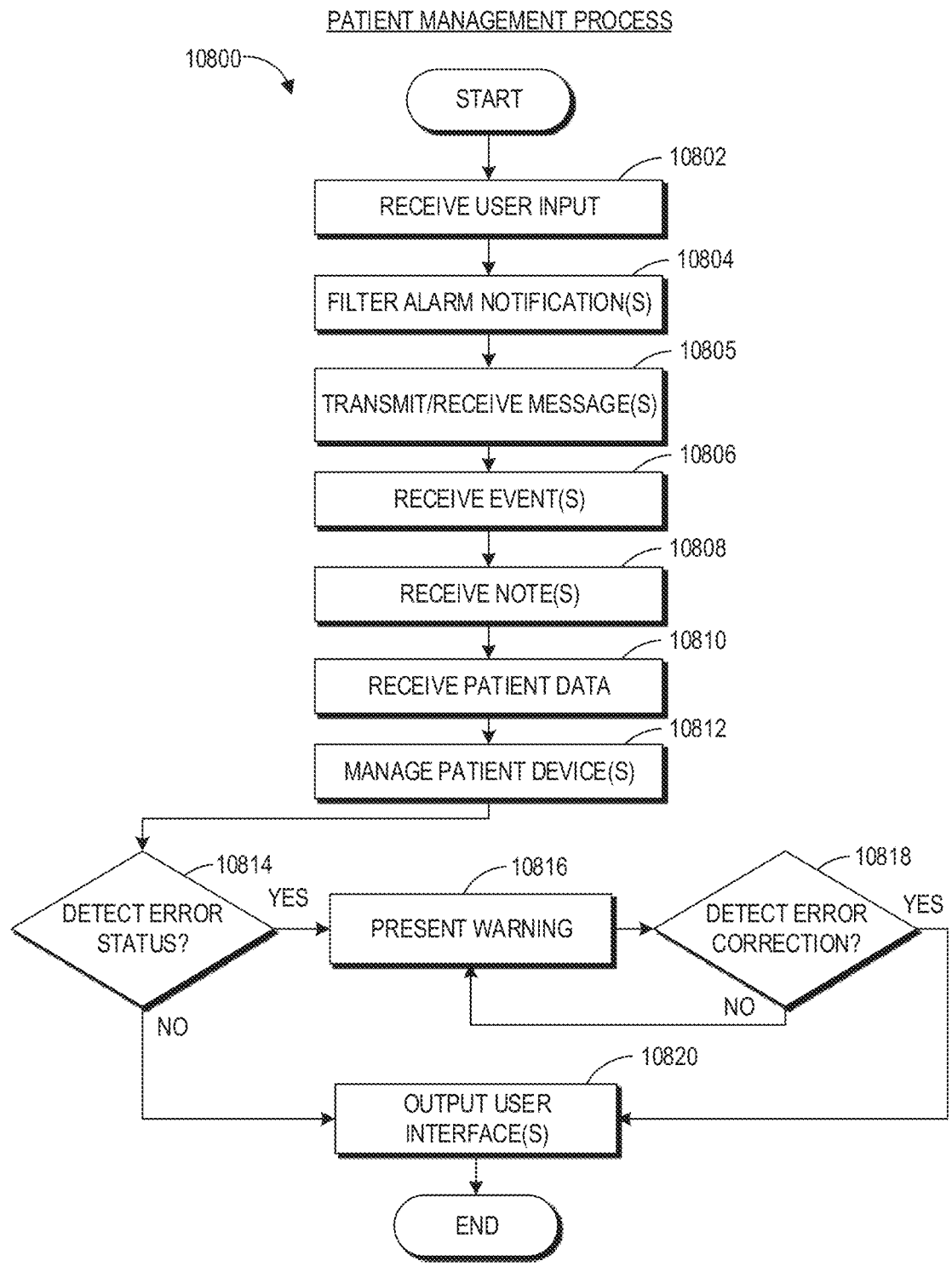
FIG. 108 depicts an example patient management process.
Figure 109:
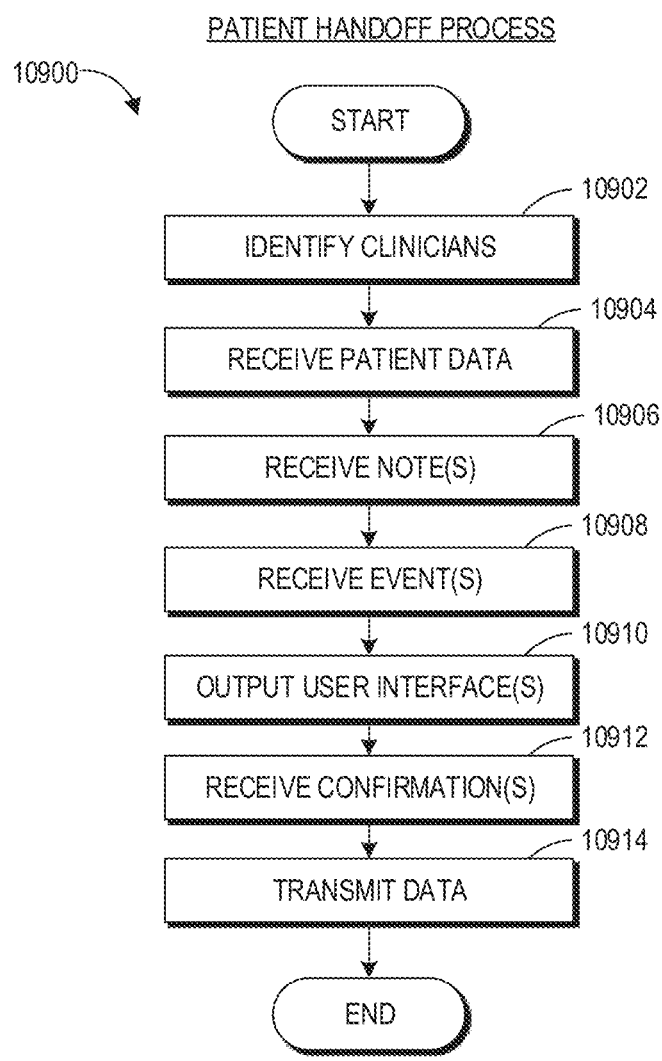
FIG. 109 depicts an example patient handoff process.

The remaining Figures, until FIGS. 108 and 109, depict user interfaces that can be output by a clinician device, such as any of the clinician devices described above. In FIGS. 49 through 53, example configuration user interfaces are shown for the clinician devices described above. The configuration user interfaces of FIGS. 49 through 53 can precede any of the other user interfaces described above and below with respect to FIGS. 8 through 48 and 54 through 107. The configuration user interfaces can allow a clinician to configure the clinician device to receive alarm notifications from a subset of patient devices. The clinician device can also receive notifications from a larger set of patient devices and the configuration data can be used to display a subset of the notifications to a clinician. A subset of patient devices can include a group of patient devices that are assigned to a particular geographical area of a clinical facility or that are grouped by some other criteria. A group of patient devices can include one or more sub-groups, the one or more sub-groups can each include one or more sub-sub-groups, etc., as described in further detail below with respect to FIGS. 51 through 53.

A group of patient devices can include a hierarchy, such as a first group with children groups, grandchildren groups, and great-grandchildren groups. If a clinician device is configured for a group of patient devices, a sub-group of patient devices, or a sub-sub-group of patient devices, etc., then the clinician device may display alarm notifications for the configured group while excluding alarm notifications or other data for other groups. A clinical benefit of configuring a clinician device for a group of patient devices can include limiting the quantity of alarm notifications or other data that can be displayed or accessed by the clinician, which can thereby improve the user interface by making data or information more easily accessible by the clinician and/or by making the user interface less cluttered.

Figure 49:
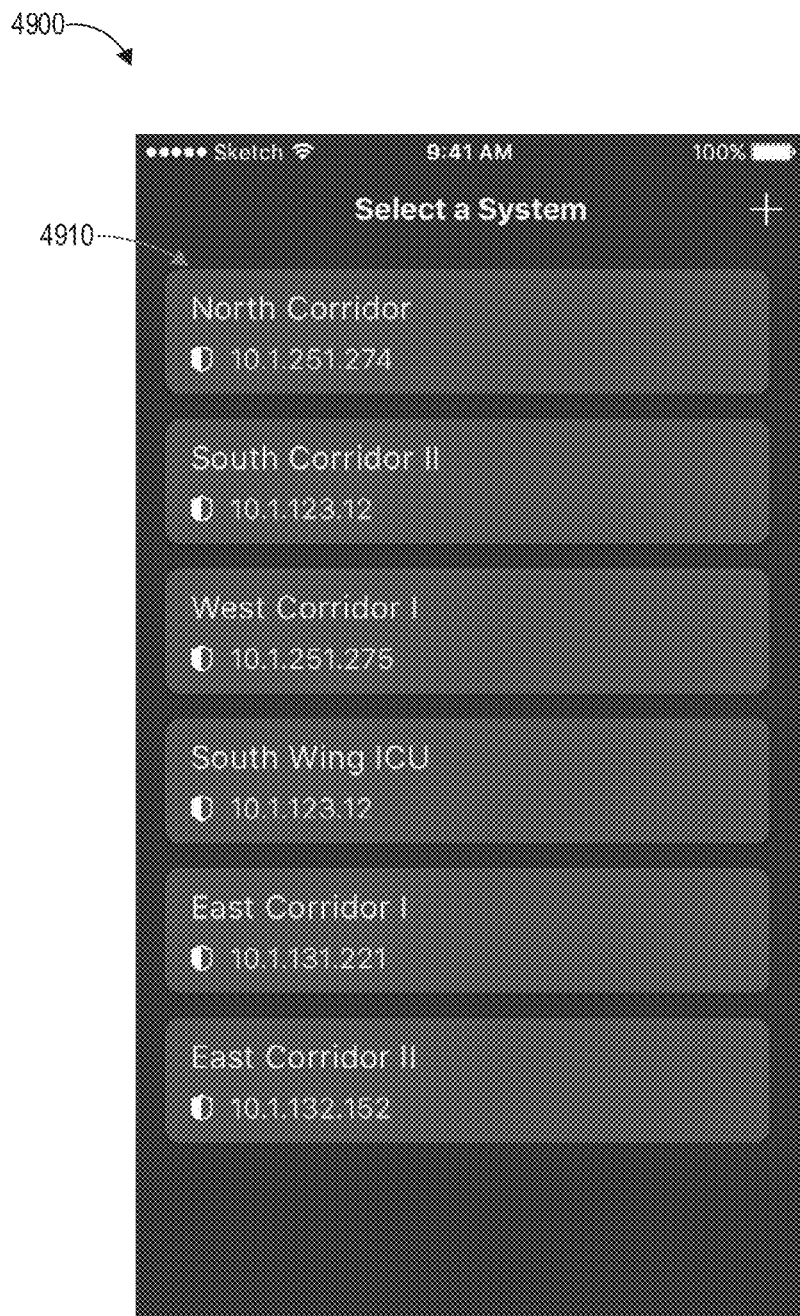
FIGS. 49 through 53 depict example configuration user interfaces for a clinician device.

Turning to FIG. 49, the user interface 4900 includes options 4910. Each of the options 4910 can be for a group of patient devices, which can also be referred to herein as a "configuration group" or a "system" with respect to FIGS. 49 through 53. In the user interface 4900, a user can be prompted to select a configuration group. In particular, in the user interface 4900, a clinician is prompted to "select a system." A configuration group can include a name, such as a name of a location. The location names for the configuration groups in the user interface 4900 can include "North Corridor," "South Corridor II," etc. A configuration group can include one or more identifiers, such as an Internet Protocol ("IP") address. The IP addresses for the configuration groups in the user interface 4900 can include "10.1.251.274," "10.1.123.12," etc.

Figure 50:
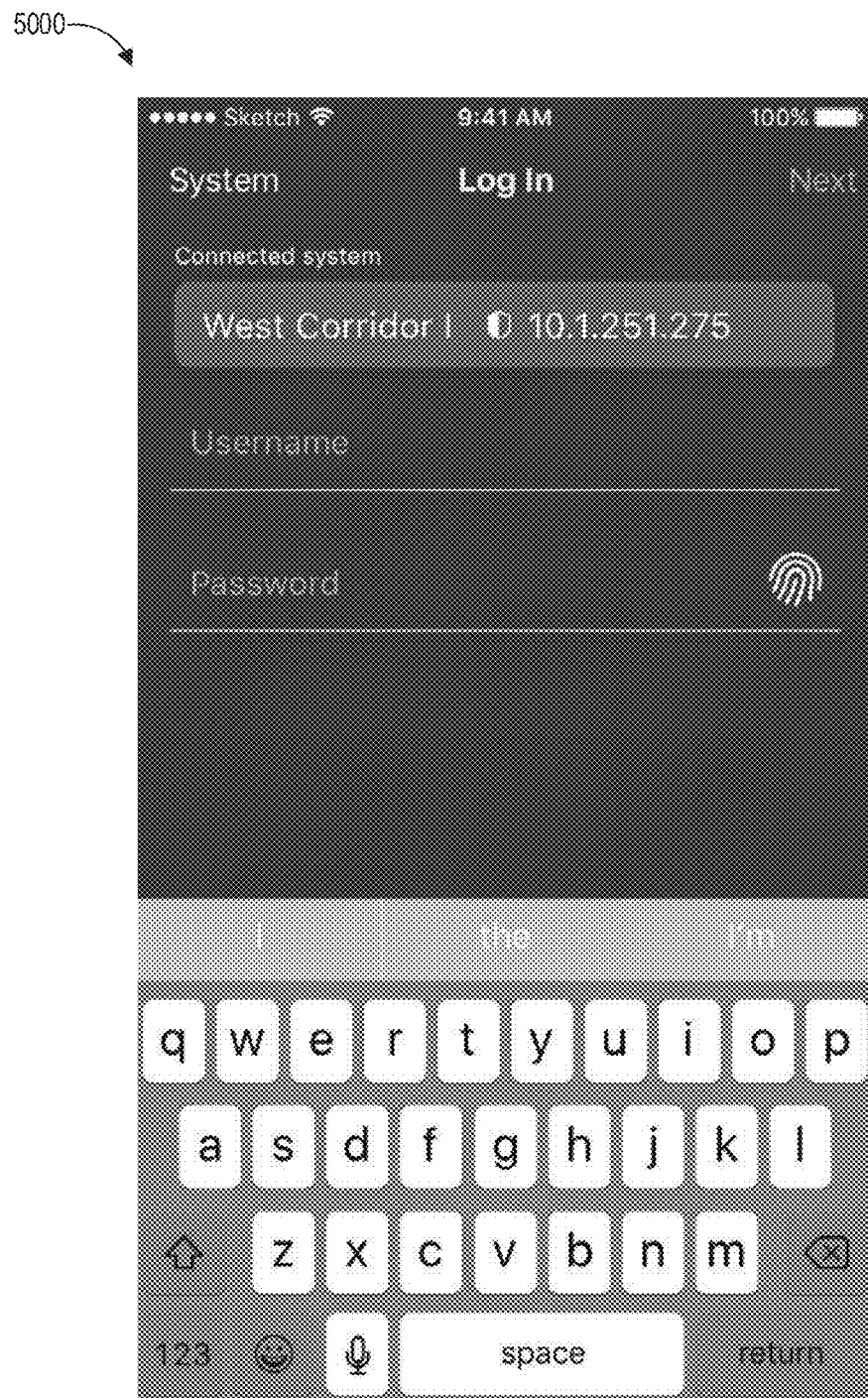

Turning to FIG. 50, the user interface 5000 can enable a clinician to log in to a configuration group. A configuration group can include access permissions, such as a list of authorized clinicians that can access or be configured for the particular configuration group. Example access permissions can include role-based access permissions, such as if a clinician has access to a particular configuration group, then the clinician is able to see all patients assigned to that configuration group. If a particular clinician is not authorized for a particular configuration group, then the clinician may be prevented from accessing data associated with the configuration group, such as notifications from patient devices assigned to the configuration group. The access permissions associated with a configuration group can provide increased patient security and/or privacy.

Figure 51:
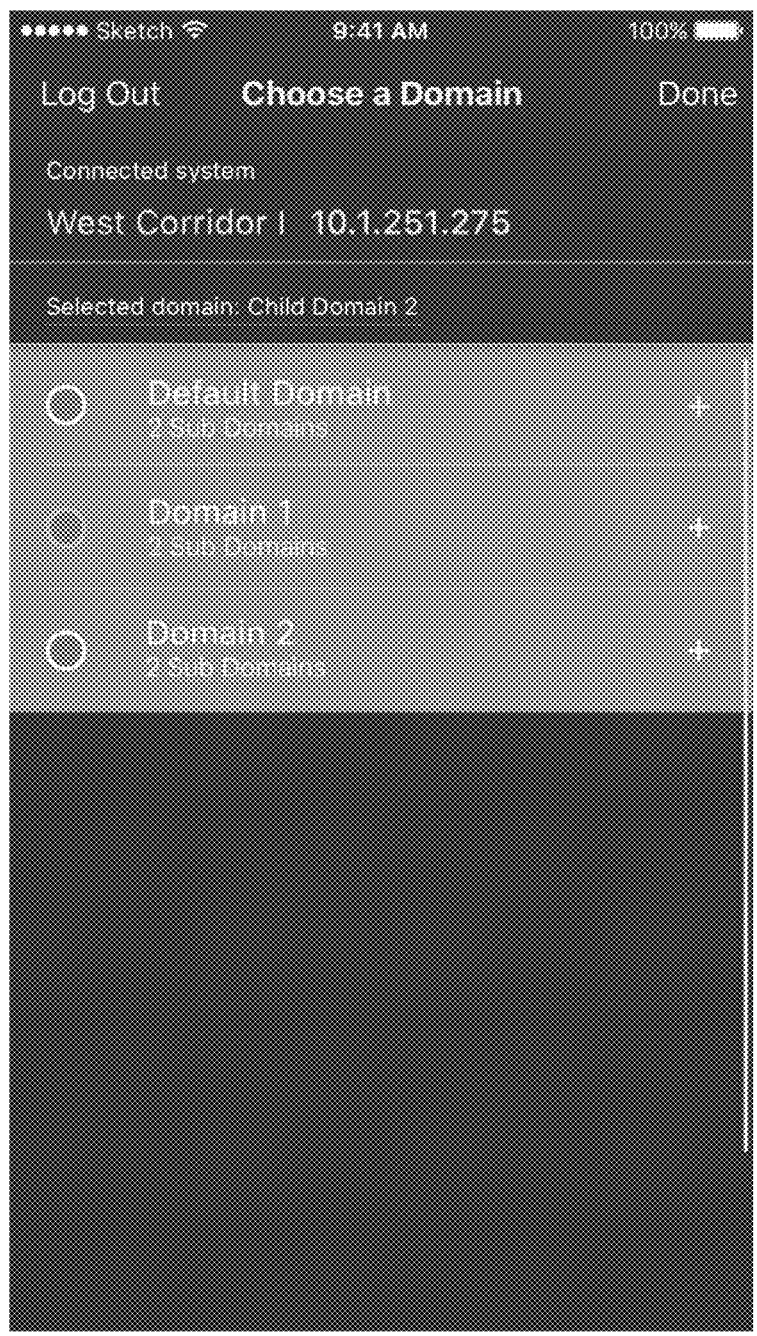

Turning to FIG. 51, the user interface 5100 can enable a clinician to select a sub-group. In the user interface 5100, the sub-groups can include the "Default Domain," "Domain 1," and "Domain 2." The selected configuration group, here "West Corridor I," can include children groups, such as the sub-groups "Default Domain," "Domain 1," and "Domain 2" shown in the user interface 5100. A clinician can select a sub-group, which can thus specify a further subset of patient devices that can be used selectively display notification information to the clinician.

Figure 52:
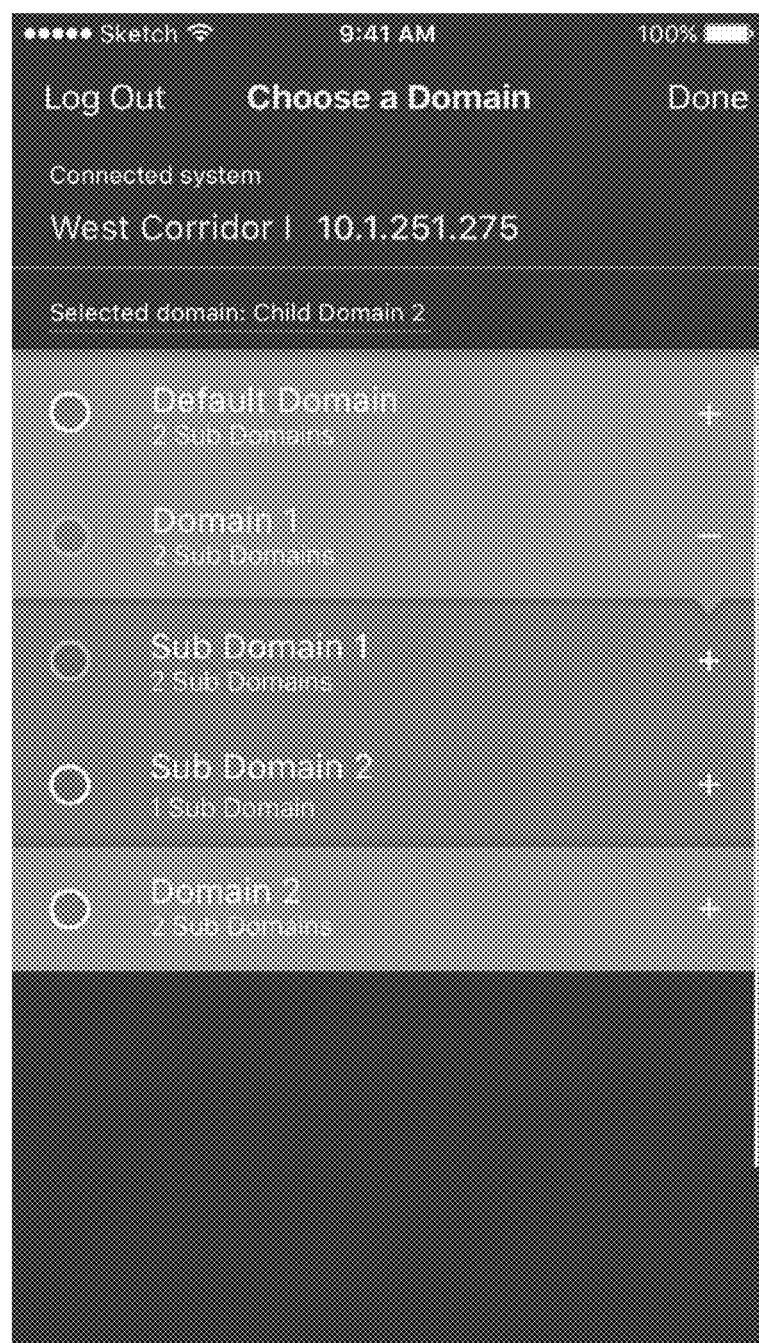

Turning to FIG. 52, the user interface 5200 can enable a clinician to select a sub-sub-group. In the user interface 5200, the sub-sub-groups can include "Sub Domain 1" and "Sub Domain 2." The selected sub-group, here "Domain 1," can include children groups, such as the sub-sub-groups "Sub Domain 1" and "Sub Domain 2" shown in the user interface 5200. A clinician can thus select a sub-sub-group, which can specify a further subset of patient devices that can be used selectively display notification information to the clinician.

Figure 53:
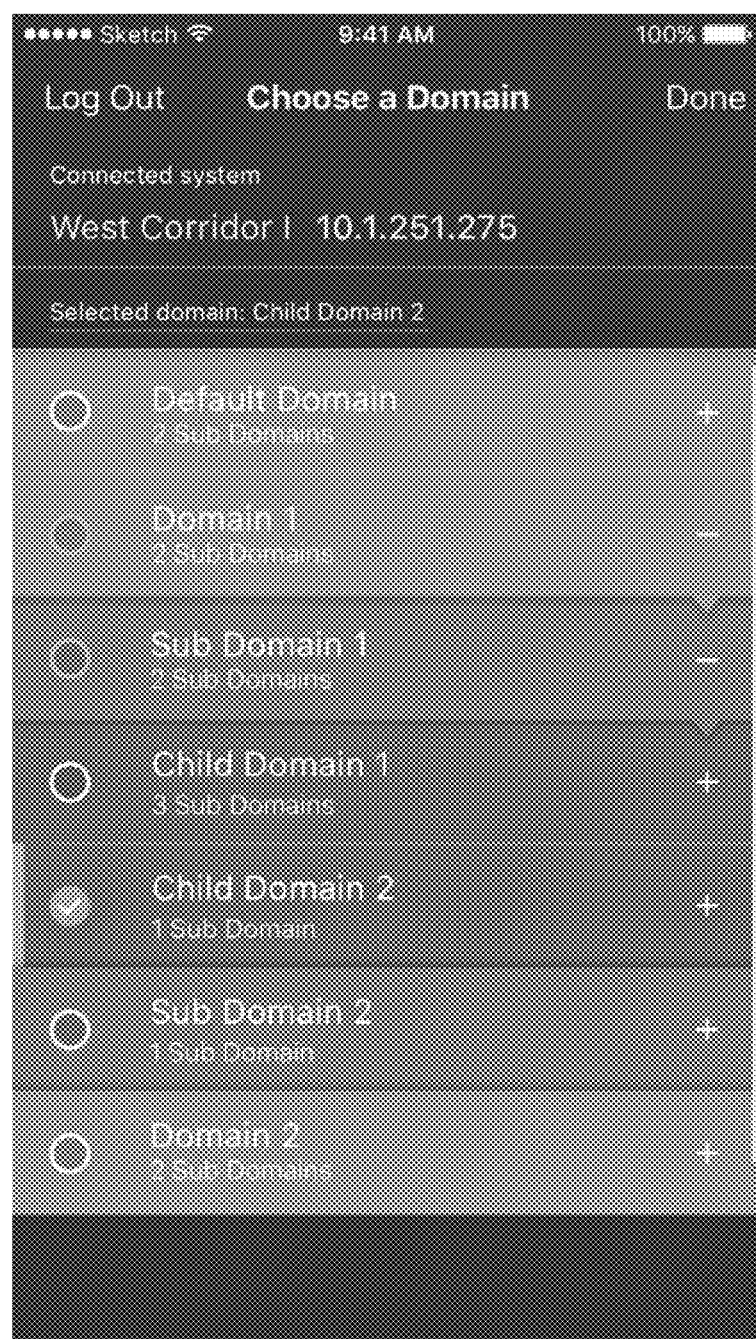

Turning to FIG. 53, the user interface 5300 can enable a clinician to select a sub-sub-sub-group. In the user interface 5300, the sub-sub-sub-groups can include "Child Domain 1" and "Child Domain 2." The selected sub-sub-group, here "Sub Domain 1," can include children groups, such as the sub-sub-sub-groups "Child Domain 1" and "Child Domain 2" shown in the user interface 5300. A clinician can thus select a sub-sub-sub-group, which can specify a further subset of patient devices that can be used selectively display notification information to the clinician.

Figure 54:
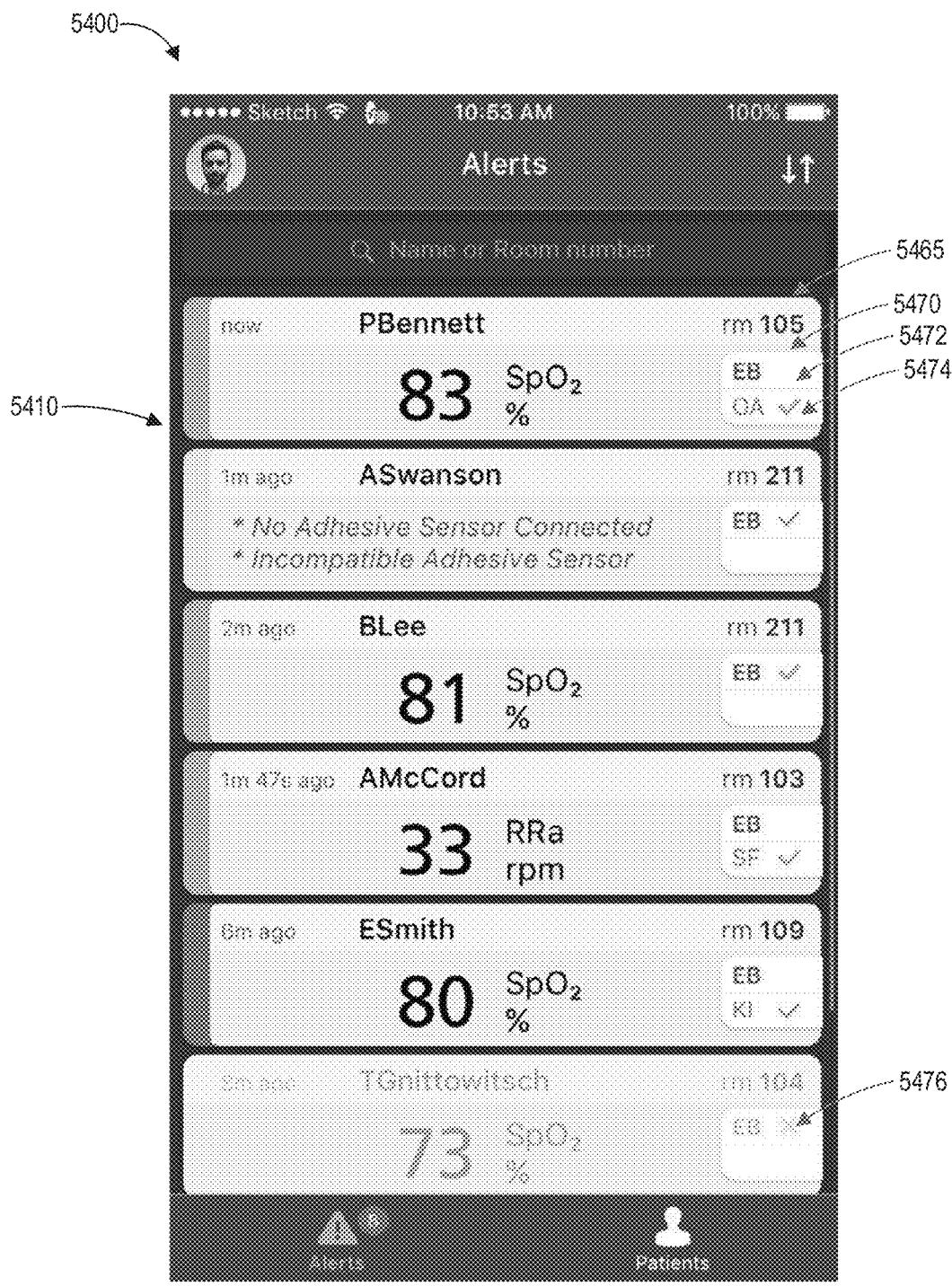
FIGS. 54 through 58 depict example notification user interfaces for a clinician device.

Turning to FIG. 54, another example notification user interface 5400 is shown which is similar to the notification user interface 1100 of FIG. 11. However, in contrast to the notification user interface 1100 of FIG. 11, the notification user interface 5400 of FIG. 54 can include a status area for each notification. The first notification 5465 can include the status area 5470. The status area 5470 can include the clinician's response status 5472 for the clinician using the clinician device and the first notification 5465. The status area 5470 can also include another clinician's response status 5474 and the first notification 5465.

As shown, the response status for a clinician can be graphically represented in the notification user interface 5400. In the notification user interface 5400, "EB" can represent the initials for the clinician using the clinician device. Accordingly, the lack of a graphical indicator for the response status 5472 can indicate that the clinician has not responded to the first notification 5465. The first notification 5465 may have been responded to by another clinician, which can be indicated by the response status 5474 for another clinician represented by the initials "OA." The response status 5474 for another clinician can include an acceptance graphical indicator that indicates that the other clinician has selected the notification 5465. Conversely, the response status 5476 can include a declined graphical indicator that indicates that a respective clinician has denied the corresponding notification. Accordingly, the response status is in the notification user interface 5400 can advantageously provide quick indications to a clinician regarding the notifications that have been accepted, denied, or that await a response.

Figure 55:
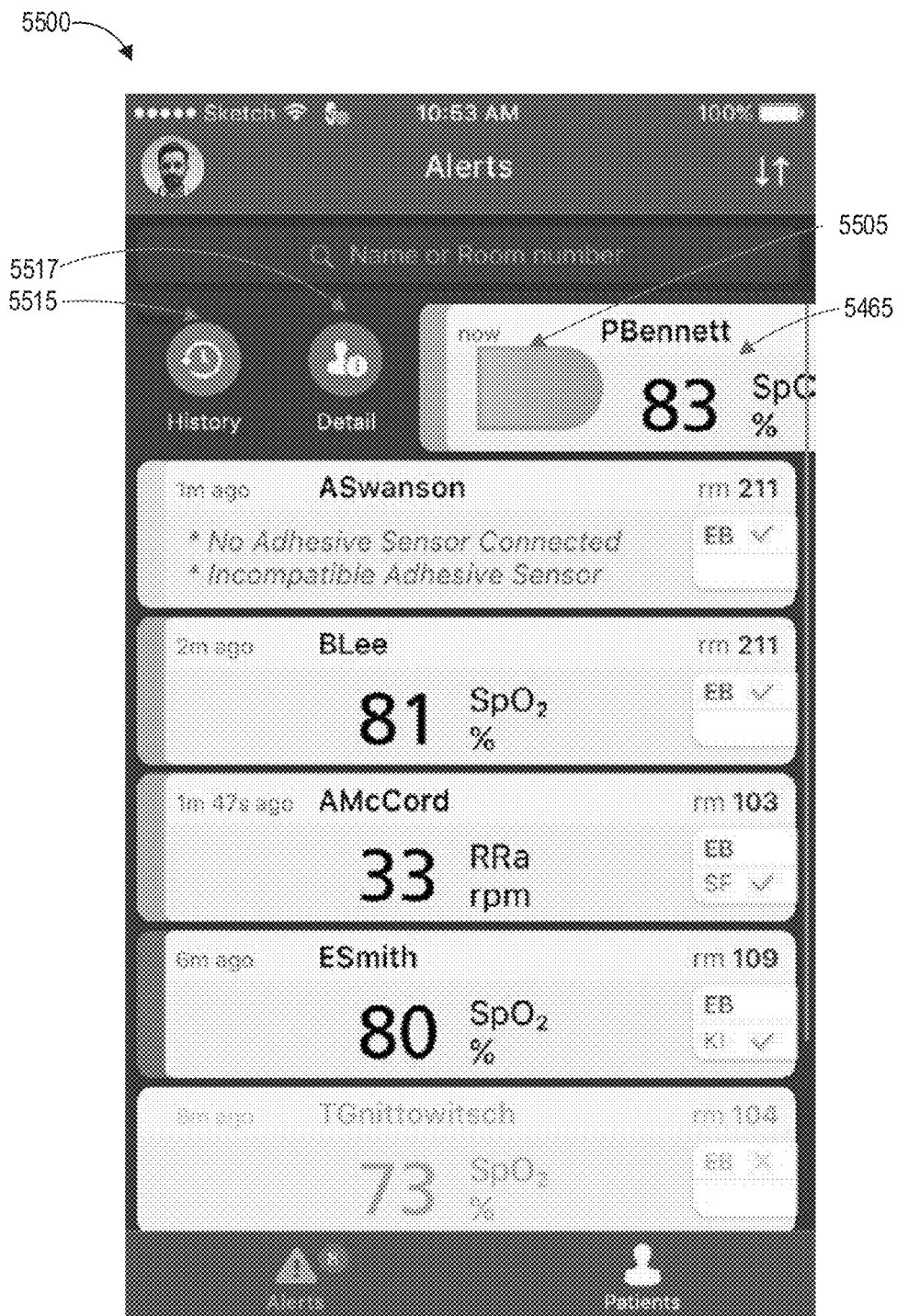

Turning to FIG. 55, another example notification user interface 5500 is shown which is similar to the notification user interface 5400 of FIG. 54. In response to a first user interaction 5505 (such as a swipe) with the first notification 5465, the user interface 5500 can update to present additional options to the clinician. The user interface 5500 can include a first selectable element 5515 and a second selectable element 5517. User selection of the first selectable element 5515 can cause the user interface 5500 to display additional information regarding the corresponding notification. User selection of the second selectable element 5517 can cause the user interface 5500 to display additional information regarding patient details for the corresponding notification.

Figure 56:
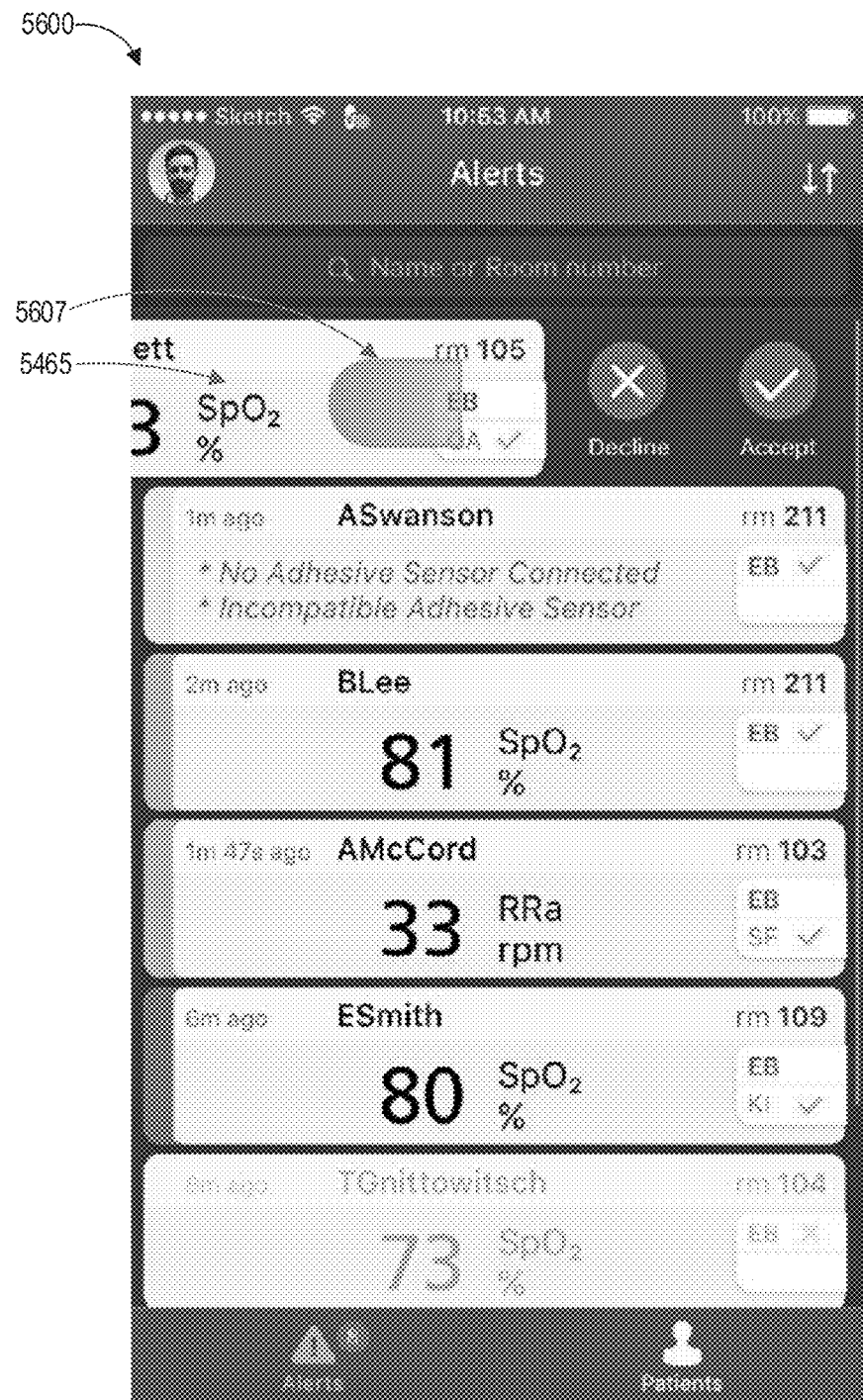

Turning to FIG. 56, another example notification user interface 5600 is shown which is similar to the notification user interface 5400 of FIG. 54. In response to a second user interaction 5607 (such as a swipe) with the first notification 5465, the user interface 5600 can update to present response options to the clinician, such as the decline and accept options for the first notification 5465.

Figure 57:

Turning to FIG. 57, another example notification user interface 5700 is shown which is similar to the notification user interface 5400 of FIG. 54. In response to a user selection of the accept element 5774 for the first notification 5465, the user interface 5700 can update and present an updated response status 5472 to indicate that the clinician has accepted the first notification 5465.

Figure 58:
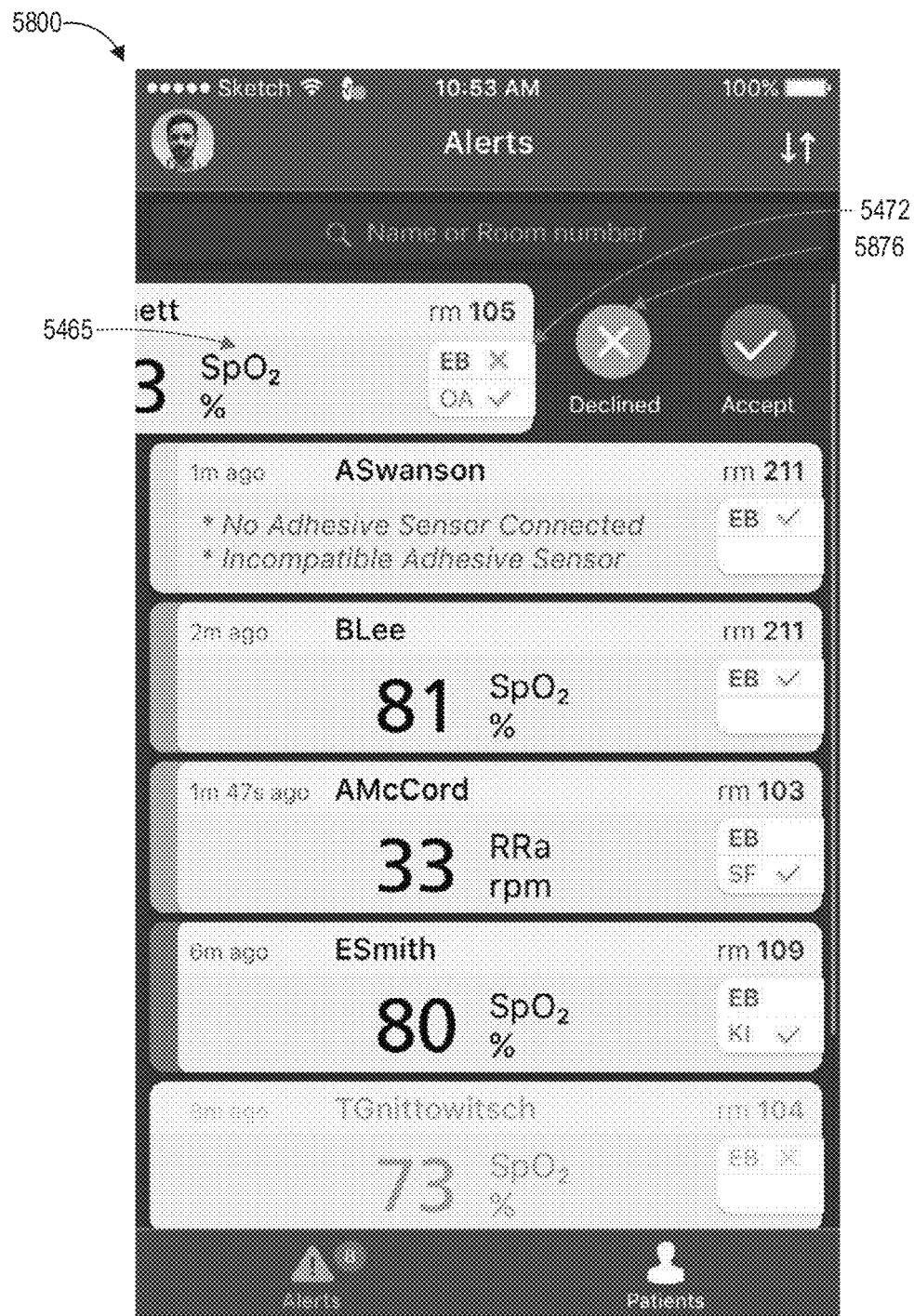

Turning to FIG. 58, another example notification user interface 5800 is shown which is similar to the notification user interface 5400 of FIG. 54. In response to a user selection of the decline element 5876 for the first notification 5465, the user interface 5800 can update and present an updated response status 5472 to indicate that the clinician has rejected the first notification 5465.

Figure 59:
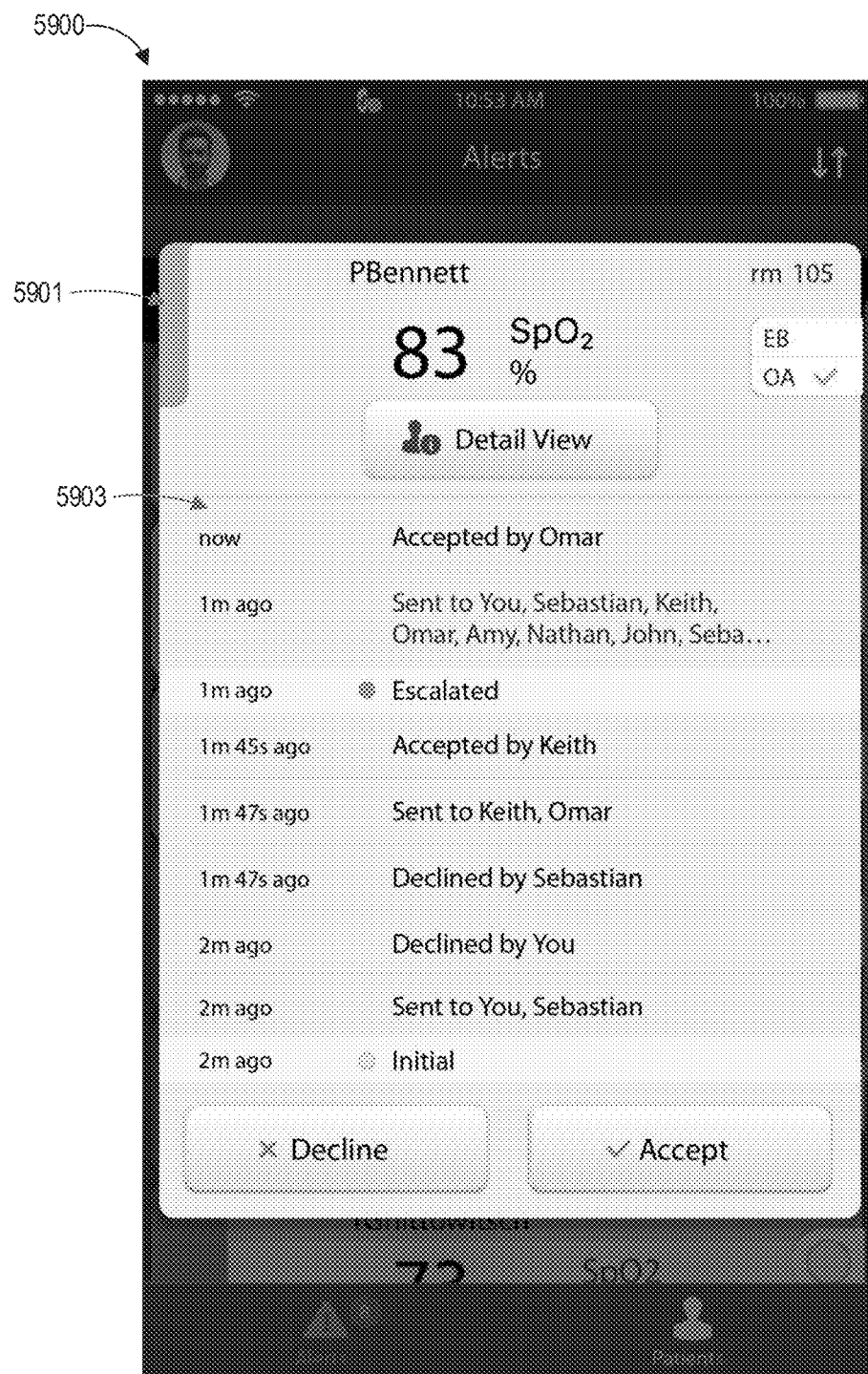
FIG. 59 depicts an example user interface for additional notification information.

Turning to FIG. 59, the example user interface 5900 can display information associated with a notification. As described above with respect to FIG. 55, a clinician can select the first selectable element 5515 that can cause the presentation of the user interface 5900 to display additional information associated with a notification. The user interface 5900 can include a notification state indicator 5901. The notification state indicator 5901 can include a color indicator, such as yellow, orange, red, or any other color. The color of the notification state indicator 5901 can represent an escalation state of the notification, such as an initial state, an escalated state, or an emergency state. Other notification states can be represented.

The user interface 5900 can include a historical view 5903 associated with a notification, such as the first notification 5465 of FIG. 55. As shown, the historical view 5903 can display a history of one or more clinician interactions with the notification 5465. The historical view 5903 can further display time information and a description associated with each interaction, such as the time of the initial notification two minutes ago, the notification being sent to one or more clinicians two minutes ago, the notification being rejected by one or more clinicians two minutes ago, an escalation of the notification one minute ago, and the notification being accepted by one or more clinicians at one or more respective times. Thus, a clinician can quickly view the history of a notification in the user interface 5900 and can respond or react as necessary.

Figure 60:
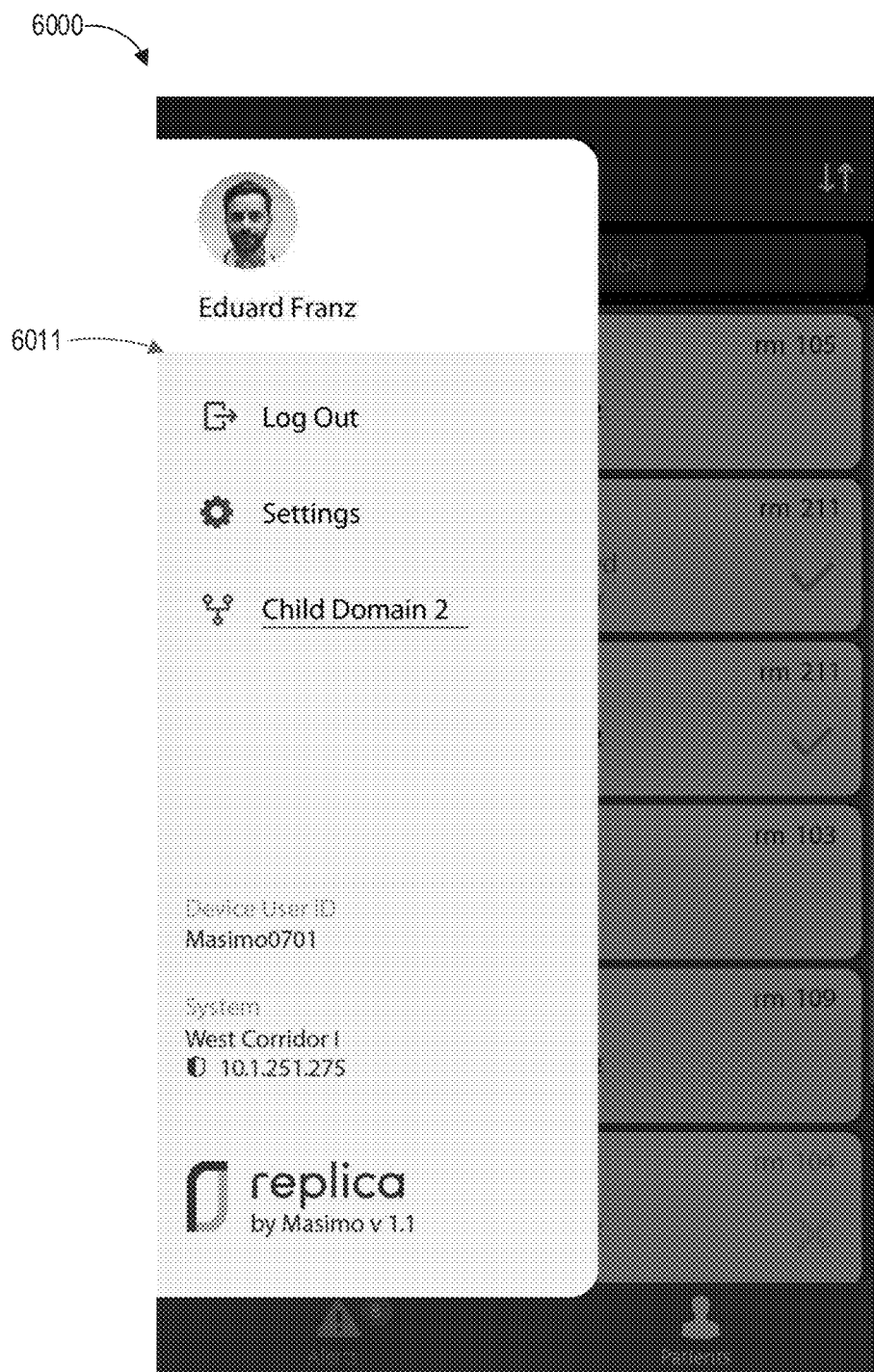
FIG. 60 depicts an example menu user interface.

Turning to FIG. 60, an example menu user interface 6000 is shown which is similar to the notification user interface 5400 of FIG. 54. However, the user interface 6000 can include a menu area 6011. The menu area 6011 can provide information and additional functions to the clinician. The menu area 6011 can display information regarding the configuration group, sub-group, sub-sub-group, etc. that the clinician is logged into with the clinician device.

Figure 61:
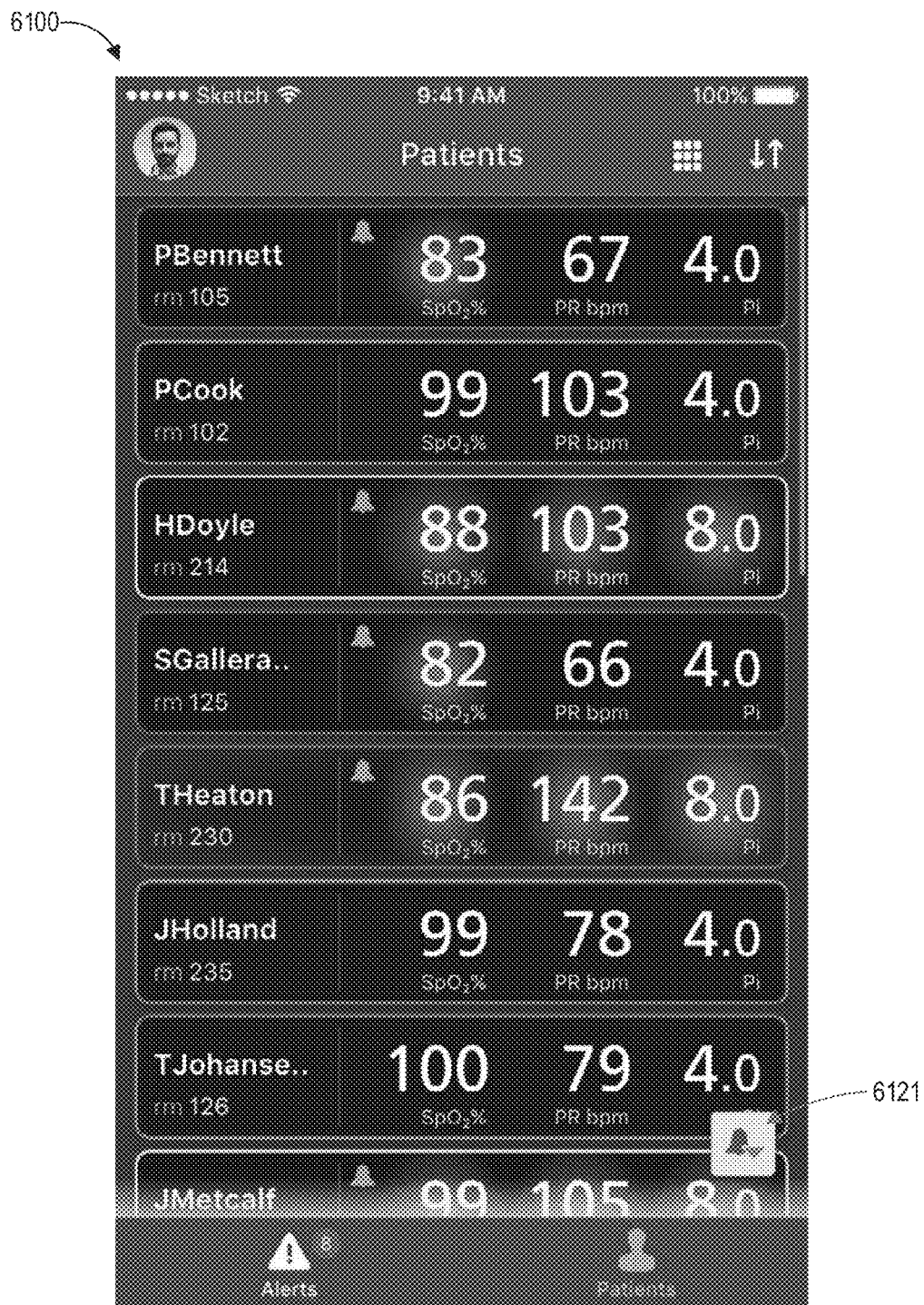
FIGS. 61 through 64 depict additional example patient user interfaces.

FIG. 61 depicts another example patient user interface 6100. The patient user interface 6100 is similar to the patients screen 1400 of FIG. 14. The patient user interface 6100 can display patient data. Similar to the patients screen 1400 of FIG. 14, the patient user interface 6100 can display indicators that indicate a status for respective patients. The patient user interface 6100 can include and display a notification indicator 6121. The notification indicator 6121 can indicate that there are one or more notifications off-screen or partially off screen, which may be accessed by scrolling down (for example, by dragging the finger upward on the display).

The notification indicator 6121 can further indicate one or more types of notifications that are off-screen. The notification indicator 6121 can be color-coded to indicate the one or more types of off-screen notifications. A notification indicator 6121 that is a first color, such as yellow, can indicate there are one or more notifications of a first type, such as notifications that correspond to a yellow color as described above. A notification indicator 6121 that is a second color, such as red, can indicate there are one or more notifications of at least a second type, such as notifications that correspond to at least one red or alarm status as described above. If the notification indicator 6121 is the second color, such as red, there can be at least one alarm status notification and additional lower status notifications, such as the first color. Additional details regarding notification statuses are described in further detail above with respect to FIG. 14. The notification indicator 6121 can advantageously notify a clinician of one or more notifications that the clinician may not otherwise see because the one or more notifications may be off-screen, thereby improving the user interface and possibly enabling a clinician to respond faster to a notification.

Figure 62:
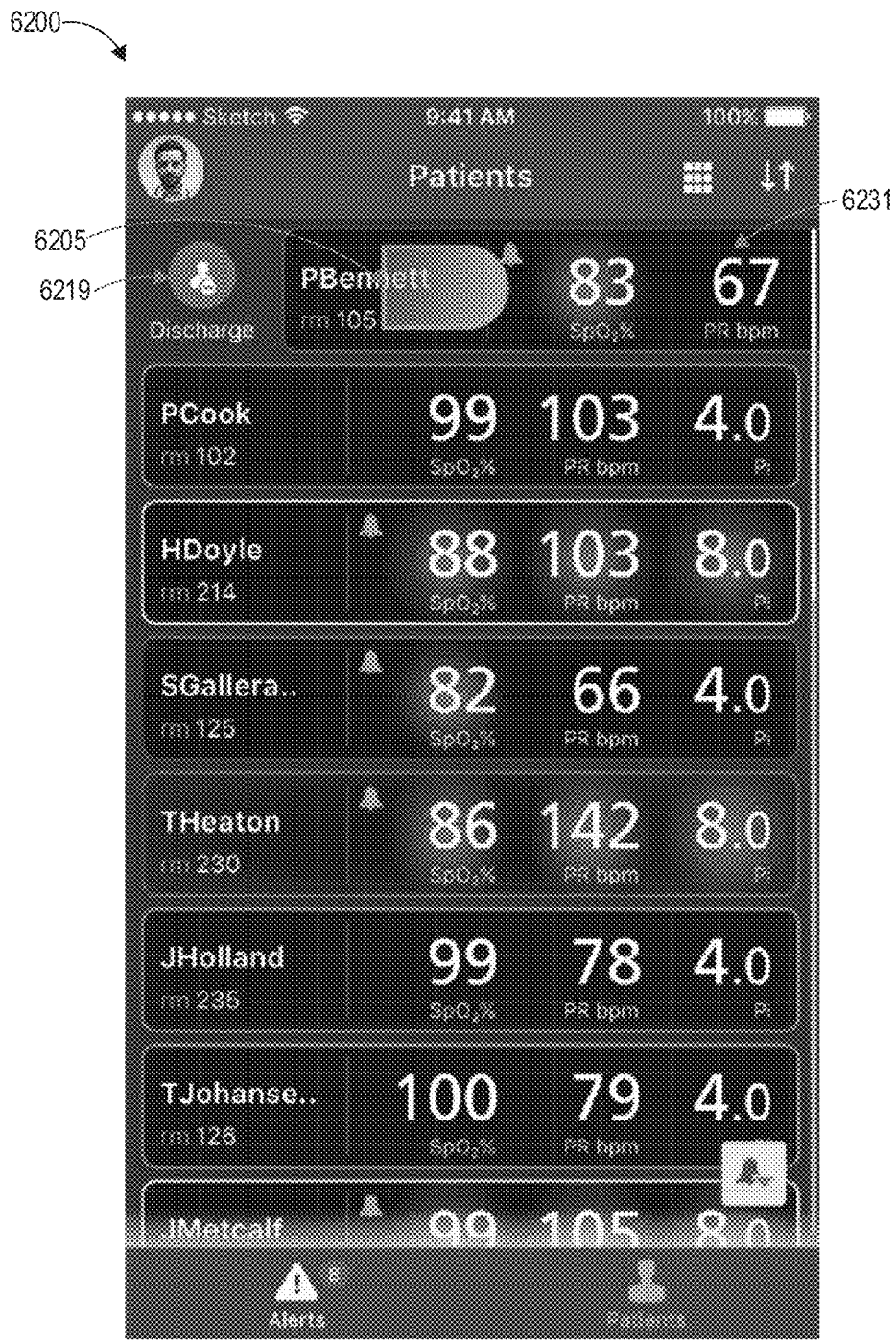

FIG. 62 depicts another example patient user interface 6200. The patient user interface 6200 is similar to the patient user interface 6100 of FIG. 61. In response to a first user interaction 6205 (such as a swipe) with the first patient tile 6231, the user interface 6200 can display a discharge element 6219 for the first patient tile 6231. As used herein, a "discharge," in addition to having its ordinary meaning, can refer to a removal of a patient from one or more patient devices. Following a discharge of a patient from a particular patient device, real or near-real time data from the patient device for the particular patient may not be available on the clinician device. Conversely, as used herein and described above, an "admit," in addition to having its ordinary meaning, can refer to an addition of a patient from a particular patient device. Following an admission of a patient to a particular patient device, real or near-real time data from the patient device for the particular patient may be available on the clinician device. Admitting or discharging a patient to or from a particular device can be different than admitting or discharging a patient to or from a healthcare facility. Accordingly, user selection of the discharge element 6219 from the clinician device can cause the particular patient (here "PBennett") to be discharged from the particular patient device (such as an optical or oximetry sensor) associated with the first patient tile 6231. The particular patient device (such as an optical or oximetry sensor) can then be physically removed from the patient. Thus, the availability of admit and discharge patient device functionality from the clinician device can improve patient care by allowing the clinician to potentially interact with fewer user interfaces or devices and to be more efficient.

Figure 63:
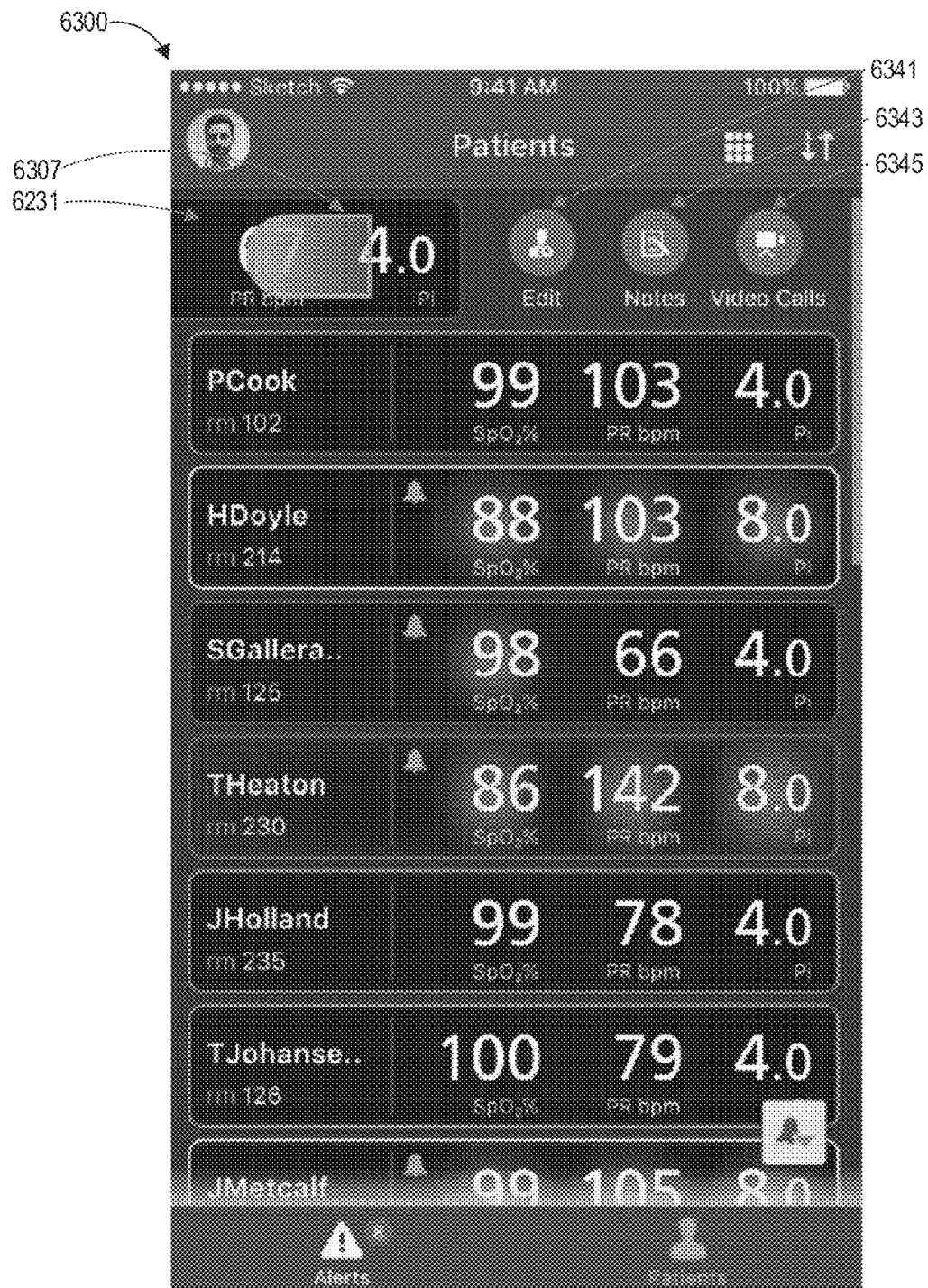

Turning to FIG. 63, another example patient user interface 6300 is shown, which is similar to the patient user interface 6100 of FIG. 61. In response to a second user interaction 6307 (such as a swipe) with the first patient tile 6231, the user interface 6300 can update to present additional options to the clinician. The user interface 6300 can include a first selectable element 6341, a second selectable element 6343, and a third selectable element 6345. User selection of the first selectable element 6341 can cause the user interface 6300 to display an additional user interface that enables a clinician to edit patient information. User selection of the second selectable element 6343 can cause the user interface 6300 to display an additional user interface that displays patient notes. User selection of the third selectable element 6345 can initiate a video call with the particular patient.

Figure 64:

FIG. 64 depicts another example patient user interface 6400. The patient user interface 6400 is similar to the patients screen 1500 of FIG. 15. Similar to the patients screen 1500 of FIG. 15, the patient user interface 6400 can display patient data in a grid view, which can advantageously display more individual patients than a list view. However, in addition to the patients screen 1500 of FIG. 15, the patient user interface 6400 can further include and display additional notification information. The patient user interface 6400 can include and display a first patient tile 6451, a second patient tile 6453, a third patient tile 6455, a fourth patient tile 6457, etc. Each of the first patient tile 6451, the second patient tile 6453, and the third patient tile 6455 can include an indicator associated with a notification status. Example indicators include a first color, a second color, and a third color for each of the first patient tile 6451, a second patient tile 6453, a third patient tile 6455, respectively. The first color, such as green, can correspond to a nominal state. The second color, such as yellow, can indicate that a notification is an initial notification or some other state. The third color, such as red, can indicate that there is a notification where one or more parameters associated with a patient device have triggered an alarm state or that a notification has been escalated. The fourth patient tile 6457 can have a fourth indicator, such as a glowing red state, which can indicate that that there is a notification where multiple parameters associated with a patient device have each triggered an alarm state.

Figure 65:
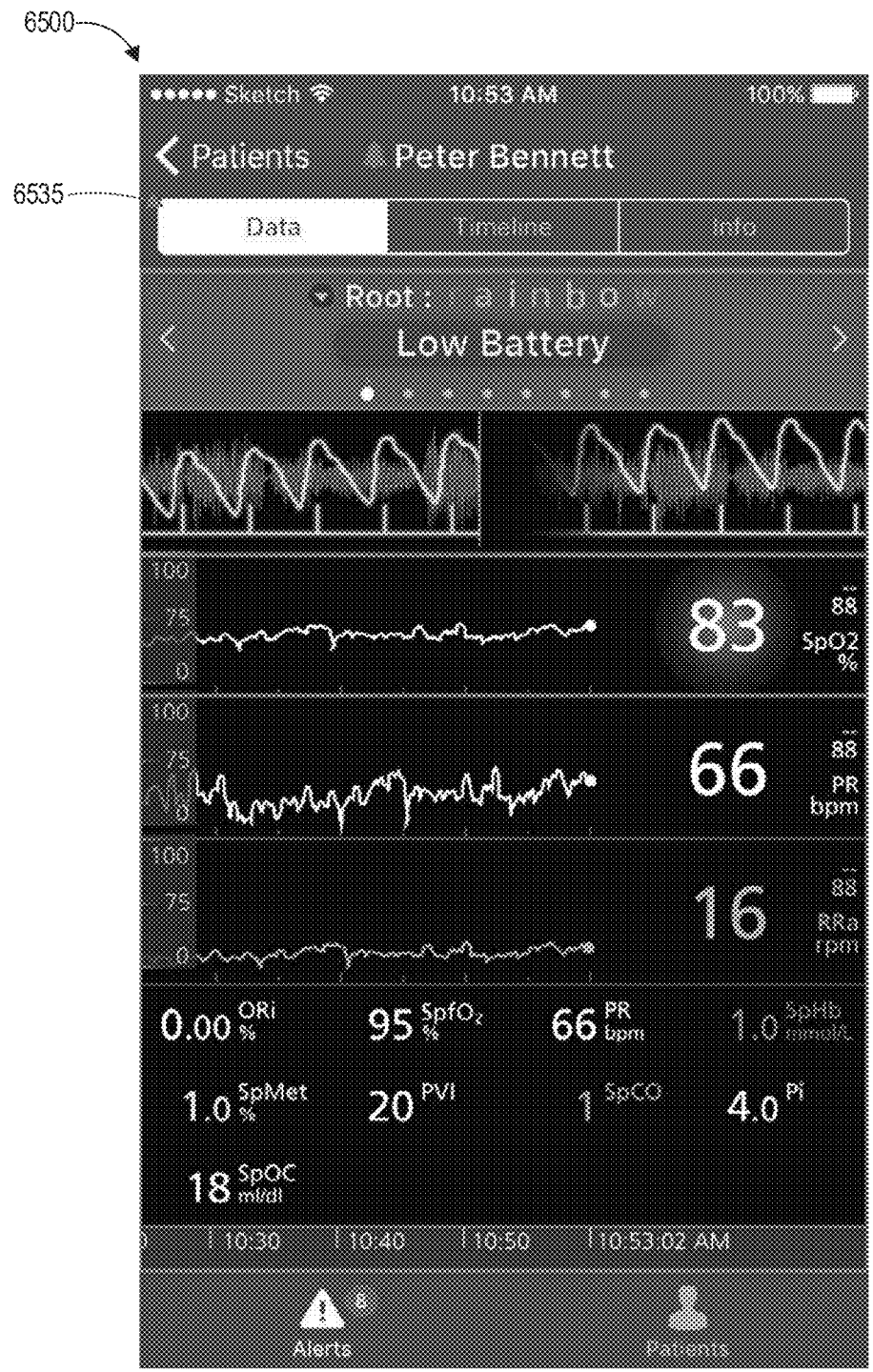
FIGS. 65 through 68 depict additional example patient data user interfaces.

FIG. 65 depicts another example patient data user interface 6500. The patient data user interface 6500 is similar to the patient data screen 1600 of FIG. 16. Similar to the patient data screen 1600 of FIG. 16, the patient data user interface 6500 can provide a more detailed view of a patient's physiological parameters, such as physiological parameter values, trend lines, and waveforms. However, in addition to the patient data screen 1600 of FIG. 16, the patient data user interface 6500 can further include a navigation bar 6535. The navigation bar 6535 can enable a user to select various user interfaces. As shown, the "Data" element of the navigation bar 6535 is selected for the patient data user interface 6500. The navigation bar 6535 can advantageously enable a clinician to easily navigate to and view different aspects and user interfaces associated with a patient device, such as a point-of-care device, for a patient.

Figure 66:
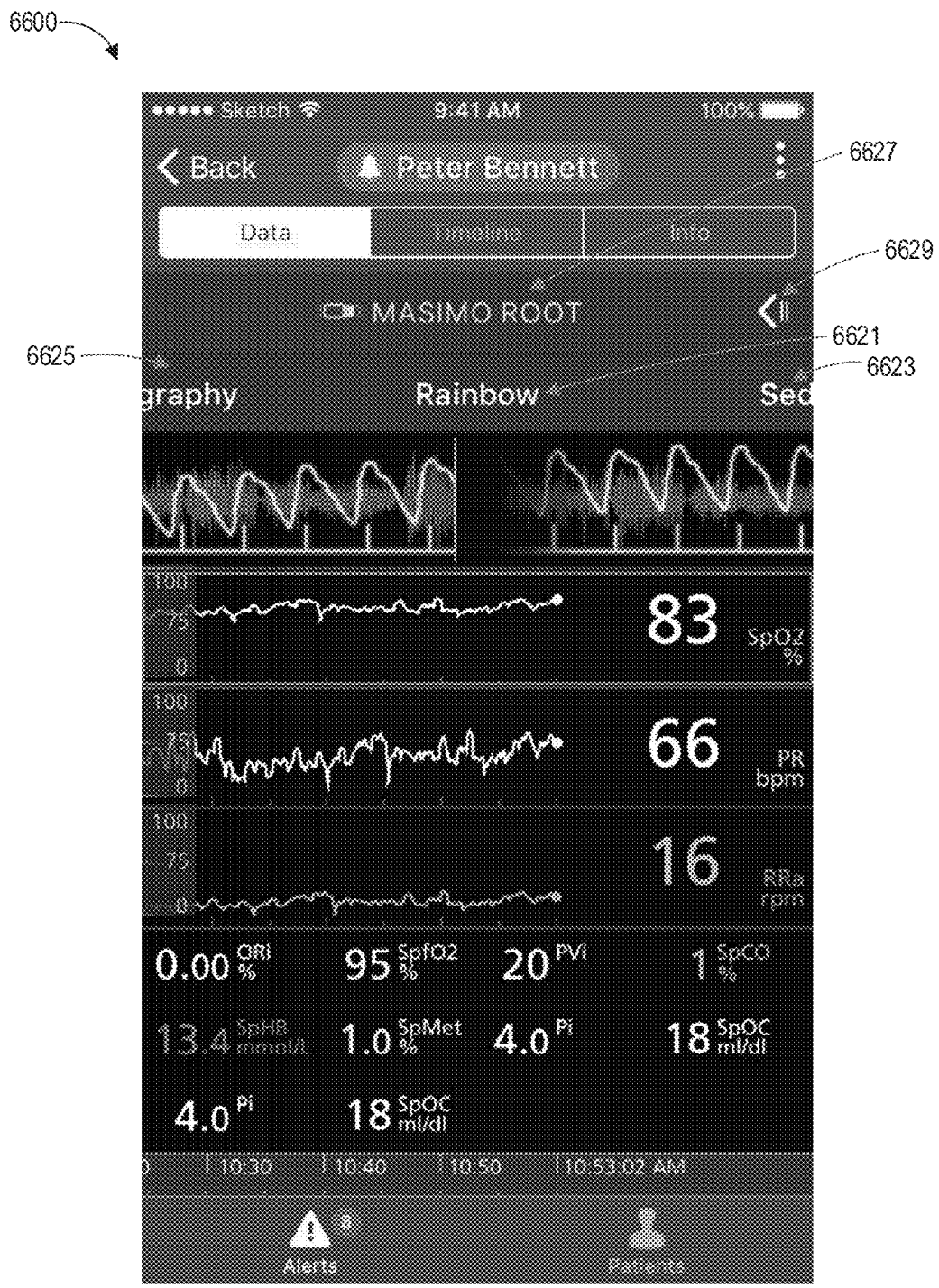

FIG. 66 depicts another example patient data user interface 6600. The patient data user interface 6600 is similar to the patient data screen 1600 of FIG. 16. Similar to the patient data screen 1600 of FIG. 16, the patient data user interface 6600 can provide a more detailed view of a patient's physiological parameters, such as physiological parameter values, trend lines, and waveforms. However, in contrast to the patient data screen 1600 of FIG. 16, the patient data user interface 6600 can further include different user interface elements for device management. The user interface 6600 can include a device descriptor 6627 that displays the name of the currently viewed device. The user interface 6600 can also include a device user interface element 6629 that enables a user to manage one or more devices, change a view of the device, or change a channel. The user interface 6600 can also include a currently selected channel indicator 6621, which is "Rainbow"™ here. The user interface 6600 can also include a first channel selector 6625, which, if selected by a clinician, can change to a first channel, such as a Capnography channel. The user interface 6600 can also include a second channel selector 6623, which, if selected by a clinician, can change to a second channel, such as a SedLine™ channel.

Figure 67:
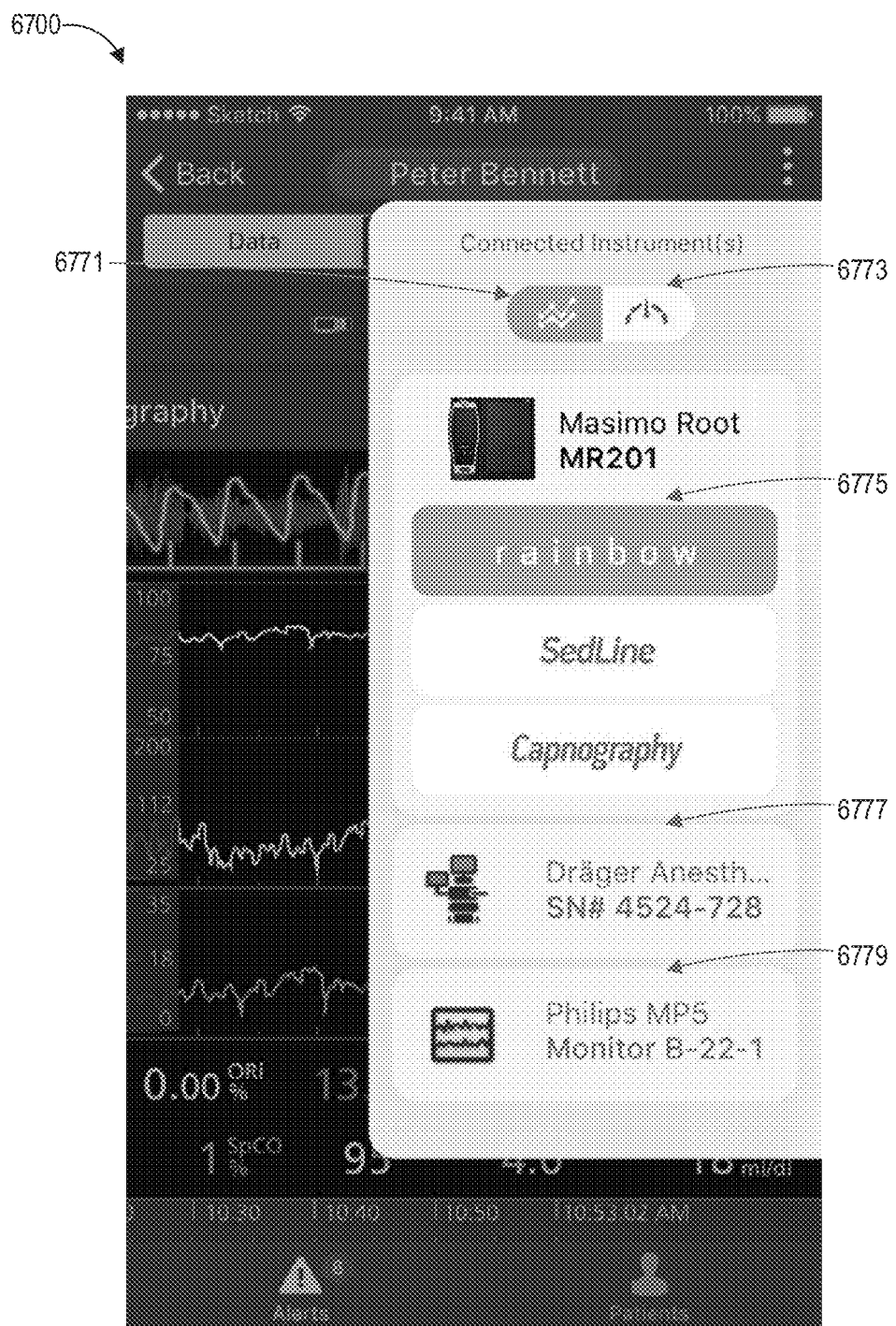

FIG. 67 depicts another example patient data user interface 6700. The patient data user interface 6700 of FIG. 67 is similar to the patient data user interface 6600 of FIG. 66. In response to a user selection of the device user interface element 6629 of FIG. 66, the patient data user interface 6700 can present use interface controls associated with one or more devices. The user interface 6700 can include a first user interface element 6771 and a second user interface element 6773, each of which can enable a clinician to change the view of the patient data user interface 6700. User selection of the first user interface element 6771 can cause presentation of a trend view and user selection of the second user interface element 6773 can cause presentation of an analog view. An analog view is described in further detail below with respect to FIG. 68. The user interface 6700 can further include a channel selector 6775 for a first device. The user interface 6700 can further include a second device selector 6777 and a third device selector 6779. Selection of additional devices can enable a clinician to manage the other devices.

Figure 68:
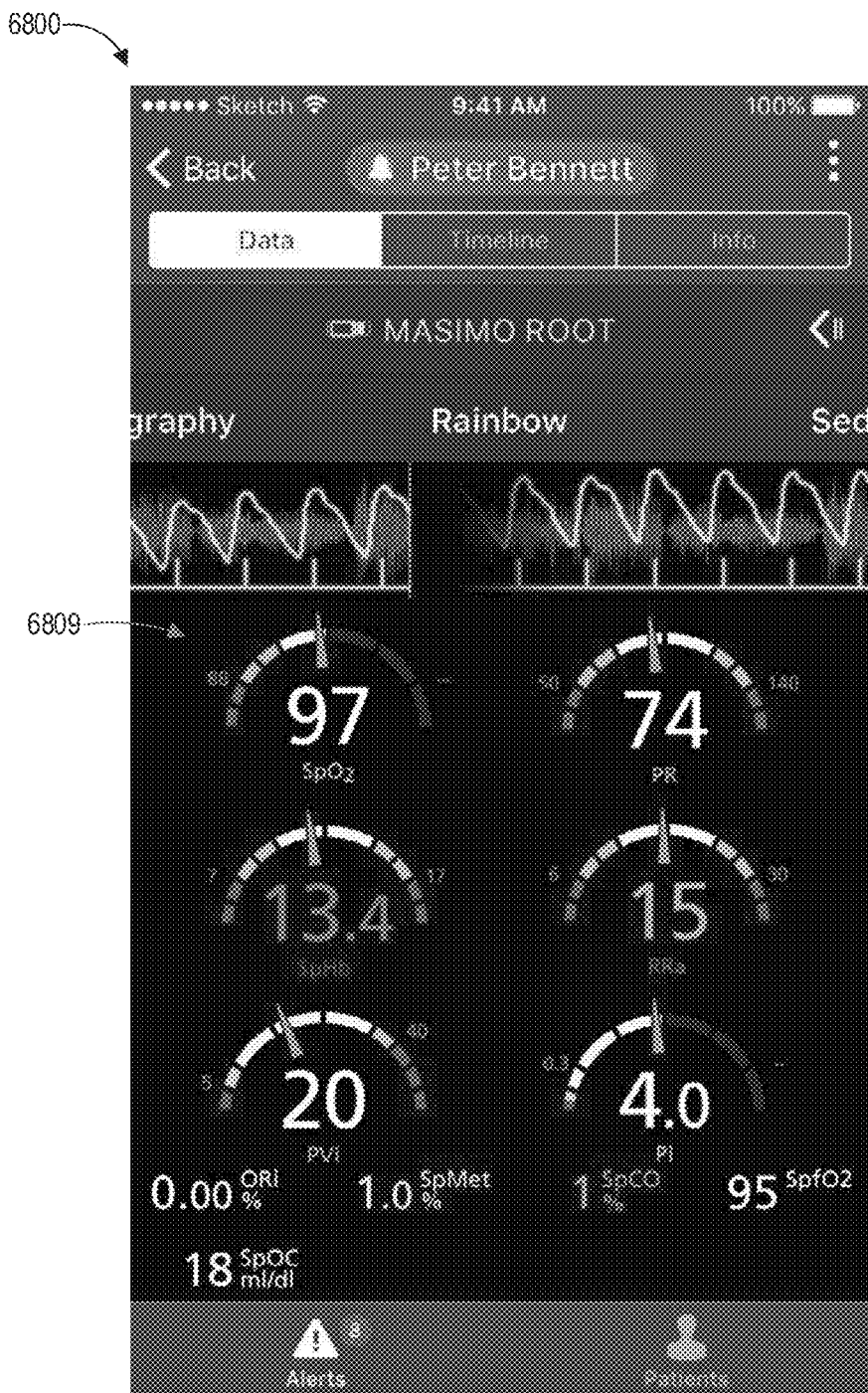

FIG. 68 depicts another example patient data user interface 6800. The patient data user interface 6800 is similar to the patient data user interface 6600 of FIG. 66. However, in contrast to the patient data user interface 6600 of FIG. 66 that presents patient data in a trend view, the patient data user interface 6800 can present patient data in an analog view. As shown, the analog view can include a physiological monitor gauge panel 6809 that can include a speedometer-style view of one or more physiological parameters. The physiological monitor gauge panel 6809 can include multiple physiological monitor gauges, such as a SpO2 (oxygen saturation) gauge and a SpHb (total hemoglobin) gauge, among others. Each physiological monitor gauge can include a semi-circular face and a parameter value indicator (such as a needle tip) that rotatably travels along each face. Each indicator can rotatably pivot around a gauge center. The indicator position on the face can correspond to a particular physiological parameter value. In some embodiments, each gauge can be advantageously configured so that the indicator is at the face mid-point when the parameter value is at a nominal value. In this visual manner, a clinician can quickly recognize that a patient has one or more abnormal readings, which can also include recognizing the degree of abnormality across multiple parameters. Additional details regarding the physiological monitor gauge panel 6809 and the speedometer-style view are described in greater detail in U.S. Pat. No. 9,778,079, titled "Physiological Monitor Gauge Panel," issued Oct. 3, 2017, and U.S. Pat. No. 9,131,881, titled "Hypersaturation Index," issued Sep. 15, 2015, each of which are hereby incorporated by reference in their entireties.

Figure 69:
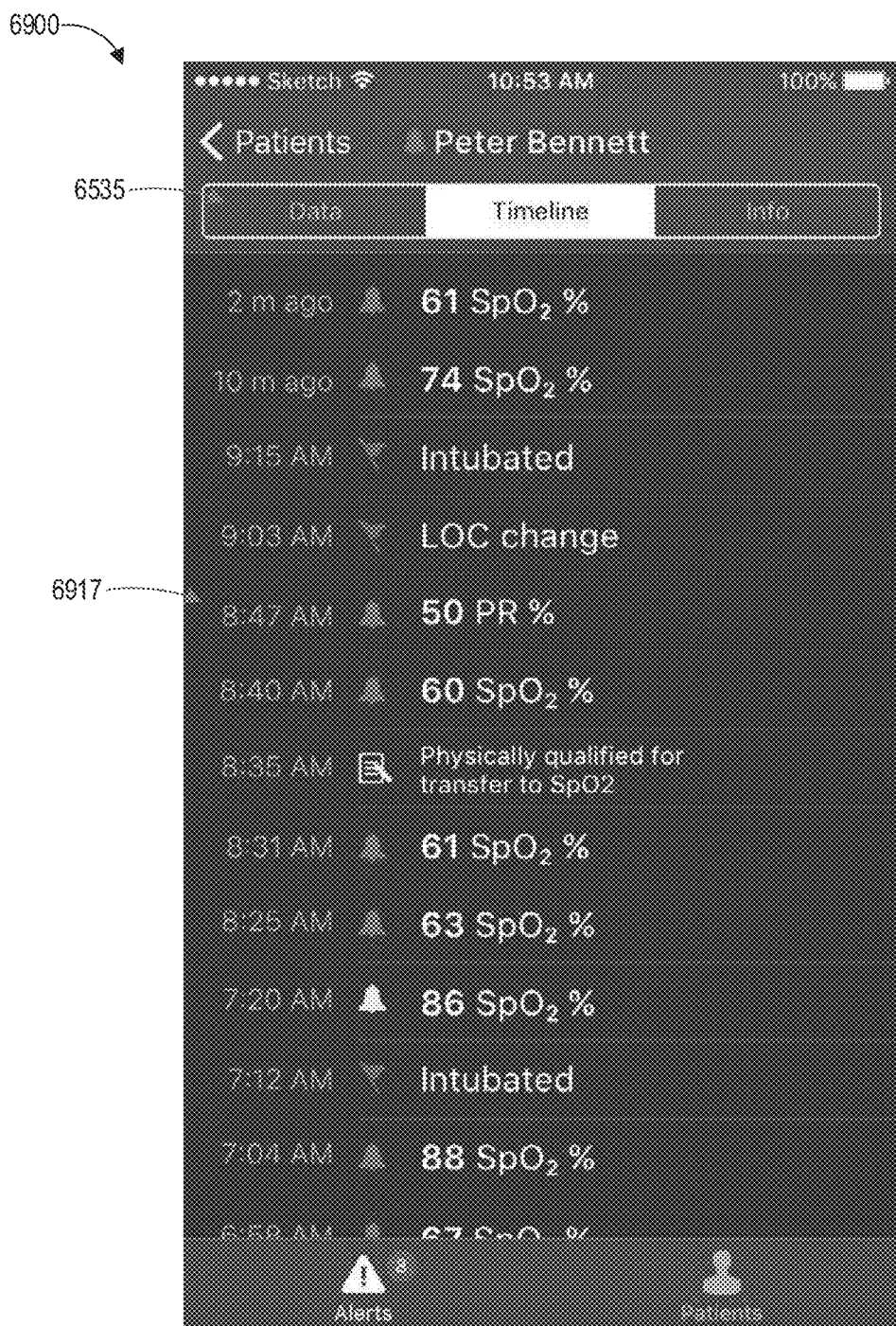
FIG. 69 depicts an example timeline user interface.

FIG. 69 depicts an example timeline user interface 6900. The timeline user interface 6900 is similar to the user interface 4700 of FIG. 47. The timeline user interface 6900 is similar to the patient data user interface 6500 of FIG. 65. Similar to the patient data user interface 6500 that can include a navigation bar, the timeline user interface 6900 can include the navigation bar 6535. As shown, the "Timeline" element of the navigation bar 6535 is selected for the timeline user interface 6900. The timeline user interface 6900 can present events. The events can be for a particular patient. The events can be received by the clinician device from a remote server in the form of event data. Some of the event data can be obtained by a patient device at the point-of-care (such as a bedside device or patient-worn monitor). The event data can include a physiological parameter value, such as a measurement value obtained by a patient device. The physiological parameter values can include measurements related to oxygen saturation or SpO2, respiratory rate, blood pressure, heart rate or pulse rate perfusion, other blood gas parameters, brain activity, brain oxygen saturation. The event data can also include alarm notifications, such as a notification associated with a physiological parameter value. As shown, the event data can also indicate textual event descriptions, such as a patient being intubated or a physical location of the patient being changed. As shown, the presentation of the events can include a respective time for the event, such as "2 m ago" or "9:15 AM". Thus, the timeline user interface 6900 can provide a historical listing of events associated with a patient, such as alarm notifications or other events, for one or more patient devices, which can advantageously improve patient care as a clinician can review the patient's physiological history in a quick and easy manner. The event data can include time data, such as a timestamp associated with the event. In other embodiments, time data can be associated with an event when the event is received by the clinician device from the remote server.

Figure 70:
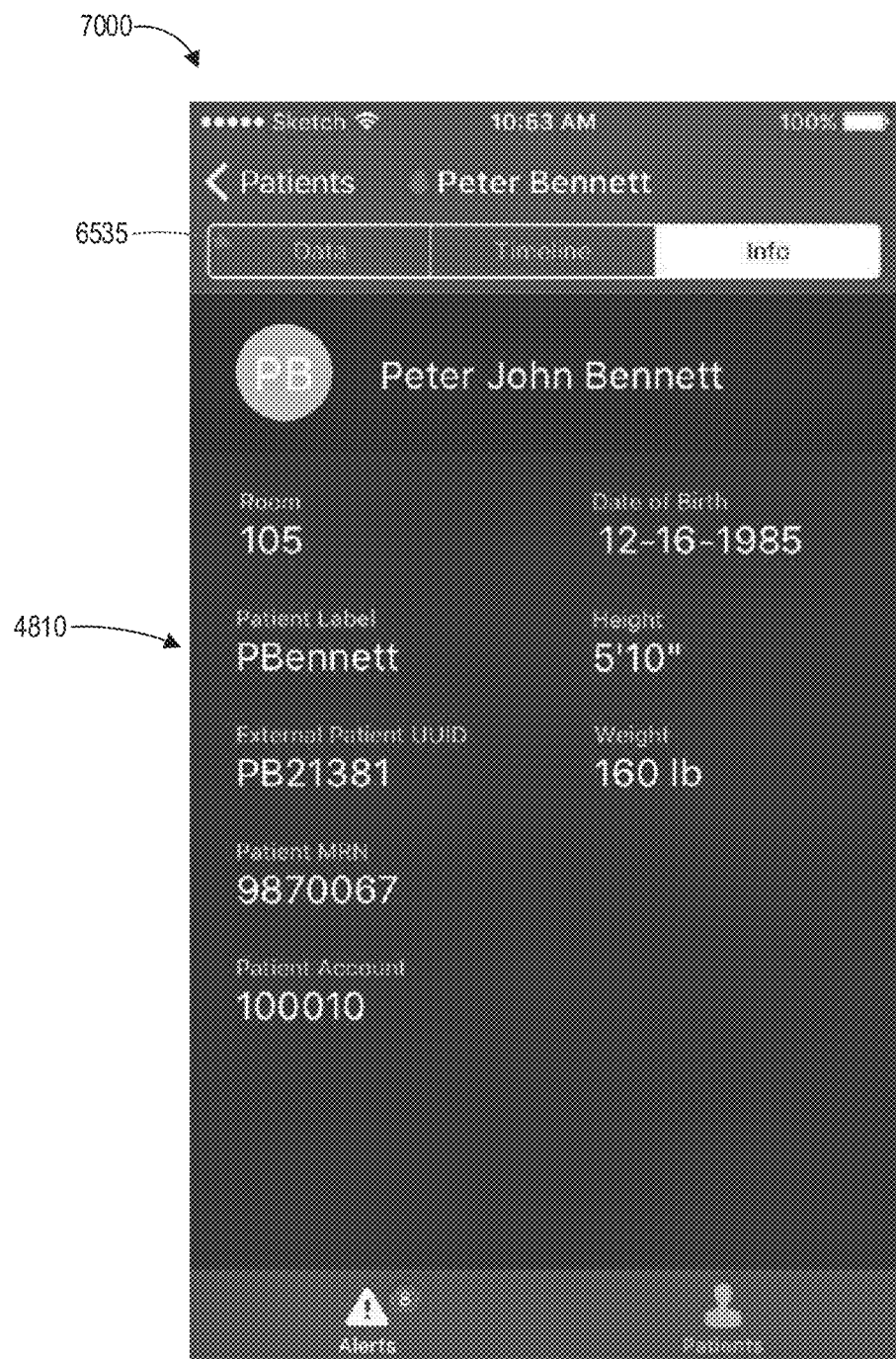
FIG. 70 depicts an example patient information user interface.

FIG. 70 depicts an example patient information user interface 7000. The patient information user interface 7000 is similar to the patient data user interface 6500 of FIG. 65. Similar to the patient data user interface 6500 that can include a navigation bar, the patient information user interface 7000 can include the navigation bar 6535. As shown, the "Info" element of the navigation bar 6535 is selected for the patient information user interface 7000. The patient information user interface 7000 is similar to the user interface 4800 of FIG. 48. Similar to the user interface 4800 of FIG. 48 that includes and can present patient information 4810, the patient information user interface 7000 can include and present patient information 4810. As shown, the patient information 4810 can include patient profile information, patient identifiers, and a current location of the patient.

Figure 71:
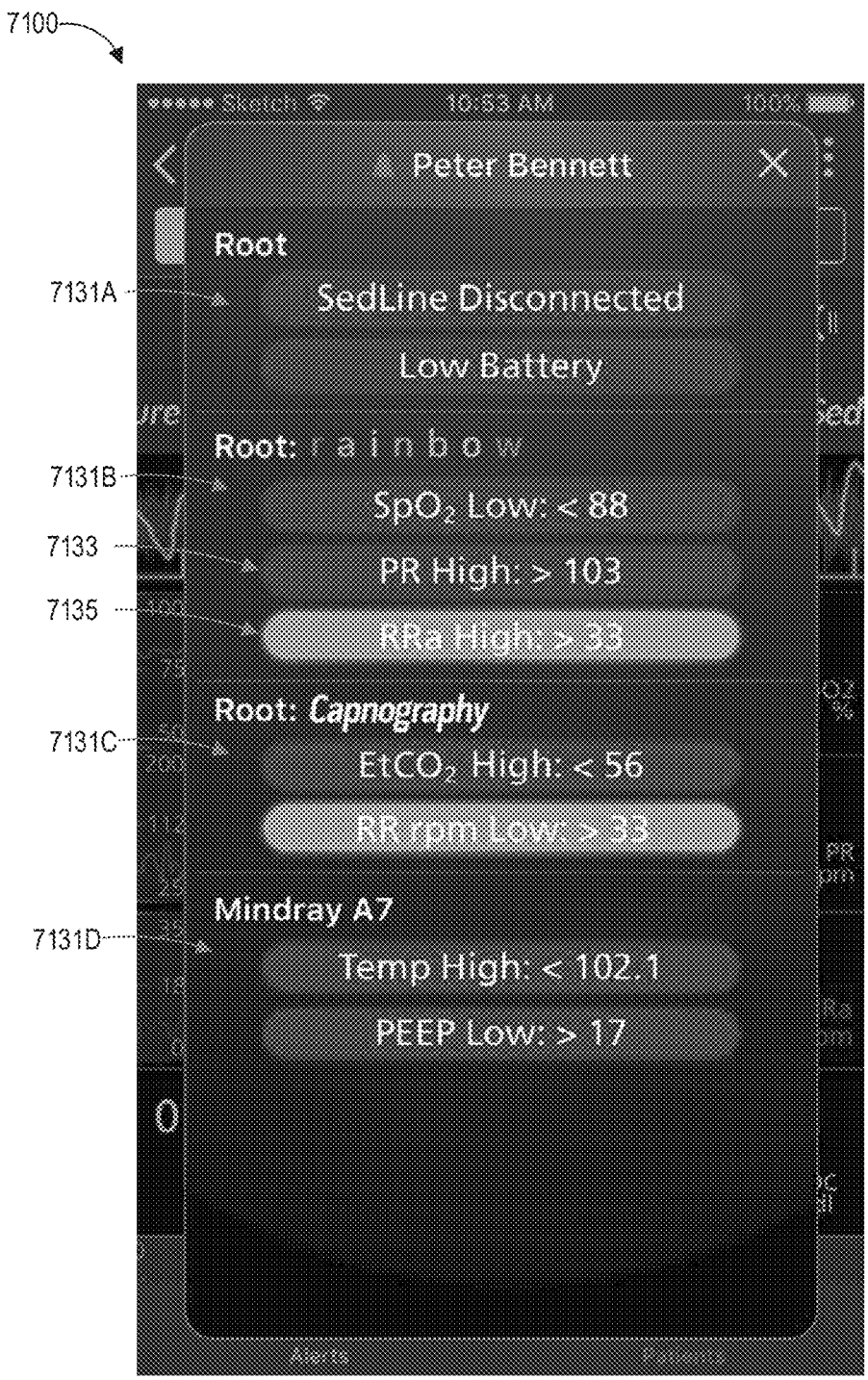
FIGS. 71 and 72 depict example notification overview user interfaces.

FIG. 71 depicts an example notification overview user interface 7100. The notification overview user interface 7100 can present multiple notifications for a particular user. The notification overview user interface 7100 can include notification sections 7131A, 7131B, 7131C, 7131D. The notification sections 7131A, 7131B, 7131C, 7131D can present system level alarm(s) or alarming parameter(s). Each of the notification sections 7131A, 7131B, 7131C, 7131D can be for (i) a particular device or (ii) a particular device and channel. The first notification section 7131A can indicate system level alarms, such as "SedLine Disconnected" and "Low Battery," for a particular device (here "Root") and patient (here "Peter Bennett"). The system level alarms can include notifications that indicate errors or issues with a device, such as the device being disconnected or a low battery. The remaining notification sections can present alarming parameter(s) for particular devices (such as "Minday A7") or particular devices and channels (such as "Root: rainbow" or "Root: Capnography") for the patient. As shown, the alarming parameter(s) can indicate parameter values being above or below a threshold, such as "SpO2 Low: <88". As described above, the alarming parameter(s) can also be presented with indicators that indicate a severity of the alarm, such as color-coded and/or glowing indicators. The first alarm notification 7133 can include a first color (such as red) that indicates a first severity of the first alarm notification 7133. The second alarm notification 7135 can include a second color (such as yellow) that indicates a second severity of the second alarm notification 7135. The notification overview user interface 7100 can present a summary of the alarm notifications for a particular patient, which can advantageously enable a clinician to review the status of the patient in a quick and easy manner.

Figure 72:
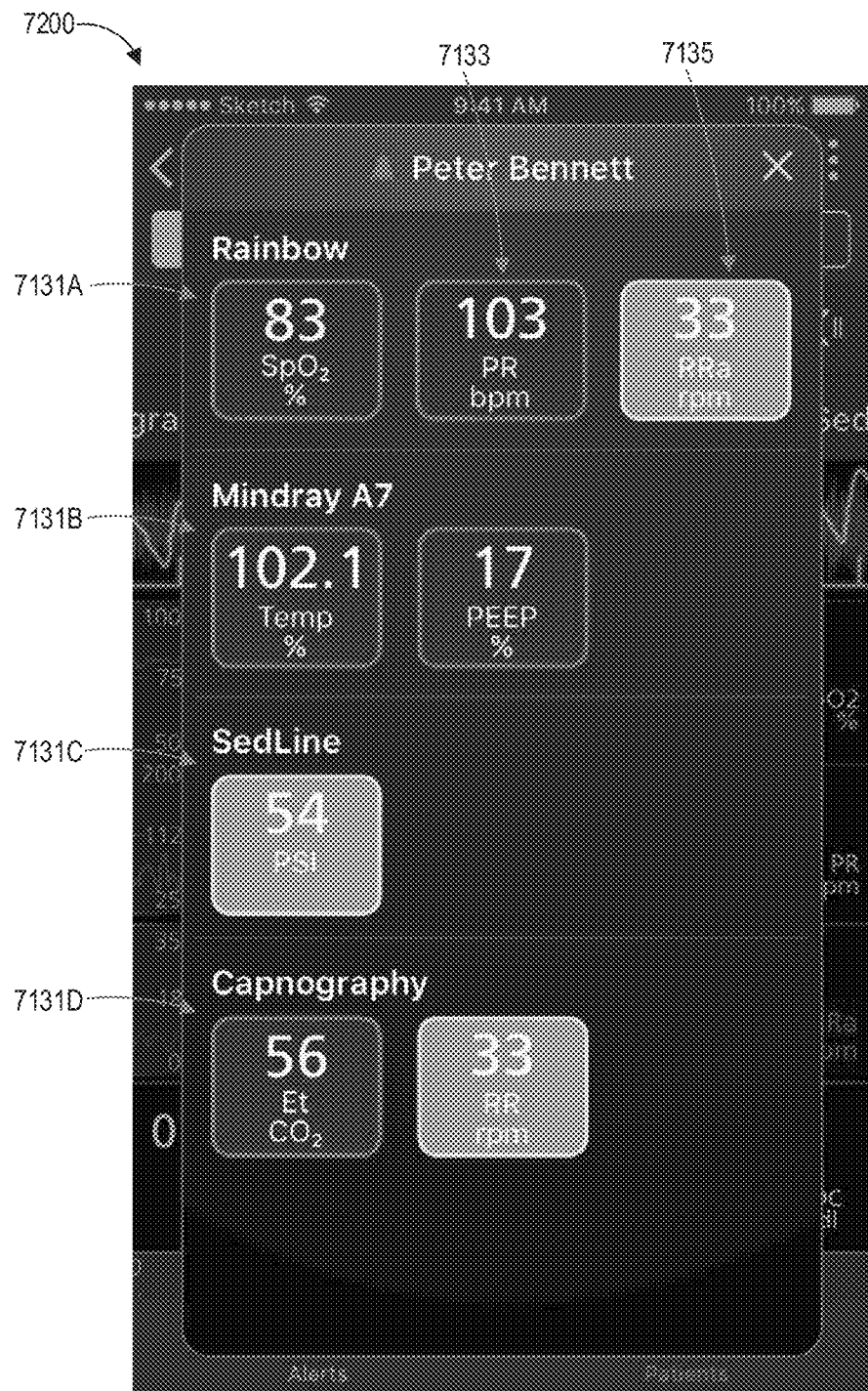

FIG. 72 depicts another example notification overview user interface 7200. The notification overview user interface 7200 is similar to the notification overview user interface 7100 of FIG. 71. Similar to the notification overview user interface 7100 of FIG. 71, the notification overview user interface 7200 can include notification sections 7131A, 7131B, 7131C, 7131D and alarm notifications, such as the first alarm notification 7133 and the second alarm notification 7135. Similar to the alarm notifications 7133, 7135 of FIG. 71, the alarm notifications 7133, 7135 of FIG. 72 can include indicators that indicate a severity of a respective alarm, such as being color-coded, pulsing, and/or glowing. However, the visual presentation of the alarm notifications 7133, 7135 of FIG. 72 can be different than the presentation of the alarm notifications 7133, 7135 of FIG. 71. The alarm notifications 7133, 7135 of FIG. 72 can be presented as larger tiles in contrast to the narrower rectangles of the alarm notifications 7133, 7135 of FIG. 71. The larger visual presentation of the alarm notifications 7133, 7135 of FIG. 72 can enable a clinician to review the notifications more quickly.

Figure 73:
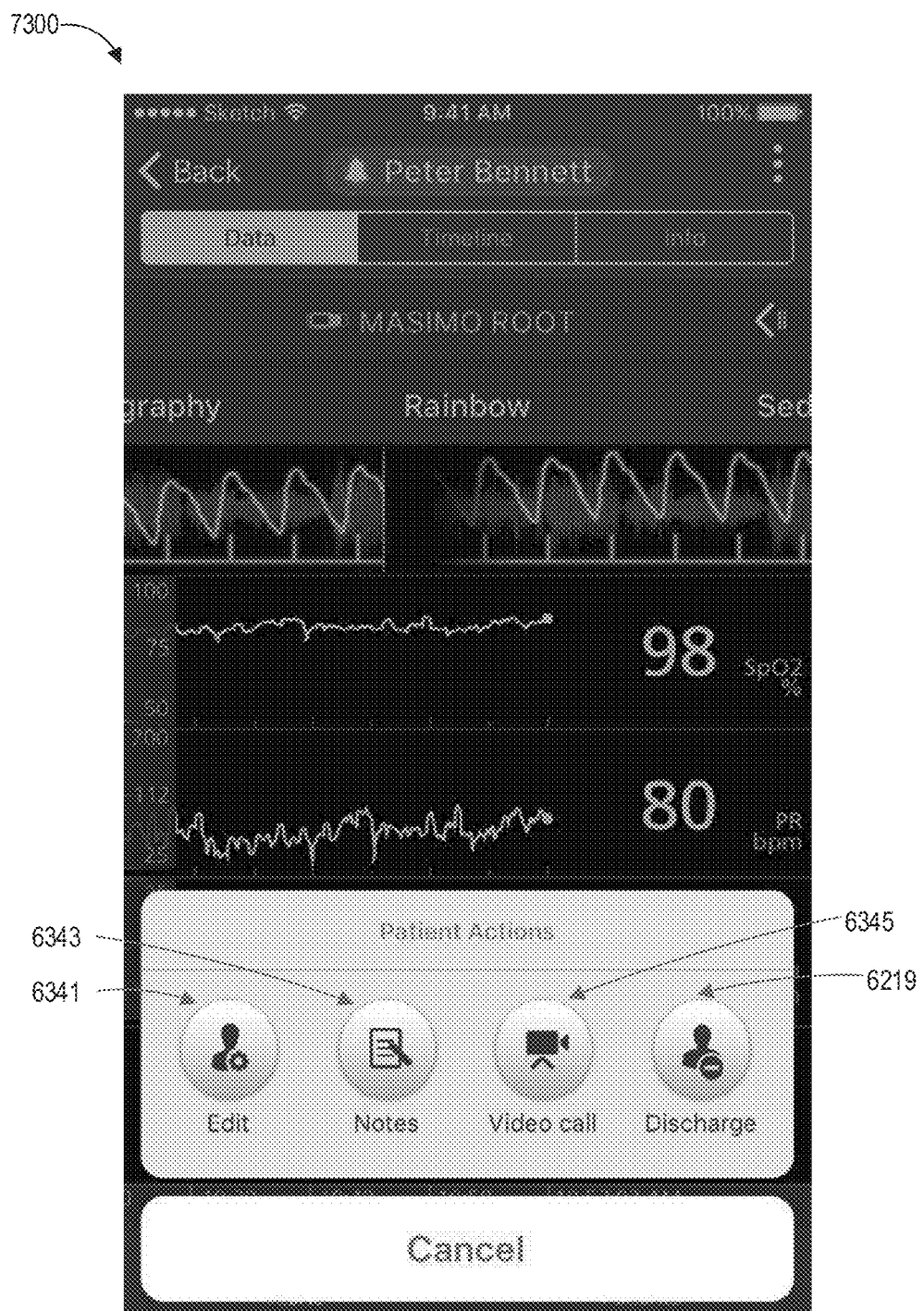
FIG. 73 depicts an example patient action user interface.

FIG. 73 depicts an example patient action user interface 7300. The patient action user interface 7300 can include elements similar to use interface elements from FIGS. 62 and 63. The patient action user interface 7300 can include a first selectable element 6341, a second selectable element 6343, a third selectable element 6345, and a fourth selectable element 6219. Similar to user selection of the selectable elements 6341, 6343, 6345 of FIG. 63, user selection of the first, second, and third selectable elements 6341 6343, 6345 of FIG. 73 can cause the presentation of additional user interfaces related to editing patient information, adding or editing patient notes, and video calling a patient, respectively. Similar to user selection of the discharge element 6219 of FIG. 62, user selection of the fourth selectable element 6219 of FIG. 73 can cause a device to discharge the patient or can cause presentation of a user interface to discharge the patient from a device.

Figure 74:
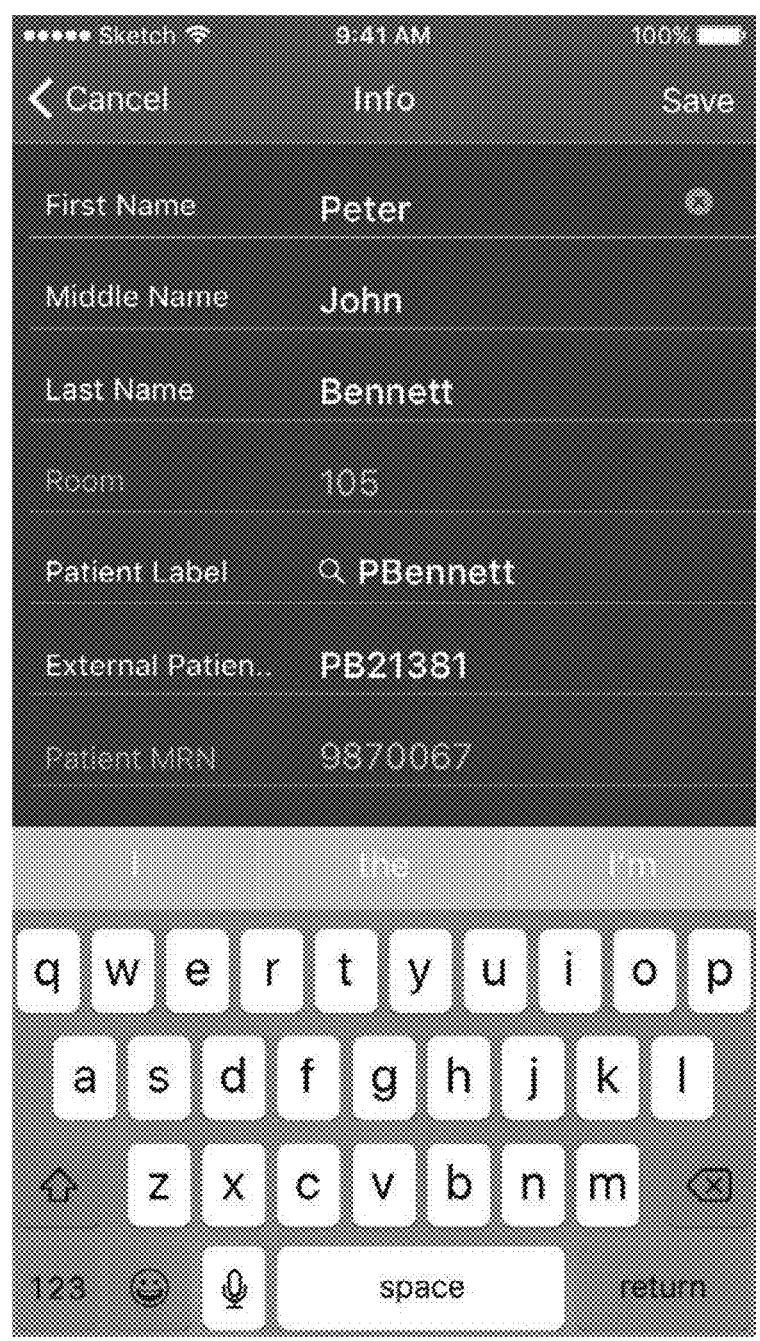
FIG. 74 depicts an example edit patient information user interface.

FIG. 74 depicts an example edit patient information user interface 7400. The edit patient information user interface 7400 can be presented in response to a user selection of the first selectable element 6341 in FIG. 73. As shown, a clinician can edit patient data using the edit patient information user interface 7400.

Figure 75:
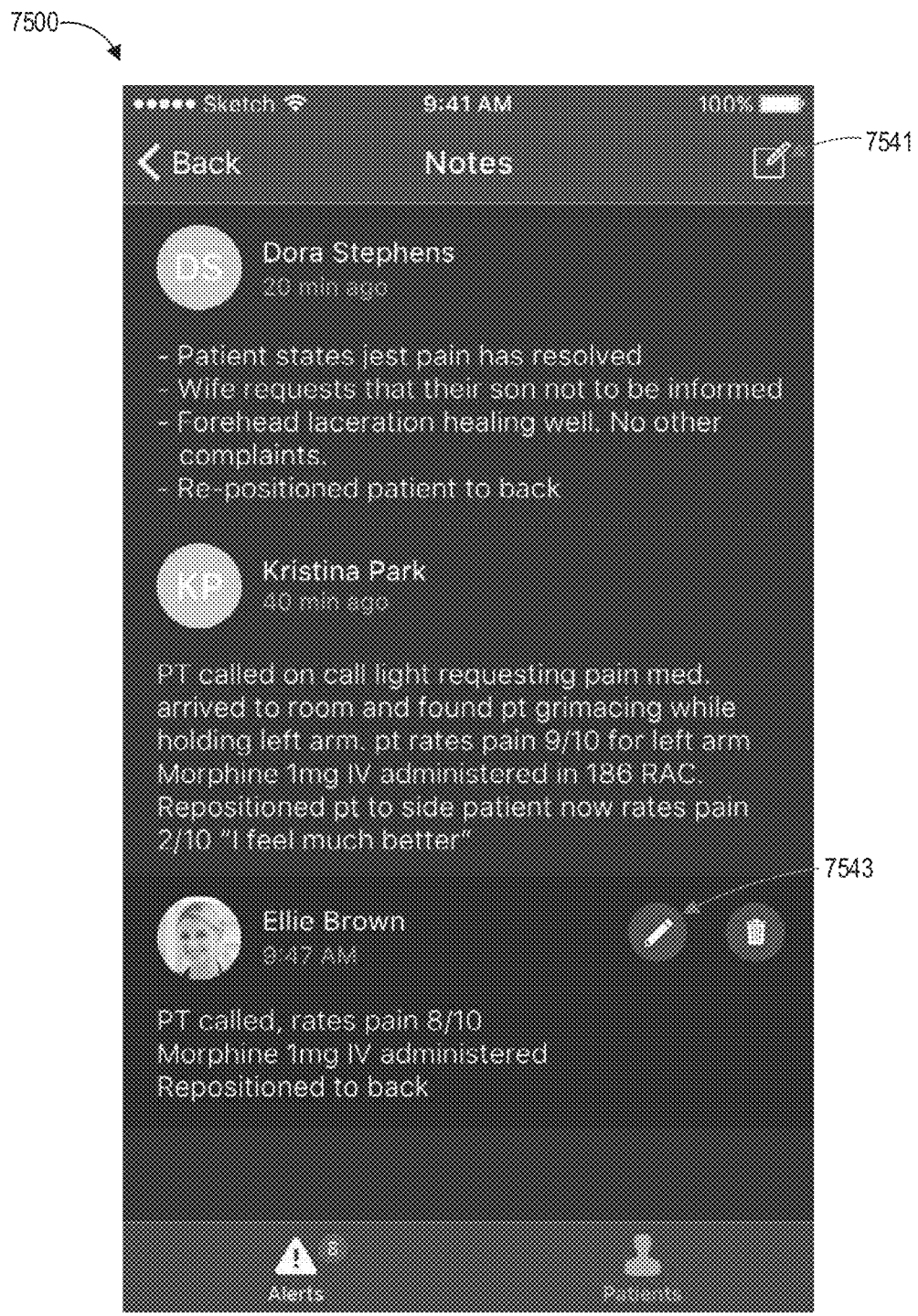
FIG. 75 depicts an example patient notes user interface.

FIG. 75 depicts an example patient notes user interface 7500, which can be reached upon user selection of the selectable element 6343 of FIG. 73. The patient notes user interface 7500 can present notes authored by one or more clinicians. The patient notes user interface 7500 can also present at least some textual data from a note. Each note can include a timestamp. The notes can be presented according to the order of corresponding timestamps, such as ascending or descending order from a most recent or an oldest note. The patient notes user interface 7500 can include user interface elements, such as an add notes user interface element 7541 and an edit notes user interface element 7543. A clinician can select the add notes user interface element 75412 to add a new note, and the clinician can edit the corresponding note by selecting the edit note user interface element 7543.

Patient notes or the patient notes user interface 7500 can be used in a patient handoff workflow between multiple clinicians, such as during a shift change. In existing clinical settings, a patient handoff can be verbal, such as a first clinician telling a second clinician what happened with the patient. Accordingly, information can be lost where the first clinician forgets to tell the second clinician something in these existing handoffs. Information loss can be exacerbated after there have been multiple handoffs for the same patient. Thus, a patient handoff workflow process using the clinician device and electronic notes can improve existing patient handoffs and thereby improve patient care. Additional details regarding patient handoffs are described in further detail below with respect to FIG. 109.

FIGS. 76 through 79 depict example error handling user interfaces. In an existing user interface for a clinician device, if the clinician device is not connected to a remote server, then the user interface will not include updated data, such as updated notifications. However, in current user interfaces, there may be no direct indication to the clinician that there is not a connection to the remote server or some other error situation. As described below with respect to FIGS. 76 through 79, the clinician device's system can detect an error situation, such as a failed connection with the remote server over a network. Upon detection of the error situation, a warning, such as a visual warning, can be output that provides an indication of the error situation. The error situation may be corrected, such as a connection being made to the remote server or the network, and the user interface can output an indicator, such as a visual indicator, that the error situation has been corrected. Accordingly, the user interface functionality related to the detecting errors, providing warnings, and providing updates that errors have been corrected can have a great clinical benefit. As mentioned above, an existing system may not provide a warning to the clinician, and, therefore, a clinician may miss some notifications without realizing that there is an issue with their clinician device. However, the systems and user interfaces described herein may provide improved warnings and notifications in such error situations to enhance patient care.

Figure 76:
FIGS. 76 through 79 depict example error handling user interfaces.

Turning to FIG. 76, an example error handling user interface 7600 is shown. The error handling user interface 7600 is similar to the notification user interface 5400 of FIG.

54. However, in addition to the notification user interface 5400 of FIG. 54, the error handling user interface 7600 can include a visual warning 7681 for an error situation. As described above, in response to detection of an error situation (such as a failed connection with a remote server over a network), the error handling user interface 7600 can present the visual warning 7681 of the error situation (such as "No server connection"). The visual warning 7681 can be an overlay or can be color coded, such as by including a first color (such as a red color) that indicates to a user that there is an error situation. While not illustrated, the visual warning 7681 can be presented for other error situations and can be in a different format, such as by being presented differently visually or by including auditory or haptic indicators. Thus, a clinician can know that their device may not be working properly and the clinician might be missing important notifications.

Figure 77:
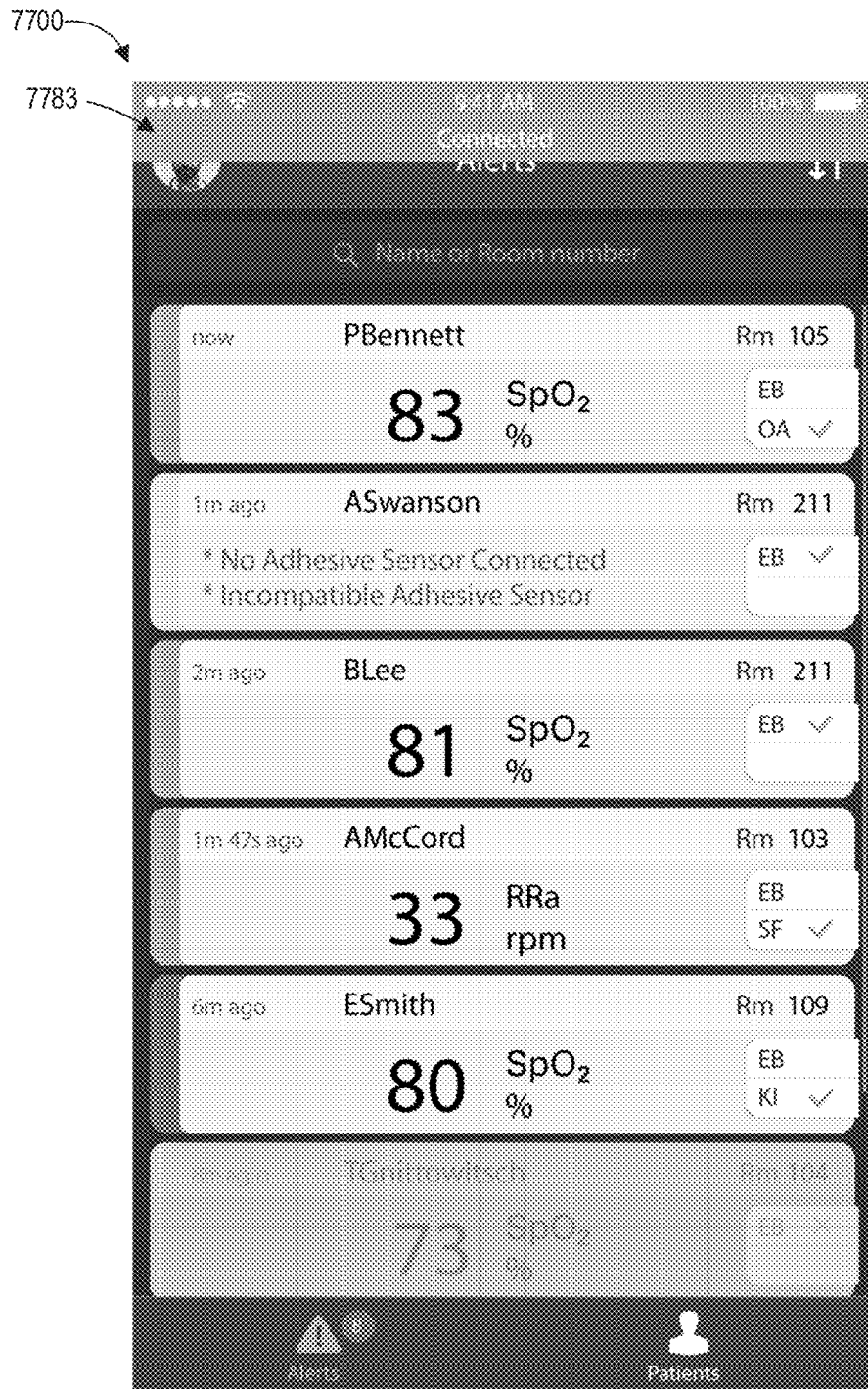

Turning to FIG. 77, another example error handling user interface 7700 is shown. The error handling user interface 7700 of FIG. 77 is similar to the error handling user interface 7600 of FIG. 76. However, instead of the presentation of the warning 7681 in the error handling user interface 7600 of FIG. 76, the error handling user interface 7700 of FIG. 77 can include a visual indicator 7783 of a correction to the error situation (such as an indicator of a connection with the remote server over the network). As described above, in response to the correction of an error situation (such as establishing a connection with a remote server over a network), the error handling user interface 7700 can present the visual indicator 7783 of the connection (such as "Connected"). The visual warning 7783 can be an overlay or can be color coded, such as by including a second color (such as a green color) that indicates to a user that the error situation has been connected. While not illustrated, the visual indicator 7783 can be presented for corrections to other error situations and can be in a different format, such as by being presented differently visually or by including auditory or haptic indicators. Thus, a clinician can know that their device may be working properly and the clinician can get updated notifications.

Figure 78:
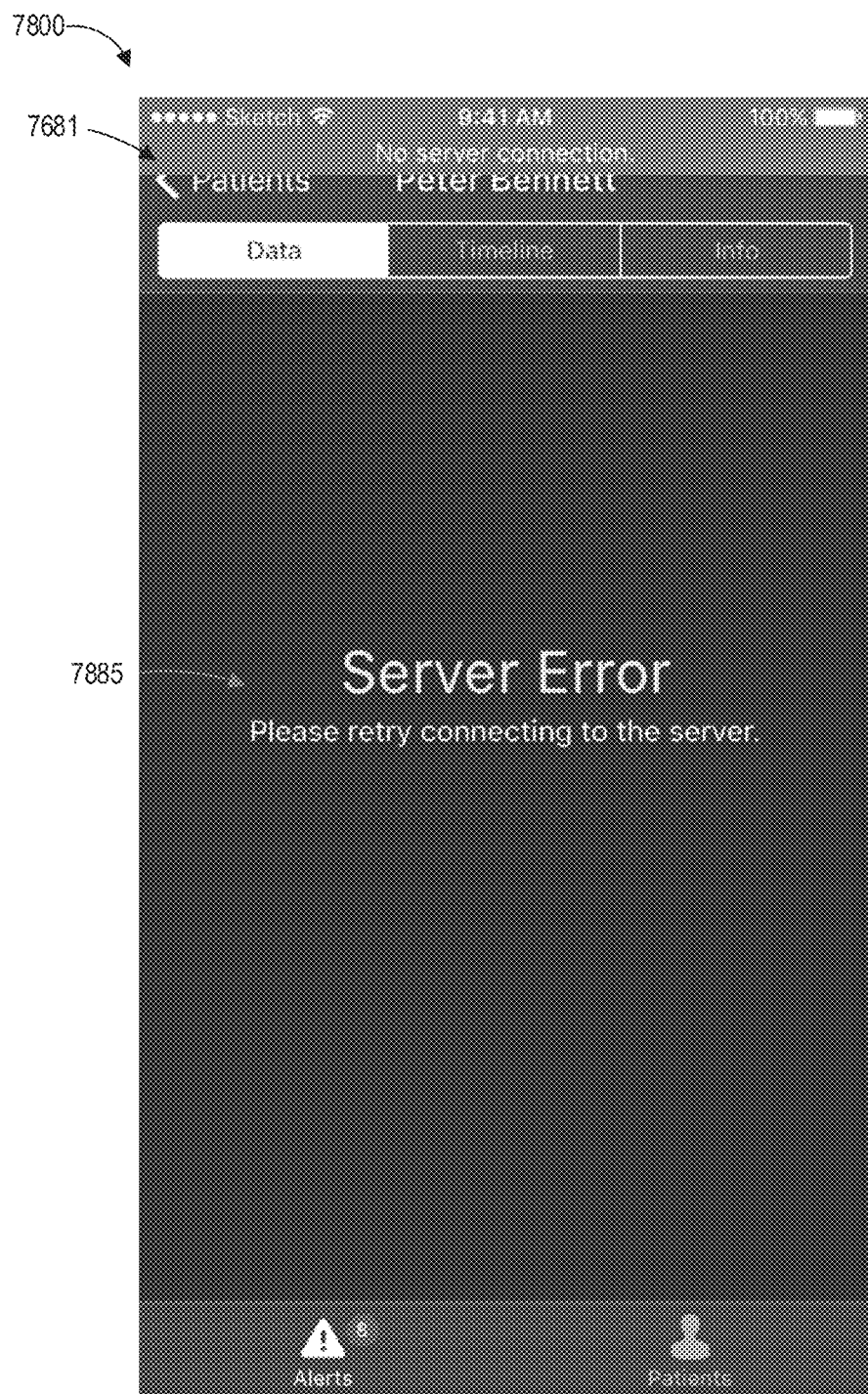

Turning to FIG. 78, another example error handling user interface 7800 is shown. The error handling user interface 7800 of FIG. 78 is similar to the error handling user interface 7600 of FIG. 76, where both user interfaces 7600, 7800 present the visual warning 7681. The error handling user interface 7800 is also similar to the patient data user interface 6500 of FIG. 65. However, instead of the presentation of near-real time or real-time patient data in the patient data user interface 6500 of FIG. 65, the error handling user interface 7800 of FIG. 78 may not present near-real time or real-time patient data (since there may be a failed connection with the remote server and near-real time or real-time patient data may be unavailable) and the error message 7885 may be presented to the user, such as the message: "Server Error" and "Please retry connecting to the server."

Figure 79:
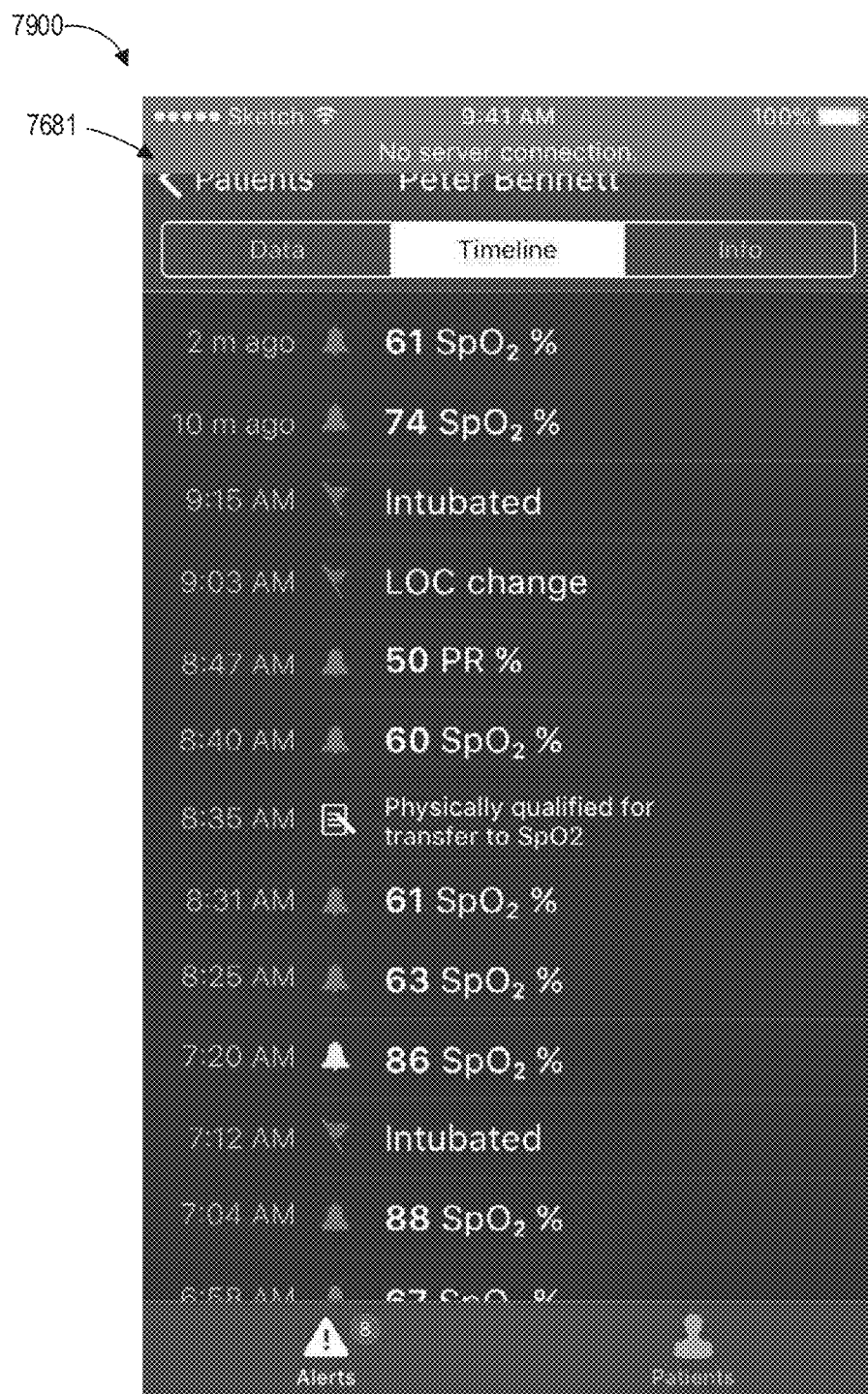

Turning to FIG. 79, another example error handling user interface 7900 is shown. The error handling user interface 7900 of FIG. 79 is similar to the error handling user interface 7600 of FIG. 76, where both user interfaces 7600, 7800 present the visual warning 7681. The error handling user interface 7800 is also similar to the timeline user interface 6900 of FIG. 69. Similar to the presentation of events in the timeline user interface 6900 of FIG. 69, the error handling user interface 7900 of FIG. 79 can also present events despite the current error situation (here, "No server connection"). The error handling user interface 7900 can be capable of presenting some event data, notification data, patient data, or other data that is available to the clinician device despite the error situation. For example, in the context of an error situation of a failed connection with the remote server over the network, the clinician device can locally store some event data, notification data, patient data, or other data to be presented to the clinician despite an ongoing error situation.

Figure 80:
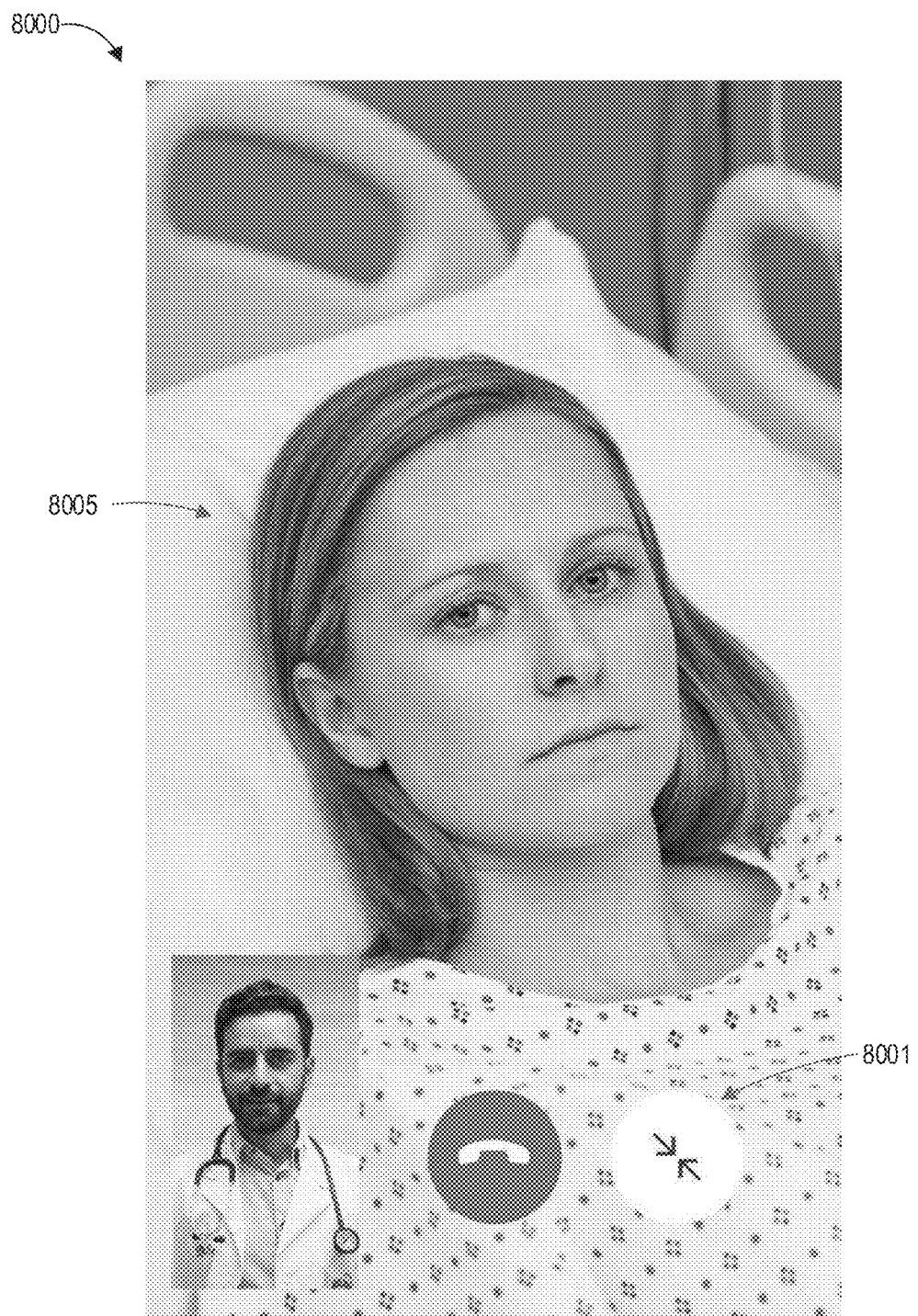
FIGS. 80 and 81 depict example video call user interfaces.

FIG. 80 depicts an example video call user interface 8000. As shown, a clinician, using the clinician device, can participate in a video call with the patient using the video call user interface 8000. The video call user interface 8000 can include a video call area 8005 that can include real-time or near-real time video of the patient. As described above, an alarm notification can be sent to the clinician, and the clinician can video call the patient to check in on the patient. Thus, the video call user interface 8000 and the alarm system described herein can improve patient care or the responsiveness of clinicians to patient alarms or notifications. The video call user interface 8000 can also include a toggle user interface element 8001. As described below in further detail with respect to FIG. 81, a user selection of the toggle user interface element 8001 can cause the user interface 8000 to update and minimize the video call area 8005 as an overlay over other user interfaces. Accordingly, the clinician can simultaneously participate in a video call with the patient and review data in other user interfaces. The improved multi-tasking capabilities of the user interfaces described herein can improve patient care and the responsiveness to medical emergencies since clinician's can possibly review and analyze patient data faster than without the improved user interface systems.

Figure 81:
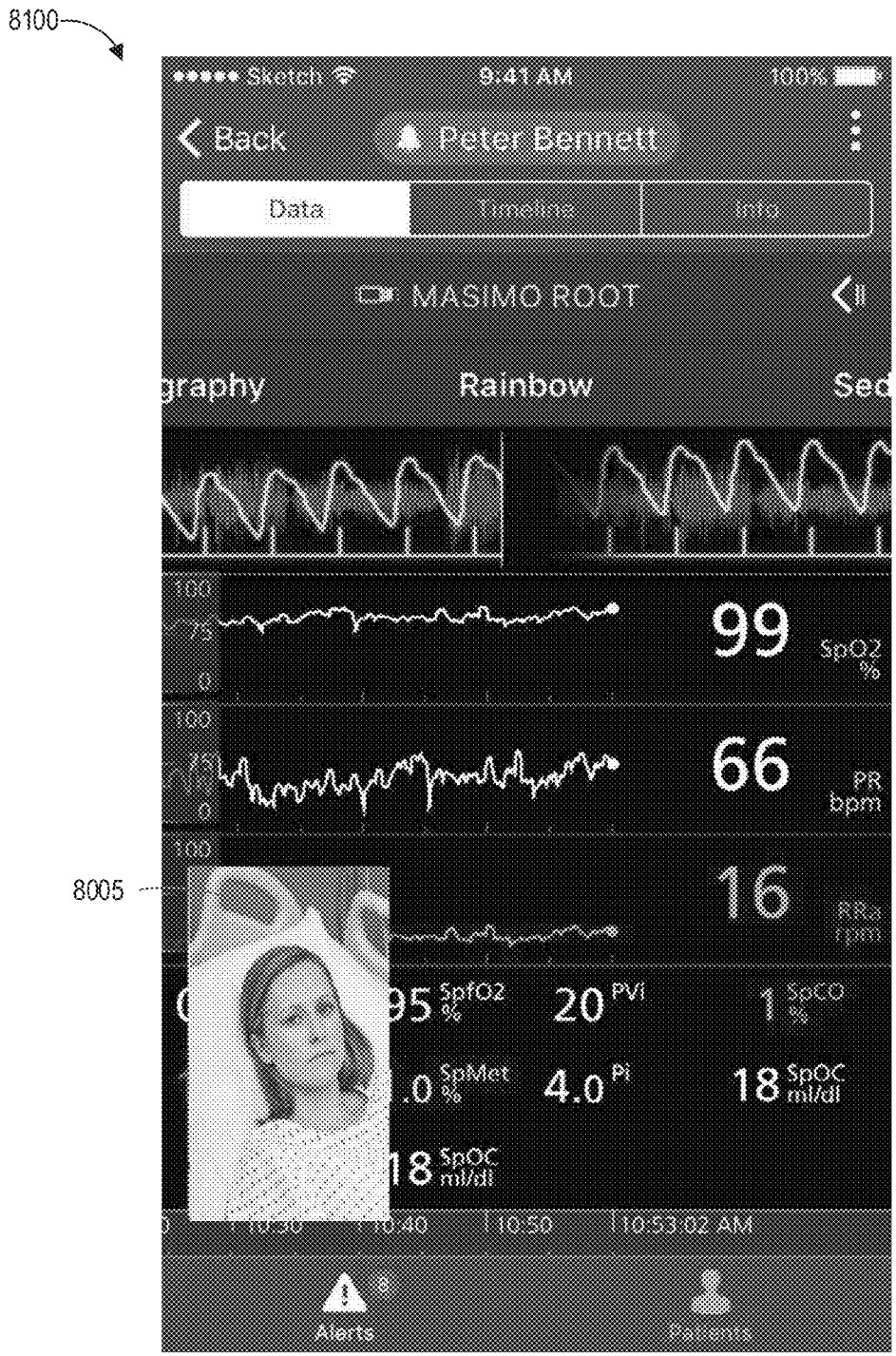

FIG. 81 depicts another example video call user interface 8100. The video call user interface 8100 is similar to the patient data user interface 6600 of FIG. 66, where both user interfaces 8100, 6600 present a patient's physiological parameters. However, in addition to the patient data user interface 6600 of FIG. 66, the video call user interface 8100 can also present the video call area 8005. As shown, the video call area 8005 can be an overlay on top of the presentation of the current user interface screen (here the patient's physiological parameters). As described above with respect to FIG. 80, user selection of the toggle user interface element 8001 in FIG. 80 can cause the presentation of the video call area 8005 in FIG. 81 as a minimized version of the larger video call area 8005 of FIG. 80, which can enable the clinician to multitask. User selection (such as a dragging user interaction) of the video call area 8005 can enable the clinician to move the video call area 8005 to a different location of the user interface 8100 (likewise, similar functionality is possible in FIG. 80).

Figure 82:
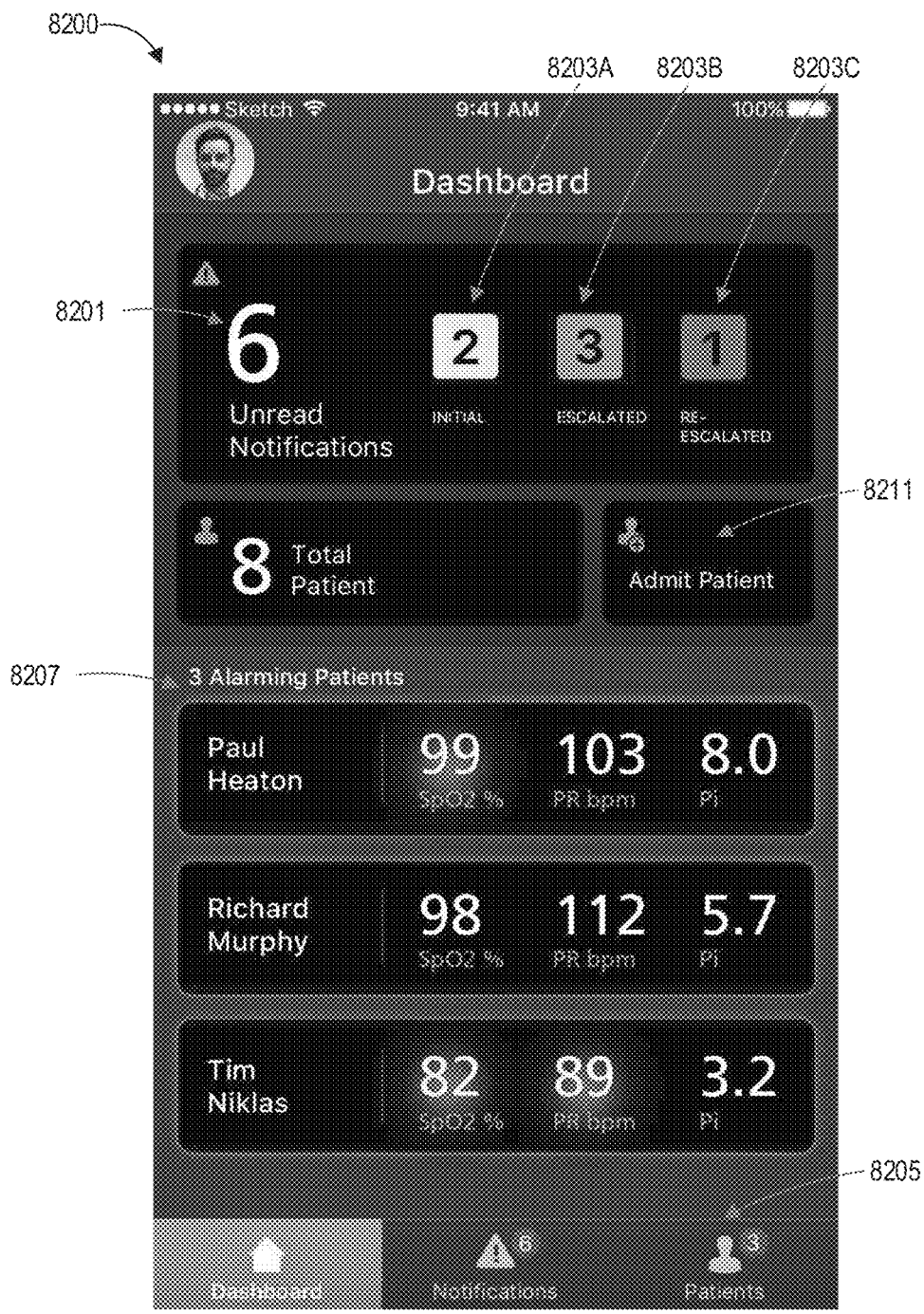
FIG. 82 depicts an example dashboard notification user interface.

FIG. 82 depicts an example dashboard user interface 8200. The dashboard user interface 8200 can provide a summary view of important information for a clinician, such as a number of notifications, the types of notifications, a number of patients, and a number of patients with notifications with an alarming status. The summary view can include summary indicators for notifications, patients, or alarms. The dashboard user interface 8200 can include a first summary indicator 8201 for a first set of notifications that include an unread status. As shown, the first summary indicator 8201 can include a quantity of unread notifications. Each of the notifications with a particular status, such as the unread status, can be categorized by escalation status (such as a status of "initial," "escalated," or "re-escalated"). The dashboard user interface 8200 can include second summary indicators 8203A, 8203B, 8203C for each of the respective categories for the escalation statuses. As described above with respect to FIG. 1, there can be different types of notifications. Different types of notifications can include notifications that correspond to alarms where physiological parameter exceeding a threshold or nonclinical notifications such as a disconnected sensor or a device with a low battery. The dashboard user interface 8200 can include a third summary indicator 8205 for a second set of notifications that include an alarming status, such as notifications that a physiological parameter exceeded a threshold. The dashboard user interface 8200 can also include alarm tiles 8207 for the second set of notifications that include an alarming status.

The dashboard user interface 8200 can also include on admit patient user interface element 8211. The admit patient user interface element 8211 can enable a clinician to admit a patient to a particular device using the clinician device. User selection of the admit patient user interface element 8211 can initiate a process to admit the patient, such as initiating a scanner process on the clinician device. Example scanner processes include barcode technology for linear or two-dimensional barcode scanners. Thus, a clinician can scan one or more of a patient wristband or a barcode on a patient device as part of the admitting process. The clinician can use a clinician device equipped with a camera, infrared scanner, or the like, or a separate optical scanner to scan the barcode.

Figure 83:
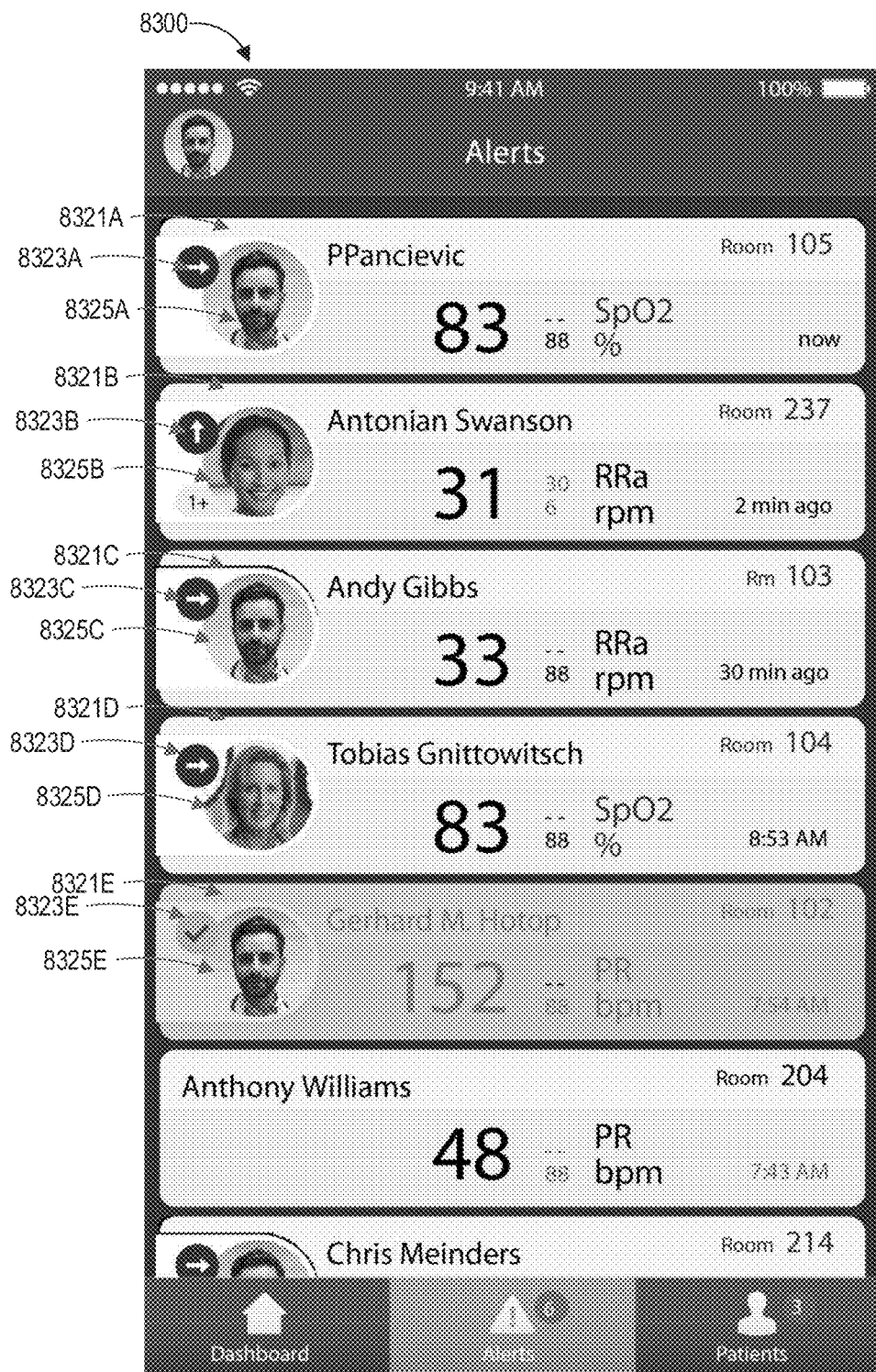
FIGS. 83 through 87 depict additional example notifications user interfaces.

FIG. 83 depicts another example notifications user interface 8300. The notifications user interface 8300 is similar to the notifications screen 800 of FIG. 8, where both the notifications user interface 8300 and the notifications screen 800 can display alarm notifications. The notifications user interface 8300 can include first, second, third, fourth, and fifth alarm notifications 8321A, 8321B, 8321C, 8321D, 8321E, which can be similar to the alarm notifications 810 of FIG. 8. In addition to the alarm notifications 810 of FIG. 8, each of the alarm notifications 8321A, 8321B, 8321C, 8321D, 8321E can include the assignment indicators 8323A, 8323B, 8323C, 8323D, 8323E, respectively. Each of the assignment indicators 8323A, 8323B, 8323C, 8323D, 8323E can indicate an assignment status for each of the alarm notifications 8321A, 8321B, 8321C, 8321D, 8321E. Each of the assignment indicators 8323A, 8323B, 8323C, 8323D, 8323E can also include a depicted clinician 8325A, 8325B, 8325C, 8325D, 8325E, respectively. The first assignment indicator 8323A (which includes a horizontal arrow) for the first notification 8321A can indicate that the first notification 8321A has been forwarded to the first depicted clinician 8325A. The second assignment indicator 8323B (which includes a vertical arrow) for the second notification 8321B can indicate that the second notification 8321B has been escalated to the second depicted clinician 8325B. The fifth assignment indicator 8323E (which includes a checkmark) for the second notification 8321E can indicate that the second notification 8321E has been accepted by the fifth depicted clinician 8325E.

Figure 84:
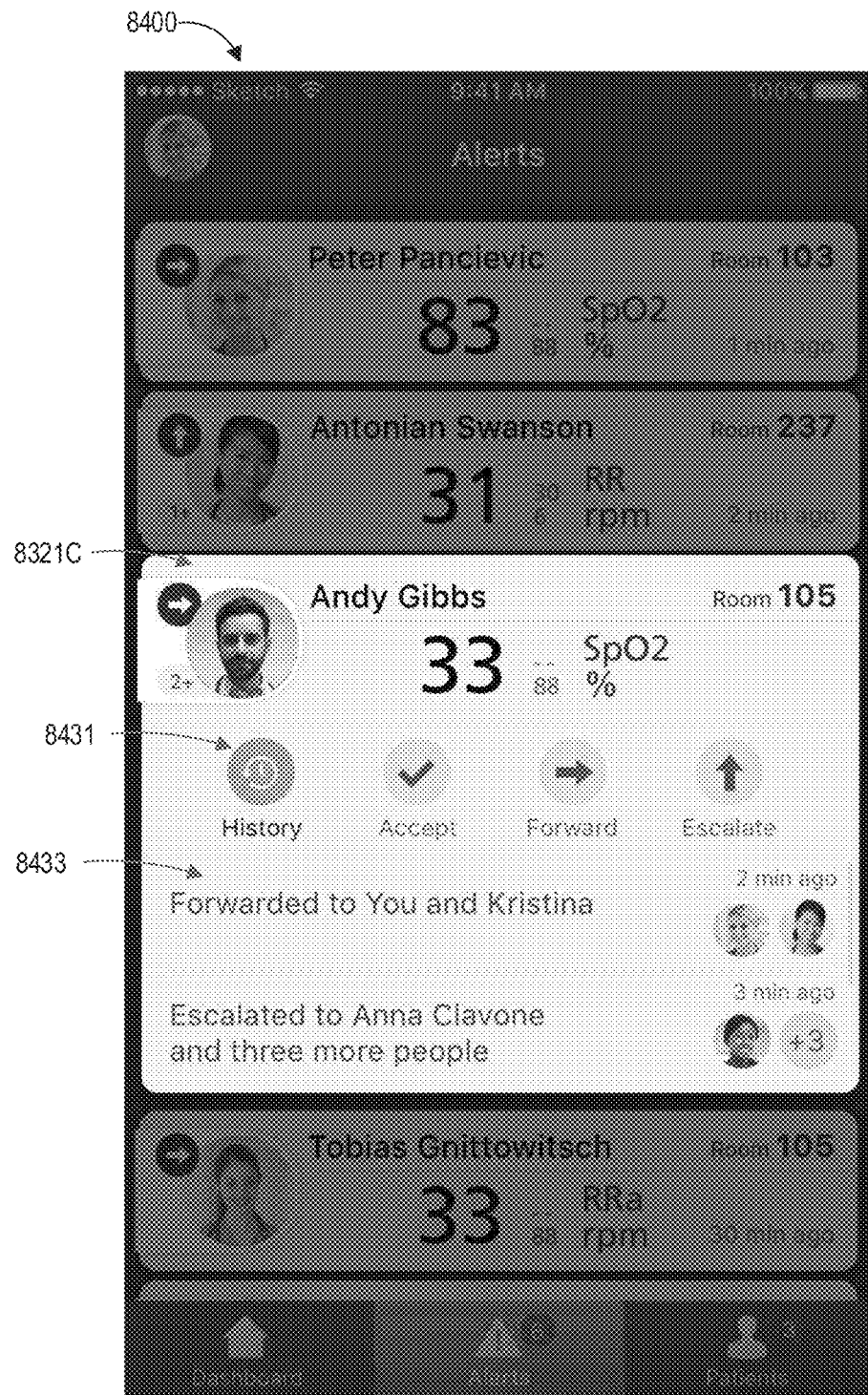

FIG. 84 depicts another example notifications user interface 8400. The notifications user interface 8400 of FIG. 84 is similar to the notifications user interface 8300 of FIG. 83. However, in addition to the notifications user interface 8300 of FIG. 83, the notifications user interface 8400 of FIG. 84 can include an expanded view of the alarm notification 8321C. In response to a user selection of the alarm notification 8321C in FIG. 83, the notifications user interface 8400 can present the expanded view of the alarm notification 8321C. The expanded view of the alarm notification 8321C can include user interface elements, such as the history user interface element 8431. In response to a user selection of the history user interface element 8431, the expanded view of the alarm notification 8321C can present the notification history of the alarm notification 8321C, such as "Forwarded to You and Kristina" and "Escalated to Anna Clavone and three more people," with corresponding time data associated with each history event.

Figure 85:
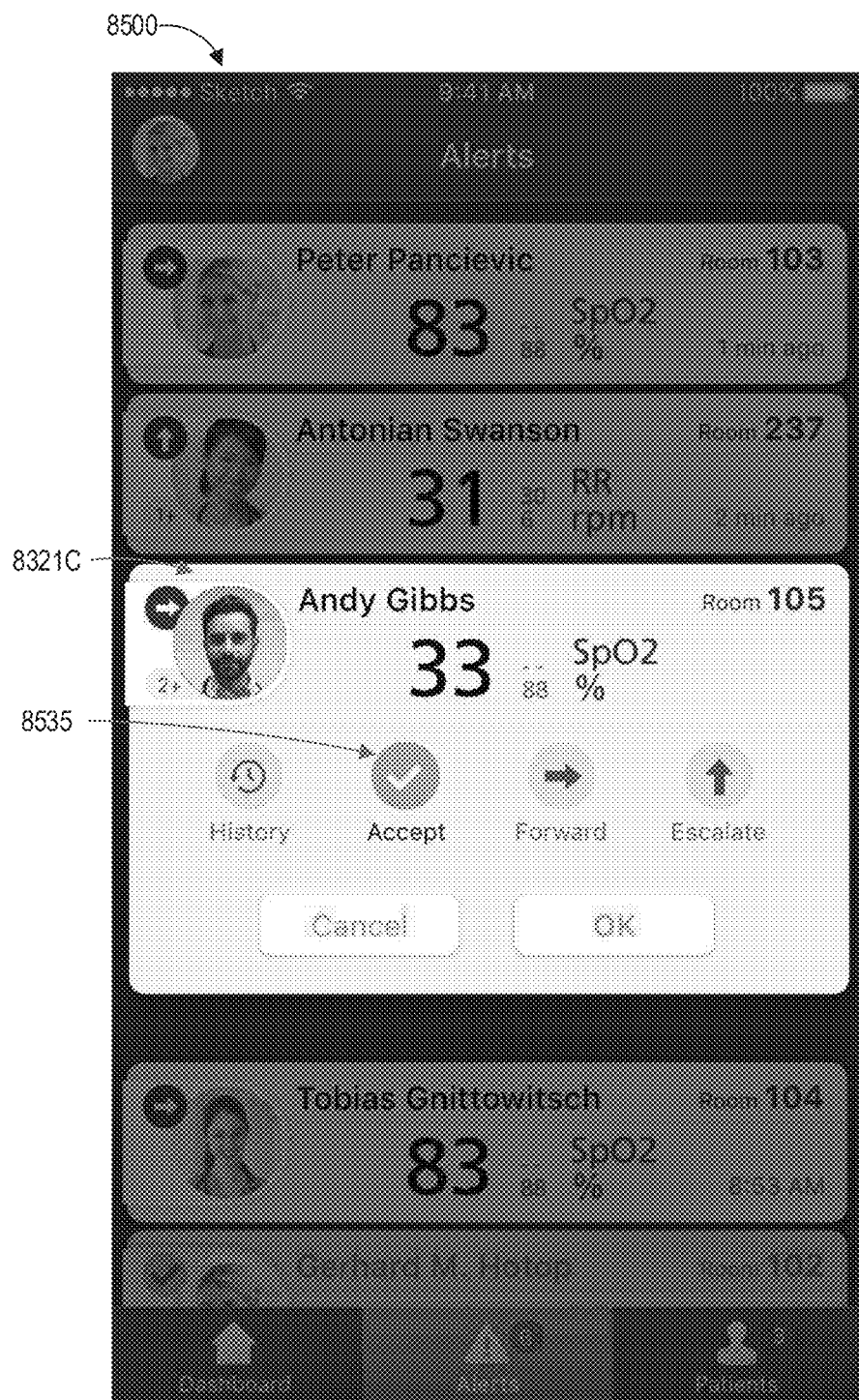

FIG. 85 depicts another example notifications user interface 8500. The notifications user interface 8500 of FIG. 85 is similar to the notifications user interface 8400 of FIG. 84. The expanded view of the alarm notification 8321C can include the accept user interface element 8535. In response to a user selection of the accept user interface element 8535, the alarm notification 8321C can be accepted. Additional details regarding acceptance of a notification are described in further detail above with respect to FIGS. 3 and 10 through 12.

Figure 86:
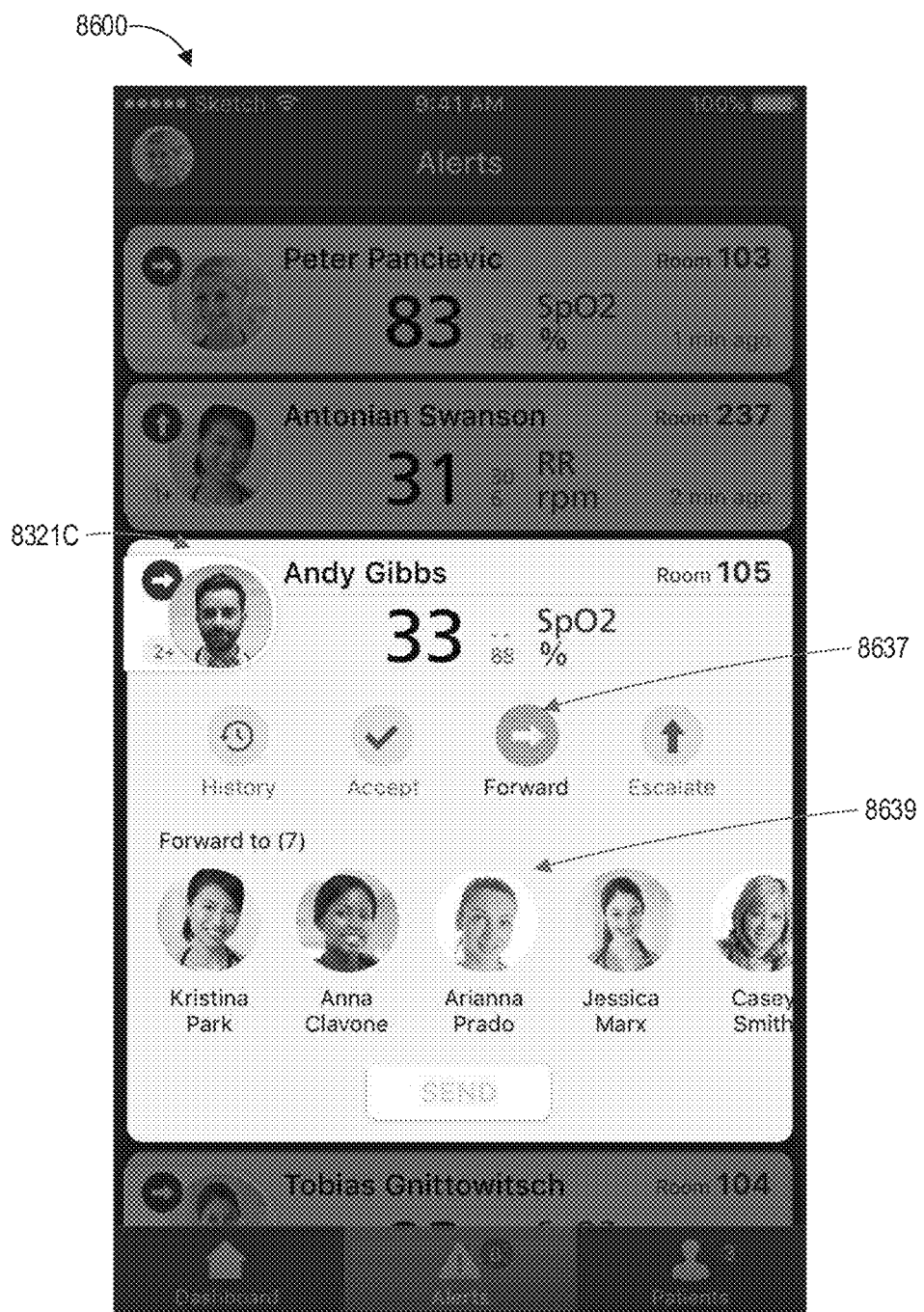

FIG. 86 depicts another example notifications user interface 8600. The notifications user interface 8600 of FIG. 86 is similar to the notifications user interface 8500 of FIG. 85. The expanded view of the alarm notification 8321C can include the forward user interface element 8637. In response to a user selection of the forward user interface element 8637, the notifications user interface 8600 can present the forward notification area 8639. As shown, the forward notification area 8639 can provide one or more other clinicians for selection by the user. The clinician can thus forward the alarm notification 8321C two other clinicians. Additional details regarding boarding a notification are described in further detail above with respect to FIGS. 3 and 10 through 12.

Figure 87:
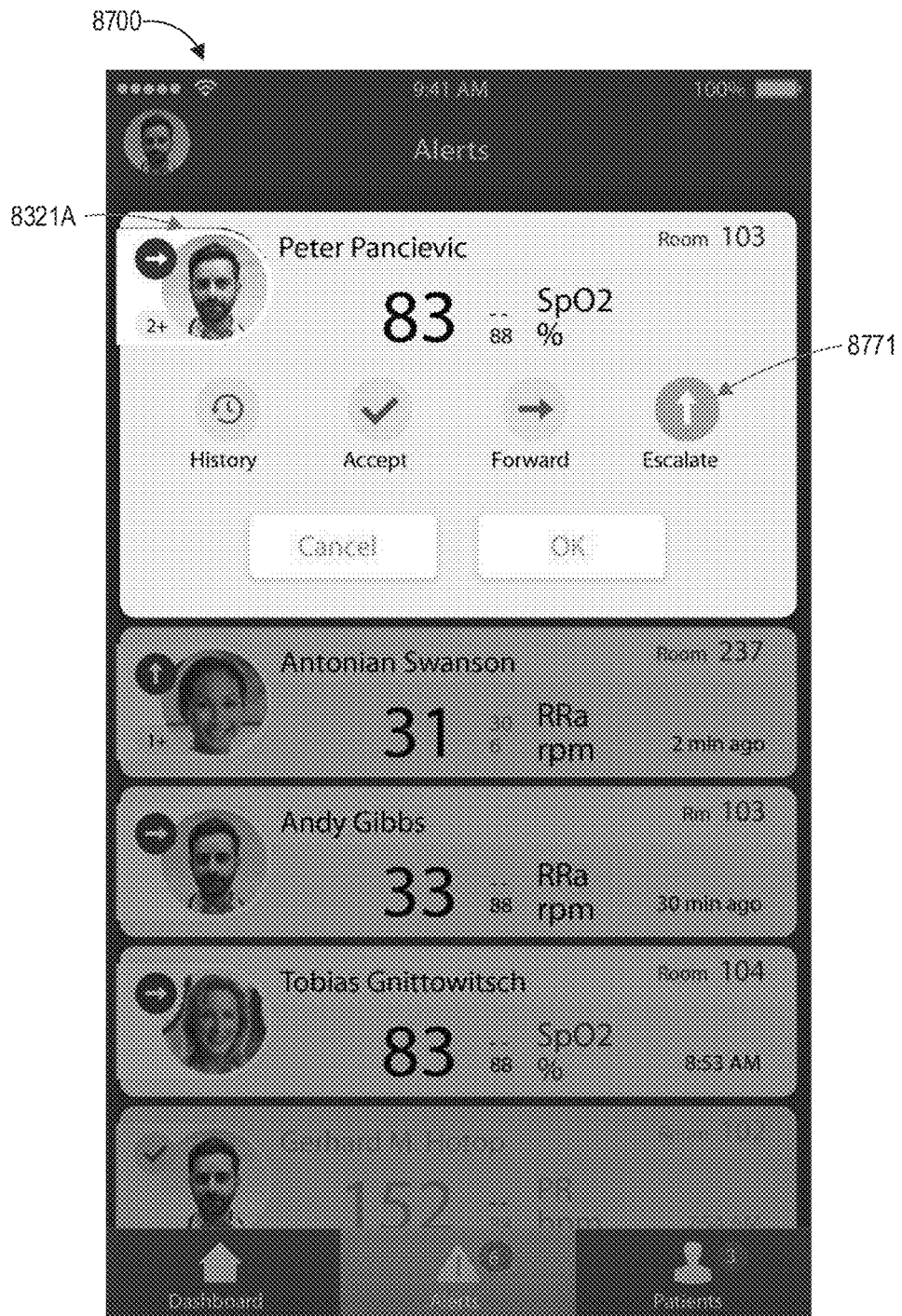

FIG. 87 depicts another example notifications user interface 8700. The notifications user interface 8700 of FIG. 87 is similar to the notifications user interface 8400 of FIG. 84. The expanded view of the alarm notification 8321A can include the escalate user interface element 8771. In response to a user selection of the escalate user interface element 8771, the alarm notification 8321C can be escalated. Additional details regarding escalation of a notification are described in further detail above with respect to FIGS. 3 and 10 through 12.

FIGS. 88 through 91 depict additional example patient data user interfaces. Each of the patient data user interfaces 8800, 8900, 9000, 9100 of FIGS. 88 through 91, respectively, are similar to the patient data user interface 6500 of FIG. 65. However, in addition to the patient data user interface 6500 of FIG. 65, each of the patient data user interfaces 8800, 8900, 9000, 9100 of FIGS. 88 through 91 can include the alarm notification area 8810. The alarm notification area 8810 can be similar to the alarm notification 810 of FIG. 8 described above, in that the alarm notification area 8810 can include an indicator (such as a color) corresponding to the severity of the corresponding alarm notification. Further, the alarm notification area 8810 is on a patient data user interface directly instead of on a separate notification user interface in this example.

Figure 88:
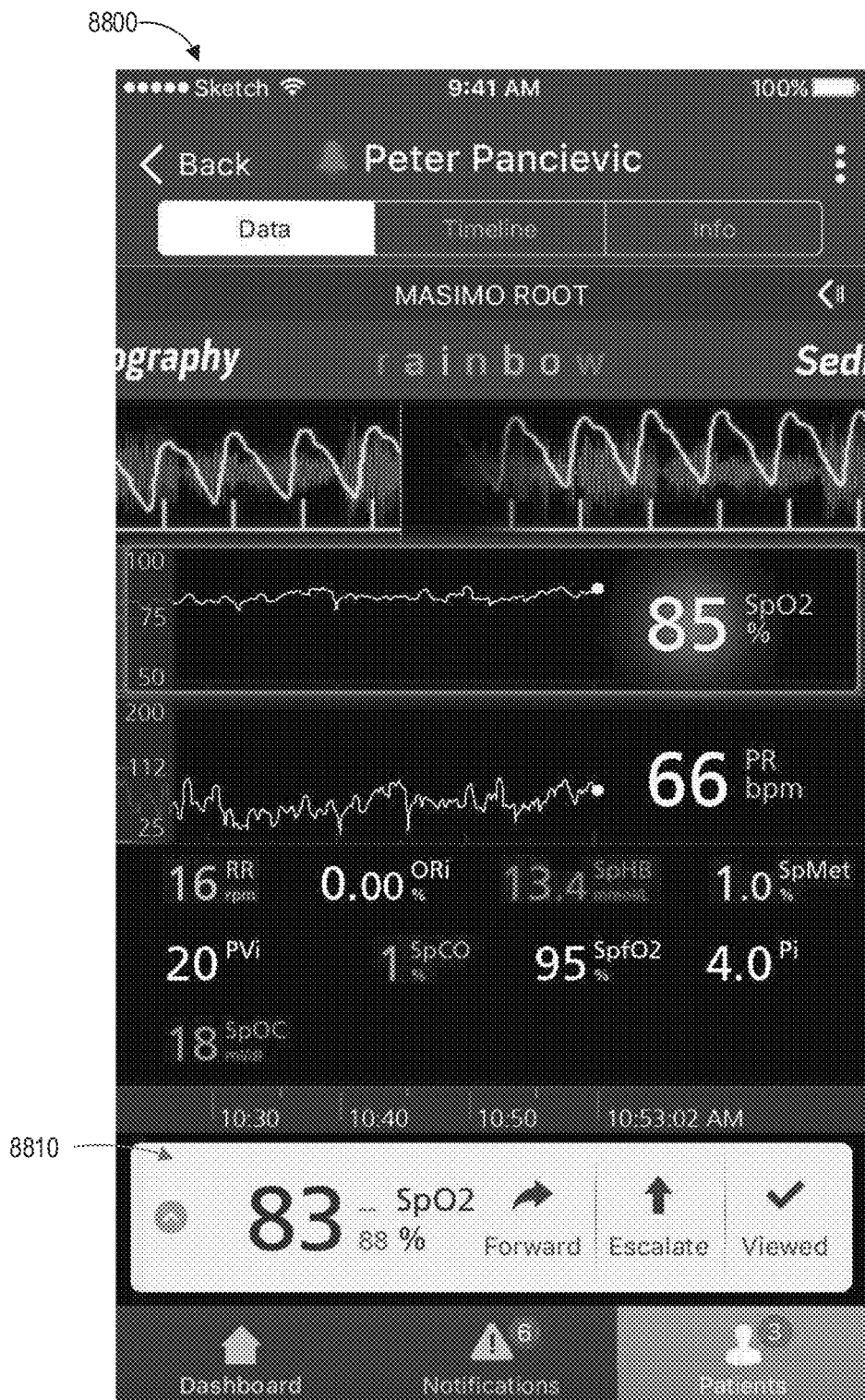
FIGS. 88 through 91 depict additional example patient data user interfaces.
Figure 89:
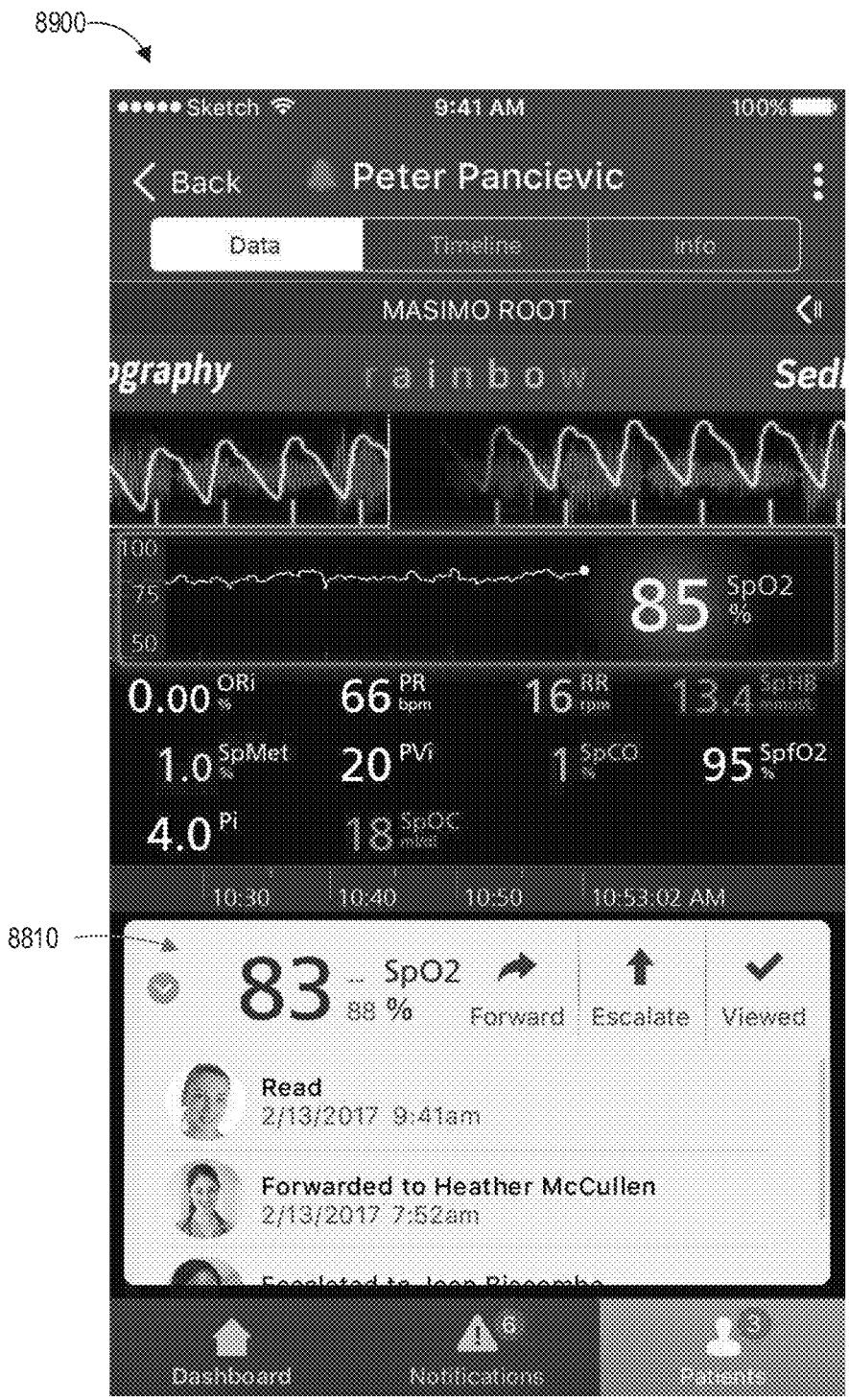
Figure 90:
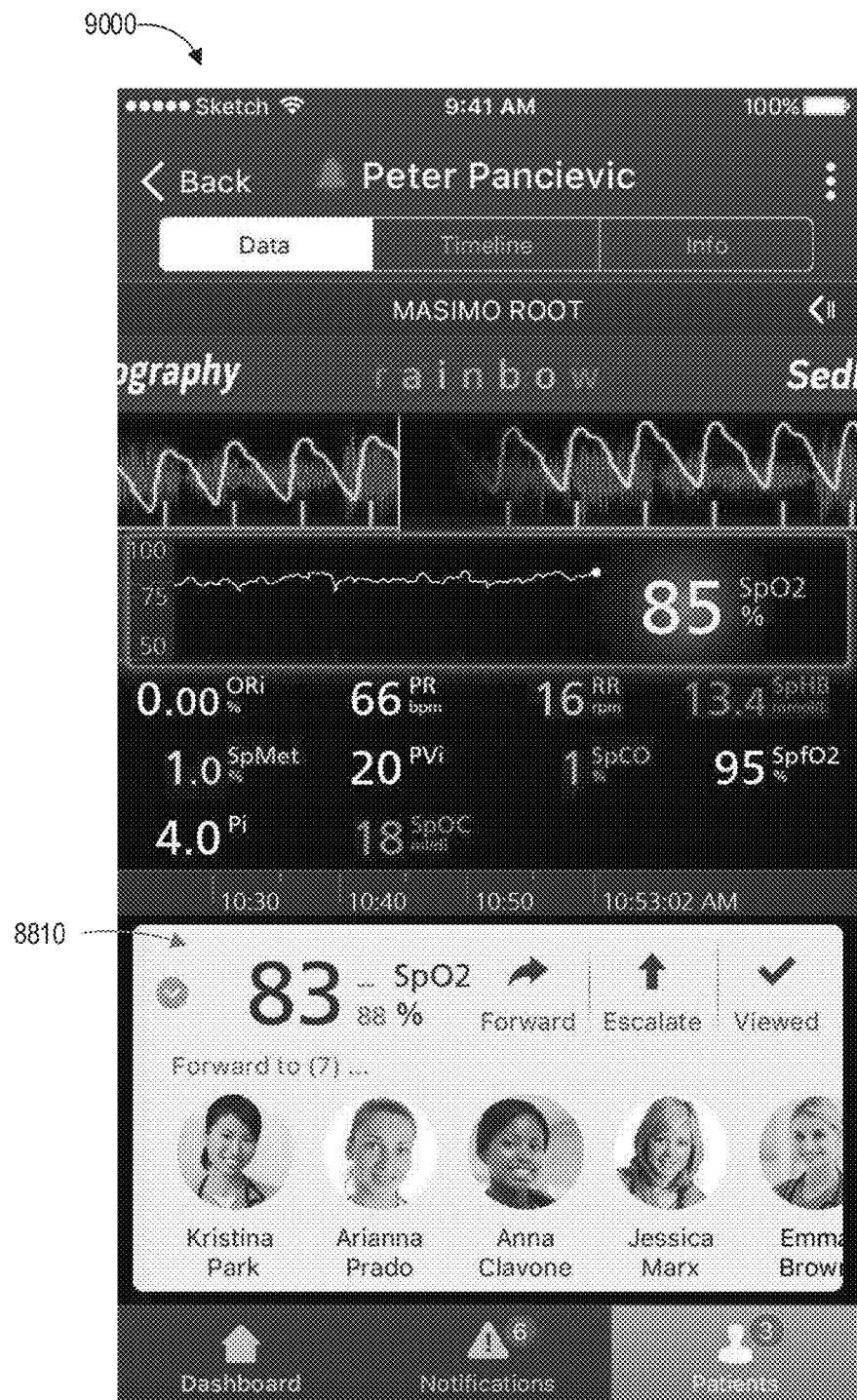
Figure 91:
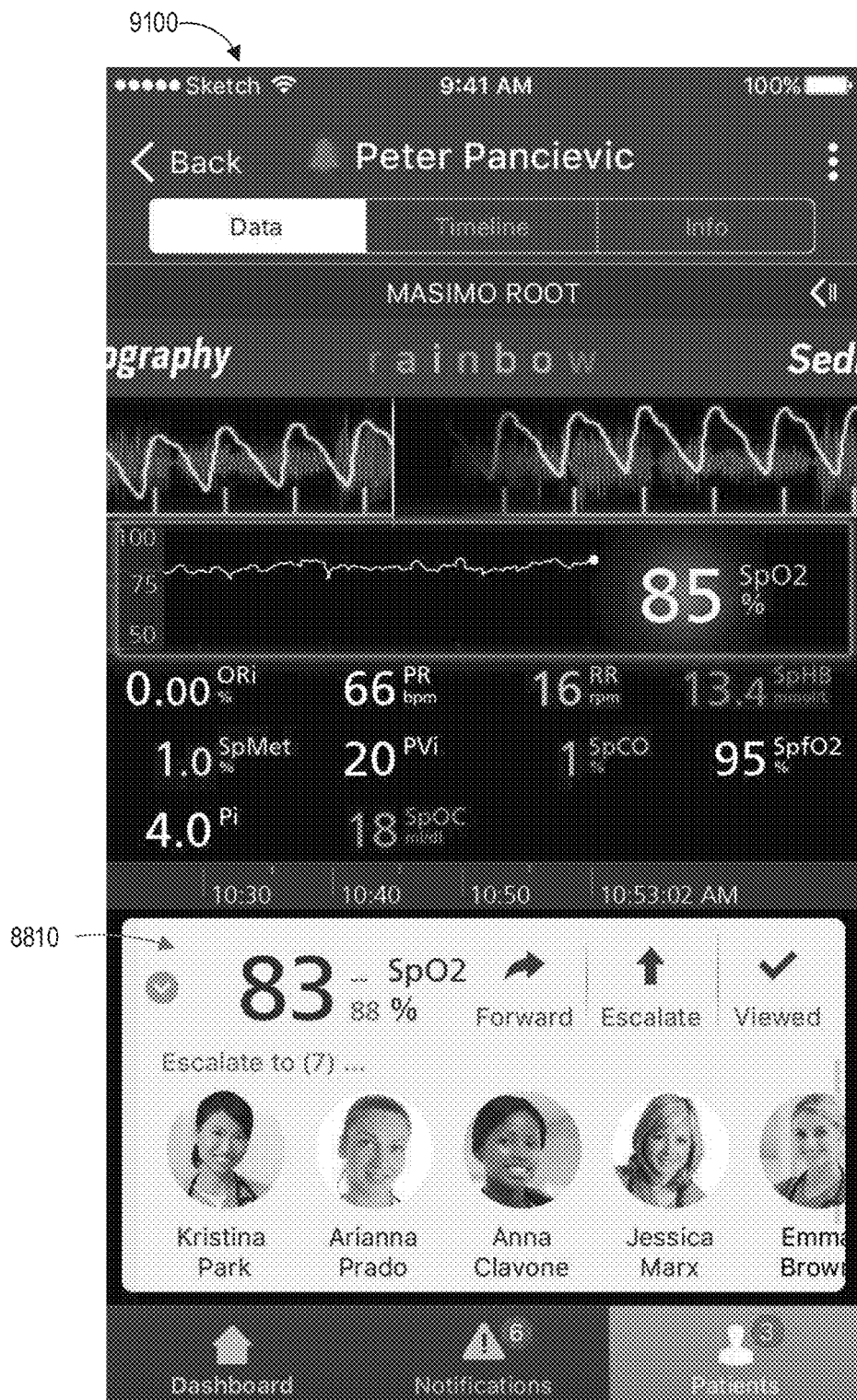

Turning to FIG. 88, the alarm notification area 8810 can include user interface elements to forward or escalate the alarm notification, which is described in further detail above with respect to FIGS. 3 and 10 through 12. Turning to FIG. 89, the alarm notification area 8810 of FIG. 89 is similar to the alarm notification area 8810 of FIG. 88. However, the alarm notification area 8810 of FIG. 89 can include an expanded view of the alarm notification area 8810 (obtained by selecting an arrow on the left of the notification area 8810 in FIG. 88). The expanded view of the alarm notification area 8810 can present a history of events associated with the corresponding alarm notification, such as when the alarm notification was read by other clinicians or was forwarded to other clinicians. Turning to FIG. 90, the alarm notification area 8810 of FIG. 90 is similar to the alarm notification area 8810 of FIG. 89. However, the expanded view of the alarm notification area 8810 of FIG. 90 can include a list of other clinicians that can be forwarded the corresponding alarm notification by the user of the clinician device. Turning to FIG. 91, the alarm notification area 8810 of FIG. 91 is similar to the alarm notification area 8810 of FIG. 89. However, the expanded view of the alarm notification area 8810 of FIG. 91 can include a list of other clinicians that can receive the corresponding alarm notification as escalated by the user of the clinician device.

Figure 92:
FIGS. 92 through 93 depict example patient card user interfaces.

FIG. 92 depicts an example patient card user interface 9200. The patient card user interface 9200 can include the patient card 9251 for the patient (in this example, "Peter Pancievic"). The patient card user interface 9200 and the patient card 9251 can include user interface elements and functionality that are similar to other user interface elements and functionality described above. Similar to the alarm notification 810 of FIG. 8 described above that can include an indicator (such as a color) corresponding to the severity of a respective alarm notification, if the patient has an alarm notification the patient card 9251 can include an indicator (such as a color or alert icon) corresponding to the severity of the respective alarm notification. Here, the patient card 8251 can include a visual indicator that includes the color red and an alert icon for a state such as an escalated state for the corresponding alarm notification. Similar to user selection of the selectable elements 6341, 6343, 6345 of FIG. 63, user selection of the first, second, and third selectable elements 6341 6343, 6345 of FIG. 92 can cause the presentation of additional user interfaces related to editing patient information, adding or editing patient notes, and video calling the patient, respectively.

Similar to user selection of the discharge element 6219 of FIG. 62, user selection of the fourth selectable element 6219 of FIG. 92 can cause a device to discharge the patient or can cause presentation of a user interface to discharge the patient from a device. The patient card 9251 can also include patient information 9253, physiological parameter values 9255, and a timeline 9257. The timeline 9257 can be similar to the timeline user interface 6900 described in greater detail above with respect to FIG. 69. The patient card 9251 can provide a summary of information that is useful to a clinician to efficiently review the status of the patient on the clinician device. The patient card user interface 9200 can include a navigation bar 9259 that enables a clinician to select an element from the navigation bar 9259 to view a different patient card. As shown, the navigation bar 9259 can further include visual indicators (such as a color-coded dot) that identify which of the corresponding patient cards that have an alarm notification.

Figure 93:
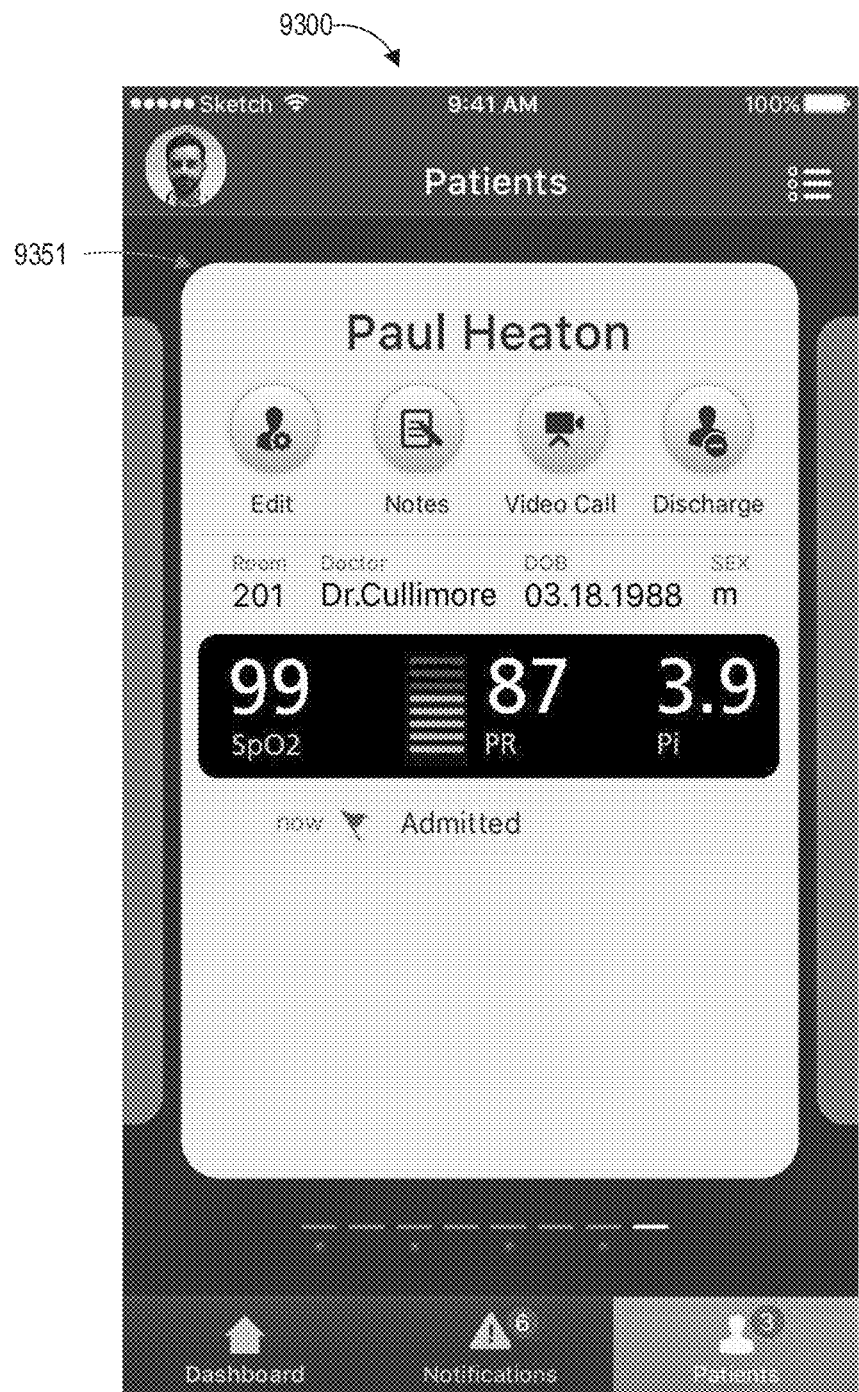

FIG. 93 depicts another example patient card user interface 9300. The patient card user interface 9300 of FIG. 93 is similar to the patient card user interface 9200 of FIG. 92. The patient card 9351 of FIG. 93 can include similar user interface elements as the user interface elements of the patient card 9251 of FIG. 92. However, in contrast to the patient card 9251 of FIG. 92 that included an alarm notification and corresponding visual indicator(s) of the alarm, the patient card 9351 of FIG. 93 may not include an alarm notification and thus corresponding visual indicator(s) for an alarm are not presented. As described above with respect to the navigation bar 9259 in FIG. 92, the patient card user interface 9300 can present the patient card 9351 in response to a user selection of a corresponding element in the navigation bar 9259.

Figure 94:
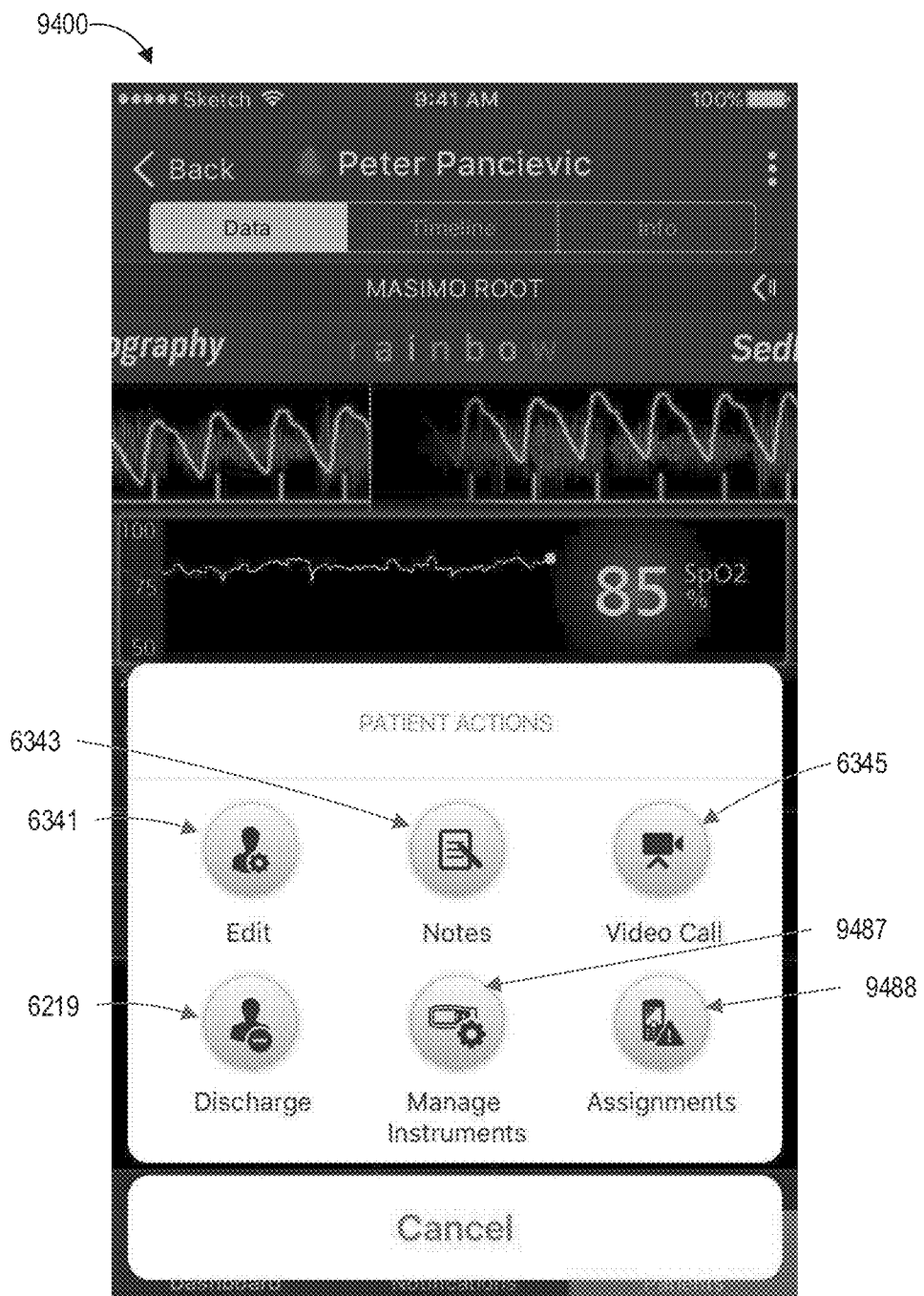
FIG. 94 depicts another example patient action user interface.

FIG. 94 depicts another example patient action user interface 9400. The patient action user interface 9400 of FIG. 94 is similar to the patient action user interface 7300 of FIG. 73. The four selectable elements 6341, 6343, 6345, 6219 of FIG. 94 for editing, note taking, video calling, and discharging, respectively, can be similar to the four selectable elements 6341, 6343, 6345, 6219 of FIG. 73. However, in addition to the user interface elements of the patient action user interface 7300 of FIG. 73, the patient action user interface 9400 of FIG. 94 can include a manage devices selectable element 9487 and an assignments selectable element 9488. In response to a user selection of the manage devices selectable element 9487, the patient action user interface 9400 can present a manage devices user interface, which is described in further detail below with respect to FIGS. 97 through 106. In response to a user selection of the assignments selectable element 9488, the patient action user interface 9400 can present an assignments user interface, which is described in further detail below with respect to FIG. 106.

Figure 95:
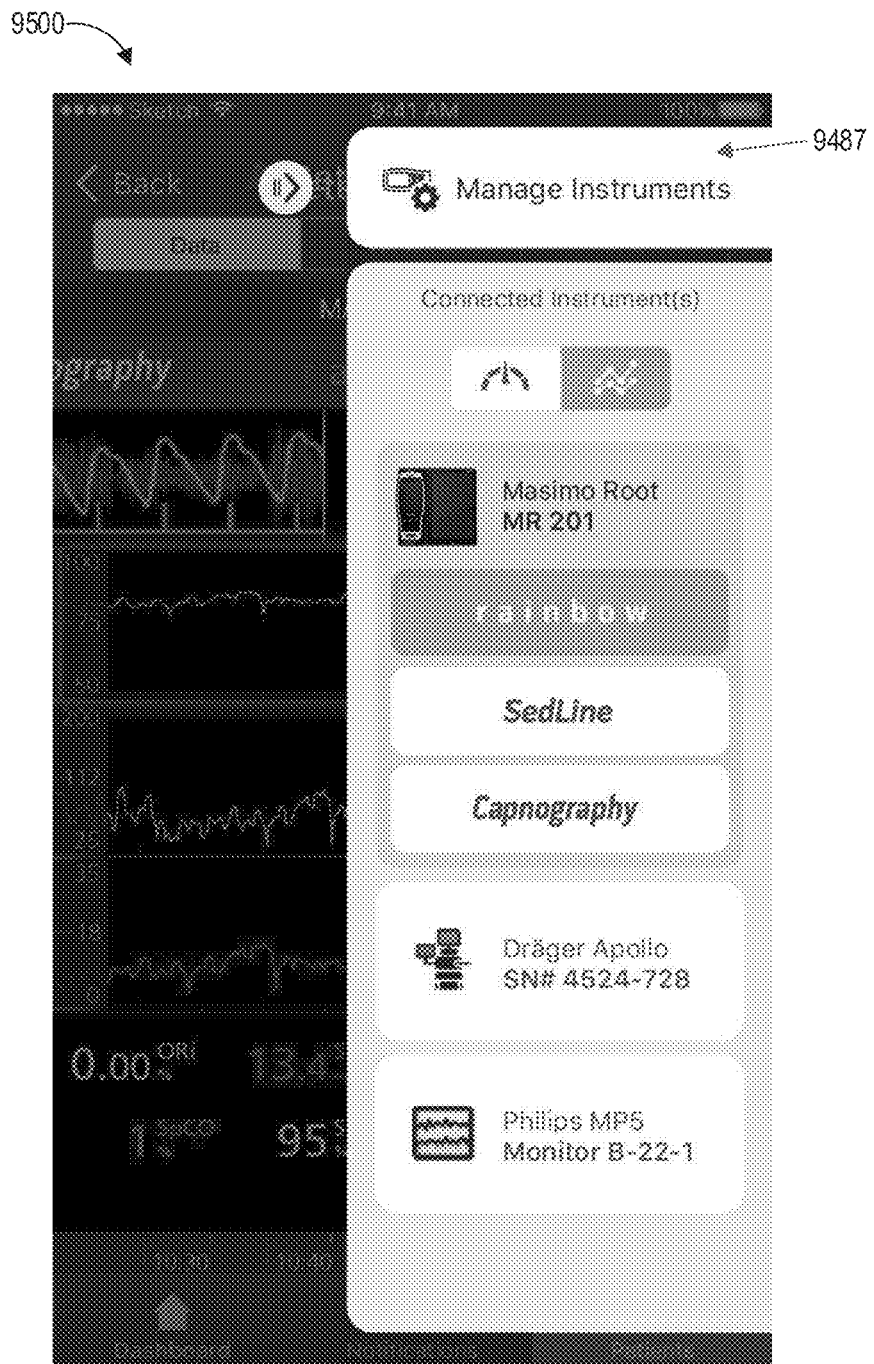
FIG. 95 depicts another example patient data user interface.

FIG. 95 depicts another example patient data user interface 9500. The patient data user interface 9500 of FIG. 95 is similar to the patient data user interface 6700 of FIG. 67, where both patient data user interfaces 9500, 6700 can present use interface controls associated with one or more devices. In addition to the patient data user interface 6700 of FIG. 67, the patient data user interface 9500 of FIG. 95 can include a manage devices selectable element 9487. The manage devices selectable element 9487 of FIG. 95 can be similar to the manage devices selectable element 9487 of FIG. 94 described above in that user selection of either element can cause presentation of a manage devices user interface, which is described in further detail below with respect to FIGS. 97 through 106.

Figure 96:
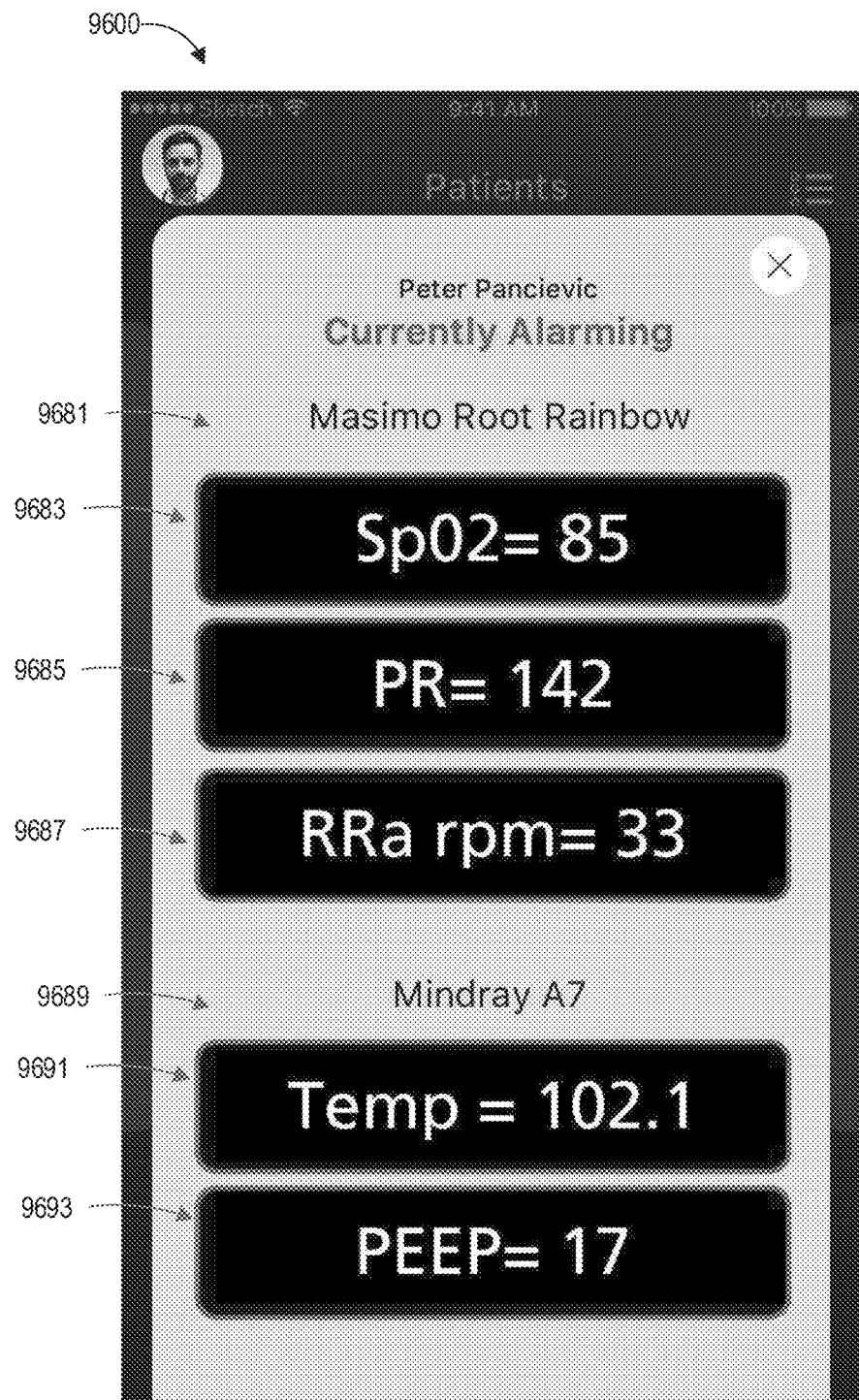
FIG. 96 depicts an example patient alarming user interface.

FIG. 96 depicts an example patient alarming user interface 9600. The patient alarming user interface 9600 can include visual representations for the alarm notifications 9683, 9685, 9687, 9691, 9693 for a particular patient (here, "Peter Pancievic"). The alarm notifications 9683, 9685, 9687, 9691, 9693 can further be for current alarms and not past historical alarms. The patient alarming user interface 9600 can further group the alarm notifications 9683, 9685, 9687, 9691, 9693 by patient device, such as a point-of-care device. The first set of alarm notifications 9683, 9685, 9687 are associated with a first patient device (here "Masimo Root Rainbow") and are grouped under the first device label 9681. The second set of alarm notifications 9691, 9693 are associated with a second patient device (here "Mindray A7") and are grouped under the second device label 9689. As shown, each of the alarm notifications 9683, 9685, 9687, 9691, 9693 include a measured physiological parameter value corresponding to the patient. The patient alarming user interface 9600 can thus provide a summary view of alarms with physiological parameter values grouped by device to the clinician, which can advantageously allow the clinician to efficiently assess and review the patient's medical condition. The patient alarming user interface 9600 can be customizable by the clinician. Further, the customization of the patient alarming user interface 9600 can be specific to a particular user and can be persisted. For example, a clinician can select which device alarms to view, the layout of the alarms, or any other type of customization. The user interface 9600 may popup and overlay any other display herein in response to the alarms being received at the clinician device from the patient devices shown.

Figure 97:
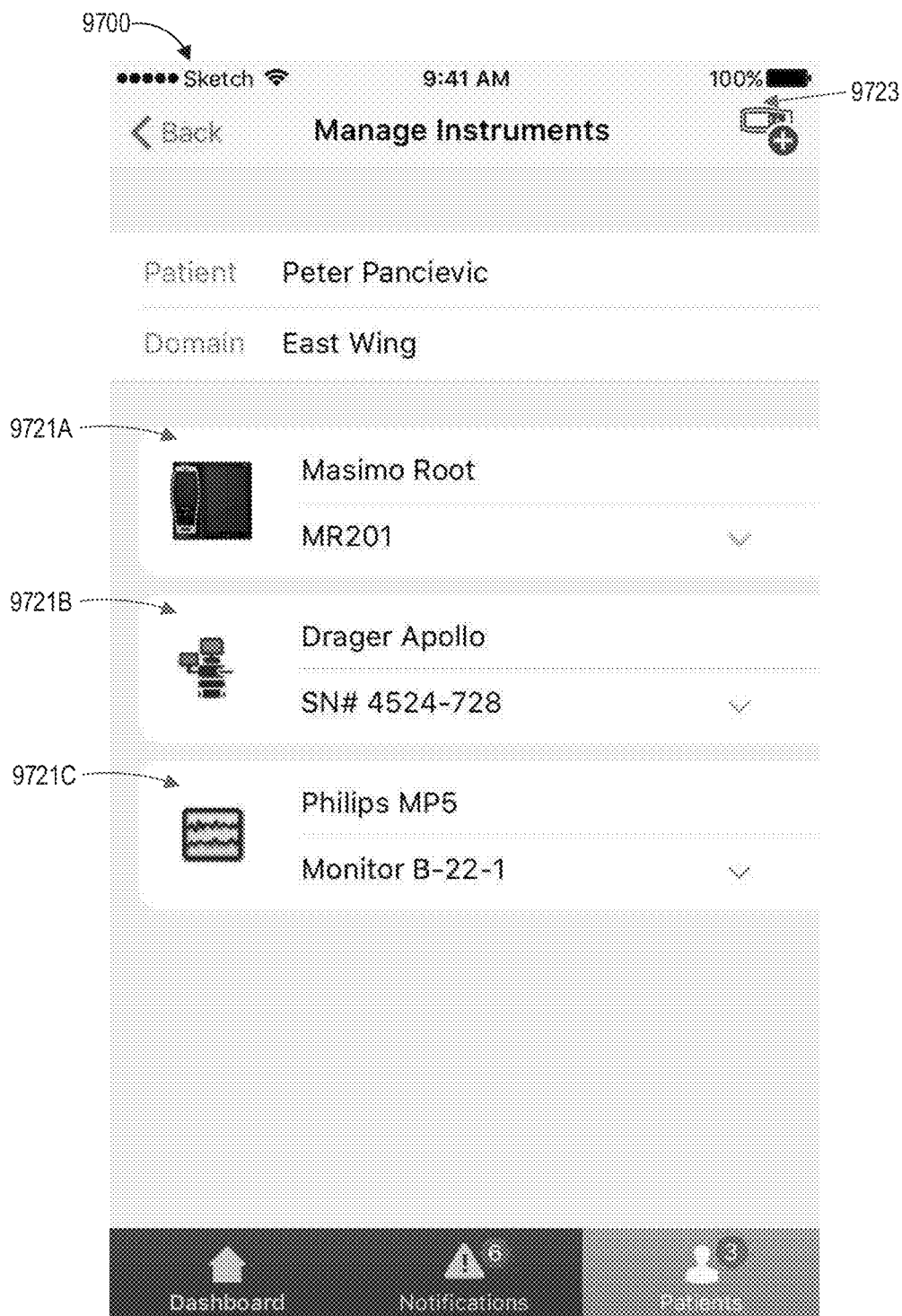
FIGS. 97 through 106 depict example manage devices user interfaces.

FIGS. 97 through 106 depict example manage devices user interfaces. A clinician using manage devices user interface(s) of FIGS. 97 through 106 can discharge a patient from a patient device, set alarm settings for the patient and patient device, admit the patient to a patient device, or assign one or more clinicians to the patient. Thus, the user interface(s) of FIGS. 97 through 106 can advantageously enable a clinician to manage patients and devices through their clinician device. Turning to FIG. 97, the manage devices user interface 9700 includes user interface elements to manage one or more patient devices for a patient (here, "Peter Pancievic"), such as the first, second, and third representations 9721A, 9721B, 9721C for first, second, and third patient devices, respectively. The manage devices user interface 9700 also includes an add device selectable element 9723.

Figure 98:
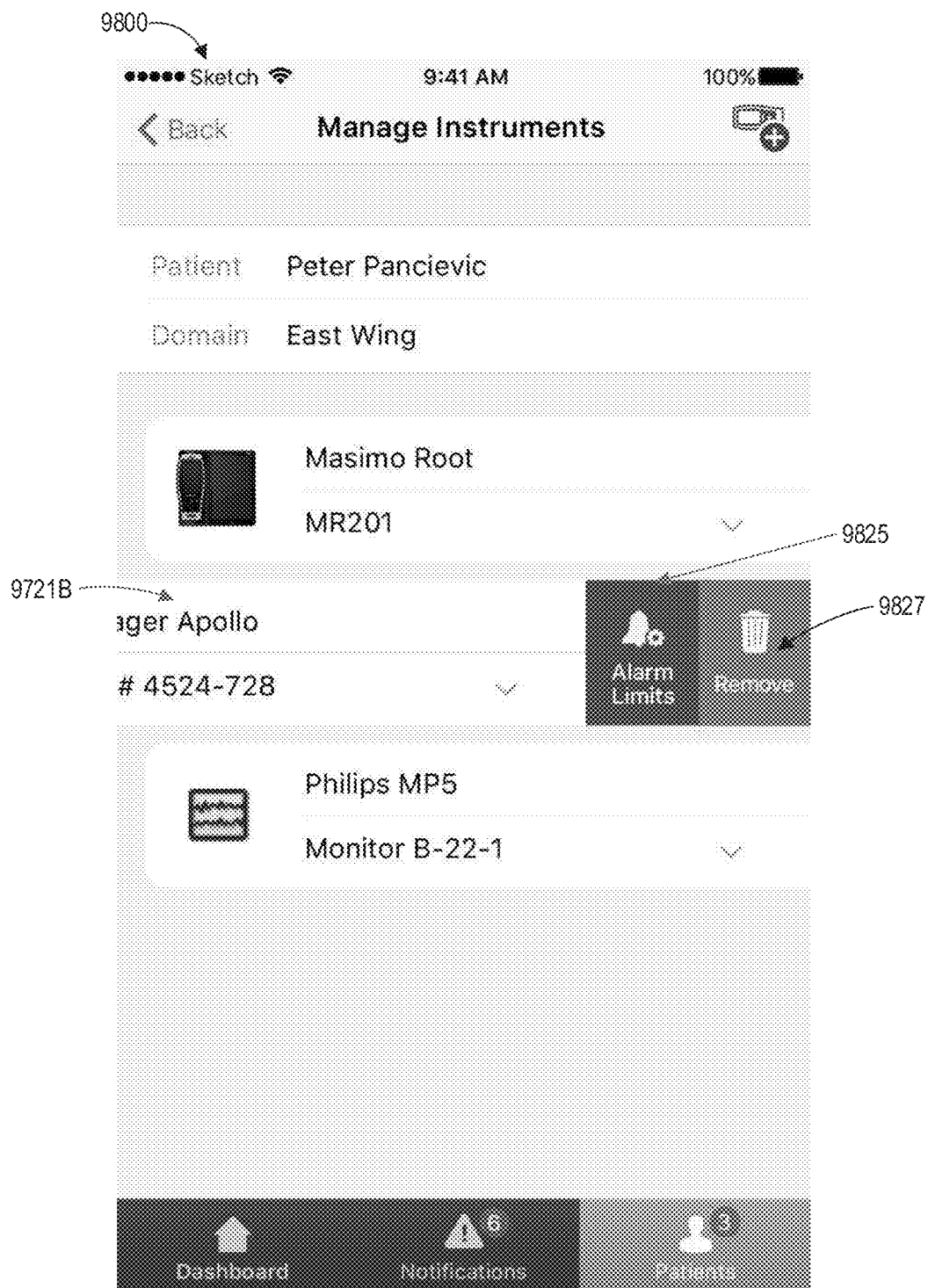

Turning to FIG. 98, another example manage devices user interface 9800 is shown which is similar to the manage devices user interface 9700 of FIG. 97. However, in addition to the manage devices user interface 9700 of FIG. 97, the manage devices user interface 9800 of FIG. 98 can include additional user interface elements 9825, 9827 associated with the second representations 9721B for the second patient device (here, "Drager Apollo"). A user selection of the alarm settings user interface element 9825 can cause the manage devices user interface 9800 to present an alarm settings user interface, which is described below with respect to FIGS. 100 through 103. The remove user interface element 9827 can be similar to the discharge element 6219 of FIG. 62 in that user selection of the user interface element 9827 can cause the patient to be discharged from the corresponding patient device.

Figure 99:
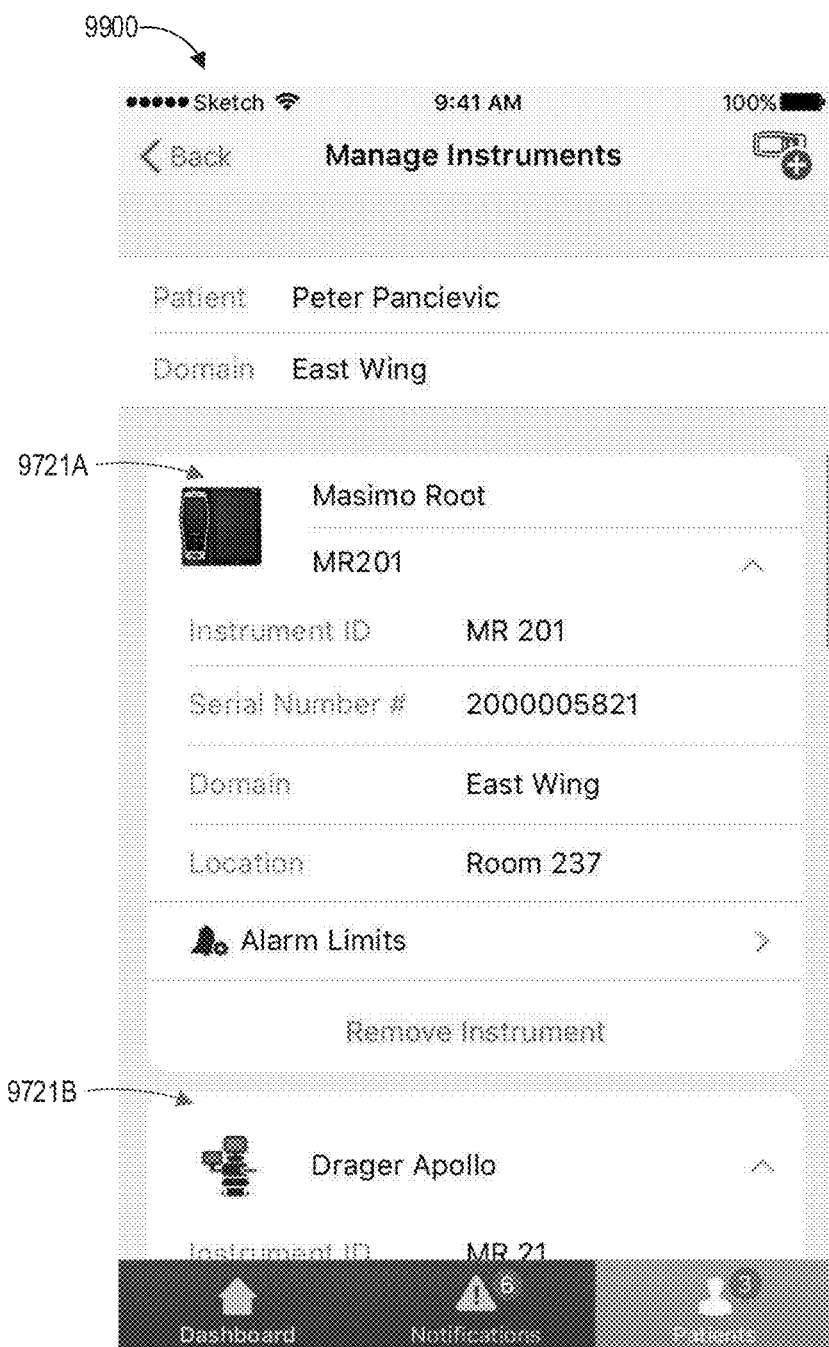

Turning to FIG. 99, another example manage devices user interface 9900 is shown which is similar to the manage devices user interface 9700 of FIG. 97. However, in contrast to the manage devices user interface 9700 of FIG. 97, the manage devices user interface 9800 of FIG. 98 can present an expanded view that includes additional information regarding patient devices. The first representation 9721A in FIG. 99 includes an expanded view for the first patient device (here, "Masimo Root") that presents additional information regarding the first patient device, such as one or more identifiers (such as an instrument identifier or a serial number), a domain, or a location (such as a room number) for the patient device. While not shown, the expanded view can include additional identifying information for the first patient device, which can facilitate device management by the clinician.

Figure 100:
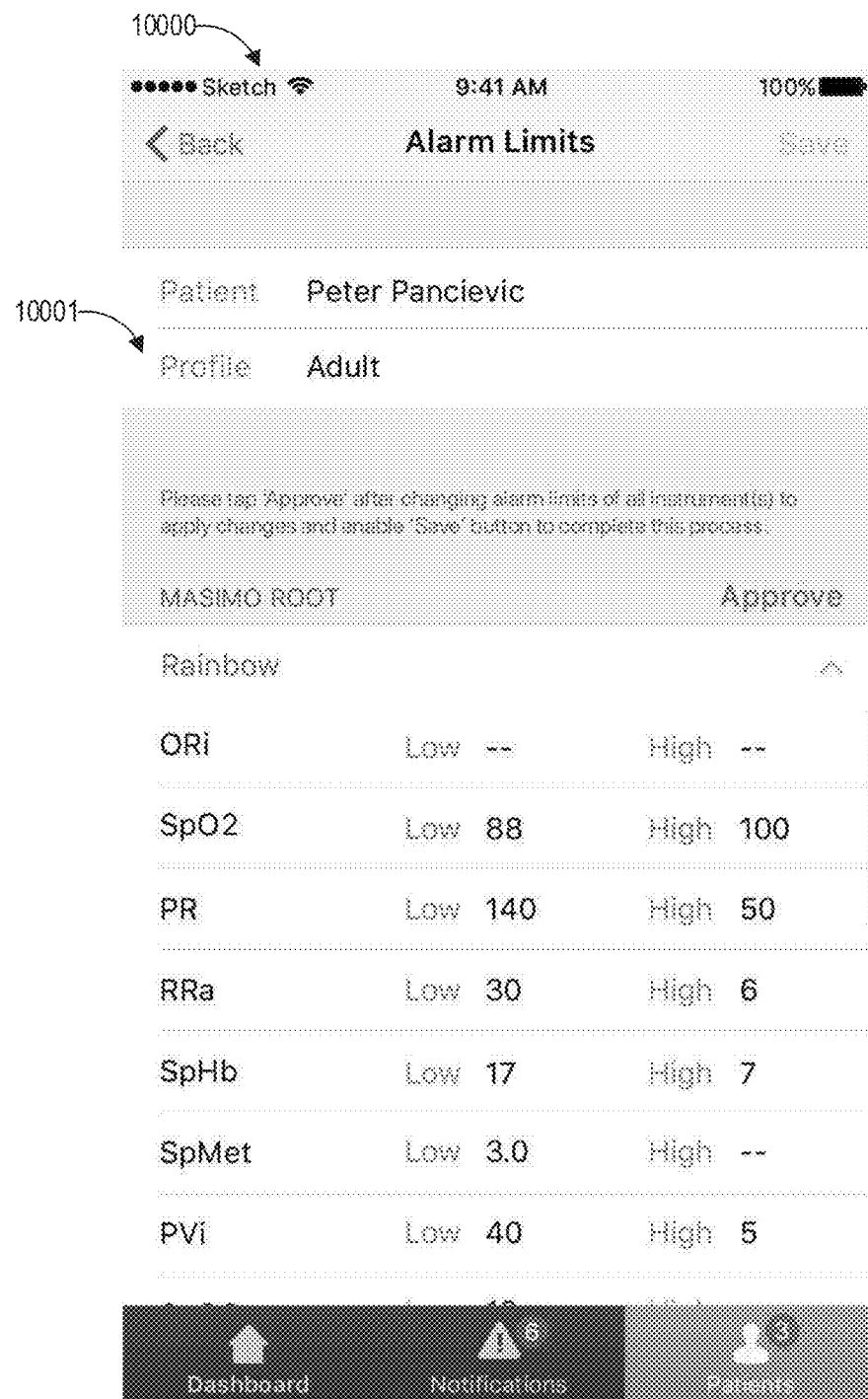

Turning to FIG. 100, an example alarm settings user interface 10000 is shown. As described above with respect to FIG. 98, a user selection of the alarm settings user interface element 9825 of FIG. 98 can cause the presentation of the alarm settings user interface 10000. The alarm settings user interface 10000 can be similar to the alarm settings screens 1900, 1950 described above with respect to FIGS. 19A and 19B. A clinician can set one or more alarm limits for the patient and the patient device using the alarm settings user interface 10000. However, in addition to the alarm settings screens 1900, 1950 of FIGS. 19A and 19B, the alarm settings user interface 10000 can include a profile element 10001. In some embodiments, a profile can be associated with predefined alarm settings such that user selection of a profile for a patient can cause the alarm settings user interface 10000 specified default threshold parameters for the alarm settings. For example, a selected adult profile can have predefined adult device settings for common thresholds of some adults. Example profiles include, but are not limited to, a pediatric profile, a neonatal profile, and the like, each of which can have different predefined settings that can be retrieved when selected for a particular patient.

Figure 101:
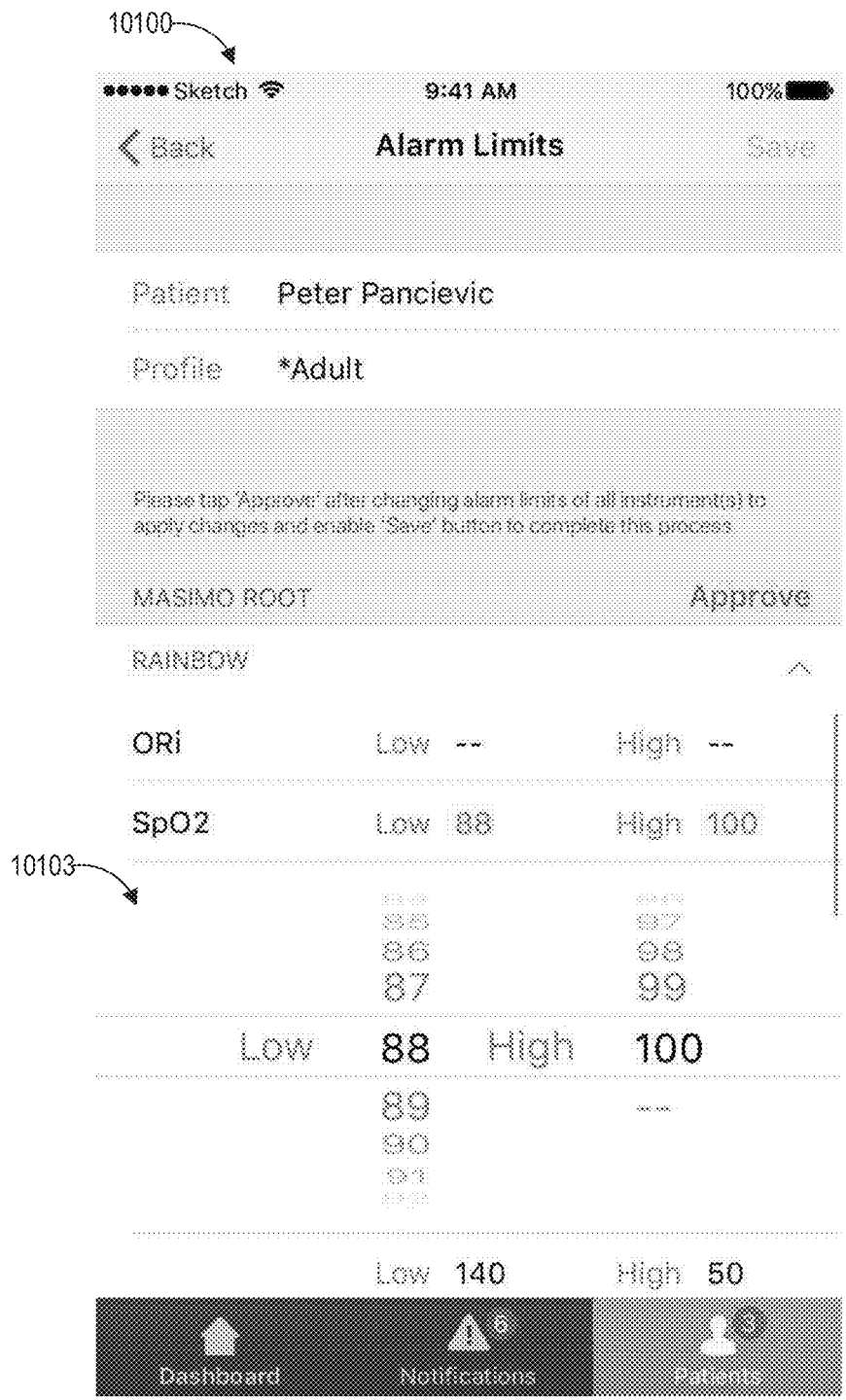

Turning to FIG. 101, another example alarm settings user interface 10100 is shown. The alarm settings user interface 10100 can be similar to alarm settings user interface 10000 of FIG. 100 and the alarm settings screens 1900, 1950 of FIGS. 19A and 19B. As shown, a clinician can adjust alarm thresholds using the threshold selector 10103 for the patient and the patient device and/or channel of that device. The alarm thresholds can include lower and upper alarm limits.

Figure 102:
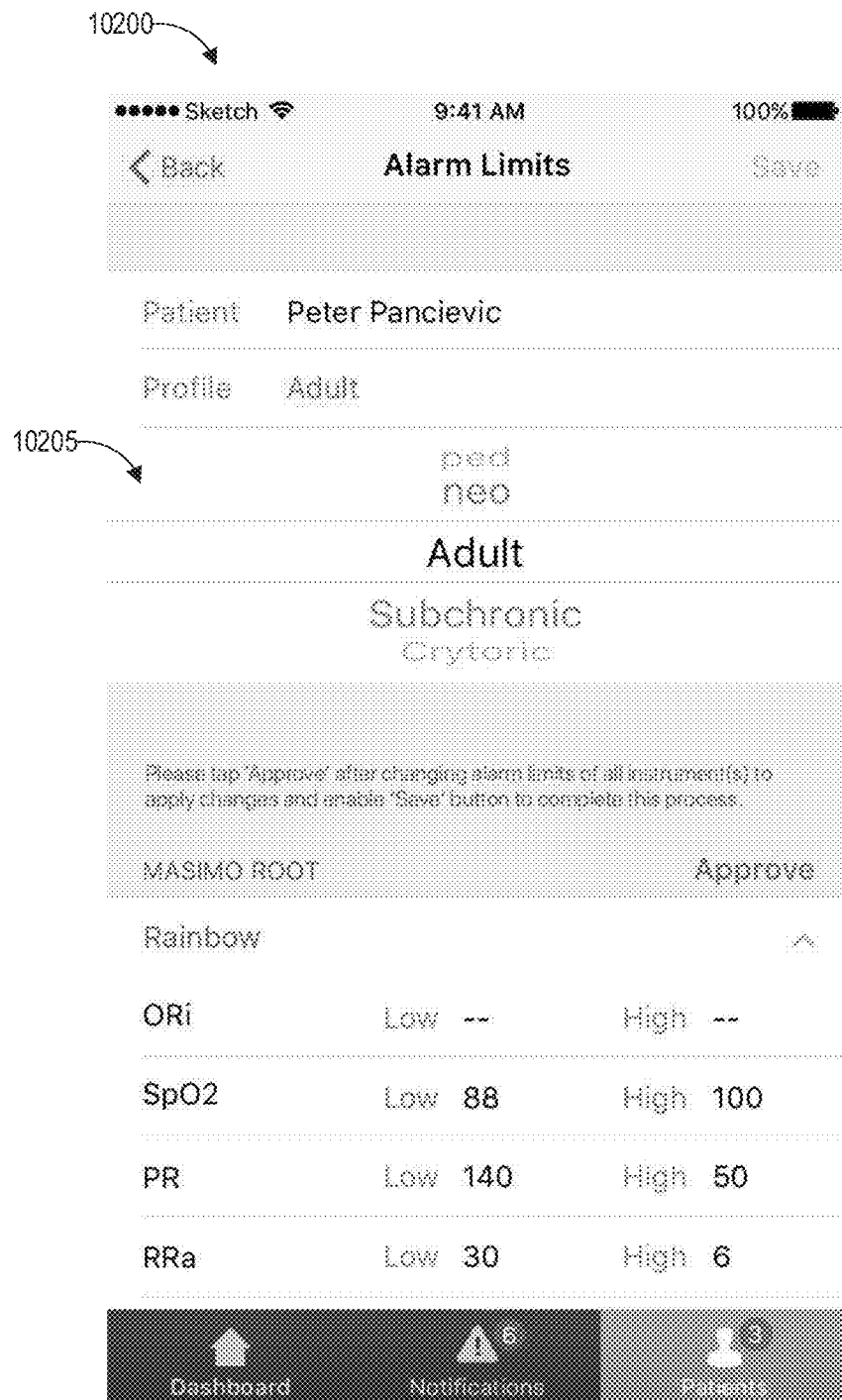

Turning to FIG. 102, another example alarm settings user interface 10200 is shown. The alarm settings user interface 10200 can be similar to the alarm settings user interface 10000 of FIG. 100. As described above with respect to FIG. 100, a clinician can select a profile for a patient, which can specify predefined threshold parameters for the alarm settings. In addition to the alarm settings user interface 10000 of FIG. 100, the alarm settings user interface 10200 can include a profile selector 10205. As shown, a clinician can select a particular profile from a group of profiles in the profile selector 10205, such as an adult profile, a pediatric profile, a neonatal profile, or the like.

Figure 103:
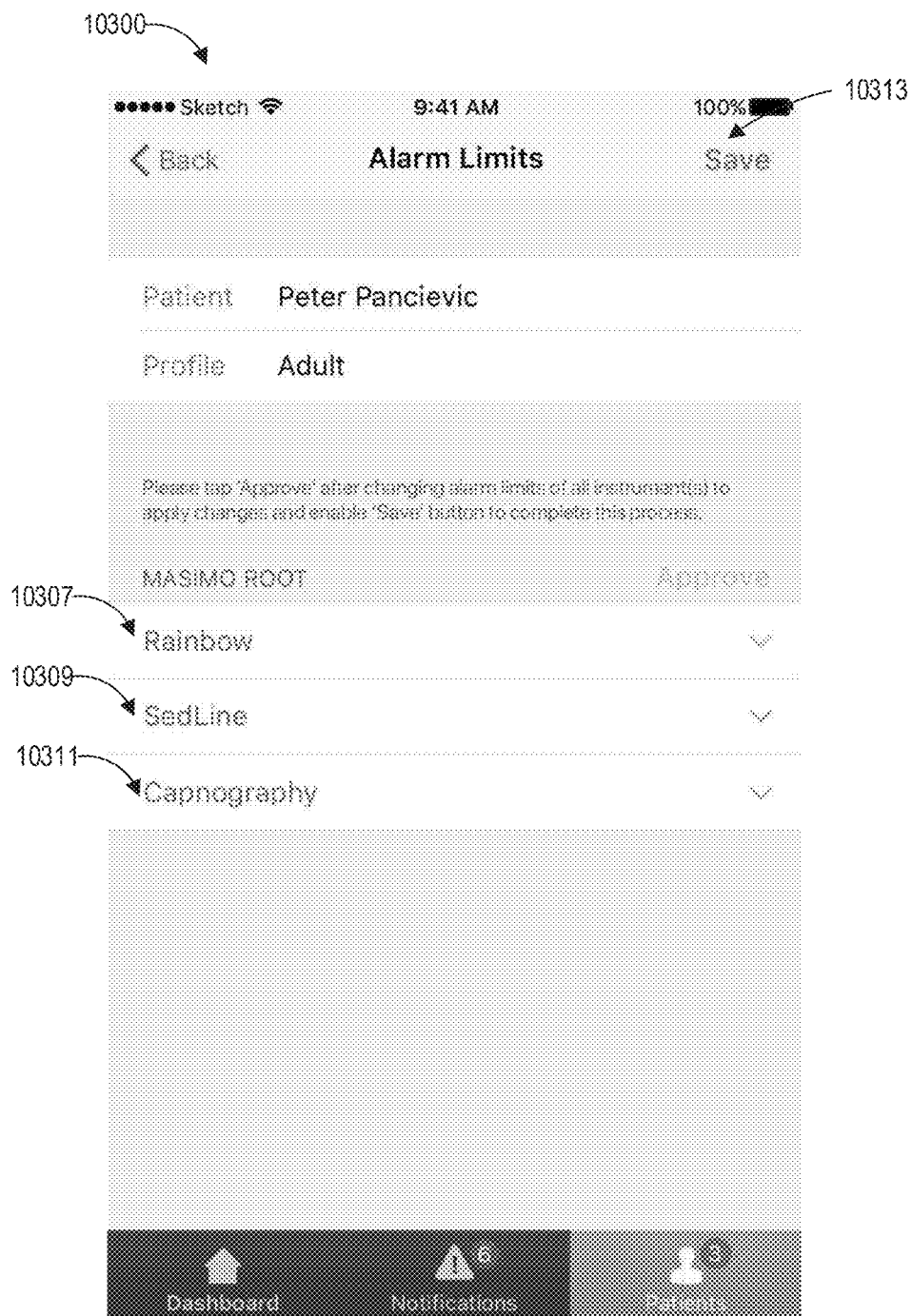

Turning to FIG. 103, another example alarm settings user interface 10300 is shown. The alarm settings user interface 10300 can be similar to the alarm settings user interface 10000 of FIG. 100. However, in contrast to the alarm settings user interface 10000 of FIG. 100, the alarm settings user interface 10300 can include multiple alarm settings categories 10307, 10309, 10311. Each category from the multiple alarm settings categories 10307, 10309, 10311 can correspond to a channel for the selected device (here, "MASIMO ROOT"). Thus, the multiple alarm settings categories 10307, 10309, 10311 can enable a clinician to configure multiple groups of alarm settings (not shown) for multiple channels of the same device. Once the settings have been configured, the clinician can select the save element 10313, which can transmit the alarm settings configuration to the remote server.

Figure 104:
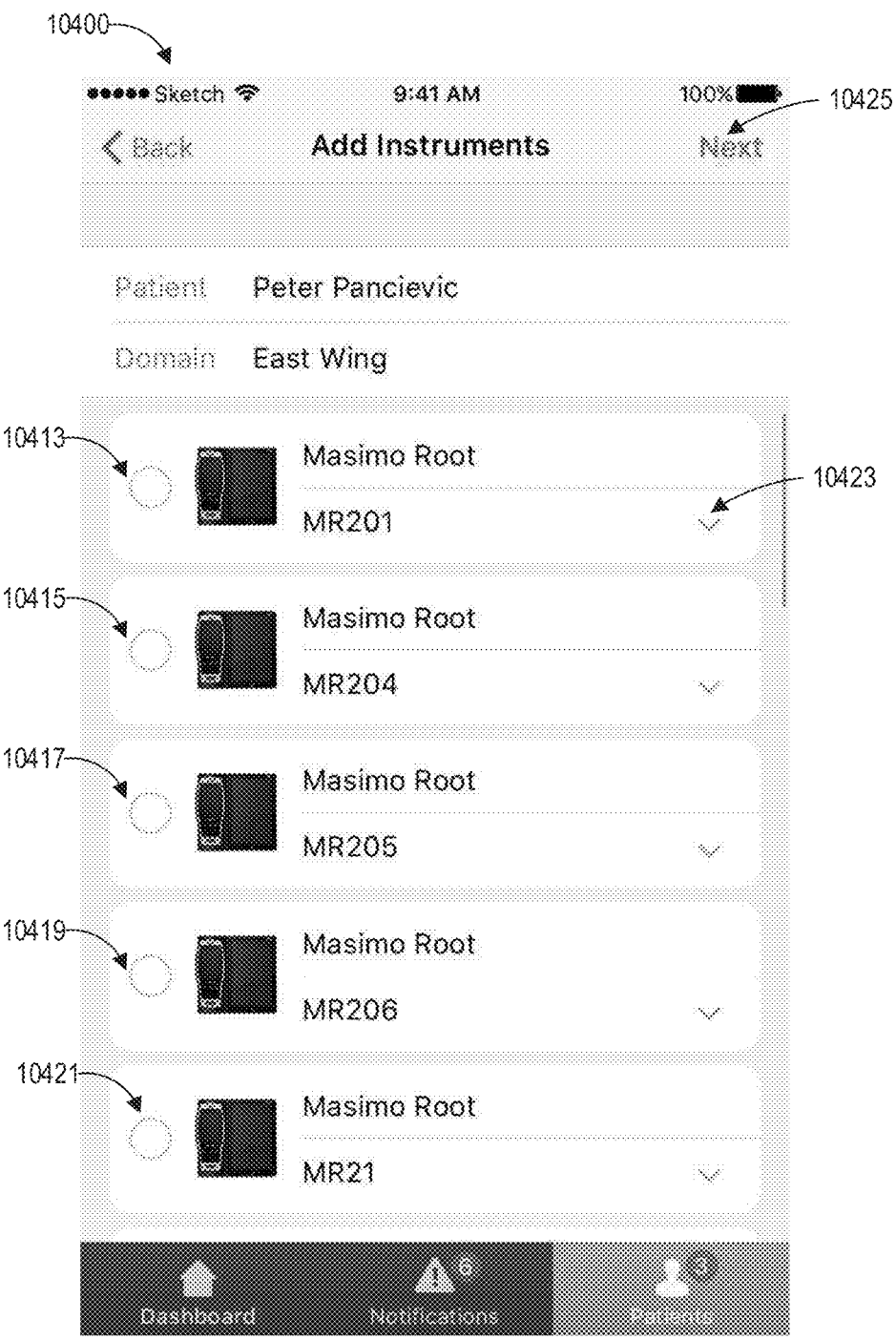

Turning to FIG. 104, an example add device user interface 10400 is shown. A clinician can add a patient device for a patient using the add device user interface 10400. A user selection of the add device selectable element 9723 of FIG. 97 can cause the presentation of the add device user interface 10400. As shown, a clinician can select a device to add from representations of a group of available devices 10413, 10415, 10417, 109, 10421. Each of the representations for the group of available devices 10413, 10415, 10417, 109, 10421 can include identifying information for the device. The representation for an available device 10413 can include an expanded element 10423, which upon selection can cause the add device 10423 to present additional information about the device, such as serial number, a domain, a location, or any other identifying information. Following selection of a patient device to be configured for a patient, the clinician can select the next element 10425, which can lead the clinician through an admit patient workflow on the clinician device.

Figure 105:
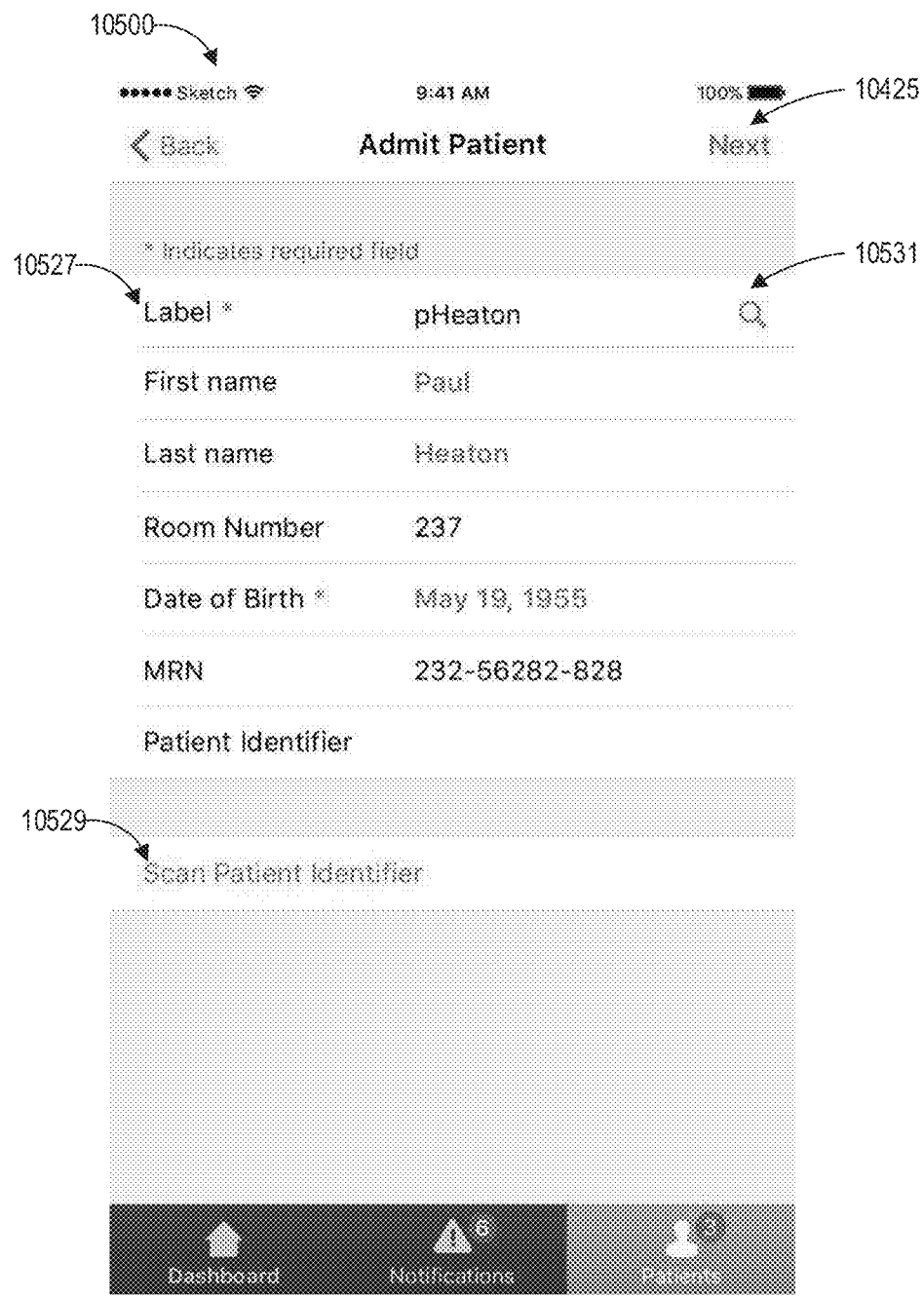

Turning to FIG. 105, an example admit patient user interface 10500 is shown. A clinician can associate a patient device with a patient using the admit patient user interface 10500. A user selection of the next element 10425 of FIG. 104 can cause the presentation of the admit patient user interface 10500, which can be a step in the admit patient workflow. The admit patient user interface 10500 can include a scanner element 10529, which can enable the clinician to use the clinician device or a separate optical scanner to scan an identifier of the patient, such as a barcode.

For example, the patient can wear a wristband with an identifying barcode. The clinician can use the clinician device which can have a camera to capture image of the barcode. In some embodiments, upon scanning a patient barcode, the patient information area 10527 in the patient user interface 10500 can automatically populate since the clinician device can retrieve patient information based on the scanned patient barcode. Additional details regarding the meeting patient and scanning barcodes are described in further detail above with respect to FIG. 82. Alternatively, the clinician can select the search element 10531 to search a particular patient by some criteria, such as any type of identifier to retrieve the patient information. In some embodiments, the patient information area 10527 is editable by the clinician and entered user input for patient information can be transmitted to the remote server. Following identification of a patient, the clinician can select the next element 10425, which can lead the clinician through a next step in the admit patient workflow on the clinician device.

Figure 106:
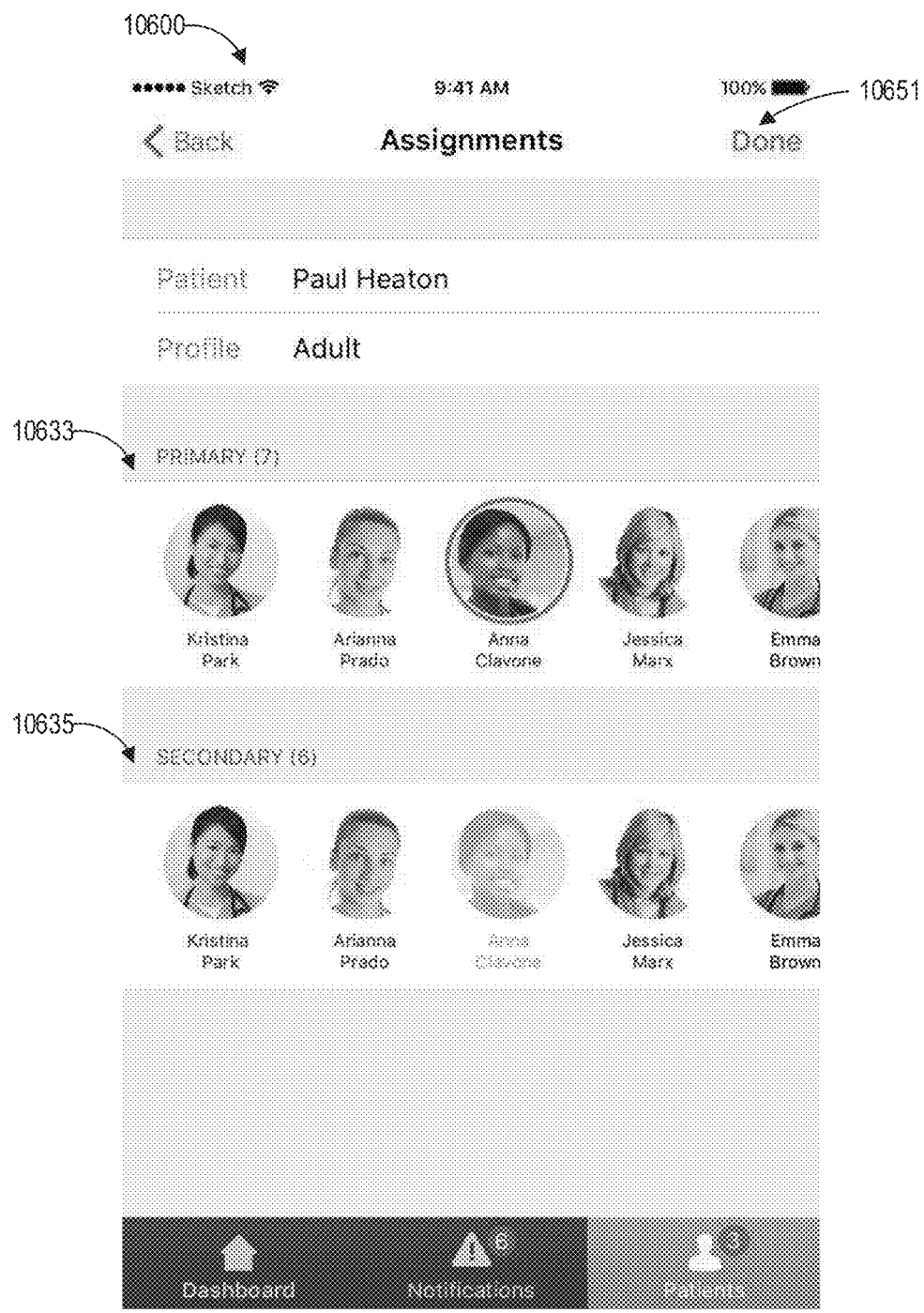

Turning to FIG. 106, an example assignments user interface 10600 is shown. A clinician can assign one or more clinicians to a patient using the assignments user interface 10600. A user selection of the next element 10425 of FIG. 105 can cause the presentation of the assignments user interface 10500, which can be a step in the admit patient workflow. Following selection of the patient device and a patient, the next step in the admit patient workflow can include assigning one or more clinicians to that patient device and patient combination. The assigned one or more clinicians can then receive alarm notifications for that patient device and patient. As shown, a clinician can select one or more primary clinicians from the primary clinicians area 10633 or one or more secondary clinicians from the secondary clinicians area 10635. As described above with respect to FIG. 2, escalating logic for alarms can include sending alarm notifications to a primary clinician and then to a secondary clinician in case the primary does not respond to the alarm notification. Following selection of one or more clinicians to be assigned to the patient, the clinician can select the done user interface element 10651, which can complete that portion of the admit patient workflow. As described above with respect to FIGS. 98 and 100 through 103, alarm settings can be set for the patient by the clinician, which can be additional steps following admission of the patient.

FIG. 107 depicts an example menu user interface 10700. The menu user interface 10700 can provide the clinician useful functions to manage the clinician device. The clinician can log out of the alarm application or the clinician device and enable another clinician to use the same clinician device. The menu user interface 10700 can include a change configuration group element 10701, which can enable the clinician to change a configuration group and view different alarm notifications for a different configuration group. Additional details regarding configuration groups are described in further detail above with respect to FIGS. 49 through 53.

Turning to FIG. 108, an example patient management process 10800 is shown. The patient management process 10800 may be implemented at least in part by any of the clinician devices described herein include the clinician device 104 of FIG. 1. Some aspects of the patient management process 10800 may be implemented at least in part by any MMSs described herein including the MMS 110 of FIG. 1, the MMS 210 of FIG. 2, or the MMS 310 of FIG. 3. For convenience, while the patient management process 10800 will be described in the context of various components of the clinician device 104 at times (such as the notification client 108 or the admit module 112), other computing systems may implement the patient management process 10800. The patient management process 10800 can provide one or more advantageous features described herein, such as, but not limited to, improved alarm notification, improved accessibility of patient data, or improved device management.

At block 10802, user input can be received. The clinician device 104 can receive user input. The clinician device 104 can receive a user selection of a first configuration group from multiple configuration groups. As described above with respect to FIGS. 49 through 53, a clinician can select a configuration group through a user interface. In some embodiments, a configuration group can be used to determine which alarm notifications to present to the clinician. For example, a selected configuration group can be a domain, such as a wing of a hospital, and the clinician device can present alarm notifications from patient devices that are assigned to the selected configuration group (such as the particular wing of the hospital).

Additional user input can be received for patient management. The clinician device 104 can receive a user selection to discharge a patient from a patient device. Based on the user input, a particular patient and patient device can be determined for discharge purposes. Examples of receiving user input to discharge a patient device are described in further detail above with respect to FIGS. 62 and 92. The clinician device 104 can receive a user input related towards admitting a patient to a patient device. The clinician device can receive a user selection identifying a patient device for admission purposes. Examples of receiving user input identifying a patient device are described in further detail above with respect to FIG. 104. The clinician device 104 can identify a patient based on user input. In some embodiments, the clinician can use an optical device to capture a patient barcode. The clinician device 104 can include or control an optical device (such as a built-in scanner or camera) to capture barcode data from a barcode for the patient. The clinician device 104 can request patient data based on a patient identifier identified from the barcode data, such as by requesting patient data from the remote server. In other embodiments, the clinician device 104 can enable a clinician to search for a particular patient. Examples of identifying a patient are described in further detail above with respect to FIG. 105. The clinician device can receive a user selection identifying one or more patients to be assigned to the patient. Multiple clinicians can be assigned to a patient, such as a primary, secondary, etc., assignment. In some embodiments, clinician assignment can be based on a group level selection. Examples of clinician assignment(s) to a patient are described in further detail above with respect to FIG. 106. Additional user input can be related to patient handoffs, such as receiving user confirmation that one or more steps in a handoff process have been completed.

Additional user input can be received for user interface customization. A clinician can customize one or more user interfaces, such as the patient alarming user interface 9600 of FIG. 96. The clinician device 104 can receive user input related to the customization of a user interface, such as the type of notifications to view in a user interface, the layout of the notifications, or any other type of customization.

At block 10804, one or more alarm notifications can be filtered. The clinician device 104 can transmit the user selection of the configuration group to a remote server over a network. In some embodiments, the remote server (such as the MMS 110) can receive the user selection and can transmit alarm notifications that correspond to the selected configuration group. Thus, the clinician device 104 can receive an alarm notification by the remote server from a patient device that is assigned to the first configuration group.

In some embodiments, the clinician device 104 can perform some alarm notification filtering. Based on the selected configuration group, the clinician device 104 can select a subset of alarm notifications to present or make available via a user interface. For example, the clinician device 104 may receive or store alarm notifications from multiple configuration groups, and the user selection can be used to select a subset of those alarm notifications. As another example, the clinician device 104 can filter alarm notifications received from the remote server over the network for a dashboard user interface. The clinician device 104 can determine, from the alarm notifications, a first subset of notifications that include an unread status. The clinician device 104 can identify categories from the first subset of notifications, where each category can correspond to an escalation status. The clinician device 104 can determine, from the alarm notifications, a second subset of notifications that can include an alarming status. Additional details regarding alarm notifications for a dashboard user interface are described above with respect to FIG. 82.

As yet another example, the clinician device 104 can filter alarm notifications received from the remote server over the network for a patient alarming user interface, which can include grouping alarm notifications based on the originating patient device. As described herein, the alarm notifications can include a measured physiological parameter value corresponding to the patient. The clinician device 104 can determine, from the alarm notifications, a first subset of notifications for the patient associated with a first patient device. The clinician device 104 can also determine, from the alarm notifications, a second subset of notifications for the patient associated with a patient device. Additional details regarding alarm notifications for a patient alarming user interface are described above with respect to FIG. 96.

At block 10805, one or more messages can be transmitted or received. The clinician device 104 can transmit or receive one or more messages with other clinician devices. The messages can include textual data, pictures, images, audio, attachments, multimedia, or any other type of data. Clinicians would like to use texting or messaging functionality, but regulations and laws regarding patient privacy, such as Health Insurance Portability and Accountability Act (HIPAA), may need to be taken into consideration. Applications running on network devices may use encryption to secure communications between devices. Accordingly, text-like messages, video, audio, images, or any other data sent to or from devices such as the patient device 102, the clinician device 104, the nurse station 106, the multi-patient monitoring system 110, or other networked devices can occur securely within an application on the device to comply with regulations and laws and maintain patient privacy. Encryption allows clinicians to securely communicate with other clinicians or patients, using, for example, text messaging, audio calling, or video calling. Encryption may also be used to communicate patient data and alarm conditions. Additional security can be used for networked devices. For example, a clinician may be required to login to the application or clinician device 104 with credentials, maintaining security of the in-application messaging. The encryption layer running at the application level allows secure communication between devices over both public and private networks and over multiple network types. For example, applications running on patient and/or clinician devices may use encryption at the application layer to encrypt text messages, images, video calling, audio calling, and/or the transmission of patient data. As another example, an application may initiation a communication with a device on a cellular network that is received by an application running on a device on an 802.11x network. Push notifications may be communicated using encryption to alert clinicians of, for example, changes in patient status or changes in patient assignments. In some embodiments, public-key encryption is used. In some embodiments, secret-key encryption is used. Digital certificates may be used to verify the identities of individuals, organizations, or devices. A device may select between multiple certificates, with the certificates being associated with, for example, different locations, different communication groups, or different users.

At block 10806, one or more events can be received. The clinician device 104 can receive an event data for a timeline user interface. The clinician device 104 can receive events from the remote server over the network, where some or all events can include a measured physiological parameter value corresponding to the patient. The events can indicate particular alarm notifications, when the alarm notifications occurred, or other patient related events such as intubation or a location change. The event data can include timestamps, such as when an event was generated or when it was received. In some embodiments, the clinician device 104 can receive events for a patient handoff. Additional information regarding events are described in further detail above with respect to FIG. 69.

At block 10808, one or more notes can be received. The clinician device 104 can receive notes data for a notes user interface or a patient handoff process. The clinician device 104 can receive notes from the remote server over the network, where each note can include textual data regarding the patient and a timestamp. The timestamp can indicate when the note was generated or received. The notes can be generated by a clinician through a clinician device, such as by typing on a keyboard, speaking into a microphone, or using some other input device. Additional information regarding notes are described in further detail above with respect to FIG. 75.

At block 10810, patient data can be received. The clinician device 104 can receive patient data from a remote server, an electronic medical record (EMR) system, or through a clinician via the clinician device 104. The clinician device 104 can request patient data from the remote server using a patient identifier. Example patient data includes a patient's name, label, room, patient medical record number (MRN), patient allergies, patient conditions, patient medication information (last medication taken, medication schedule, next scheduled medication), patient medical history, medical records, lab data, x-rays, blood work, or any other patient related information. Patient data or any data sent to or from the clinician device 104 can be transmitted according to a Health Level-7 or HL7 format, which refers to a set of international standards for transfer of clinical and administrative data between software applications used by various healthcare providers. In some embodiments, the clinician can use his or her clinician device 104 to edit or enter any patient data. Additional information regarding patient information are described in further detail with respect to FIGS. 48 and 70.

At block 10812, one or more patient devices can be managed. The clinician device 104 can manage a patient device by transmitting instructions to the remote server. The clinician device 104 can transmit the user selection to discharge the patient from a patient device to the remote server over the network. The remote server, such as the MMS 110, can remove an association between a patient (such as a patient profile) and a particular patient device, such that physiological data regarding the patient may no longer be captured or transmitted by the patient device. Additional information regarding discharging a patient are described in further detail above with respect to FIGS. 62 and 98. The clinician device 104 can transmit, to the remote server over the network, admit data identifying the patient device, the patient, and the clinician to admit the patient to the patient device. The remote server, such as the MMS 110, can add an association between the patient (such as a patient profile) and the particular patient device, such that physiological data regarding the patient can be captured or transmitted by the patient device to the remote server or the clinician device 104. Additional information regarding admitting a patient are described in further detail above with respect to FIGS. 104 through 106.

Blocks 10814, 10816, and 10818 relate to error handling. At block 10814, an error status can be determined. The clinician device 104 can determine an error status. The clinician device 104 can detect a failed connection with the remote server over the network. Detection of a failed connection can include detecting that a network card is not working or that a network connection with the remote server cannot be made. Additional examples of error detection include detection of failed device hardware on the clinician device 104. If an error state has been detected, the process 10800 can proceed to block 10816; otherwise, the process can proceed to block 10820 where an error state has not been detected. At block 10816, a warning can be presented. The clinician device 104 can present a visual warning of the failed connection. At block 10818, a correction to the error can be detected. The clinician device 104 can detect that the error state has been corrected. In the context of a failed network connection, the clinician device 104 can detect a correction where the clinician device 104 successfully establishes a connection with the remote server over the network. If a correction has been detected, the clinician device 104 can proceed to block 10822; otherwise, the clinician device 104 can return to block 10818 and can continue checking for a correction of the error state. While the clinician device 105 keeps checking, the warning at block 10816 can persist, which can advantageously continue to inform the clinician that the clinician device 104 or the remote server is experiencing errors. Additional information regarding warnings, error states, and error correction are described in further detail above with respect to FIGS. 76 through 79.

At block 10820, a user interface can be output. Example output user interfaces are described above with respect to FIGS. 8 through 107. In the context of an error state correction, the clinician device 104 can present a visual indicator of the error state correction (such as an indication that a connection has been established). The clinician device 104 can also output a timeline user interface that presents events, which is described in further detail above with respect to FIG. 69. The clinician device 104 can output a messaging user interface that includes messages sent to or by the clinician. The messaging user interface can include user input elements that enable a clinician to compose and send messages to other clinicians within an application. The clinician device 104 can output a video call user interface, an example of which is described in further detail above with respect to FIGS. 80 and 81.

The clinician device 104 can output a dashboard user interface. The dashboard user interface can include a first summary indicator of a first subset of notifications (such as unread notifications), a plurality of second summary indicators for each category (such as initial, escalated, and re-escalated statuses), and a third summary indicator of another subset of notifications (such as notifications that are alarming). Thus, in the dashboard user interface, the clinician can view how many notifications are unread, how many unread notifications there are of each category type, the alarming notifications and how many are alarming. The summary indicators can include a quantity of notifications or a number of notifications. Additional information regarding a dashboard user interface is described in further detail above with respect to FIG. 82.

The clinician device 104 can also output a patient alarming user interface. The patient alarming user interface can include patient alarms segregated by originating patient device. Further, the patient alarming user interface can include multiple patient alarms grouped by device from multiple patient devices. In particular, the patient alarming user interface can include a first visual representation for each first measured physiological parameter value from a first subset of notifications grouped by a first patient device, and a second visual representation for each second measured physiological parameter value from a second subset of notifications grouped by a second patient device. Additional details regarding a patient alarming user interface are described in further detail with respect to FIG. 96.

In some embodiments, the clinician device 104 can output a user interface based on customization input. The clinician device 104 can use user-specified customization to dynamically output a user interface, such as the type of notifications to view in a user interface, the layout of the notifications, or any other type of customization. Further, a dynamically output user interface can be further customized for particular patients. A clinician can have a different patient alarming user interface for a first patient than a second patient based on customization parameters specific to particular patients.

Turning to FIG. 109, an example patient handoff process 10900 is shown. A patient handoff may occur, for example, when there are shift changes for one or more members of a clinical team. The handoff may occur as part of a transfer of responsibility and/or accountability for care of a patient to another individual. Information related to the handoff may include, for example, the location of patient(s), current status, problems or concerns, background information, reason for admission, summary of treatment to date, baseline observations, vital sign data, clinical assessment, recommendations, and identification of possible risks. The patient handoff process 10900 may be implemented at least in part by any of the clinician devices described herein include the clinician device 104 of FIG. 1. Some aspects of the patient handoff process 10900 may be implemented at least in part by any MMS s described herein including the MMS 110 of FIG. 1, the MMS 210 of FIG. 2, or the MMS 310 of FIG. 3. For convenience, while the patient handoff process 10900 will be described in the context of various components of the clinician device 104 at times, other computing systems may implement the patient handoff process 10900. The patient management process 10900 can provide one or more advantageous features described herein, such as, but not limited to, an improved patient handoff workflow.

At block 10902, one or more clinicians for the patient handoff can be identified. For example, the clinician device 104 can identify a first clinician and a second clinician for a handoff workflow for a patient. For example, the clinician leaving for shift change can conduct the patient handoff with the clinician device 104. In some embodiments, the patient handoff may be associated with multiple clinicians. As part of the handoff process, each of the transitioning clinicians can be specified to the clinician device 104 in addition to a particular patient.

At block 10904, patient data can be received. The clinician device 104 can receive patient data from the remote server over the network. The block 10904 for receiving patient data can be similar to the block 10810 of FIG. 108 for receiving patient data.

At block 10906, notes can be received. The clinician device 104 can receive notes for the patient from the remote server over the network. Each note can include, for example, (i) textual data regarding the patient, and (ii) a timestamp. In some embodiments, notes can be stored locally on the clinician device 104 and can be retrieved from local storage. The block 10906 can be similar to the block 10808 of FIG. 108 for receiving notes.

At block 10908, events can be received. The clinician device 104 can receive events for the patient from the remote server over the network. Each event can include (i) a measured physiological parameter value corresponding to the patient, and (ii) a timestamp. In some embodiments, events can be stored locally on the clinician device 104 and can be retrieved from local storage. The block 10908 can be similar to the block 10806 of FIG. 108 for receiving events.

At block 10910, one or more user interfaces can be output. The clinician device 104 can output a first user interface including, for example, (i) the notes ordered by each respective timestamp, and (ii) a visual representation of at least some of the textual data regarding the patient. The clinician device 104 can output a second user interface including, for example, (i) the events ordered by each respective timestamp, and (ii) a visual representation for each measured physiological parameter value. The clinician device 104 can output a third user interface including patient data. In some embodiments, the clinician device 104 can output a user interface that integrates notes, events, or patient data. For example, the user interface can include a feed such that notes, events, or patient data can be ordered by timestamps and reviewed by the handoff clinicians.

At block 10912, one or more confirmations can be received. The clinician device 104 can receive confirmations that indicate the clinicians have reviewed the handoff data. In some embodiments, a confirmation can include a clinician simply selecting a next user interface element to proceed through the handoff workflow. The clinician device 104 can receive a confirmation that a review of the user interface including the notes has been completed. The clinician device 104 can receive a confirmation that a review of the user interface including the events have been completed. The clinician device 104 can receive a confirmation that a review of the user interface including patient data has been completed.

At block 10914, data can be transmitted that indicates completion of the handoff workflow. In response to receiving one or more confirmations, the clinician device 104 can transmit an indication to the remote server that the handoff workflow for the patient has been completed by the clinicians. The indication can include a patient identifier, identifiers for clinicians, or a timestamp indicating a time that the handoff was completed. In some embodiments, the remote server does not need to be notified of the handoff completion. Handoff completion data may not need to be transmitted to the remote server or may not need to be stored at all.

VIII. Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A system for managing patient alarms, the system comprising:
  a server comprising a first hardware processor configured to execute first instructions to:
    receive a first alarm notification for a first alarm, the first alarm notification comprising a measured physiological parameter value for a patient;
    determine a first clinician device to notify;
    transmit the first alarm notification to the first clinician device;
    determine a plurality of historical entries associated with the first alarm; and
  the first clinician device comprising a second hardware processor configured to execute second instructions to:
    receive, from the server, a plurality of alarm notifications comprising the first alarm notification;
    cause presentation, in a display of the first clinician device, of a first user interface comprising:
      a plurality of visual representations,
      wherein each visual representation from the plurality of visual representations corresponds to an alarm notification from the plurality of alarm notifications,
      wherein a first visual representation of the plurality of visual representations corresponds to the first alarm notification, the first visual representation comprising:
        (i) the measured physiological parameter value,
        (ii) at least one of a patient identifier or a room identifier associated with the patient,
        (iii) a first option to accept the first alarm, and
        (iv) a second option to reject the first alarm,
        wherein user selection of the first option for accepting the first alarm causes the first clinician device to transmit an indication of an acceptance of the first alarm to the server, and
        wherein user selection of the second option for rejecting the first alarm causes the first clinician device to transmit an indication of a rejection of the first alarm to the server;
      receive selection of a selectable element associated with the first alarm notification; and
      in response to receiving the selection of the selectable element, cause presentation of a historical view for the first alarm, wherein the historical view comprises the plurality of historical entries,
      wherein the plurality of historical entries comprises at least one of a forward, accept, reject, or escalation of the first alarm, and a different one of the forward, accept, reject, or escalation of the first alarm.

2. The system of claim 1, wherein the first hardware processor of the server is configured to execute further instructions to:
  receive, from the first clinician device, the indication of the rejection of the first alarm;
  identify a second clinician device to notify; and
  transmit the first alarm notification to the second clinician device.

3. The system of claim 1, wherein the first hardware processor of the server is configured to execute further instructions to:
  Determine that, after a period of time, a response to the first alarm has not been received from the first clinician device;
  identify a second clinician device to notify; and
  transmit the first alarm notification to the second clinician device.

4. The system of claim 1, wherein the first visual representation of the first alarm at least includes a textual description of a physiological parameter corresponding to the physiological parameter value.

5. The system of claim 1, wherein the server receives the first alarm notification from a patient monitoring device.

6. The system of claim 1, wherein the first hardware processor of the server is configured to execute further instructions to:
  receive, from an electronic medical records (EMR) system, patient data for the patient; and
  transmit the patient data to the first clinician device, wherein the second hardware processor of the first clinician device is configured to execute further instructions to:
    cause presentation, in the display of the first clinician device, of a second user interface comprising the patient data.

7. The system of claim 6, wherein the patient data comprises at least one of: patient allergy data, patient conditions data, patient medication data, patient medical history data, medical records data, lab data, x-rays data, or blood work data.

8. The system of claim 1, wherein the first clinician device comprises a mobile computing device.

9. A method for managing patient alarms, the method comprising:
  under control of one or more hardware processors,
  receiving, at a server, a plurality of alarm notifications comprising a first alarm notification for a first alarm, the first alarm notification comprising a measured physiological parameter value for a patient;

determining a first clinician device to notify;

transmitting the plurality of alarm notifications to the first clinician device;

determining a plurality of historical entries associated with the first alarm;

receiving, at the first clinician device, the plurality of alarm notifications;

causing presentation, in a display of the first clinician device, of a first user interface comprising:
 a plurality of visual representations,
  wherein each visual representation from the plurality of visual representations corresponds to an alarm notification from the plurality of alarm notifications,
  wherein a first visual representation of the plurality of visual representations corresponds to the first alarm notification, the first visual representation comprising:
   (i) the measured physiological parameter value,
   (ii) at least one of a patient identifier or a room identifier associated with the patient,
   (iii) a first option to accept the first alarm, and
   (iv) a second option to reject the first alarm,
  wherein user selection of the first option for accepting the first alarm causes the first clinician device to transmit an indication of an acceptance of the first alarm to the server, and
  wherein user selection of the second option for rejecting the first alarm causes the first clinician device to transmit an indication of a rejection of the first alarm to the server;

receiving, at the first clinician device, selection of a selectable element associated with the first alarm notification; and in response to receiving the selection of the selectable element, causing presentation, in the display of the first clinician device, of a historical view for the first alarm, wherein the historical view comprises the plurality of historical entries, wherein the plurality of historical entries comprises at least one of a forward, accept, reject, or escalation of the first alarm, and a different one of the forward, accept, reject, or escalation of the first alarm.

10. The method of claim 9, further comprising:

receiving, from the first clinician device, the indication of the rejection of the first alarm;

identifying a second clinician device to notify; and transmitting the first alarm notification to the second clinician device.

11. The method of claim 9, further comprising:

determining that, after a period of time, a response to the first alarm has not been received from the first clinician device;

identifying a second clinician device to notify; and transmitting the first alarm notification to the second clinician device.

12. The method of claim 9, wherein the first visual representation of the first alarm at least includes a textual description of a physiological parameter corresponding to the physiological parameter value.

13. The method of claim 9, wherein the server receives the first alarm notification from a patient monitoring device.

14. The method of claim 9, further comprising:

receiving, at the server, patient data for the patient from an electronic medical records (EMR) system;

transmitting the patient data to the first clinician device; and causing presentation, in the display of the first clinician device, of a second user interface comprising the patient data.

15. The method of claim 14, wherein the patient data comprises at least one of: patient allergy data, patient conditions data, patient medication data, patient medical history data, medical records data, lab data, x-rays data, or blood work data.

* * * * *